United States Patent
Stamatoyannopoulos et al.

(10) Patent No.: US 12,253,468 B2
(45) Date of Patent: *Mar. 18, 2025

(54) METHODS FOR FLUORESCENCE IMAGING MICROSCOPY AND NANO-FISH

(71) Applicant: Altius Institute for Biomedical Sciences, Seattle, WA (US)

(72) Inventors: John A. Stamatoyannopoulos, Seattle, WA (US); Shreeram Akilesh, Seattle, WA (US); Vivek Nandakumar, Seattle, WA (US)

(73) Assignee: Altius Institute for Biomedical Sciences, Seattle, WA (US)

( * ) Notice: Subject to any disclaimer, the term of this patent is extended or adjusted under 35 U.S.C. 154(b) by 353 days.

This patent is subject to a terminal disclaimer.

(21) Appl. No.: 17/736,684

(22) Filed: May 4, 2022

(65) Prior Publication Data

US 2022/0397526 A1 Dec. 15, 2022

Related U.S. Application Data

(63) Continuation of application No. 16/319,157, filed as application No. PCT/US2017/042946 on Jul. 19, 2017, now Pat. No. 11,353,400.

(60) Provisional application No. 62/364,245, filed on Jul. 19, 2016.

(51) Int. Cl.
| | |
|---|---|
| G01N 21/64 | (2006.01) |
| A01N 1/02 | (2006.01) |
| C12N 5/078 | (2010.01) |
| C12N 5/09 | (2010.01) |
| C12P 19/34 | (2006.01) |
| C12Q 1/6837 | (2018.01) |
| C12Q 1/6841 | (2018.01) |
| C40B 40/06 | (2006.01) |
| G01N 1/30 | (2006.01) |
| G01N 21/78 | (2006.01) |
| G01N 33/569 | (2006.01) |
| G01N 33/574 | (2006.01) |
| G01N 33/58 | (2006.01) |
| C40B 30/04 | (2006.01) |
| G01N 15/00 | (2006.01) |

(52) U.S. Cl.
CPC ........... *G01N 21/64* (2013.01); *A01N 1/0221* (2013.01); *C12N 5/0634* (2013.01); *C12N 5/0694* (2013.01); *C12P 19/34* (2013.01); *C12Q 1/6837* (2013.01); *C12Q 1/6841* (2013.01); *C40B 40/06* (2013.01); *G01N 1/30* (2013.01); *G01N 21/6458* (2013.01); *G01N 21/78* (2013.01); *G01N 33/56966* (2013.01); *G01N 33/574* (2013.01); *G01N 33/582* (2013.01); *C40B 30/04* (2013.01); *G01N 2015/0038* (2013.01)

(58) Field of Classification Search
CPC ...... G01N 21/64; G01N 1/30; G01N 21/6458; G01N 21/78; G01N 33/56966; G01N 33/574; G01N 33/582; G01N 2015/0038; A01N 1/0221; C12N 5/0634; C12N 5/0694; C12P 19/34; C12Q 1/6837; C12Q 1/6841; C12Q 2521/301; C12Q 2563/107; C40B 40/06; C40B 30/04
See application file for complete search history.

(56) References Cited

U.S. PATENT DOCUMENTS

| | | | |
|---|---|---|---|
| 5,474,796 | A | 12/1995 | Brennan |
| 6,107,088 | A | 8/2000 | Korneluk et al. |
| 11,353,400 | B2 | 6/2022 | Stamatoyannopoulos et al. |
| 2003/0027159 | A1 | 2/2003 | Ward et al. |
| 2003/0087279 | A1 | 5/2003 | Shao et al. |
| 2003/0170689 | A1 | 9/2003 | Stamatoyannopoulous et al. |
| 2005/0244863 | A1* | 11/2005 | Mir .................... B82Y 5/00 435/7.1 |
| 2007/0204354 | A1 | 8/2007 | Nomura |
| 2008/0094614 | A1* | 4/2008 | Tuschel .................. G01J 3/44 356/213 |
| 2009/0029378 | A1* | 1/2009 | Connelly ........... G01N 33/5091 435/7.1 |
| 2012/0322692 | A1 | 12/2012 | Pham et al. |
| 2014/0073520 | A1 | 3/2014 | Cai et al. |
| 2015/0252412 | A1* | 9/2015 | Van Oudenaarden ............... C12Q 1/6841 506/5 |
| 2016/0046984 | A1 | 2/2016 | Nguyen et al. |
| 2021/0310058 | A1 | 10/2021 | Akilesh et al. |

FOREIGN PATENT DOCUMENTS

| | | |
|---|---|---|
| DE | 4038293 A1 | 6/1992 |
| WO | 2013101893 A1 | 7/2013 |
| WO | WO 2014036525 | 3/2014 |

(Continued)

OTHER PUBLICATIONS

Alonas, et al., "Imaging Viral RNA Using Multiply Labeled Tetravalent RNA Imaging Probes in Live Cells", Methods, Apr. 2016, 98:91-98. (18 pages).

(Continued)

*Primary Examiner* — Narayan K Bhat
(74) *Attorney, Agent, or Firm* — Bozicevic, Field & Francis LLP; Shweta Chandra

(57) ABSTRACT

Disclosed herein are methods of detecting a target nucleic acid sequence, determining the localization of the target nucleic acid sequence, and/or quantifying the number of target nucleic acid sequences in a cell. This method may be used on small target nucleic acid sequences, and may be referred to as Nano-FISH.

14 Claims, 39 Drawing Sheets
Specification includes a Sequence Listing.

(56) References Cited

FOREIGN PATENT DOCUMENTS

| WO | 2014204727 A1 | 12/2014 |
|---|---|---|
| WO | WO 2015002978 | 1/2015 |
| WO | WO 2018017774 | 1/2018 |
| WO | WO 2018035387 | 2/2018 |

OTHER PUBLICATIONS

Baranyi, et al., "Rapid generation of stable cell lines expressing high levels of erythropoietin, factor VIII, and an antihuman CD20 antibody using lentiviral vectors", Hum Gene Ther Methods, Aug. 2013, 24(4):214-227.
Beliveau, et al., "Single-molecule super-resolution imaging of chromosomes and in situ haplotype visualization using Oligopaint FISH probes", Nature Communications, May 2015, 6(1):7147. (14 pages).
Beliveau, et al., "Versatile design and synthesis platform for visualizing genomes with Oligopaint FISH probes", PNAS, Dec. 11, 2012, 109(52):21301-21306.
Goel, et al., "Molecular beacon: a multitask probe", Journal of Applied Microbiology, Sep. 2005, 99(3):435-442.
Ma, et al., "Multicolor CRISPR labeling of chromosomal loci in human cells", PNAS, Mar. 10, 2015, 112(10):3002-3007.
Ni, et al., "Super-resolution imaging of a 2.5 kb non-repetitive DNA in situ in the nuclear genome using molecular beacon probes", eLife, May 9, 2017, 6:e21660. (23 pages).
Reisinger, et al., "Visualization of episomal and integrated Epstein-Barr virus DNA by fiber fluorescence in situ hybridization", Int J Cancer., Apr. 1, 2006, 118(7):1603-1608.
Zufferey, et al., "Self-Inactivating Lentivirus Vector for Safe and Efficient In Vivo Gene Delivery", Journal of Virology, Dec. 1998, 72(12):9873-9880.
Corrigan et al., (2016) "A continuum model of transcriptional bursting," elife, 5(e13051):1-38.
GenBank data sheet, H1N1 Influenza segment 4, printed on Aug. 20, 2020, pp. 1-2 (Year: 2020).
GenBank data sheet, H1N1 Influenza segment 5, printed on Aug. 21, 2020, pp. 1-2 (Year: 2020).
GenBank data sheet, H1N1 Influenza segment 6, printed on Aug. 20, 2020, pp. 1-2 (Year: 2020).
Raj et al., (2008) "Imaging individual mRNA molecules using multiple singly labeled probes," Nature Methods, 5(10) 877-879.
"Apoptosis" from Wikipedia, 28 pages. Printed on Jan. 10, 2023.
Chimeric nuclease from Wikipedia, 2 pages. Printed on Jun. 10, 2022.
Fu et al., (2014) "Promises and Pitfalls of Intracellular Delivery of Proteins" Bioconjugate Chemistry, vol. 25, 1602-1608.
Kotterman et.al., (2014) "Engineering adeno-associated viruses for clinical gene therapy" Nature Reviews, vol. 15, 445-451.
Lenzi et al., (2014) NCBI Bookshelf, A Service of the National Library of Medicine, National Institute of Health, Oversight and Review of Clinical Gene Transfer Protocols: Assessing the Role of the Recombinant DNA Advisory Committee, Washington(DC): National Academies Press (US), pp. 1-16.
Namdev et al., (2016) "Challenges and approaches for Oral protein and peptide drug delivery" Research J. Pharm. and Tech., 9(3), 305-312.
Rehman et al., (2016) "Delivery of Therapeutic Proteins: Challenges and Strategies. Current Drug Targets" 17, 1172-1188.
Shim et al., (2018) "Nonviral Delivery Systems for Cancer Gene Therapy: Strategies and Challenges" Current Gene Therapy, 18,3-20.

* cited by examiner

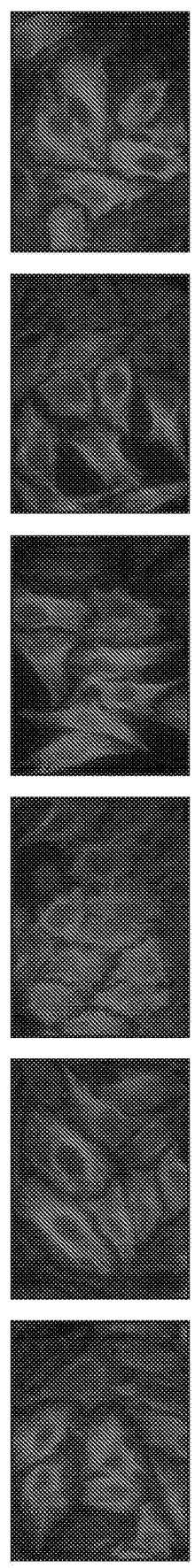
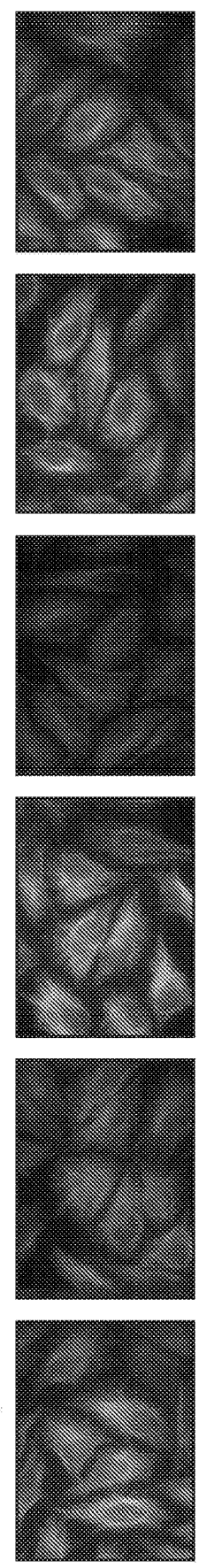
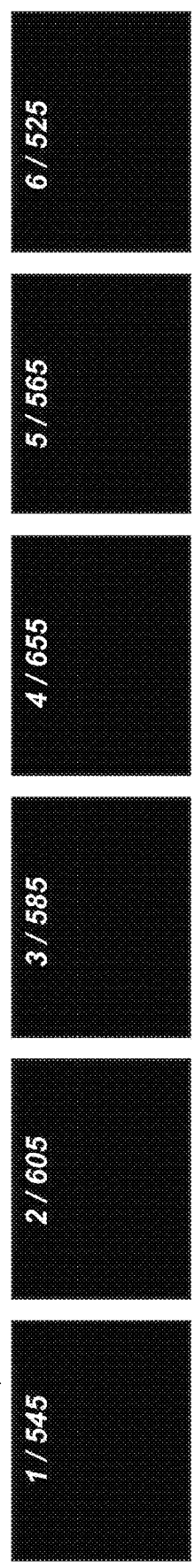
FIG. 9
FIG. 9A  β-Tubulin (M) -> RaM-ssDNA -> QDot655-Rb
FIG. 9B  β-Tubulin (M) -> RaM-ssDNA -> QDot-ssDNA'
FIG. 9C  Control -> QDot-ssDNA'

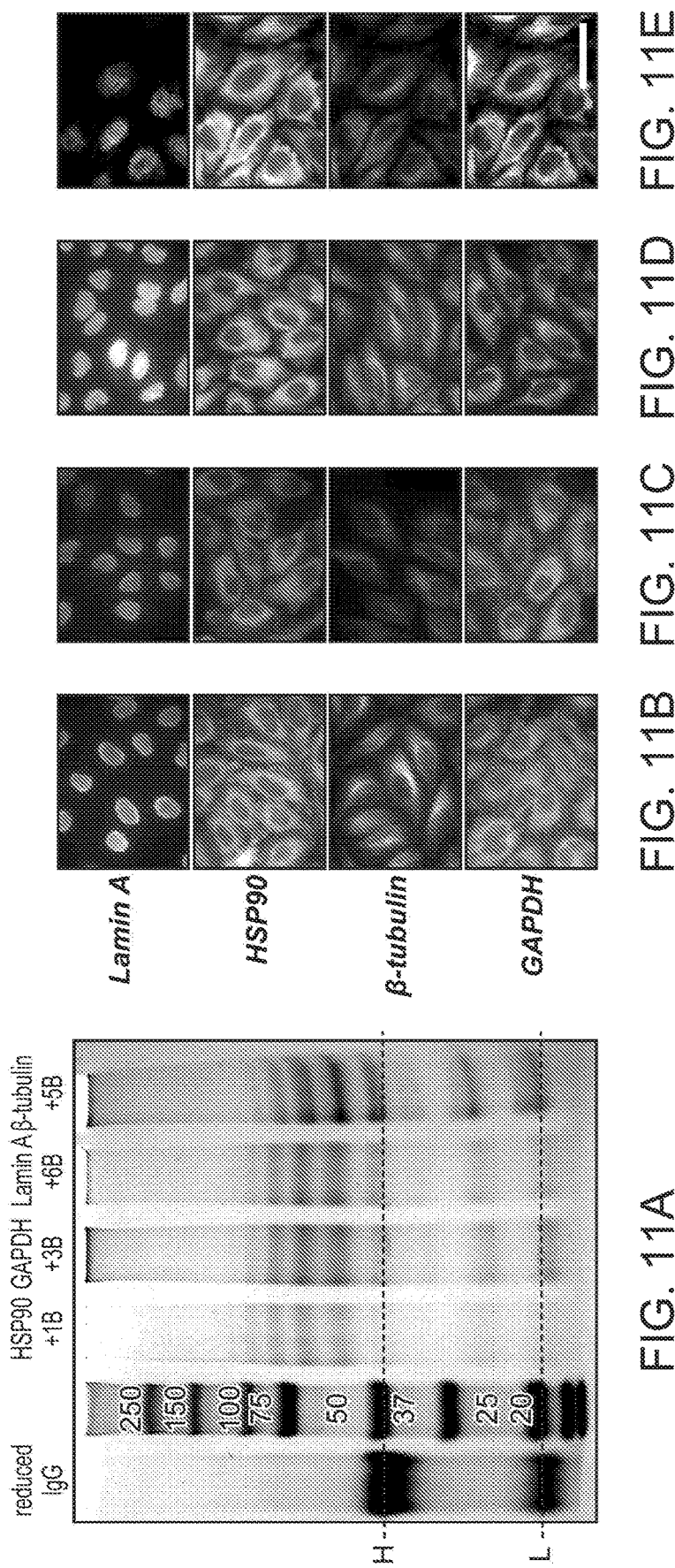

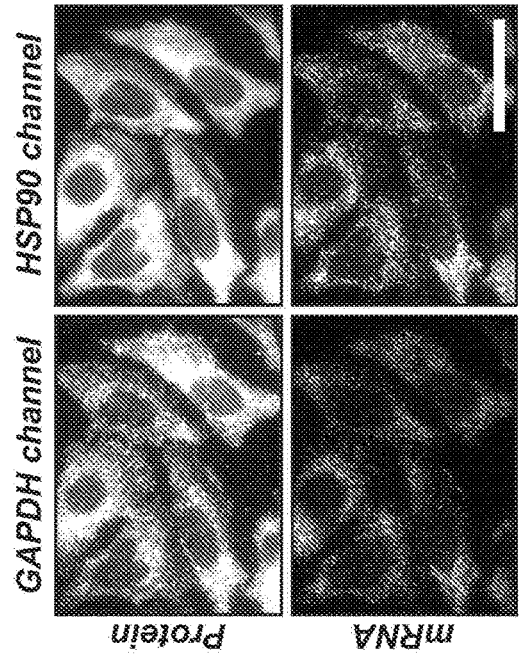
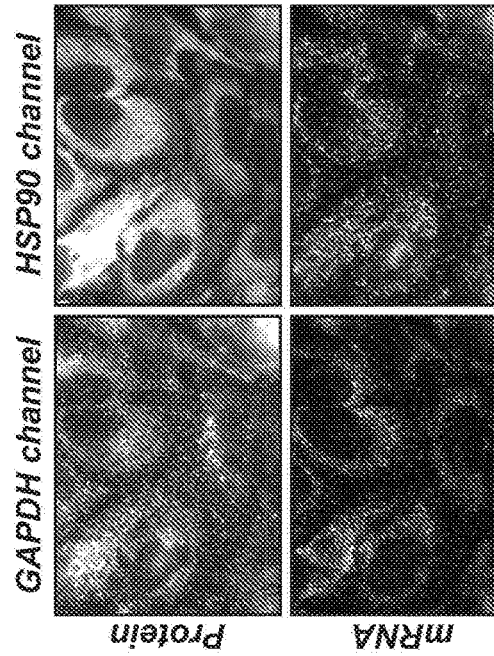
FIG. 22A
FIG. 22B

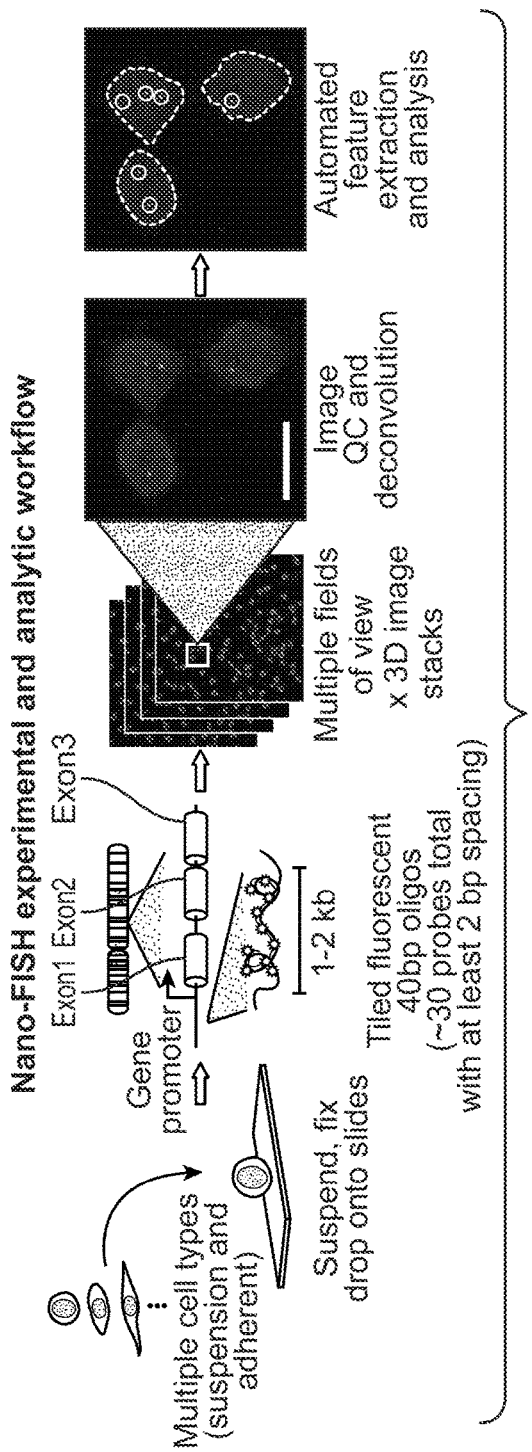
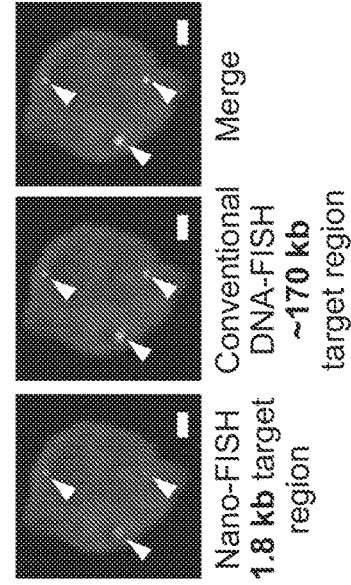
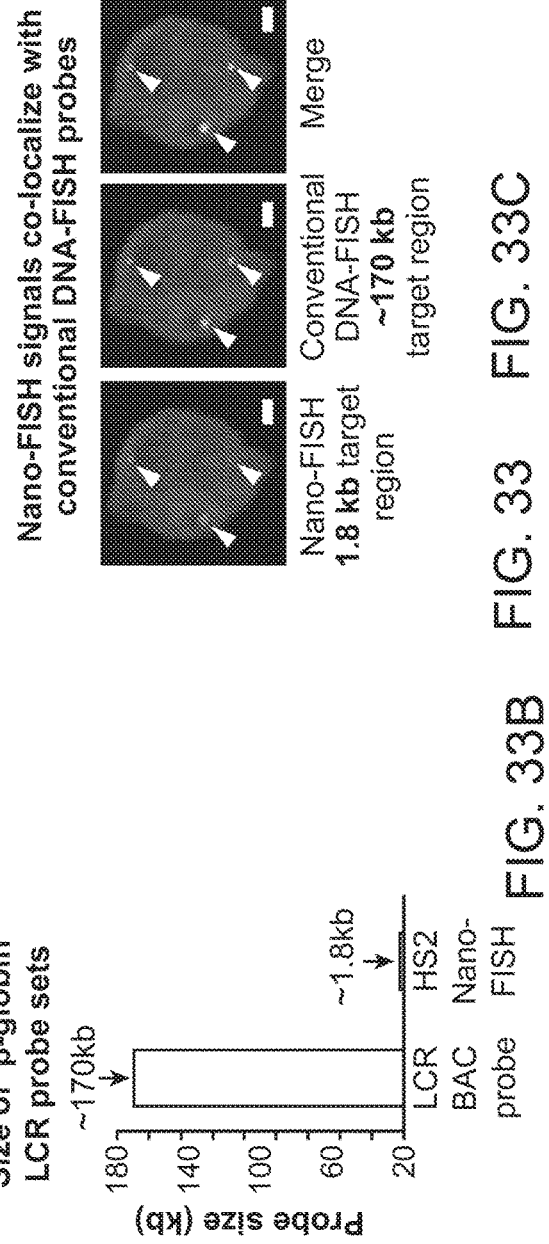
FIG. 33A
FIG. 33B   FIG. 33C
FIG. 33

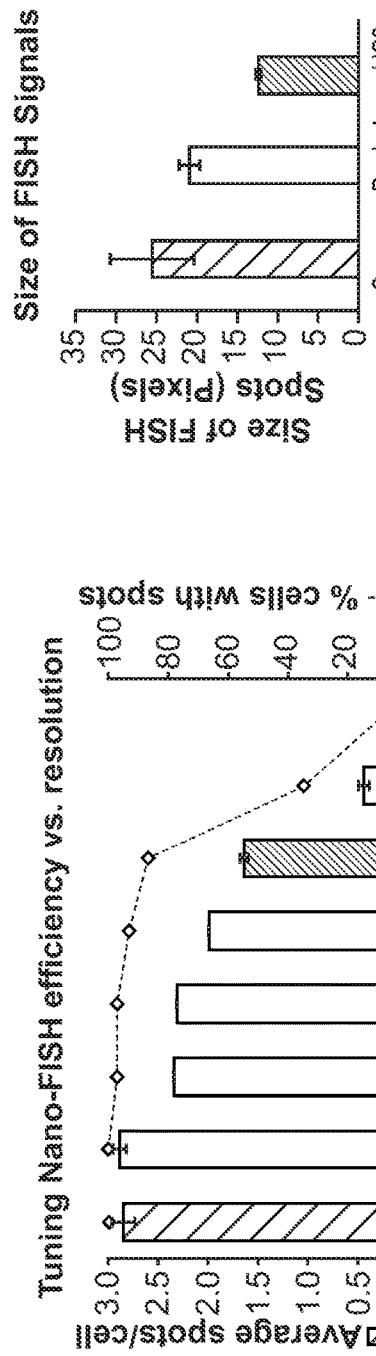
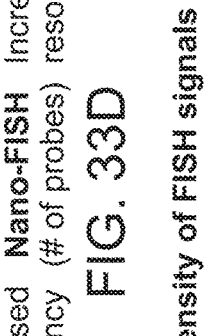
FIG. 33

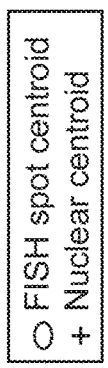
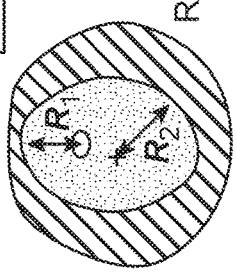
FIG. 34A
FIG. 34B
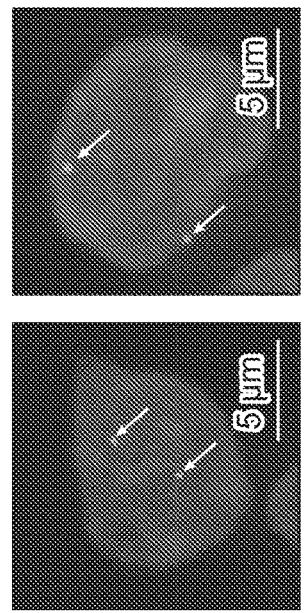
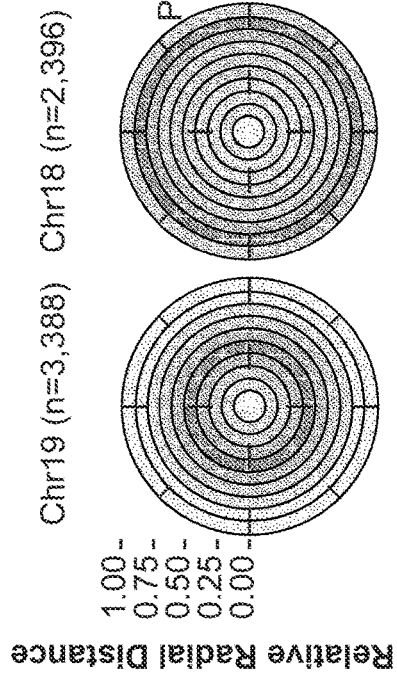
FIG. 34C
FIG. 34D
FIG. 34

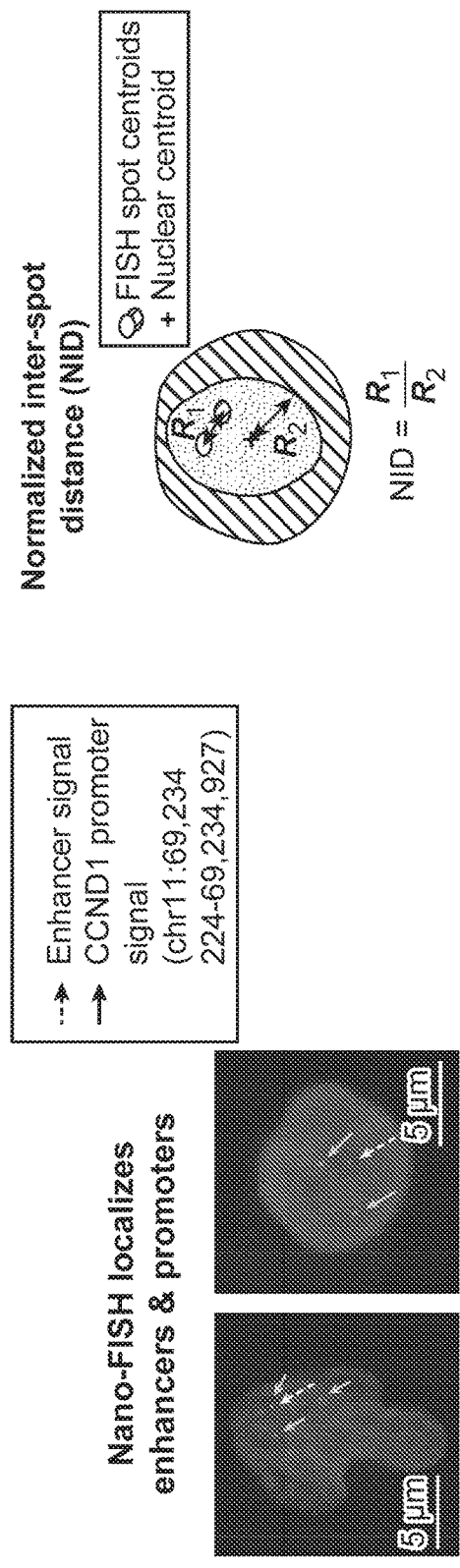
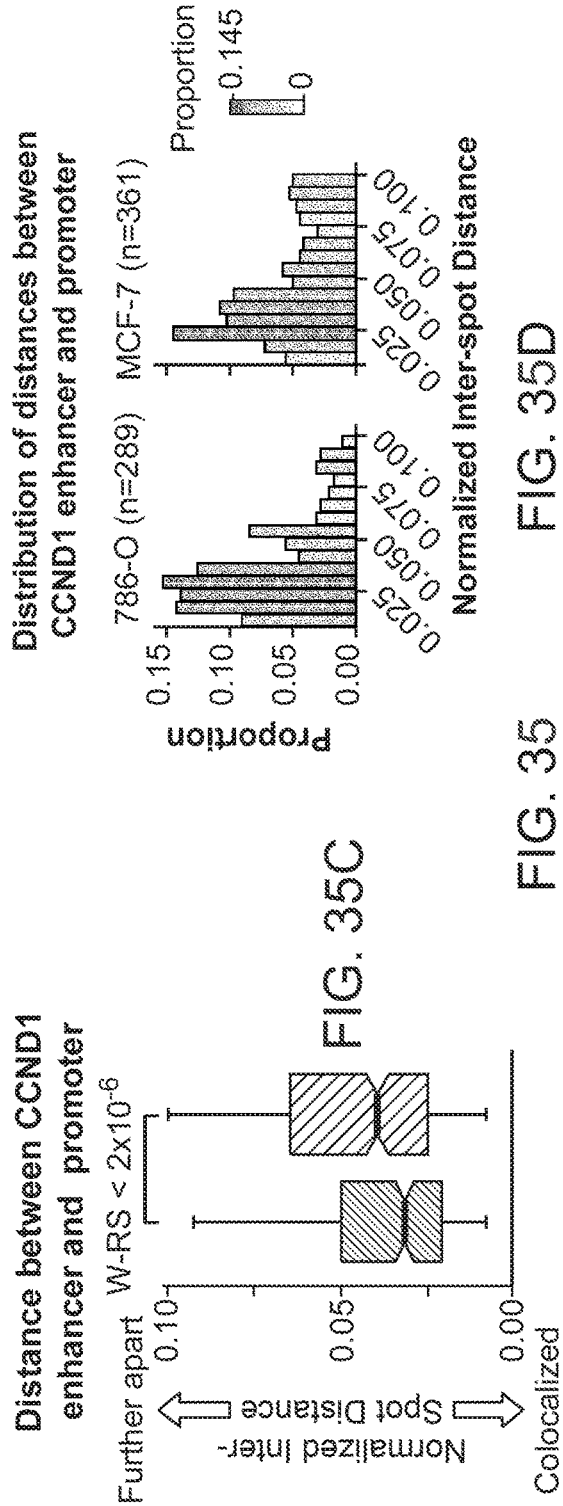
FIG. 35A
FIG. 35B
FIG. 35C
FIG. 35D
FIG. 35

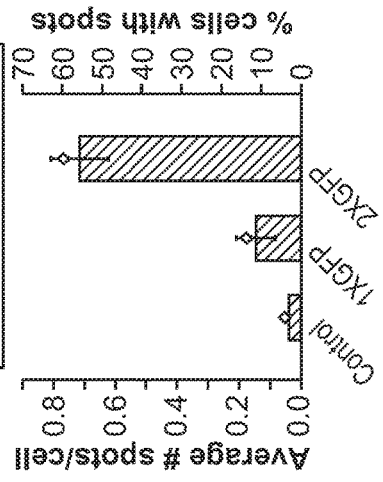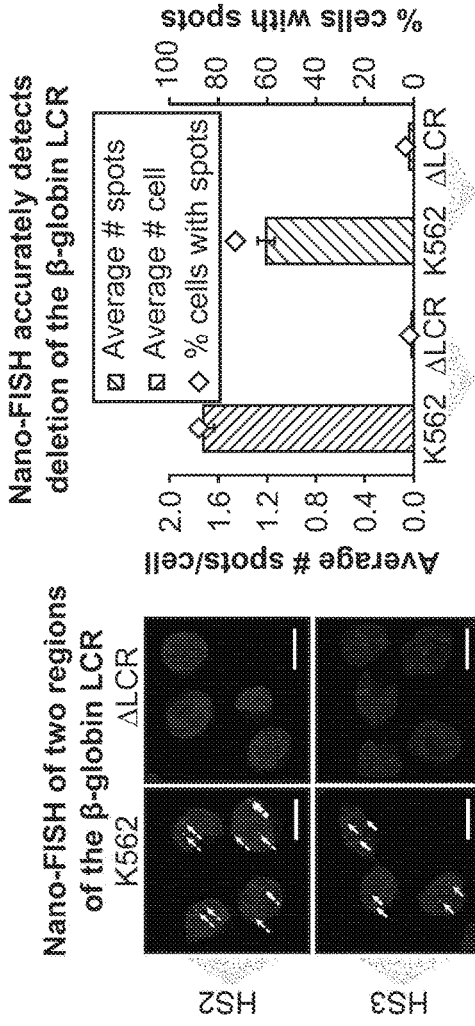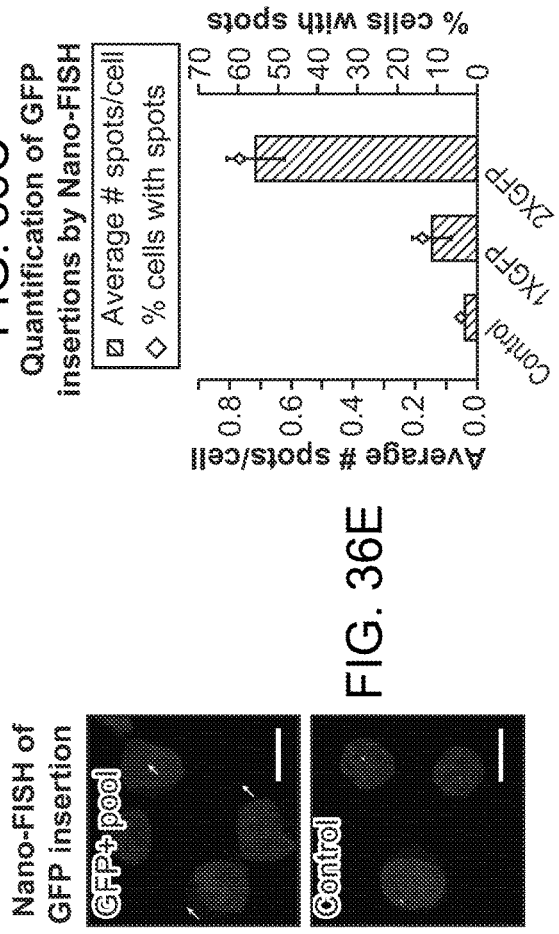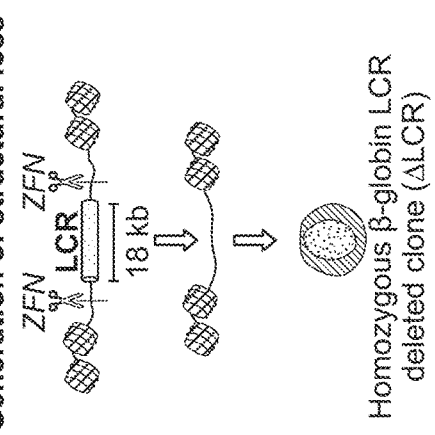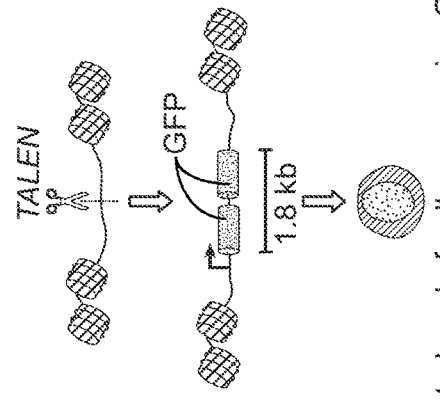
FIG. 36

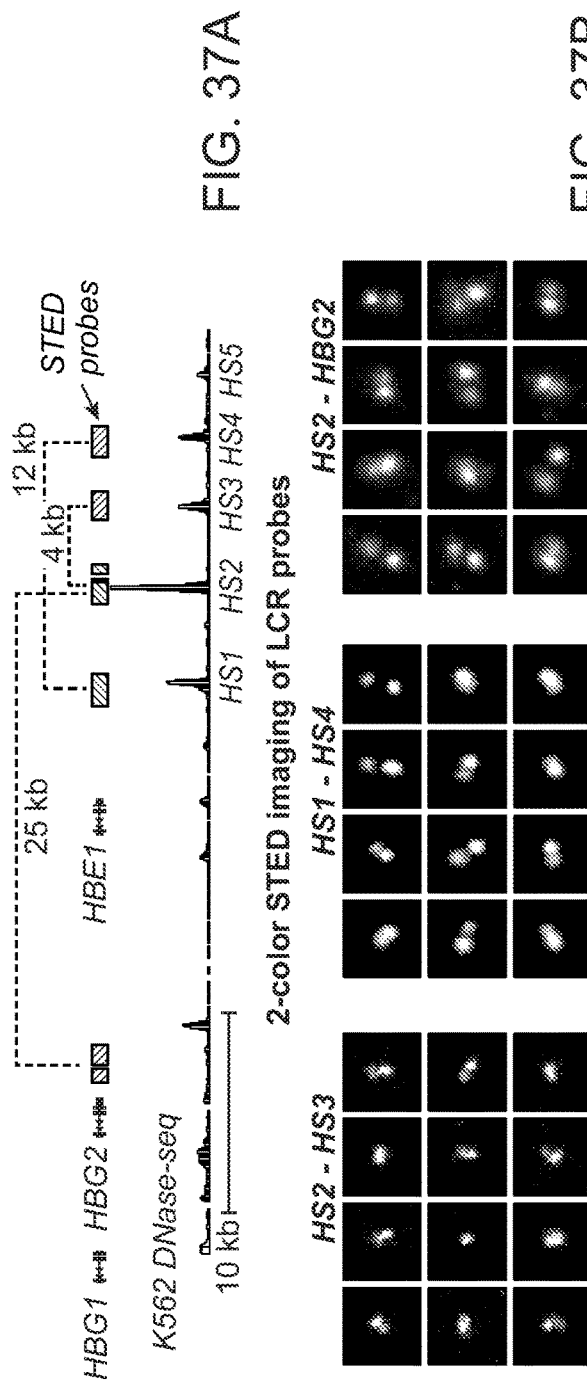
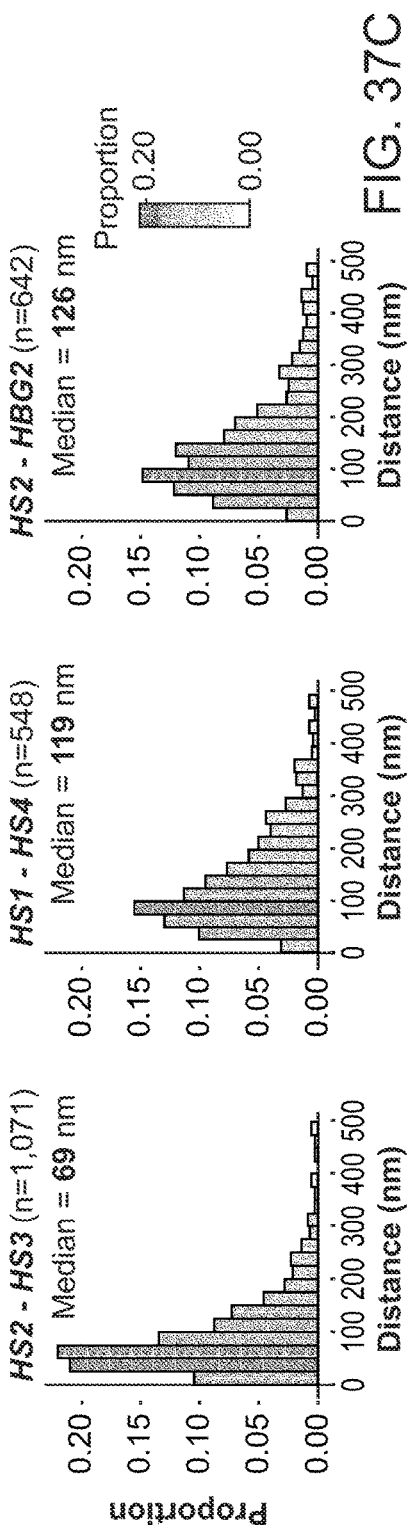
FIG. 37A
FIG. 37B
FIG. 37C
FIG. 37

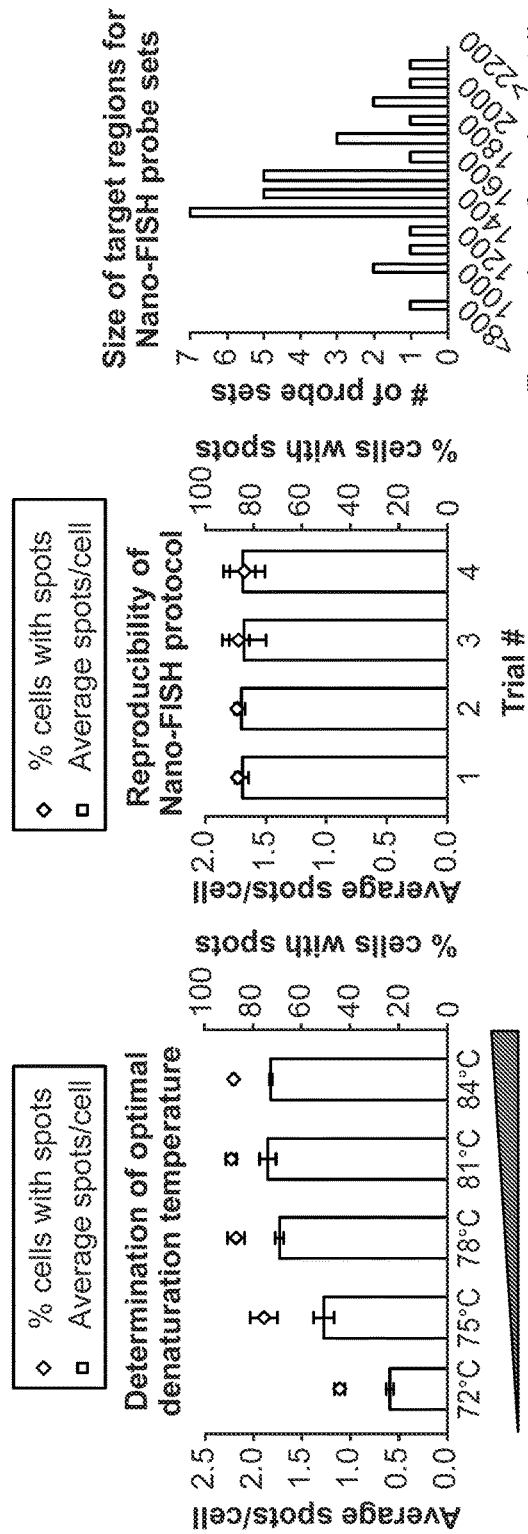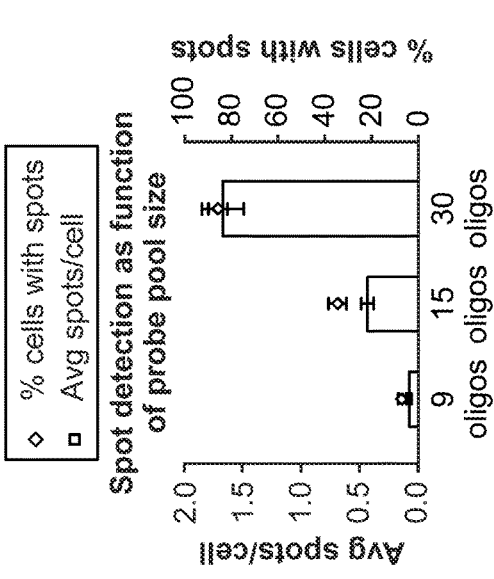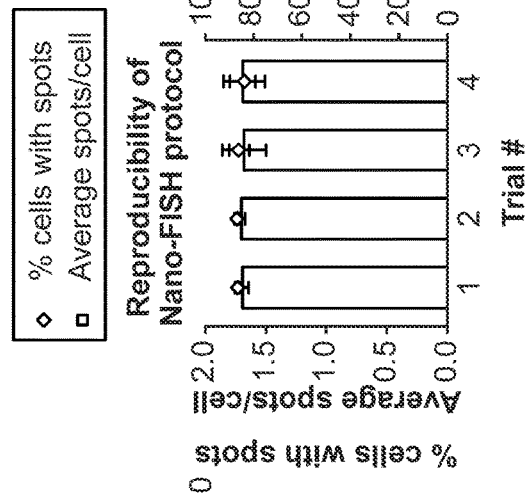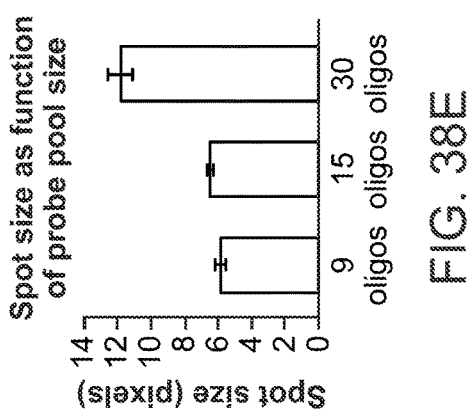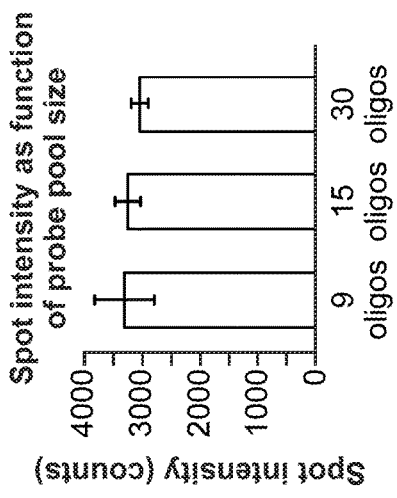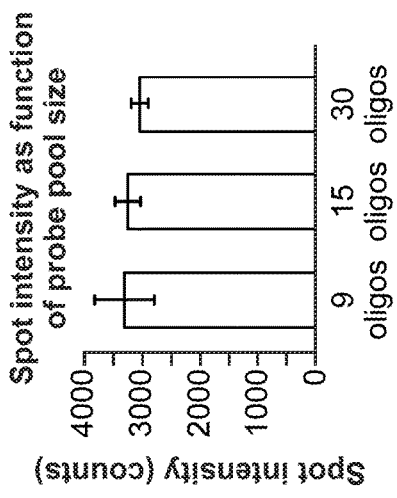
FIG. 38

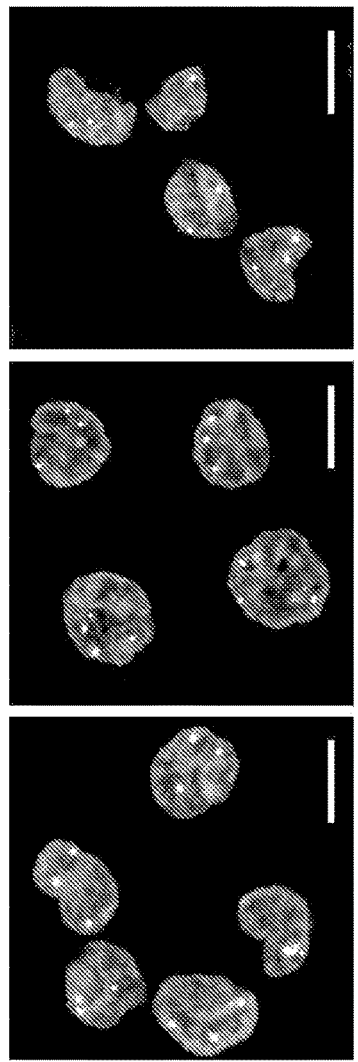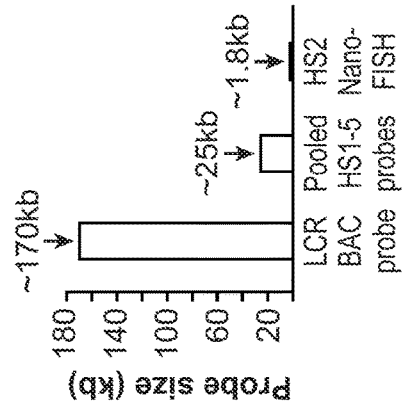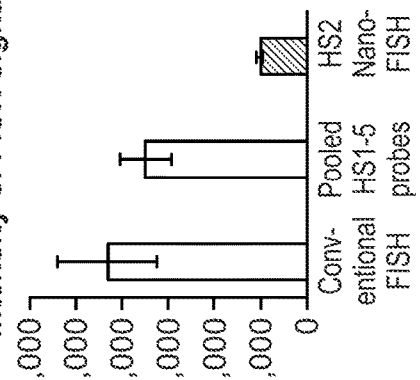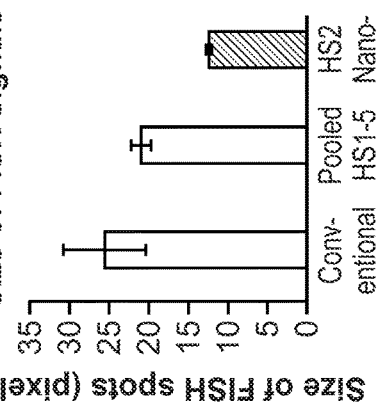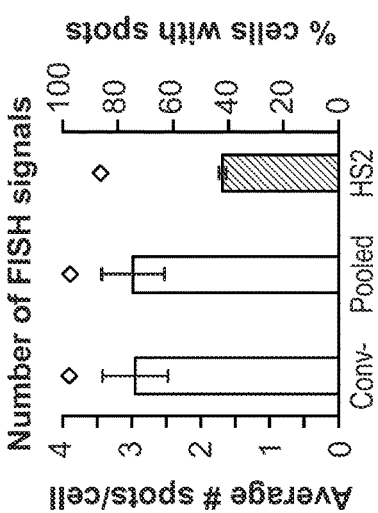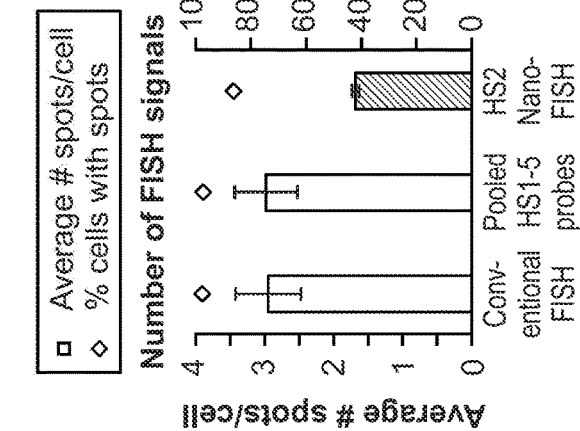
FIG. 39A
FIG. 39B
FIG. 39C
FIG. 39D
FIG. 39E
FIG. 39

SEQUENCE LISTING

```
<160> NUMBER OF SEQ ID NOS: 1037

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
```
tttcccttgc tcttcatgat tttaacaaca tgatggattt                                  40

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ccctgccccc cattaactca catcctgaat tttatgttta                                  40

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
gcacttcatc atcgtctttg aagtcccctt cttgtcctcc                                  40

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tatgatgaac accatgcacc acatgcaggt tctggtgaag                                  40

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
gatacaaaag aatattggta tgtatgttgc acagactcat                                  40

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cctatttccc ccacacagcc ttcccacatt ggccaaccct                                  40

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tacaaagggc ttctctggcc agagagagcc ggtgtctgct                40

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tgggggggtt aatggagtta tggactggga tgggcagcct                40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
acctacctag ggaactcttt ctccctggca ctaggctagt                40

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
actgactgag ctgacctcca gtacagggcc tgaggccact                40

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
ctgggagcta aatagaagca aatatcccca ggcctgggtg                40

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
atgcgtcaag caactacact cccacagtaa actgggaacc                40

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
cagctccttg gcagcctagg ctctagctca acatctgctt                40

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
tgctggagtc gcaccaacct ggctctgcct atctccagca                              40

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
ctctgtaggc tgcacaacgt ggaacagatg aaaggaacca                              40

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tggggtaaat tataatcatg aaattccgtc aagcttgaat                              40

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
aacatattta atatggcata ttcaaatgac agaaagtacg                              40

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
ctttattctt gctaatgttg actccttagc aaagataatt                              40

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
tgatctttgc taaactcttc aggaataaat gaacatttcc                              40

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
ttttcaagca gttaagaagc aagaattaat gactcgaata                      40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
atgagagtgt tgactgatga agggctccta tacgcgggtt                      40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
tctttcccat ctgtttcccg gcccctacca gaaataagtg                      40

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
atgaacctcc ctcgctccaa gaccagagct cctaggaagt                      40

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
tctttatttt attggccaca attgaacata ggtataattt                      40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
cagaagcaag ccctgatcaa ggaaaccatt cacacttgat                      40

```
<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
gtggcttttg ctcaaagtga ggacgttatc agctctgccc                             40

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
ctttaaacaa aaactaaagg cgtaaggaaa gataactact                             40

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
cagttgccac acttttttc actgctaaag ttcgtaatga                              40

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ggcaatcaga agtattttgg ttgcttctag gtcagaatga                             40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
ggcagcaaac ttgtttaggt atgattcatc attgtctgct                             40

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
ctacaaaaca atgagtctga ttacgaccca cagaaatgaa                             40

<210> SEQ ID NO 32
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
cctcccacag acccaaacat gctgctgcaa atgtctcact                            40

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
ggacaagcac acacatcgct gggaagatct gcaagcctcc                            40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
taaacctgga taacaagaac actgtttcca ctgcgctagt                            40

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
tcatcacgat gacaatggac aagccatatc cctaacaggg                            40

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
tttccatgac accaggaccg taaagcacct tttacaccgt                            40

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
aattgggatg tgcaaaacct cttaacttgt agcaccaagt                            40

<210> SEQ ID NO 38
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
tcttgtgtta ttcgcctgca ttgaaatccc atcccaatcc                              40

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
tgagtgatct ctttgctgat cataaacata ttcctccatc                              40

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
tgcattcatt actaaataca cagggcatag cacatagtaa                              40

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
cttcaatgtt gccaggaaaa tccttgcagg aatcacaccc                              40

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42 attttttct aaagctttag gaaatacaca cgtttcccct                               40

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
agagtaatct tcaacaatcc ttggtctaaa cacacacaag                              40

<210> SEQ ID NO 44
<211> LENGTH: 40
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 44
cccagggacc cacgccaagc tcaccgcacc ttccaccaaa                          40

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
agctcctgta ctagctggtg gggtgtggag cacacagccc                          40

<210> SEQ ID NO 46
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
tcacacaggg aaagtgaggc ttggtggttg atttgagcaa                          40

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
ccttccaaca gccgtgtgag acaagaggtc ttatcctctt                          40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
acaagggtca ctgagcacat gccatgtgtt gggcacagtg                          40

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
gtctcctaag tctcattctt ttcttaggat tcttcagatc                          40

<210> SEQ ID NO 50
<211> LENGTH: 40
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 50
tccgcctaag taaaacataa aattacttaa gctgcgtaaa                              40

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
cattttgacc tgattatctt tgtctataag tcttaagcca                              40

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
ccggttcctc caccctcact gccccaacaa ctgaaagaag                              40

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
acagtgtgtt gaaagaatcc ataactcttt ctttccagcc                              40

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
gaagtttcat ctttatcaaa atctccattc ccaggcggac                              40

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
aagtccattt ttttaagctt tgcgcttcag ctccagaaca                              40

<210> SEQ ID NO 56
<211> LENGTH: 40
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 56
tcttcgttat gaatacaaat aggaaaacaa tcagacccaa                         40

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
tcctcggggc attctagaac cgtagcagac ctgcttacat                         40

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
tccttatgtg ggaaaataaa gaggatagac agatttgatt                         40

<210> SEQ ID NO 59
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
agctgcgagt ccctaacaga cttccaggac agctgaaaaa                         40

<210> SEQ ID NO 60
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
aggacaaggg agagacgccc acccgcctct gtcagggata                         40

<210> SEQ ID NO 61
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
aatccatgag ggtgacatac acatccttac tgttcccaca                         40

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 62
acttccttcc ctgagatgcc catcctttga ttctgggatt                40

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
gctcccggat aaattaatta ccgtgaccct gagctgcttc                40

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
tagactaaga gaatctaatt tgtggcaaag atcttgagtg                40

<210> SEQ ID NO 65
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
tgaaggatga ctaagagctt ccctataaac cccatactgg                40

<210> SEQ ID NO 66
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
agccaggact atagagtttc agaaaaggga gaaaattcta                40

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
tgctgctaat ttaagtttct ggcaagtcaa aataaatctc                40

<210> SEQ ID NO 68
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
cgaaaaccat caattaacta gaatgatcag gaaattgcgt                                    40

<210> SEQ ID NO 69
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
tttatttagt ccccagggtg tatgaagtgc tcttccaggc                                    40

<210> SEQ ID NO 70
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
ggtccttctt ggtaccgata ttgccatatt ggctggacat                                    40

<210> SEQ ID NO 71
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
tggcttggta ggatgcactc acatgggctg tagtaatact                                    40

<210> SEQ ID NO 72
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
tatcaccagc ataacttgtg gttcttcagc cagtaatttc                                    40

<210> SEQ ID NO 73
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
gaacaactgg gtatctacag gcaaagaaat gaaccttgac                                    40

<210> SEQ ID NO 74
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 74
taggtactgt tgtgtcccta tatatttgac ttggtaataa                              40

<210> SEQ ID NO 75
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
tatgtgaaca tcggtgaata tcataattta ttatgcaaac                              40

<210> SEQ ID NO 76
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
agctgaacac tctttgtggt cctcttgaag cctagaatta                              40

<210> SEQ ID NO 77
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
ccccacctca ctgcccccca gttctgactc acggtgtccc                              40

<210> SEQ ID NO 78
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
actcccatca cctggccagc ttggctgtcc cctgacccac                              40

<210> SEQ ID NO 79
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
ggctgcccag ctgcccagca gcaaaactgc ataggaactc                              40

<210> SEQ ID NO 80
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
```
gcccaggacg ccaagtgtca ccaccctctc cccaggcagg                            40

<210> SEQ ID NO 81
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
cacaaggtca gctccacccg tgggtcagtg tgccccagat                            40

<210> SEQ ID NO 82
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
ggagacaaaa cgggcaccca gcccagtcat gcccgtgcct                            40

<210> SEQ ID NO 83
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
ctgaaatcag tcagcagttt cggtgagtct gcagctgaca                            40

<210> SEQ ID NO 84
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
cgccacattt ggggctggga gagatgtcac aggggctgac                            40

<210> SEQ ID NO 85
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
cacatgttct ctgcataggt ttttaagcag ccagcagctg                            40

<210> SEQ ID NO 86
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
tttaaaatga aaacccacac ttccaaaata gcacttgagt        40

<210> SEQ ID NO 87
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
aacatgtttg tgtaattaag cattttaaaa tcataaccat        40

<210> SEQ ID NO 88
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
tgcttatctg tgcttttat gttccacccc cccaccacca        40

<210> SEQ ID NO 89
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
attaataata attctgtgtt tatggggatt gcagatacat        40

<210> SEQ ID NO 90
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
ccagctttgt gtcttcatga cccaactgga gtaagaatgg        40

<210> SEQ ID NO 91
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
aaagacctca tttgcagcat ggttagcagt gtcaaacatt        40

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
tctcgtagca ctggctgcag ccggcctgtg tgtgcccacc        40

<210> SEQ ID NO 93
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
gccttcatcc tgaacggctg accagcggaa acaaaagatc                              40

<210> SEQ ID NO 94
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
atggccagat aacagtgttt agacatgtct ttgatgtttt                              40

<210> SEQ ID NO 95
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
ccctgactgt gtaaggggtc tctctccatg gggaatagag                              40

<210> SEQ ID NO 96
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
ctgagcttag cttctactgt gctgttaatt tcaggcaaga                              40

<210> SEQ ID NO 97
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
agatcaataa tatttgcatt agctacttac atcagtctct                              40

<210> SEQ ID NO 98
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
taattgcaga aaacttataa agcatggaag aatacaaaac                              40

<210> SEQ ID NO 99
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
aaacaaattc ctctacctgg acatgactgt tgttagcatt                40

<210> SEQ ID NO 100
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
gggagattct tcatatcctt ttaatgtaga tatgcacatt                40

<210> SEQ ID NO 101
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
acaaaaaagg ctatcatatt gtacatataa ctttgctgta                40

<210> SEQ ID NO 102
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
tctgctagga acctgtaccc atgtcattac tgtaagcatt                40

<210> SEQ ID NO 103
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
actactcaaa ttttagtatc tgcagatatc agatatcctt                40

<210> SEQ ID NO 104
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
tgaaatggta ttgttgccct ttctgattag taaagtatac                40

```
<210> SEQ ID NO 105
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
ttataatcta gcaaggttag agatcatgga tcactttcag                              40

<210> SEQ ID NO 106
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
acagcttgcc tccgataagc cagaattcca gagcttctgg                              40

<210> SEQ ID NO 107
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
tcaatcaacc tgatagctta ggggataaac taatttgaag                              40

<210> SEQ ID NO 108
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
gatcatgaag gatgaaagaa tttcaccaat attataataa                              40

<210> SEQ ID NO 109
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
tttagccatc tgtatcaatg agcagatata agctttacac                              40

<210> SEQ ID NO 110
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
aggggtagat tatttatgct gcccatttt agaccataaa                               40

<210> SEQ ID NO 111
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
cactaccatt tcacaattcg cactttcttt ctttgtcctt                          40

<210> SEQ ID NO 112
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
gctccatcaa atcataaagg acccacttca aatgccatca                          40

<210> SEQ ID NO 113
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
tcctactttc aggaacttct ttctccaaac gtcttctgcc                          40

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
aattctattt tttcttcaac gtactttagg cttgtaatgt                          40

<210> SEQ ID NO 115
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
taagatgcaa atagtaagcc tgagcccttc tgtctaactt                          40

<210> SEQ ID NO 116
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
ctgtgtttca gaataaaata ccaactctac tactctcatc                          40

<210> SEQ ID NO 117
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
gaaaccatgt ttatctcagg tttacaaatc tccacttgtc                              40

<210> SEQ ID NO 118
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
ctttggaaaa gtaatcaggt ttagaggagc tcatgagagc                              40

<210> SEQ ID NO 119
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
gctgaatccc caactcccaa ttggctccat ttgtggggga                              40

<210> SEQ ID NO 120
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
ggtgttatga acttaacgct tgtgtctcca gaaaattcac                              40

<210> SEQ ID NO 121
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 121
agttaatgca cgttaataag caagagttta gtttaatgtg                              40

<210> SEQ ID NO 122
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 122
taattgagaa ggcagattca ctggagttct tatataattg                              40

<210> SEQ ID NO 123
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 123
cacggtcaga tgaaaatata gtgtgaagaa tttgtataac                            40

<210> SEQ ID NO 124
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 124
cacaagtcag catcagcgtg tcatgtctca gcagcagaac                            40

<210> SEQ ID NO 125
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 125
ggaggtgggg acttaggtga aggaaatgag ccagcagaag                            40

<210> SEQ ID NO 126
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126
gtcacagcat ttcaaggagg agacctcatt gtaagcttct                            40

<210> SEQ ID NO 127
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 127
aaagaggtga aattaatccc ataccyttaa gtctacagac                            40

<210> SEQ ID NO 128
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 128
ctttactaag gaactttca ttttaagtgt tgacgcatgc                             40

<210> SEQ ID NO 129
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 129
caggtttttc tttccacggt aactacaatg aagtgatcct                          40

<210> SEQ ID NO 130
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 130
gctctacagg gaggttgagg tgttagagat cagagcagga                          40

<210> SEQ ID NO 131
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 131
tactatttcc aacggcatct ggcttttctc agcccttgtg                          40

<210> SEQ ID NO 132
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 132
aaggtttagg cagggatagc cattctattt tattaggggc                          40

<210> SEQ ID NO 133
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 133
aggggctcaa cgaagaaaaa gtgttccaag ctttaggaag                          40

<210> SEQ ID NO 134
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 134
gggctgaacc cccttccctg gattgcagca cagcagcgag                          40

<210> SEQ ID NO 135
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 135
ctgacgtcat aatctaccaa ggtcatggat cgagttcaga                              40

<210> SEQ ID NO 136
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 136
gaaggtagag ctctcctcca ataagccaga tttccagagt                              40

<210> SEQ ID NO 137
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 137
caccaatatt attataattc ctatcaacct gataggttag                              40

<210> SEQ ID NO 138
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 138
agatataagc cttacacagg attatgaagt ctgaaaggat                              40

<210> SEQ ID NO 139
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 139
acatgtatct ttctggtctt ttagccgcct aacactttga                              40

<210> SEQ ID NO 140
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140
caaagaacaa gtgcaatatg tgcagctttg ttgcgcaggt                              40

<210> SEQ ID NO 141
<211> LENGTH: 40
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 141
tattattatg tgagtaactg gaagatactg ataagttgac          40

<210> SEQ ID NO 142
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 142
taaaaatctt tctcacccat ccttagattg agagaagtca          40

<210> SEQ ID NO 143
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 143
ttgggttcac ctcagtctct ataatctgta ccagcatacc          40

<210> SEQ ID NO 144
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
cacacccatc tcacagatcc cctatcttaa agagaccta          40

<210> SEQ ID NO 145
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 145
atggaaccca accagactct cagatatggc caaagatcta          40

<210> SEQ ID NO 146
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 146
gacaccagtc tctgacacat tcttaaaggt caggctctac          40

<210> SEQ ID NO 147
<211> LENGTH: 40
<212> TYPE: DNA
<213> ORGANISM: Artificial Sequence
<220> FEATURE:
<223> OTHER INFORMATION: Description of Artificial Sequence: Synthetic
      probe -continued

<400> SEQUENCE: 147
agagattcaa aagattcact tgtttaggcc ttagcgggct                          40

<210> SEQ ID NO 148
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148
tccttagtct gaggaggagc aattaagatt cacttgttta                          40

<210> SEQ ID NO 149
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 149
taaatgggga agttgtttga aaacaggagg gatcctagat                          40

<210> SEQ ID NO 150
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
gggtttatac atgactttta gaacactgcc ttggttttg                           40

<210> SEQ ID NO 151
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 151
aactcttaaa agatattgcc tcaaaagcat aagaggaaat                          40

<210> SEQ ID NO 152
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
aaatcgagga ataagacagt tatggataag gagaaatcaa                          40

<210> SEQ ID NO 153
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 153
tcagttagga tttaatcaat gtcagaagca atgatatagg                          40

<210> SEQ ID NO 154
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 154
cttgaaaaca cttgaaattg cttgtgtaaa gaaacagttt                          40

<210> SEQ ID NO 155
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 155
ataatcttca gaggaaagtt ttattctctg acttatttaa                          40

<210> SEQ ID NO 156
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
agattccttc tgtcattttg cctctgttcg aatactttct                          40

<210> SEQ ID NO 157
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 157
atttcagctt ctaaacttta tttggcaatg ccttcccatg                          40

<210> SEQ ID NO 158
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 158
gcaggagttt gttttcttct gcttcagagc tttgaattta                          40

<210> SEQ ID NO 159
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159
```
acatatcaac ggcactggtt ctttatctaa ctctctggca                                40

<210> SEQ ID NO 160
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 160
ttatgcttcc ctgaaacaat accacctgct attctccact                                40

<210> SEQ ID NO 161
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 161
ttctcactcc ctaccactga ggacaagttt atgtccttag                                40

<210> SEQ ID NO 162
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 162
ttagagatta tgtcattacc agagttaaaa ttctataatg                                40

<210> SEQ ID NO 163
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 163
ggtcattctt agaatagtaa tccagccaat agtacaggtt                                40

<210> SEQ ID NO 164
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 164
caggcaataa gggcttttta agcaaaacag ttgtgataaa                                40

<210> SEQ ID NO 165
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 165
atgatgggca ctgaaggtta aaacttgagt ctgtcaactt                                  40

<210> SEQ ID NO 166
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 166
aactcataaa tatcccattt tccgctgaaa tatagcttta                                  40

<210> SEQ ID NO 167
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 167
cctggtttct ttgacctttt gggaccttga gtaagtaaag                                  40

<210> SEQ ID NO 168
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
cttcatttat tttcatgatt aaaattctaa gaaattcttg                                  40

<210> SEQ ID NO 169
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 169
tttttaatta aattgcattg cctaatgtat ttatgaacta                                  40

<210> SEQ ID NO 170
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 170
catagaaata aaacaatact ctgaagtagt tcagaatgtg                                  40

<210> SEQ ID NO 171
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
caatttatat aaagagttaa ttcaaatgag actattttaa                                  40

<210> SEQ ID NO 172
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172
agggctttga atcttatgtc tagaaatttt gaaaaacctc                              40

<210> SEQ ID NO 173
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173
tatatgctaa gattccacct ctagtgctag aactgagaag                              40

<210> SEQ ID NO 174
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
tgacttggtg atctttttta aattctgaaa caacagcaac                              40

<210> SEQ ID NO 175
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 175
agctaaggac tttttcttgc ctatgcatgc tatcttcagt                              40

<210> SEQ ID NO 176
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
tgattattta gtattgaaac tataacatag tatgtttcct                              40

<210> SEQ ID NO 177
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
aaaaaatgtg tatttctctg gagaaggtta aaactgagga                              40

<210> SEQ ID NO 178
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
caagtgagca aggcttaaat ggaagaagca atgatctcgt                         40

<210> SEQ ID NO 179
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 179
ccaccttcat taacgagatc atccatcatg aggaaatatg                         40

<210> SEQ ID NO 180
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 180
accaggcccc ctctgttttg tgtcactaag ggtgaggatg                         40

<210> SEQ ID NO 181
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 181
atgatttttc cctcccccgg gcttctttta gccatcaata                         40

<210> SEQ ID NO 182
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 182
tagccccaca ggagtttgtt ctgaaagtaa acttccacaa                         40

<210> SEQ ID NO 183
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 183
aagcttattg aggctaaggc atctgtgaag gaaagaaaca                         40

```
<210> SEQ ID NO 184
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 184
ctctaaacca ctatgctgct agagcctctt ttctgtactc                              40

<210> SEQ ID NO 185
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 185
ctcattcaga cactagtgtc accagtctcc tcatatacct                              40

<210> SEQ ID NO 186
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
tattttcttc ttcttgctgg tttagtcatg ttttctggga                              40

<210> SEQ ID NO 187
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 187
ggcaaaccca ttattttttt ctttagactt gggatggtga                              40

<210> SEQ ID NO 188
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 188
tgggcagcgt cagaaactgt gtgtggatat agataagagc                              40

<210> SEQ ID NO 189
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
gactatgctg agctgtgatg agggaggggc ctagctaaag                              40

<210> SEQ ID NO 190
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 190
tgagagtcag aatgctcctg ctattgcctt ctcagtcccc                          40

<210> SEQ ID NO 191
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 191
ttggtttcta cacaagtaga tacatagaaa aggctatagg                          40

<210> SEQ ID NO 192
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
tgtttgagag tcctgcatga ttagttgctc agaaatgccc                          40

<210> SEQ ID NO 193
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 193
ttacaaatat gtgattatca tcaaaacgtg agggctaaag                          40

<210> SEQ ID NO 194
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 194
cagataactt gcaagtccta ggataccagg aaaataaatt                          40

<210> SEQ ID NO 195
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
agcattatgt ctgtctgtca ttgtttttca tcctcttgta                          40

<210> SEQ ID NO 196
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 196
ttcacagtta cccacacagg tgaacccttt tagctctcct                              40

<210> SEQ ID NO 197
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 197
gaatgtttct ttcctctcag gatcagagtt gcctacatct                             40

<210> SEQ ID NO 198
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 198
aatgcaccaa gactggcctg agatgtatcc ttaagatgag                             40

<210> SEQ ID NO 199
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 199
tcccagtagc accccaagtc agatctgacc ccgtatgtga                             40

<210> SEQ ID NO 200
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 200
gtgtcctcta acagcacagg ccttttgcca cctagctgtc                             40

<210> SEQ ID NO 201
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 201
ggcaaacaag gtttgttttc ttttcctgtt ttcatgcctt                             40

<210> SEQ ID NO 202
<211> LENGTH: 40
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 202
ttccatatcc ttgtttcata ttaatacatg tgtatagatc                          40

<210> SEQ ID NO 203
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 203
aaatctatac acatgtatta ataaagcctg attctgccgc                          40

<210> SEQ ID NO 204
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 204
aggtatagag gccacctgca agataaatat ttgattcaca                          40

<210> SEQ ID NO 205
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 205
ctaatcattc tatggcaatt gataacaaca aatatatata                          40

<210> SEQ ID NO 206
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 206
ataatatatt ctagaatatg tcacattctg tctcaggcat                          40

<210> SEQ ID NO 207
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 207
tttctttatg atgccgtttg aggtggagtt ttagtcaggt                          40

<210> SEQ ID NO 208
<211> LENGTH: 40
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 208
agcttctcct ttttttttgcc atctgccctg taagcatcct                           40

<210> SEQ ID NO 209
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 209
gggacccaga taggagtcat cactctaggc tgagaacatc                            40

<210> SEQ ID NO 210
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 210
cacacaccct aagcctcagc atgactcatc atgactcagc                            40

<210> SEQ ID NO 211
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 211
ctgtgcttga gccagaaggt ttgcttagaa ggttacacag                            40

<210> SEQ ID NO 212
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 212
aactgctcat gcttggacta tgggaggtca ctaatggaga                            40

<210> SEQ ID NO 213
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 213
cagaaatgta acaggaacta aggaaaaact gaagcttatt                            40

<210> SEQ ID NO 214
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 214
cagagatgag gatgctggaa gggatagagg gagctgagct                            40

<210> SEQ ID NO 215
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 215
aaaagtatag taatcattca gcaaatggtt ttgaagcacc                            40

<210> SEQ ID NO 216
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 216
gtatcttatt ccccacaaga gtccaagtaa aaaataacag                            40

<210> SEQ ID NO 217
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 217
gaaaagaatg tttctctcac tgtggattat tttagagagt                            40

<210> SEQ ID NO 218
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 218
aatggtcaag atttttttaa aaattaagaa aacataagtt                            40

<210> SEQ ID NO 219
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 219
cttgagaaat gaaaatttat tttttgttg gaggataccc                             40

<210> SEQ ID NO 220
<211> LENGTH: 40
<212> TYPE: DNA
<213> ORGANISM: Artificial Sequence
<220> FEATURE:
<223> OTHER INFORMATION: Description of Artificial Sequence: Synthetic
```

```
                                          -continued
    probe

<400> SEQUENCE: 220
tctatctccc atcagggcaa gctgtaagga actggctaag                                  40

<210> SEQ ID NO 221
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 221
agtgagacag agtgacttag tcttagaggc cccactggta                                  40

<210> SEQ ID NO 222
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 222
gatgagaagg caccttcatc actcatcaca gtcagctctg                                  40

<210> SEQ ID NO 223
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 223
tctcctctct cctttctcat cagaaatttc ataagtctac                                  40

<210> SEQ ID NO 224
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 224
gtcaggcaga tcacataaga aaagaggatg ccagttaagg                                  40

<210> SEQ ID NO 225
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 225
gttgctgtta gacaatttca tctgtgccct gcttaggagc                                  40

<210> SEQ ID NO 226
<211> LENGTH: 40
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 226
tctttaatga aagctaagct ttcattaaaa aaagtctaac          40

<210> SEQ ID NO 227
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 227
tgcattcgac tttgactgca gcagctggtt agaaggttct          40

<210> SEQ ID NO 228
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 228
gaggagggtc ccagcccatt gctaaattaa catcaggctc          40

<210> SEQ ID NO 229
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 229
actggcagta tatctctaac agtggttgat gctatcttct          40

<210> SEQ ID NO 230
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 230
cttgcctgct acattgagac cactgaccca tacataggaa          40

<210> SEQ ID NO 231
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 231
atagctctgt cctgaactgt taggccactg gtccagagag          40

<210> SEQ ID NO 232
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 232
catctccttt gatcctcata ataaccctat gagatagaca                              40

<210> SEQ ID NO 233
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 233
tattactctt actttataga tgatgatcct gaaaacatag                              40

<210> SEQ ID NO 234
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 234
caaggcactt gcccctagct gggggtatag gggagcagtc                              40

<210> SEQ ID NO 235
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 235
gtagtagtag aatgaaaaat gctgctatgc tgtgcctccc                              40

<210> SEQ ID NO 236
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 236
ctttcccatg tctgccctct actcatggtc tatctctcct                              40

<210> SEQ ID NO 237
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 237
cctgggagtc atggactcca cccagcacca ccaacctgac                              40

<210> SEQ ID NO 238
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 238

```
ccacctatct gagcctgcca gcctataacc catctgggcc                          40
```

<210> SEQ ID NO 239
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 239

```
tagctggtgg ccagccctga ccccacccca ccctccctgg                          40
```

<210> SEQ ID NO 240
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 240

```
tctgatagac acatctggca caccagctcg caaagtcacc                          40
```

<210> SEQ ID NO 241
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 241

```
gggtcttgtg tttgctgagt caaaattcct tgaaatccaa                          40
```

<210> SEQ ID NO 242
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 242

```
ttagagactc ctgctcccaa atttacagtc atagacttct                          40
```

<210> SEQ ID NO 243
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 243

```
ggctgtctcc tttatccaca gaatgattcc tttgcttcat                          40
```

<210> SEQ ID NO 244
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 244
ccatccatct gatcctcctc atcagtgcag cacagggccc                              40

<210> SEQ ID NO 245
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 245
gcagtagctg cagagtctca cataggtctg gcactgcctc                              40

<210> SEQ ID NO 246
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 246
atgtccgacc ttaggcaaat gcttgactct tctgagctca                              40

<210> SEQ ID NO 247
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 247
tgtcatggca aaataaagat aataatagtg ttttttatg                               40

<210> SEQ ID NO 248
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 248
tagcgtgagg atggaaaaca atagcaaaat tgattagact                              40

<210> SEQ ID NO 249
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 249
aaggtctcaa caaatagtag tagattttat cgtccattaa                              40

<210> SEQ ID NO 250
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 250
tccctctcct ctcttactca tcccatcacg tatgcctctt                              40

<210> SEQ ID NO 251
<211> LENGTH: 40
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 251
ttcccttacc tataataaga gttattcctc ttattatatt                            40

<210> SEQ ID NO 252
<211> LENGTH: 40
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 252
ttatagtgat tctggatatt aaagtgggaa tgaggggcag                            40

<210> SEQ ID NO 253
<211> LENGTH: 40
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 253
ctaacgaaga agatgtttct caaagaagcc attctcccca                            40

<210> SEQ ID NO 254
<211> LENGTH: 40
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 254
gatcatctca gcagggttca ggaagataaa ggaggatcaa                            40

<210> SEQ ID NO 255
<211> LENGTH: 40
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 255
tgttgaggtg ggaggaccgc ttgagcctgg gaagtgcaag                            40

<210> SEQ ID NO 256
<211> LENGTH: 40
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 256
agtgagccga gattttgcca ctacactccc atttgggtga                            40

<210> SEQ ID NO 257
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 257
gtgagaccct ttctcaaaaa caaactaatt aaaaaaccct                           40

<210> SEQ ID NO 258
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 258
tttacagatg aagaaactga gtcatacaac tactaagaga                           40

<210> SEQ ID NO 259
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 259
gagtcactaa tcactcaggt ggtctggctc cagcatctgt                           40

<210> SEQ ID NO 260
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 260
ttaatctctg ctctatactg cccaagactt ttataaagtc                           40

<210> SEQ ID NO 261
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 261
gttgagtcac tgaaatgagt tattgggatg gctgtgtggg                           40

<210> SEQ ID NO 262
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 262
gtgctaagtt ctttcctaaa ggtatgtgag aatacaaagg                           40

```
<210> SEQ ID NO 263
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 263
aagcatcctc cttttacac acgtgaacta gtgcatgcaa                          40

<210> SEQ ID NO 264
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 264
gacactcagt gggcctgggt gaaggtgaga attttattgc                         40

<210> SEQ ID NO 265
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 265
tgagagcctc tggggacatc ttgccagtca atgagtctca                         40

<210> SEQ ID NO 266
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 266
caatttcctt ctcagtcttg gagtaacaga agctcatgca                         40

<210> SEQ ID NO 267
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 267
ataaacggaa attttgtatt gaaatgagag ccattggaaa                         40

<210> SEQ ID NO 268
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 268
ttactccaga ctcctactta taaaagaga aactgaggct                          40

<210> SEQ ID NO 269
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 269
gaagggtggg gactttctca gtatgacatg gaaatgatca                             40

<210> SEQ ID NO 270
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 270
tggattcaaa gctcctgact ttctgtctag tgtatgtgca                             40

<210> SEQ ID NO 271
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 271 gcccctttc ctctaactga aagaaggaaa aaaaaatgga                              40

<210> SEQ ID NO 272
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 272
aaaatattct acatagtttc catgtcacag ccagggctgg                             40

<210> SEQ ID NO 273
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 273
tctcctgtta tttcttttaa aataaatata tcatttaaat                             40

<210> SEQ ID NO 274
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 274
aaataagcaa accctgctcg ggaatgggag ggagagtctc                             40

<210> SEQ ID NO 275
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 275
gtccacccct tctcggccct ggctctgcag atagtgctat                               40

<210> SEQ ID NO 276
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 276
gccctgacag agccctgccc attgctgggc cttggagtga                               40

<210> SEQ ID NO 277
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 277
gcctagtaga gaggcagggc aagccatctc atagctgctg                               40

<210> SEQ ID NO 278
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 278
ggagagagaa aagggctcat tgtctataaa ctcaggtcat                               40

<210> SEQ ID NO 279
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 279
attcttattc tcacactaag aaaaagaatg agatgtctac                               40

<210> SEQ ID NO 280
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 280
accctgcgtc ccctcttgtg tactggggtc cccaagagct                               40

<210> SEQ ID NO 281
<211> LENGTH: 40
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 281
aaaagtgatg gcaaagtcat tgcgctagat gccatcccat                               40

<210> SEQ ID NO 282
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 282
tataaacctg catttgtctc cacacaccag tcatggacaa                               40

<210> SEQ ID NO 283
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 283
cctcctccca ggtccacgtg cttgtctttg tataatactc                               40

<210> SEQ ID NO 284
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 284
aatttcggaa aatgtattct ttcaatcttg ttctgttatt                               40

<210> SEQ ID NO 285
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 285
tttcaatggc ttagtagaaa aagtacatac ttgttttccc                               40

<210> SEQ ID NO 286
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 286
attgacaata gacaatttca catcaatgtc tatatgggtc                               40

<210> SEQ ID NO 287
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 287
tgtttgctgt gtttgcaaaa actcacaata actttatatt                              40

<210> SEQ ID NO 288
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 288
ctactctaag aaagttacaa catggtgaat acaagagaaa                              40

<210> SEQ ID NO 289
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 289
ttacaagtcc agaaaataaa agttatcatc ttgaggcctc                              40

<210> SEQ ID NO 290
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 290
ttctaggaat aatatcaata ttacaaaatt aatctaacaa                              40

<210> SEQ ID NO 291
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 291
gaacagcaat gagataatgt gtacaaagta cccagaccta                              40

<210> SEQ ID NO 292
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 292
gtagagcatc aaggaagcgc attgcggagc agtttttgt                               40

<210> SEQ ID NO 293
<211> LENGTH: 40
<212> TYPE: DNA
<213> ORGANISM: Artificial Sequence
<220> FEATURE:

```
<223> OTHER INFORMATION: Description of Artificial Sequence: Synthetic
      probe

<400> SEQUENCE: 293
ttgtttttgt attctgtttc gtgaggcaag gtttcactct                            40

<210> SEQ ID NO 294
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 294
tccaggctgg agtgcagtgg caagatcatg tctcactgca                            40

<210> SEQ ID NO 295
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 295
tgacctcctg agctcaaggg atcctcccat ttcggcctcc                            40

<210> SEQ ID NO 296
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 296
tagctgggac tacaggtgta catcacatgc ctggctaatt                            40

<210> SEQ ID NO 297
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 297
tttttttttt aagtagagac gaggtcttgc tatgttgtcc                            40

<210> SEQ ID NO 298
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 298
taatatcaaa ctcttgagct caagcagtcc tcccacttct                            40

<210> SEQ ID NO 299
<211> LENGTH: 40
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 299
tggaggtatc cagtatgaaa tttagataat acctgccttc                    40

<210> SEQ ID NO 300
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 300
gttgaaatta gaacttaatg atataatgca tcaatgaact                    40

<210> SEQ ID NO 301
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 301
atagttccta gcacaaagta agaatccttt caatgtgtgt                    40

<210> SEQ ID NO 302
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 302
gtgtatgtat ttatctgtta ttaataggaa tcttatgggc                    40

<210> SEQ ID NO 303
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 303
tctcacttaa tccttattaa taactatgaa gcaggtattt                    40

<210> SEQ ID NO 304
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 304
gagttttcca agtgagttaa gtatagcttg taatacttaa                    40

<210> SEQ ID NO 305
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 305
atatccacag gttacatagc tagtatataa ctgagaaata                40

<210> SEQ ID NO 306
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 306
tatttatatt ataaaacatt ctaacaatac agatgtatat                40

<210> SEQ ID NO 307
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 307
taaaaaactg aaagggctca tgcaacccta ccttctcaat                40

<210> SEQ ID NO 308
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 308
cttcttcact tagaaaaaac cagccttagc tgtctgctat                40

<210> SEQ ID NO 309
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 309
cctttcaaaa tatacttctg agaaatgaga gagagaaatg                40

<210> SEQ ID NO 310
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 310
gggtagaagg aaggaagata gggtaagaga cagggaagga                40

<210> SEQ ID NO 311
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 311
tggggaaaga aattaaatta ttcttttctc tgtctcttga                            40

<210> SEQ ID NO 312
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 312
gctctttcca ttacattgaa tcaaaggtaa tgttgccatt                            40

<210> SEQ ID NO 313
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 313
gactcttgaa ataagaaag accgatgtat gaaataattt                             40

<210> SEQ ID NO 314
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 314
agtctatggc attttcaaaa tgcaaggtga tgtcttacta                            40

<210> SEQ ID NO 315
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 315
gcctttgctt tattattaga aatggggaag tgagtataga                            40

<210> SEQ ID NO 316
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 316
ttatcaggag atatattagg aaaaagggaa actggagaaa                            40

<210> SEQ ID NO 317
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 317
```
gaggagtatc cagatgtcct gtccctgtaa ggtgggggca                              40

<210> SEQ ID NO 318
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 318
ccttcaatca aaagggctcc ttaacaactt ccttgcttgg                              40

<210> SEQ ID NO 319
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 319
ccaccatctt ggaccattag ctccacaggt atcttcttcc                              40

<210> SEQ ID NO 320
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 320
agtggtcata acagcagctt cagctacctc tctaaagagt                              40

<210> SEQ ID NO 321
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 321
ccagatatag gtcaggaaat ataatccact aataaaaga                               40

<210> SEQ ID NO 322
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 322
cattttgact gtagttgttt gttttttgtc attgtgacta                              40

<210> SEQ ID NO 323
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 323
taacattctc actctttcat cagtaatcac tcaggttatt                            40

<210> SEQ ID NO 324
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 324
gaccaacaga ctgtgggaaa aatcagagaa ggaggcatcc                            40

<210> SEQ ID NO 325
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 325
gcttactagc ctaaactgaa attgctatag cagagtgaac                            40

<210> SEQ ID NO 326
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 326
aggtttacag atattttcca caaagagtaa aaggattgaa                            40

<210> SEQ ID NO 327
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 327
tctccagatc aatgcatagg aaataataat ggaccataaa                            40

<210> SEQ ID NO 328
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 328
atattatgac gaacaacatt aggataagtc catatcaatt                            40

<210> SEQ ID NO 329
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 329
atccagtcat aagcacagac tacgtgaagc acgtccaagt                            40

<210> SEQ ID NO 330
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 330
gcaggagaaa tgagaggagc aagaaagagg agccatttga                            40

<210> SEQ ID NO 331
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 331
gaatagcaga aaaggaaag gcaagtcata ttaacaaatg                             40

<210> SEQ ID NO 332
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 332
tcatgccaac agtacagata actctgctaa taaaggtaga                            40

<210> SEQ ID NO 333
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 333
taatacaggt agtagcagat atctacatag tagttaaagg                            40

<210> SEQ ID NO 334
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 334
ggccatcagt acagaagatt ccataaagga gaacctaaag                            40

<210> SEQ ID NO 335
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 335
agaataattt gtcagaagct taaaagctga actctgaggc                            40

<210> SEQ ID NO 336
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 336
aactacaata tccttttgac tgtggaaagg gtggtgaaag                           40

<210> SEQ ID NO 337
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 337
gttcaaggac atttgagcca acatagagag gaacattggc                           40

<210> SEQ ID NO 338
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 338
tgagggatat ctgtcctgat gttgtccagg atggtgatga                           40

<210> SEQ ID NO 339
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 339
catataaata acgtagagaa aacaggaggg gatagagatc                           40

<210> SEQ ID NO 340
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 340
caaagaggca tcaaagatag ggatgtttgt aaggatgaaa                           40

<210> SEQ ID NO 341
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 341
ctgttcttct ctgagtagcc aagctcagct tggttcaagc                           40

<210> SEQ ID NO 342
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 342
catactgtgg atctgtagca aattcccct gaaaacccag                              40

<210> SEQ ID NO 343
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 343
tctgaccctc acattcaagt tctgaggaag ggccactgcc                             40

<210> SEQ ID NO 344
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 344
gccttgagat acctggtcct tattccttgg actttggcaa                             40

<210> SEQ ID NO 345
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 345
atagggcttg ttttagggag aaacctgttc tccaaactct                             40

<210> SEQ ID NO 346
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 346
ctggtgtcca tactctgaat gggaagaatg atgggattac                             40

<210> SEQ ID NO 347
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 347
agcaggagag gatcaacccc atactctgaa tctaagagaa                             40

<210> SEQ ID NO 348

<210> SEQ ID NO 348
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 348
tcagatccct ggatgcaagc caggtctgga accataggca                          40

<210> SEQ ID NO 349
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 349
ctcctcccta ccacctttag ccataaggaa acatggaatg                          40

<210> SEQ ID NO 350
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 350
gacacaaacc tgggcctttc aatgctataa cctttcttga                          40

<210> SEQ ID NO 351
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 351
ctacctgact tctgagtcag gatttataag ccttgttact                          40

<210> SEQ ID NO 352
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 352
tgaaccaaca agcatcgaag caataatgag actgcccgca                          40

<210> SEQ ID NO 353
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 353
gaaaagcaat aatccatttt tcatggtatc tcatatgata                          40

<210> SEQ ID NO 354
<211> LENGTH: 40

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 354
taacacttat ctctctgaac tttgggcttt taatatagga                          40

<210> SEQ ID NO 355
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 355
ttttctgact gtctaatctt tctgatctat cctggatggc                          40

<210> SEQ ID NO 356
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 356
atcttcatcg aatttgggtg tttctttcta aaagtccttt                          40

<210> SEQ ID NO 357
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 357
gaaattacaa atgctaaagc aaacccaaac aggcaggaat                          40

<210> SEQ ID NO 358
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 358
attaggcatc ttacagtttt tagaatcctg catagaactt                          40

<210> SEQ ID NO 359
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 359
tacaatattt gactcttcag gttaaacata tgtcataaat                          40

<210> SEQ ID NO 360
<211> LENGTH: 40
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 360
aacattcagt gaagtgaagg gcctactta cttaacaaga                                40

<210> SEQ ID NO 361
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 361
tcttttccta tcagtggttt acaagccttg tttatatttt                               40

<210> SEQ ID NO 362
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 362 tattttttgtt ctgagaatat agatttagat acataatgga                              40

<210> SEQ ID NO 363
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 363
caaaatctaa cacaaaatct agtagaatca tttgcttaca                               40

<210> SEQ ID NO 364
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 364
agaatttatg acttgtgata tccaagtcat tcctggataa                               40

<210> SEQ ID NO 365
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 365
ttacactaga aaatagccac aggcttcctg caaggcagcc                               40

<210> SEQ ID NO 366
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 366
agtttgaaca cttgttatgg tctattctct cattctttac                              40

<210> SEQ ID NO 367
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 367
acttcgtgag agatgaggca gaggtacact acgaaagcaa                              40

<210> SEQ ID NO 368
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 368
tcttgagaat gagcctcagc cctggctcaa actcacctgc                              40

<210> SEQ ID NO 369
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 369
aataggatgt ctgtgctcca agttgccaga gagagagatt                              40

<210> SEQ ID NO 370
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 370
attaaagatc cctcctgctt aattaacatt cacaagtaac                              40

<210> SEQ ID NO 371
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 371
acttaaagta gcgataccct ttcaccctgt cctaatcaca                              40

<210> SEQ ID NO 372
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 372
tctcaggtgt aactttata gtgaggactt tcctgccata                                40

<210> SEQ ID NO 373
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 373
atagtttcat ataaatgggt tcctcatcat ctatgggtac                               40

<210> SEQ ID NO 374
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 374
ggtatttaca tttgccattc cctatgccct aaatatttaa                               40

<210> SEQ ID NO 375
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 375
tattgatatt ccttgaaaat tctaagcatc ttacatcttt                               40

<210> SEQ ID NO 376
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 376
cttttattct ccccttcacc gaatctcatc ctacattggc                               40

<210> SEQ ID NO 377
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 377
tagtgtccca aattttataa tttaggactt ctatgatctc                               40

<210> SEQ ID NO 378
<211> LENGTH: 40
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 378
atatggtcac ctctttgttc aaagtcttct gatagtttcc                                40

<210> SEQ ID NO 379
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 379
acaatcttcc tgcttctacc actgccccac tacaatttct                                40

<210> SEQ ID NO 380
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 380
agtcactgtc accaccacct aaattatagc tgttgactca                                40

<210> SEQ ID NO 381
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 381 ctgaccccctt gccttcacct ccaatgctac cactctggtc                               40

<210> SEQ ID NO 382
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 382
agaaaatcct gttggttttt cgtgaaagga tgttttcaga                                40

<210> SEQ ID NO 383
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 383
acatatactc acagccagaa attagcatgc actagagtgt                                40

<210> SEQ ID NO 384
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 384
acccaaagac tcactttgcc tagcttcaaa atccttactc                                40

<210> SEQ ID NO 385
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 385
tgaggtagag actgtgatga acaaacacct tgacaaaatt                                40

<210> SEQ ID NO 386
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 386
tccatatcca cccacccagc tttccaattt taaagccaat                                40

<210> SEQ ID NO 387
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 387
aaggtatgat gtgtagacaa gctccagaga tggtttctca                                40

<210> SEQ ID NO 388
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 388
ctctggtcag catccaagaa atacttgatg tcactttggc                                40

<210> SEQ ID NO 389
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 389
aactgtgaac ttccttcagc tagaggggcc tggctcagaa                                40

<210> SEQ ID NO 390
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 390
tgattgttct ctgacttatc taccattttc cctccttaaa                            40

<210> SEQ ID NO 391
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 391
aaacaaaacc catcaaattc cctgaccgaa cagaattctg                            40

<210> SEQ ID NO 392
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 392
cagaggtcac agcctaaaca tcaaattcct tgaggtgcgg                            40

<210> SEQ ID NO 393
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 393
gaaggcaggt gtggctctgc agtgtgattg ggtacttgca                            40

<210> SEQ ID NO 394
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 394
catggaggaa aaactcatca gggatggagg cacgcctcta                            40

<210> SEQ ID NO 395
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 395
agcttgttaa attgaattct atccttctta ttcaattcta                            40

<210> SEQ ID NO 396
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 396
```
catagttgtc agcacaatgc ctaggctata ggaagtactc 40

<210> SEQ ID NO 397
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 397
gcagatatag cttgatggcc ccatgcttgg tttaacatcc 40

<210> SEQ ID NO 398
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 398
ctaaataact agaatactct ttattttttc gtatcatgaa 40

<210> SEQ ID NO 399
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 399
agtgtttaaa gggtgatatc agactaaact tgaaatatgt 40

<210> SEQ ID NO 400
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 400
ggatgggtct agaaagacta gcattgtttt aggttgagtg 40

<210> SEQ ID NO 401
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 401
tgctgccaac attaacagtc aagaaatacc tccgaataac 40

<210> SEQ ID NO 402
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 402
tattgtgaga ggtctgaata gtgttgtaaa ataagctgaa         40

<210> SEQ ID NO 403
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 403
ttacaacatg atggcttgtt gtctaaatat ctcctaggga         40

<210> SEQ ID NO 404
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 404
ctaagtagaa gggtactttc acaggaacag agagcaaaag         40

<210> SEQ ID NO 405
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 405
gtcttgtatt gcccagtgac atgcacactg gtcaaaagta         40

<210> SEQ ID NO 406
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 406
ccctatgtct tccctgatgg gctagagttc ctctttctca         40

<210> SEQ ID NO 407
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 407
aaagtttccc caaattttac caatgcaagc catttctcca         40

<210> SEQ ID NO 408
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 408
aactgcagat tctctgcatc tccctttgcc gggtctgaca         40

```
<210> SEQ ID NO 409
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 409
tagtgctgtg gtgctgtgat aggtacacaa gaaatgagaa                              40

<210> SEQ ID NO 410
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 410
taactagcgt caagaactga gggccctaaa ctatgctagg                              40

<210> SEQ ID NO 411
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 411
cattggctcc gtcttcatcc tgcagtgacc tcagtgcctc                              40

<210> SEQ ID NO 412
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 412
tgtttatgtg ttatagtgtt catttactct tctggtctaa                              40

<210> SEQ ID NO 413
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 413
cctttgaccc cttggtcaag ctgcaacttt ggttaaaggg                              40

<210> SEQ ID NO 414
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 414
ttctcttggg ttacagagat tgtcatatga caaattataa                              40
```

<210> SEQ ID NO 415
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 415
tggaagttgt ggtccaagcc acagttgcag accatacttc                        40

<210> SEQ ID NO 416
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 416
ctgccctgtg gcccttgctt cttacttttca cttcttgtcg                       40

<210> SEQ ID NO 417
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 417
aactcagata ttgtggatgc gagaaattag aagtagatat                        40

<210> SEQ ID NO 418
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 418
tacagaacca ccaagtagta aggctaggat gtagacccag                        40

<210> SEQ ID NO 419
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 419
tgagctctcc tactgtctac attacatgag ctcttattaa                        40

<210> SEQ ID NO 420
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 420
aagctaataa gtagacaatt agtaattaga agtcagatgg                        40

```
<210> SEQ ID NO 421
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 421
agcccaatgt acttgtagtg tagatcaact tattgaaagc                              40

<210> SEQ ID NO 422
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 422
ccaatactca gaagtagatt attacctcat ttattgatga                              40

<210> SEQ ID NO 423
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 423
gctagaatca aatttaagtt tatcatatga ggccgggcac                              40

<210> SEQ ID NO 424
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 424
taatactaat gataagtaac acctcttgag tacttagtat                              40

<210> SEQ ID NO 425
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 425
atggtaattc tgtgagatat gtattattga acatactata                              40

<210> SEQ ID NO 426
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 426
tgaaagagaa gtgggaatta atacttactg aaatctttct                              40

<210> SEQ ID NO 427
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 427
gagagacacg aggaaatagt gtagatttag gctggaggta                          40

<210> SEQ ID NO 428
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 428
gttgagaggg aaacaagatg gtgaagggac tagaaaccac                          40

<210> SEQ ID NO 429
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 429
caaggttctg aacatgagaa atttttagga atctgcacag                          40

<210> SEQ ID NO 430
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 430
tgccatctaa aaaaatctga cttcactgga aacatggaag                          40

<210> SEQ ID NO 431
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 431
gggatcctct cttaagtgtt tcctgctgga atctcctcac                          40

<210> SEQ ID NO 432
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 432
gtttccttca tgtgacaggg agcctcctgc cccgaacttc                          40

<210> SEQ ID NO 433
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 433
ttggataaga gtagggaaga acctagagcc tacgctgagc                            40

<210> SEQ ID NO 434
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 434
atctggggct ttgtgaagac tggcttaaaa tcagaagccc                            40

<210> SEQ ID NO 435
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 435
accgcaatgc ttcctgccca ttcagggctc cagcatgtag                            40

<210> SEQ ID NO 436
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 436
tatggggaag cagggtatga aagagctctg aatgaaatgg                            40

<210> SEQ ID NO 437
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 437
ggttgcatga atcagattat caacagaaat gttgagacaa                            40

<210> SEQ ID NO 438
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 438
aatgcaggcc taggcatgac tgaaggctct ctcataattc                            40

<210> SEQ ID NO 439
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 439
taacgttttc ttgtctgcta ccccatcata tgcacaacaa                            40

<210> SEQ ID NO 440
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 440
ttaattccca aactcatata gctctgagaa agtctatgct                            40

<210> SEQ ID NO 441
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 441
ccctataggg gatttctacc ctgagcaaaa ggctggtctt                            40

<210> SEQ ID NO 442
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 442
tcctcaccat atagaaagct tttaacccat cattgaataa                            40

<210> SEQ ID NO 443
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 443
taagctgtct agcaaaagca agggcttgga aaatctgtga                            40

<210> SEQ ID NO 444
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 444
aggattagaa gattcttctg tgtgtaagaa tttcataaac                            40

<210> SEQ ID NO 445
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 445
attatcttct ggaataggga atcaagttat attatgtaac                           40

<210> SEQ ID NO 446
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 446
ctctctggtt gactgttaga gttctggcac ttgtcactat                           40

<210> SEQ ID NO 447
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 447
tcttcagtta gatggttaac tttgtgaagt tgaaaactgt                           40

<210> SEQ ID NO 448
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 448
ctacaccatg tggagaaggg gtggtggttt tgattgctgc                           40

<210> SEQ ID NO 449
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 449
actttcctaa cctgagccta acatccctga catcaggaaa                           40

<210> SEQ ID NO 450
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 450
tacactttat tcgtctgtgt cctgctctgg gatgatagtc                           40

<210> SEQ ID NO 451
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 451
tactctttgc attccactgt ttttcctaag tgactaaaaa                           40

<210> SEQ ID NO 452
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 452
aaaggcctcc caggccaagt tatccattca gaaagcattt                           40

<210> SEQ ID NO 453
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 453
tattgacatg tacttcttgg cagtctgtat gctggatgct                           40

<210> SEQ ID NO 454
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 454
tttggtccta attatgtctt tgctcactat ccaataaata                           40

<210> SEQ ID NO 455
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 455
gttaaaaaaa ctacctctca acttgctcaa gcatacactc                           40

<210> SEQ ID NO 456
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 456
taattagtgc tttgcataat taatcatatt taatactctt                           40

<210> SEQ ID NO 457
<211> LENGTH: 40
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 457
actagtgttc tgtactttat gcccattcat ctttaactgt                                40

<210> SEQ ID NO 458
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 458 gtatttttg tttaactgca atcattcttg ctgcaggtga                                 40

<210> SEQ ID NO 459
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 459
gcagtgactt ataaatgcta actactctag aaatgtttgc                                40

<210> SEQ ID NO 460
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 460
ttataagcat gattacagga gttttaacag gctcataaga                                40

<210> SEQ ID NO 461
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 461
agtatccctc aagtagtgtc aggaattagt catttaaata                                40

<210> SEQ ID NO 462
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 462
agtcacccat ttggtatatt aaagatgtgt tgtctactgt                                40

<210> SEQ ID NO 463
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 463
tggtcataaa acattgaatt ctaatctccc tctcaaccct                              40

<210> SEQ ID NO 464
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 464
acagttgaaa agacctaagc ttgtgcctga tttaagcctt                              40

<210> SEQ ID NO 465
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 465
caactacagg gccttgaact gcacactttc agtccggtcc                              40

<210> SEQ ID NO 466
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 466
gtggttcttt gaagagactt ccacctggga acagttaaac                              40

<210> SEQ ID NO 467
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 467
tggaggaaat atttatcccc aggtagttcc cttttttgcac                             40

<210> SEQ ID NO 468
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 468
gcctggtgct tttggtaggg gagcttgcac tttcccccctt                             40

<210> SEQ ID NO 469
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 469
tctcatttct ttgagaactt cagggaaaat agacaaggac                             40

<210> SEQ ID NO 470
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 470
caaacttttc aagccttctc taatcttaaa ggtaaacaag                             40

<210> SEQ ID NO 471
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 471
tcaacaaagg agaaaagttt gttggcctcc aaaggcacag                             40

<210> SEQ ID NO 472
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 472
gatgcaacag accttggaag catacaggag agctgaactt                             40

<210> SEQ ID NO 473
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 473
catctgagat cccagcttct aagaccttca attctcactc                             40

<210> SEQ ID NO 474
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 474
tatcttaaca gtgagtgaac aggaaatctc ctcttttccc                             40

<210> SEQ ID NO 475
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 475
```
aactcatgct ttgtagatga ctagatcaaa aaatttcagc        40

<210> SEQ ID NO 476
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 476
tcaaaggaag tcaaaagatg tgaaaaacaa tttctgaccc        40

<210> SEQ ID NO 477
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 477
tgccttcact taagtaatca attcctaggt tatattctga        40

<210> SEQ ID NO 478
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 478
ccctaccttg ttcaaaatgt tcctgtccag accaaagtac        40

<210> SEQ ID NO 479
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 479
gcacttacaa attatactac gctctatact ttttgtttaa        40

<210> SEQ ID NO 480
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 480
ctttagtttc atttcaaaca atccatacac acacagccct        40

<210> SEQ ID NO 481
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 481

```
tagggaccac agggttaagg gggcagtaga attatactcc                              40
```

<210> SEQ ID NO 482
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 482

```
ctcacaatta agctaagcag ctaagagtct tgcagggtag                              40
```

<210> SEQ ID NO 483
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 483

```
gttgaaagac agagaggatg gggtgctatg ccccaaatca                              40
```

<210> SEQ ID NO 484
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 484

```
gcttgtctaa ttttatatat caccctactg aacatgaccc                              40
```

<210> SEQ ID NO 485
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 485

```
aatattgtac acgtacacca aagcatcatg ttgtacccca                              40
```

<210> SEQ ID NO 486
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 486

```
tgtgaagtgg tggatttgtt aattagccct atttaaccat                              40
```

<210> SEQ ID NO 487
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 487

```
tgacacatat gacattttaa ctatgttcca gatttttgaa                              40
```

<210> SEQ ID NO 488
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 488
gcaaggaatc attcaatgtt ttctaaatct attactgcat                          40

<210> SEQ ID NO 489
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 489
cattttcata ggttttcctc gattgatcat tattcatgat                          40

<210> SEQ ID NO 490
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 490
aaagtgatca agatattttt agttcaggct ccaaaatttt                          40

<210> SEQ ID NO 491
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 491
ctttacaggc cgagaaaaat gaatctgaat tcctgacctc                          40

<210> SEQ ID NO 492
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 492
tccactcaag gcctacattc tgctataatg caatttcaag                          40

<210> SEQ ID NO 493
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 493
aactgcttaa aattaatggc acaagtcatg tttttgatgt                          40

<210> SEQ ID NO 494
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 494
ctgactgtga cgtagcaata aagaaaccca cgtttcatat                          40

<210> SEQ ID NO 495
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 495
ctggcccact gcttggagga gagcactcag gaccatgaac                          40

<210> SEQ ID NO 496
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 496
ttctgaaatg ataaagtcaa tcacaggaag gcacctggac                          40

<210> SEQ ID NO 497
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 497
atcattctct ttcccttcct ctatgtggca gaaagtaaaa                          40

<210> SEQ ID NO 498
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 498
ggagataata atgtgttact ccctaaggca gagtgccctt                          40

<210> SEQ ID NO 499
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 499
caattaactt ggccatgtga ctggttgtga ctaaaataat                          40

```
<210> SEQ ID NO 500
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 500
cactaaatca atatacttct caacaatttc caacagccct                             40

<210> SEQ ID NO 501
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 501
ctaggctcct gagtttgctg gggatgcgaa gaacccttat                             40

<210> SEQ ID NO 502
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 502
ccgaggaccc cgcactcgga gccgccagcc ggccccaccg                             40

<210> SEQ ID NO 503
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 503
ttggaagcac agggtgtggg ataatgctaa ttactagtga                             40

<210> SEQ ID NO 504
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 504
gttcagtatg cctttgattt tacaataata ttcctgttat                             40

<210> SEQ ID NO 505
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 505
agattccatg aagtattaca gcatttggta gtcttttgc                              40

<210> SEQ ID NO 506
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 506
tatttgctct gaaataagac ataatttggg gtgagaaagc                             40

<210> SEQ ID NO 507
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 507
actcatgata tttggctcta gaatacatgc tctgaatcat                             40

<210> SEQ ID NO 508
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 508
tccaagatga agtggctact aactgacaga gggcataatt                             40

<210> SEQ ID NO 509
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 509
tattcacagt aactctgtgc ctcaagtact attgtaatac                             40

<210> SEQ ID NO 510
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 510
acatcctcaa tctacacact aggatagtat aaaagtaata                             40

<210> SEQ ID NO 511
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 511
gtctacccat atgtgacctt catgtctttg ctctaagccc                             40

<210> SEQ ID NO 512
<211> LENGTH: 40
```

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 512
cgtgtaatcc ttgacaatgt catctcatct atttattccc                              40

<210> SEQ ID NO 513
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 513
tctgaaagag actaaccttc cctcgctttg cagagaaaga                              40

<210> SEQ ID NO 514
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 514
atgcatggat tctcttgaaa aaatgtttct gccatgatgt                              40

<210> SEQ ID NO 515
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 515
tagttgaaga cctactgtgt tcagggccgt gagccagggc                              40

<210> SEQ ID NO 516
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 516
caacgtggag agctgtcctg gcaccatttc ttcctgctgt                              40

<210> SEQ ID NO 517
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 517
atcctcaaag gagcctggct tgggctaaca aggaagaact                              40

<210> SEQ ID NO 518
<211> LENGTH: 40
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 518
tgcctgggac cctgccccaa gcaaagtaat aatctgaatg                              40

<210> SEQ ID NO 519
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 519
ctggtgtgtc cagtgtgatc cctgcaccca tgcccggagc                              40

<210> SEQ ID NO 520
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 520 ctgcccctg cagcagggaa ggggctctgg aagggtctga                               40

<210> SEQ ID NO 521
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 521
tagctgctgc cccactatgc accatcgctt atctgttctt                              40

<210> SEQ ID NO 522
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 522
gaaacccgaa aaatgtcctg gtcctcttct taagtctggg                              40

<210> SEQ ID NO 523
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 523
gctgagaaca tgactctgct tggcgttcca tttaattgac                              40

<210> SEQ ID NO 524
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 524
gagagggtgt gcatttgaag tatagatttg ttaaacatag                          40

<210> SEQ ID NO 525
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 525
catcaggcaa aaatacttcg atgggactgt gttctttcag                          40

<210> SEQ ID NO 526
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 526
tctaaagtga tgtaatgttg ccacggaaat tctaatccct                          40

<210> SEQ ID NO 527
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 527
cgtgcagaac cagctctgtc ttcccagaca ctgtcgcttt                          40

<210> SEQ ID NO 528
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 528
acccctgagc acctcagtgt ccgtgactgt ggagcggagg                          40

<210> SEQ ID NO 529
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 529
ctgcctggga cacgtacggc tgcccagtga tcctgagcgc                          40

<210> SEQ ID NO 530
<211> LENGTH: 40
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 530
cacagccgga tggtgtggga gctggcactg ccggggctcc                               40

<210> SEQ ID NO 531
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 531
cgtcttggca gaggctccct gtcatcaagg acctgaggtt                               40

<210> SEQ ID NO 532
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 532
gaccccacaa agatgagcgg gtccccttcc caattttcgg                               40

<210> SEQ ID NO 533
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 533
tcaggaagcc ggtgctcagc aaacttatct gaagctcttg                               40

<210> SEQ ID NO 534
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 534
gaggctgcag aggaacatcg tttggtcaaa tgtgaaatgt                               40

<210> SEQ ID NO 535
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 535
ctagcttcta gaaagtgctg ccaatttggg gaccaaggga                               40

<210> SEQ ID NO 536
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 536
ggaaacactt cttttccct tgacaaagga catcctctgc                                    40

<210> SEQ ID NO 537
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 537
gcatgtgcat aaacactcgt gtgtgtgtcc ttttatccca                                    40

<210> SEQ ID NO 538
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 538
ccaaatctct atacatgtcc atagagagag gcagacgtat                                    40

<210> SEQ ID NO 539
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 539
gggttgaaga caaggggctc agagcttgct ttttatacac                                    40

<210> SEQ ID NO 540
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 540
agattcatct tcatggcagg acttcaggca agagaggccc                                    40

<210> SEQ ID NO 541
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 541 ctcaccccctt agcaggaccc tgacggaact gggtacaggc                                    40

<210> SEQ ID NO 542
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 542
ggttgggaga caatgggtgg cccctcggtg tggtgtcctc        40

<210> SEQ ID NO 543
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 543
agagtctaga gggcccgtgg ggacgggagt cctgggaacc        40

<210> SEQ ID NO 544
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 544
gcggcatgtc cggcttcacc ctgcccagaa tcacagcctc        40

<210> SEQ ID NO 545
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 545
atggttaaaa aattctccta cttaagactc ccagacccct        40

<210> SEQ ID NO 546
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 546
gggttgaaga caaggggctc agagcttgct ttttatacac        40

<210> SEQ ID NO 547
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 547
agattcatct tcatggcagg acttcaggca agagaggccc        40

<210> SEQ ID NO 548
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 548 ctcaccccctt agcaggaccc tgacggaact gggtacaggc                              40

<210> SEQ ID NO 549
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 549
ggttgggaga caatgggtgg ccccctcggtg tggtgtcctc                              40

<210> SEQ ID NO 550
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 550
agagtctaga gggcccgtgg ggacgggagt cctgggaacc                               40

<210> SEQ ID NO 551
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 551
gcggcatgtc cggcttcacc ctgcccagaa tcacagcctc                               40

<210> SEQ ID NO 552
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 552
tgagattcca gggctggttc cacaacggcc ggcatcggcc                               40

<210> SEQ ID NO 553
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 553
ctgagtcact aacaaagctc aggcctgacc acaggacatt                               40

<210> SEQ ID NO 554
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 554
```
ggctggccta cctgccacgg ggccagggct gggtgctttc 40

<210> SEQ ID NO 555
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 555
gggctctgga cgctggaggc ctgaggctgc accccaggtt 40

<210> SEQ ID NO 556
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 556
acagtggcca ctcacccact gggcccacat ccccacaggc 40

<210> SEQ ID NO 557
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 557
actctgccag cctttgatgc ctcgctgaga cagagggtct 40

<210> SEQ ID NO 558
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 558
agccggggct ctggccccat ccaggggctc ccccagcagc 40

<210> SEQ ID NO 559
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 559
ccttggaagt cagtcagcag gtcaggacac agttcagccc 40

<210> SEQ ID NO 560
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 560
ttacatgcag ttggtcttct cctgtgaatg gggaaactga                 40

<210> SEQ ID NO 561
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 561
ctgcatcaca gaacagctgc atttctaatg tcaggcttct                 40

<210> SEQ ID NO 562
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 562
cagcctggga ggcttgtcaa cctcctttga caagcacgcc                 40

<210> SEQ ID NO 563
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 563
agaaactggg gctccagggc atggaggctg cctgtggcca                 40

<210> SEQ ID NO 564
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 564
tcccggcctg gaggaagtct tattagcctc atttcatgga                 40

<210> SEQ ID NO 565
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 565
tcctgccagc cccctcacgc tcacgaattc agtcccaggg                 40

<210> SEQ ID NO 566
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 566
aattctaaag gtgaagggac gtctacaccc ccaacaaaac                 40

<210> SEQ ID NO 567
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 567
ggaaatatta gtcccctctg cctgggacaa gaccaccgaa                40

<210> SEQ ID NO 568
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 568
aaacacacct ctgaatggaa agctgagaaa cagtgatctc                40

<210> SEQ ID NO 569
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 569
actgcacccc ctcccttccc gtgccggcaa tttaaccggg                40

<210> SEQ ID NO 570
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 570
tgccttccta ccttgaccag tcggtccttg cggggggtccc                40

<210> SEQ ID NO 571
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 571
atttccttca tcttgtcctt ctagcctgga gactcttcgg                40

<210> SEQ ID NO 572
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 572
aatgcccgaa aattccagca gcagcccaag atggtggcca                40

<210> SEQ ID NO 573
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 573
cgttgcaaat gcccaagggg gtaaccctaa aagttaaagg        40

<210> SEQ ID NO 574
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 574
acacaacccc tgtgcaagtt tcattccggc gcacaggggc        40

<210> SEQ ID NO 575
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 575
tgcaagaact aatttagcat gcaaggacgg ggaggaccgg        40

<210> SEQ ID NO 576
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 576
gccacgaggg cacccacggg cggacagacg gccaaagaat        40

<210> SEQ ID NO 577
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 577
accccatatc caagccggca gaatgggcgc atttccaaga        40

<210> SEQ ID NO 578
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 578
gcctggggag accacgagaa ggggtgactg gggcgcggcg        40

```
<210> SEQ ID NO 579
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 579
ctgcagtagg ggacaactag gaaggccggc aggccacacg                              40

<210> SEQ ID NO 580
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 580
gagtgggtcc cccgggattt aggggtgag gtggaggtgg                               40

<210> SEQ ID NO 581
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 581
tccccgccag ggaagagggg tgcaggggc cccgtccgcc                               40

<210> SEQ ID NO 582
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 582
tgaggcgccg cgcctgccct gcggcggagt tgcccctgta                              40

<210> SEQ ID NO 583
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 583
aaacgccggg agcagcgagg ggcagagccc aaaagccatc                              40

<210> SEQ ID NO 584
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 584
ttgttaagca aagatcaaag cccggcagag aatgggagcg                              40

<210> SEQ ID NO 585
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 585
caacttcaac aaaactcccc tgtagtccgt gtgacgttac                          40

<210> SEQ ID NO 586
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 586
ctgctactgc gccgacagcc ctctggaggc tccaggactt                          40

<210> SEQ ID NO 587
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 587
gctcttctgc ccctcgccgg agcgtgcgga ctctgctgct                          40

<210> SEQ ID NO 588
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 588
tccgcgctcg gctctcgctt ctgctgcccc gcgctccctc                          40

<210> SEQ ID NO 589
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 589
tttccacttc gcagcacagg agctggtgtt ccatggctgg                          40

<210> SEQ ID NO 590
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 590
ggtcgttgag gaggttggca tcggggtacg cgcggcggat                          40

<210> SEQ ID NO 591
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 591
tgtcctactt caaatgtgtg cagaaggagg tcctgccgtc                              40

<210> SEQ ID NO 592
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 592
tcgggcggct ctcttaagac ttccctgcaa cttgttgccc                              40

<210> SEQ ID NO 593
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 593
acccacgttt ctttgctact caccccctc ccttctctcc                               40

<210> SEQ ID NO 594
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 594
ctagaacttt gaagtttgcc gtggtgtttc tagggatccg                              40

<210> SEQ ID NO 595
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 595 agaaggggt ccgggagggg tgccttcggg agaagccagt                               40

<210> SEQ ID NO 596
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 596 cagggcacc ccaatgggcc cgagggtgcg ggctggcagg                               40

<210> SEQ ID NO 597
<211> LENGTH: 40
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 597
gggtgcgctt tgtgtccccc gcctgcgccc cagcccggct                40

<210> SEQ ID NO 598
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 598
gcctcagcgg ccgggagccg ccaactccgg ggggaggggg                40

<210> SEQ ID NO 599
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 599
aaagtgcagt aatacccttg atcagagttg atgacttgaa                40

<210> SEQ ID NO 600
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 600
gagagaaata aagtagttgc tctatttgta aattgaaaag                40

<210> SEQ ID NO 601
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 601
ggtagcagtg attgctgtat atttgtgaaa aggaggcaag                40

<210> SEQ ID NO 602
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 602
tgctgataat ggaagtgcag tgggttagct ttgtttccat                40

<210> SEQ ID NO 603
<211> LENGTH: 40
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 603
ccgttctacc gtgactagta tggaattgtg ggaaccagaa                              40

<210> SEQ ID NO 604
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 604
ttaacatcag tgtcaactgc agtgttgttt ctgagtaata                              40

<210> SEQ ID NO 605
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 605
cataactcca tgctctcaaa ccaatcactc cttcattcat                              40

<210> SEQ ID NO 606
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 606
ttctcctatg ctgcaccaga aagggttttg tgggttatca                              40

<210> SEQ ID NO 607
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 607
atcgttcagc atctttagga aatatccaga gactgcattg                              40

<210> SEQ ID NO 608
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 608
tttattaaga gcaaaaaaag cctgtttcgt tagccagtca                              40

<210> SEQ ID NO 609
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 609
ttgttcatat gcctaactta ataaattctt catacagaaa                                 40

<210> SEQ ID NO 610
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 610
ataactttta aacccaaaca cctagagatt tcattatgta                                 40

<210> SEQ ID NO 611
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 611
ttcttaccat taagtcttcc aaatgataat ttattataaa                                 40

<210> SEQ ID NO 612
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 612
tatgtaagga caacttcatt atatgcttga agaaattgtt                                 40

<210> SEQ ID NO 613
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 613
aatcttaaaa gtgacactag tcacattcca cacggttaaa                                 40

<210> SEQ ID NO 614
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 614
attttgaaaa ctattccttt atctggaatg aatgtaaacc                                 40

<210> SEQ ID NO 615
<211> LENGTH: 40
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 615
ttgcattaag ggcaccagaa acttatagaa aaccaaaaag                              40

<210> SEQ ID NO 616
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 616
taaaagacag tgaactgaac agtaattaac attacatcca                              40

<210> SEQ ID NO 617
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 617
caaaaaactg tgtttatcat ataccaaaca ttttcaagtt                              40

<210> SEQ ID NO 618
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 618
tctcaggata ttttgttctc tgacacaaat acaccagtca                              40

<210> SEQ ID NO 619
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 619
tagctttaca tctcagaatg aatcaatgtg ggggcagaaa                              40

<210> SEQ ID NO 620
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 620
agacctatat acctatagtg cctaatagac aataagccac                              40

<210> SEQ ID NO 621
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 621
tctctcccct gcctagacta aggtaagtgg gtcttacctt        40

<210> SEQ ID NO 622
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 622
catcctgctt ttaaaaccct tagtgctcag cggcttgtct        40

<210> SEQ ID NO 623
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 623
agcttataaa cttcagagta atgtagcaca aatgtctgtc        40

<210> SEQ ID NO 624
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 624
aacttgaaat aaaactttaa acgttgattg attctttccc        40

<210> SEQ ID NO 625
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 625
gacaggctta gagtccataa caaacaatct tagctggaaa        40

<210> SEQ ID NO 626
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 626
tgctcaacaa cacttgtgga agagcagggc aagctatttc        40

<210> SEQ ID NO 627
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 627
ttacaacatc actgtagaca ttacttttac ccacagtgcc                                 40

<210> SEQ ID NO 628
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 628
atcctagttg tatatacttc ttggataaag tatcttcgta                                 40

<210> SEQ ID NO 629
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 629
atttttgggg agtgccattc ctgcaggtct tgaagacagg                                 40

<210> SEQ ID NO 630
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 630
cacacagcca atgaaactga cagagccaat gcaaccaaaa                                 40

<210> SEQ ID NO 631
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 631
acgacttcaa tcaagagaaa caggcaggtc agagtgtgaa                                 40

<210> SEQ ID NO 632
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 632
ctggttatca gggttcatag cacataggtt tgacaaccac                                 40

<210> SEQ ID NO 633
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 633
```
tttattattc agctgggtaa gccaagtgac agtcttcccc					40

<210> SEQ ID NO 634
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 634
gttttattct aggaatcaac tgctttctaa aaatgtctaa					40

<210> SEQ ID NO 635
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 635
tttactgatg gtacttattc ccccaattat tgattattga					40

<210> SEQ ID NO 636
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 636
gcatttagga atattcaata ttgatactaa ggtcatcttt					40

<210> SEQ ID NO 637
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 637
tactctgtaa tgtagtaatc tttatgaaga aataaatttg					40

<210> SEQ ID NO 638
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 638
attttgaaaa aatgtttcac tgcattttac tatacaagct					40

<210> SEQ ID NO 639
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 639
accacacatt catcaaaaaa tacctcaaag aaaattctgc                                40

<210> SEQ ID NO 640
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 640
gttgtcacaa taaactcagt actgagtaaa atatcacaaa                                40

<210> SEQ ID NO 641
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 641
gagtatatat tgtattactt acctgatgcg caaagaccca                                40

<210> SEQ ID NO 642
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 642
aaaatgacag caacataggt gccacctgag gtccacatct                                40

<210> SEQ ID NO 643
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 643
tggagagagt ggggttaatc tgttactaca ctttgctact                                40

<210> SEQ ID NO 644
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 644
atttccatca ttttgtcttt cagtaagcat gtacgaagta                                40

<210> SEQ ID NO 645
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 645
gagatgaaga tggtacatca gtagggagcc cctctactgg                                40

<210> SEQ ID NO 646
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 646
tctaattcat caaagtattc tgggttgatt ccaggtacgt                           40

<210> SEQ ID NO 647
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 647
acaaactcgt tttgtacaga gaggaaaata ttaaaacacc                           40

<210> SEQ ID NO 648
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 648
atgttaatta taaacactgt tataagtttt acaaatgtaa                           40

<210> SEQ ID NO 649
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 649
tccactggca gagagaatat atgtttccat tacggtccca                           40

<210> SEQ ID NO 650
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 650
tcaaaggttt tctatcacgt tttctattat ttactcacat                           40

<210> SEQ ID NO 651
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 651
aaaaacaaga gtcacacaac ctatgctcca caatatctgc                           40

<210> SEQ ID NO 652
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 652
ataggttatt ctacaatcga caccaactat cagcggcttt                          40

<210> SEQ ID NO 653
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 653
attgaattaa atgatggctt gattatccag gaatcagcca                          40

<210> SEQ ID NO 654
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 654
cttaccataa cagagtaatc tctagcttat tccaaggata                          40

<210> SEQ ID NO 655
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 655
acctaaaatt taactagaat cacttttcaa tgaagctgct                          40

<210> SEQ ID NO 656
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 656
taaactaaga gcctttgatc ttgccttatt ctgataaaat                          40

<210> SEQ ID NO 657
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 657
aaataataat tcacaaggaa atccttattg tttatttaaa                          40

```
<210> SEQ ID NO 658
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 658
gtaatatgta ggttaaacag aaatgttggt tgaatcatgt                              40

<210> SEQ ID NO 659
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 659
tgcagacact aatcaaacca aacagggcca attaaaattg                              40

<210> SEQ ID NO 660
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 660
taaagtgcaa tgggacagag caacttcatt ttcacaaaca                              40

<210> SEQ ID NO 661
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 661
taatctaatt gccagaaatg cttgcccatt gcaatgggag                              40

<210> SEQ ID NO 662
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 662
agttgacaat gactgcttag tttagggttt tgaagtaaac                              40

<210> SEQ ID NO 663
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 663
cagatggcag gtattctgtg aattaacact gatgcttctg                              40

<210> SEQ ID NO 664
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 664
agtcaagttc agaaatgatc tgttatgacc ccatgaaacg                            40

<210> SEQ ID NO 665
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 665
gggatgctct gatacatcat tcagtaaaat gatagaaaaa                            40

<210> SEQ ID NO 666
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 666
tagctgtatt gcttgatagc ttcatagctt gataaccatt                            40

<210> SEQ ID NO 667
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 667
ttttagcagg gaattaacac aggtatataa atgaagaaaa                            40

<210> SEQ ID NO 668
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 668
ttgattgttt atgaagctga gattgtttac tggtttcgag                            40

<210> SEQ ID NO 669
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 669
tctgtgtttt tatgtttggg aacatgaggg aatcagttct                            40

<210> SEQ ID NO 670
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 670
ttcttaagct ttcattttc cagtggtgaa tgtagagaga                              40

<210> SEQ ID NO 671
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 671
acggtaactg aataaactta agaactgagg taaagttttc                             40

<210> SEQ ID NO 672
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 672
tcaatatgta aaattgatca attcagacac ctttatatgg                             40

<210> SEQ ID NO 673
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 673
tgtctctttc atgctgtaaa tagagcattg catgaaagat                             40

<210> SEQ ID NO 674
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 674
ttcatagcac agtttataaa cctaagaaag caaagatgaa                             40

<210> SEQ ID NO 675
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 675
aaccaagcag gattctatga ctaaaaaagt gtatttgtat                             40

<210> SEQ ID NO 676
<211> LENGTH: 40
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 676
agatagagaa tttcaaagaa accatcttta tcagctgcac                             40

<210> SEQ ID NO 677
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 677
ccaagaatga aaagatgcac taattcgact gaaagccaag                             40

<210> SEQ ID NO 678
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 678
tcatagttga gacatataac aaccataaag gtccgcatat                             40

<210> SEQ ID NO 679
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 679
aggaaagggt ggaaaggcaa gcagcgggga gtgttggctg                             40

<210> SEQ ID NO 680
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 680
ctataaattg acctatcctg taaaaaagga tgtcacagca                             40

<210> SEQ ID NO 681
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 681
acaattgacc taagactgta aattgtaaat tgactataaa                             40

<210> SEQ ID NO 682
<211> LENGTH: 40
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 682
gcaagactgg gtatactatt aataggaaaa aatgaacttc                              40

<210> SEQ ID NO 683
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 683
attgctttga tattgattga atcacagaga aaatcctaag                              40

<210> SEQ ID NO 684
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 684
tagattatgc tggcaaatct cagtgatcag agaattatat                              40

<210> SEQ ID NO 685
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 685
attcagaaat ggaataggaa gatatttatg tgccatcctg                              40

<210> SEQ ID NO 686
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 686
gtttgaatta ttattcaaac agtgtatgtt tgtttgtact                              40

<210> SEQ ID NO 687
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 687
aatgcaacag agacaggtat ttatagcatc tgttttccat                              40

<210> SEQ ID NO 688
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 688
tttaatatcc aaatatgtat ggacacatac aattgtacat                              40

<210> SEQ ID NO 689
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 689
acgtctaccg tcattttcgt aattattcgg tttccctgtc                              40

<210> SEQ ID NO 690
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 690
ggagcgctcc tgcgcgcctt gttcgttagg atttattttt                              40

<210> SEQ ID NO 691
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 691
ggtggctccc taatgcctgc tcgtttcagg tctcagctct                              40

<210> SEQ ID NO 692
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 692
ccttagtgtg ttgaggacgc tgcagaaggt acagaggaga                              40

<210> SEQ ID NO 693
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 693
gaccagatgg taggacagtc attctcctct gcgtctccgc                              40

<210> SEQ ID NO 694
<211> LENGTH: 40
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 694
cgtgaggcat ggagtttttg tcctgcccct gcctggttag                             40

<210> SEQ ID NO 695
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 695
tttaagtctc tggcaccgtg catagcagaa ttggttggga                             40

<210> SEQ ID NO 696
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 696
tctttctcca agtgcctcta tgttggcaca tctctgaaat                             40

<210> SEQ ID NO 697
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 697
tgcgtcccgg ccaggtaagc agcttccctc tcagctgcct                             40

<210> SEQ ID NO 698
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 698
gggtgtatgt agctggcaga agtgggactt ggtcgcaacc                             40

<210> SEQ ID NO 699
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 699
cgtggcgagt gggcggtagc tgctcgtaga gcgtgtgaaa                             40

<210> SEQ ID NO 700
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 700
gttggcccta aaagttatca ttcatgctag tttgaccaat        40

<210> SEQ ID NO 701
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 701
aagtgggagg agctgggcaa gaaagtccac ccctttttct        40

<210> SEQ ID NO 702
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 702
gccgagccga agtcatctgc caatcaaaac agccacaggg        40

<210> SEQ ID NO 703
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 703
cgcgtaccta atgggagaca gacaggtgcc tttaaagcgg        40

<210> SEQ ID NO 704
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 704
tggggaaagc ggaggaaggc atggagtgtg ggcgttaggg        40

<210> SEQ ID NO 705
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 705
gcatattctg ccttgaagtc attggttggt cctggaagtg        40

<210> SEQ ID NO 706
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 706
aattggtctg ggggaggagc tacgacagtc caggggcggg          40

<210> SEQ ID NO 707
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 707
gtgtcgtgct gattggatgt atccgccccc ctctcttaaa          40

<210> SEQ ID NO 708
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 708
caacacgcca gcgcgaggac ccgaacgtca atcaagagac          40

<210> SEQ ID NO 709
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 709
gcgttcgatt ggcctcccgc gcaggctgct aggattggct          40

<210> SEQ ID NO 710
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 710
ccctgccccc tttcgcggat tgggtgatcg ctccaaggcg          40

<210> SEQ ID NO 711
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 711
ctgacccttg gaggctttct attggttcct ggcagggatg          40

<210> SEQ ID NO 712
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 712
tcccgaatat aggccagtca ttgctcctgc tgaacgtcgc                                  40

<210> SEQ ID NO 713
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 713
cccctcctct cttctcgtct ctggcgccga cccgccccg                                   40

<210> SEQ ID NO 714
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 714
gctcaaggga ggccgcggcg tctgccgatg gctccgcgga                                  40

<210> SEQ ID NO 715
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 715
tgggggagtg ggcccggggt tgttctgacg acggggtcg                                   40

<210> SEQ ID NO 716
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 716
cccgggcgct atcgcgatag cggcgcgaag cggaagtggg                                  40

<210> SEQ ID NO 717
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 717
cgggggaggc gagcgcccgc cgccttttc tcgcgcccg                                    40

<210> SEQ ID NO 718
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 718

```
cacaggagct ggcgccgccg ctgaggagcg tatcgcgaca                      40
```

<210> SEQ ID NO 719
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 719

```
gttgccgact cgcgctctcg gcttctgctc cggggcttct                      40
```

<210> SEQ ID NO 720
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 720

```
actcggagct cggatcccag tgtggacctg gactcgaatc                      40
```

<210> SEQ ID NO 721
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 721

```
ggctcctcct tgttccgagc ccgaaggccc gcccttcac                       40
```

<210> SEQ ID NO 722
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 722

```
ctttccggag cccgtctgtt cccttcggg tccaaagctt                       40
```

<210> SEQ ID NO 723
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 723

```
gaccccgcct cattcctcac ggcgagctcc agacccccgcc                     40
```

<210> SEQ ID NO 724
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 724

```
agaactcaag ctcccgattg tgcccgaagg aacccgaagg                      40
```

```
<210> SEQ ID NO 725
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 725
actattgccg aagtgagccg aagtttgtgg ccccgcttcc                              40

<210> SEQ ID NO 726
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 726
acatgtggct ccgcccacac tggcctcagc tctccgttct                              40

<210> SEQ ID NO 727
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 727
acagtgaccc taaggactcg actacctccg aagaaagccg                              40

<210> SEQ ID NO 728
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 728
cttgtaccca actatctacg aagtaaaccg aagcttgtgg                              40

<210> SEQ ID NO 729
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 729
tatctggcga acctgttgac tccgcctatc atcctagcgt                              40

<210> SEQ ID NO 730
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 730
ggcaagtcgc tttcgccccg ccccttgta aatactcatg                              40
```

<210> SEQ ID NO 731
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 731
ctcctctact tgggaacttg aggatcgtca ccctggcccg     40

<210> SEQ ID NO 732
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 732
ttggctccgc cccactgagc gcacctccct ctgccgcttc     40

<210> SEQ ID NO 733
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 733
tccttgctcc acccctcat gccgacaccc tcgtcaactt     40

<210> SEQ ID NO 734
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 734
tccaccgata gaaccagcga gtcacctcat aaacagtaat     40

<210> SEQ ID NO 735
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 735
cgctcagtcc gcctccttgc ctcccttcag aatgtcccac     40

<210> SEQ ID NO 736
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 736
gccgtccact ctccgctcgg gcgggctcac cccaattggg     40

```
<210> SEQ ID NO 737
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 737
cgaccgaacc ccacagccga aagccccgcc ccctggacac                          40

<210> SEQ ID NO 738
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 738
ctccgagcgc cagcgcaccc cagttgggga gttcccgccc                          40

<210> SEQ ID NO 739
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 739
agccccgcct cctcccggac gcaataggtt cggcgttcgg                          40

<210> SEQ ID NO 740
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 740
agcaatttga cgttcgggtg ttctcggctc ggccgaatcc                          40

<210> SEQ ID NO 741
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 741
tgccccctcc cgagcacagg aagttcggcg ttcgggcgtc                          40

<210> SEQ ID NO 742
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 742
tttcggacct cctcgctctc agactcccac agtacaaaac                          40

<210> SEQ ID NO 743
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 743
cgagccttcg ctcctcctct ttccgaacga ctgtgattcg                              40

<210> SEQ ID NO 744
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 744
gaggctaagg caccgccgag gccacaccct cttccggacg                              40

<210> SEQ ID NO 745
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 745
gcgtccccct tcgggtgttc ccgtcagcgg tcagaagctc                              40

<210> SEQ ID NO 746
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 746
ccttacaaag gtccattttg gcaccaccct cttgcaaagt                              40

<210> SEQ ID NO 747
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 747
ggagcgtgaa aaacaaacct ccgcaagcgc ggcgacacgc                              40

<210> SEQ ID NO 748
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 748
acccgctctg tgcccgcact gccgtaccta ccattgcgcc                              40

<210> SEQ ID NO 749
<211> LENGTH: 40
```

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 749
ggtcctcagc atctgcatat gtagcccctc ccgctggtca                                40

<210> SEQ ID NO 750
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 750
cccaacccct acccccaatc catcttagag ctgattctct                                40

<210> SEQ ID NO 751
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 751
actccagtga ttcttcctta tgctagggac tcgaggaccc                                40

<210> SEQ ID NO 752
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 752
gagaattgag aagtcagtgt gggaggggat gtcccagtac                                40

<210> SEQ ID NO 753
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 753
tttctggttc gcgttggctg cattgtggag ctgagggatg                                40

<210> SEQ ID NO 754
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 754
tagcttctta atctccttct ttaggtcagc ctcatacttt                                40

<210> SEQ ID NO 755
<211> LENGTH: 40
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 755
ttctccctgg gacccagcag tccactctcc cagttccctc                                40

<210> SEQ ID NO 756
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 756
aaagtcagac ctcaggaccc aggaactggg gcccacagct                                40

<210> SEQ ID NO 757
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 757
tcttgatttg gtccctcagc cgctgcagat gggaaaagca                                40

<210> SEQ ID NO 758
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 758
taagctgcct cttgtccttg atctcgttgg acgctaccca                                40

<210> SEQ ID NO 759
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 759
ggctctgggc tcctaccgtc tcaatgagct tgcggttgtc                                40

<210> SEQ ID NO 760
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 760
tgaggacctc tggggtctgg ccgctctgcc tccgcccctt                                40

<210> SEQ ID NO 761
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 761
ctgcctcttc acttccctta ggtgcagaaa ccttacttct                           40

<210> SEQ ID NO 762
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 762
cgacctgagc ctcgtgaccc tactttctga gctctgagtc                           40

<210> SEQ ID NO 763
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 763
tcaaaggtgg gaaaggagct gactaagggc cagcagacac                           40

<210> SEQ ID NO 764
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 764
ccgttccatt tgctgtagag agtgcagttg gcagggggc                            40

<210> SEQ ID NO 765
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 765
gctgtaagct ttggttttgg tctctcgttc cacaactttg                           40

<210> SEQ ID NO 766
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 766
ccaactcacc gtgagccact ggccaacctc ttccttctcc                           40

<210> SEQ ID NO 767
<211> LENGTH: 40
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 767
ccagggctca ggatcctcag agttcacctc ctcttctcta                              40

<210> SEQ ID NO 768
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 768
gtccacctgc atgttgagcg tgtcgatggt attctagggg                              40

<210> SEQ ID NO 769
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 769
gcgtgtctgc actgacagtg actccacttc actctcaaac                              40

<210> SEQ ID NO 770
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 770
tgtcgggtct ccctcactca catccttgtc gcccttcttc                              40

<210> SEQ ID NO 771
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 771
ctgctggcca gcccattccc atgcccatcc ccatcccaaa                              40

<210> SEQ ID NO 772
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 772
gaatccaggc cccaactccc aggagcataa atgactggcc                              40

<210> SEQ ID NO 773
<211> LENGTH: 40
<212> TYPE: DNA
<213> ORGANISM: Artificial Sequence
<220> FEATURE:
<223> OTHER INFORMATION: Description of Artificial Sequence: Synthetic probe

<400> SEQUENCE: 773
tctcaaatcc ctaatcccgg ctgttggccc tgtccgcctg            40

<210> SEQ ID NO 774
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 774
cctgccccac gcgtgcagct gctaagccct cccaatcctg            40

<210> SEQ ID NO 775
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 775
cccagacacc caggggaccc tgagattctg tctgacctcc            40

<210> SEQ ID NO 776
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 776
cttcccccaa gtcgctcctc ttcacaaagg ccccacggtc            40

<210> SEQ ID NO 777
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 777
cctctgggtg ccaggaggcc tcttgccatg ggtgtccttc            40

<210> SEQ ID NO 778
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 778
ctgccttgtc tctacccact gtgctctccc taggaccagg            40

<210> SEQ ID NO 779
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 779
ggcgaggggg aggtcctgca gctgctcgcg tgggctgccc                                  40

<210> SEQ ID NO 780
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 780
tgcgctcgat ctcatccttc agttcgtagc ccacctgggg                                  40

<210> SEQ ID NO 781
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 781
tcacctgctt cacaggcggc ggctcctgcc acttgtcgaa                                  40

<210> SEQ ID NO 782
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 782
ctcgcttctt ccgctgtcca tccaggggcg caggcagcgg                                  40

<210> SEQ ID NO 783
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 783
cccatgccta ccggaccccc agggcccctc acctgcggcc                                  40

<210> SEQ ID NO 784
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 784
agtcggctgg gaggaggacg ccggcttctc ccctccatga                                  40

<210> SEQ ID NO 785
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 785
atcttgcggt acctggggac gggtgggtgg gcggcgccag        40

<210> SEQ ID NO 786
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 786
ttggcctgct tccggatctc cgtcagcccc agccgctcct        40

<210> SEQ ID NO 787
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 787
ggagggcgct ctgggagtct gacctctccg aagctcatac        40

<210> SEQ ID NO 788
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 788
aggaggcaga gggcggtggc ggctggctgg ctgtggggtt        40

<210> SEQ ID NO 789
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 789
agacatgagc cagggccaca ggacgagagg aggggcggtg        40

<210> SEQ ID NO 790
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 790
ccaagggccg cgagggtcgc tttggggctg aatggatgga        40

<210> SEQ ID NO 791
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 791
gatgggaagc cgcgggggct ctaagcagcg gagacacagg                40

<210> SEQ ID NO 792
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 792
ggagcctctg ggcagggagg aaccggccaa ggagcccggg                40

<210> SEQ ID NO 793
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 793
ggcggggccc agggacgggg cggccgtgca gcagggcact                40

<210> SEQ ID NO 794
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 794
ctgcaggacc aagggatga cgctgggata acagaggaga                40

<210> SEQ ID NO 795
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 795
cagaacaggt ttataggat gaggtggcct ctgagttcgg                40

<210> SEQ ID NO 796
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 796
ccattccttc cttactcgtg tgggtcgggg gatgtcagga                40

<210> SEQ ID NO 797
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 797

```
ggcccggtcc cagcactgct ctgtgagctc agagttggga                              40
```

<210> SEQ ID NO 798
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 798

```
tgggggccca cacacgcggg ggatgccggg gagcctgaga                              40
```

<210> SEQ ID NO 799
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 799

```
cacgggcacc tgctccggta cccactcggc ccggctgagg                              40
```

<210> SEQ ID NO 800
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 800

```
ctccaccagc cggaagccca gcggtcacca gccggccggt                              40
```

<210> SEQ ID NO 801
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 801

```
aggcgtcctc ctcgatctag ggggaagagg aggcgccctg                              40
```

<210> SEQ ID NO 802
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 802

```
acttgcccag gtggcccagg ctgaatccca ggtcctcctg                              40
```

<210> SEQ ID NO 803
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 803

```
tggcctcgtt tacctgtgtc tgccgcacac gcccactgcc                              40
```

<210> SEQ ID NO 804
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 804
gtctggccca tacctgcagc gtcttggaga tcctggcctt                                40

<210> SEQ ID NO 805
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 805 gctccccca ccttgtgtcc ctcggtcccc agccccacct                                 40

<210> SEQ ID NO 806
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 806
tgcagggtcc gctgtgggga ggacaggag gctgcgatct                                 40

<210> SEQ ID NO 807
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 807
tcgcggatgg tggacttccc gccatatacg acgctctgct                                40

<210> SEQ ID NO 808
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 808
agtggggtga aggccacgct ggaggccgtg cccgaggagc                                40

<210> SEQ ID NO 809
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 809
cggctgctga gcctaaccac ctcctgggct tctttccagc                                40

<210> SEQ ID NO 810
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 810
gctcatggta tccctaccgc aggcaatctg tggacagcac                           40

<210> SEQ ID NO 811
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 811
ctgaatgtca cctgaagggt cacagaagct actcacaggg                           40

<210> SEQ ID NO 812
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 812
ttaagtgttc tcaatatgag attagctgga gccgcctaat                           40

<210> SEQ ID NO 813
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 813
gaagatccat ctgttggaag ccagaggact agtgggaaac                           40

<210> SEQ ID NO 814
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 814
cccccacagg gatctgacac acaacttagg ttgtcagcca                           40

<210> SEQ ID NO 815
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 815
gcccagcttc ccaagtcctg cctggacacc gccccatgga                           40

```
<210> SEQ ID NO 816
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 816
aatcaccttc atgcttaaaa cactcacact gatttccagc                          40

<210> SEQ ID NO 817
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 817
cctcttgggg acctgggtga ccttactcac cctcatggct                          40

<210> SEQ ID NO 818
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 818
gttgctgtgg acaggcttgg agccgttttt ggctggagac                          40

<210> SEQ ID NO 819
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 819
ggaggggtag gtgggcggca cagctgggga ctgagggtgc                          40

<210> SEQ ID NO 820
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 820
gccaggagtg gtgctcaagg cagaggcagc aggcggggggg                          40

<210> SEQ ID NO 821
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 821
cagggcactt gggggtgctg cggggggcggg gaccccattg                          40

<210> SEQ ID NO 822
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 822
ggtgcccgag ttgtggctgg gagctggact ggccttgggg                          40

<210> SEQ ID NO 823
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 823
ctgcttgcca gcccctccac cggcactgct gttactactg                          40

<210> SEQ ID NO 824
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 824 gcccccacc ccgctgcctc ctcactcact ggtggcgcca                           40

<210> SEQ ID NO 825
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 825
cgggctgtct gccacaactg agctgtaacc tgggaacaaa                          40

<210> SEQ ID NO 826
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 826
gctggcattg ttgcccccac tgctgctcaa agccacctct                          40

<210> SEQ ID NO 827
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 827
aggtgggttg tgggggccgg aaggggggcc caaggcctgg                          40

<210> SEQ ID NO 828
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 828
tcccaaccct gccgatggcc gagacactca cgaggtgctg                                 40

<210> SEQ ID NO 829
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 829
gggggtgagg cgcctgcgcc tctctgtttc aaaaggctgc                                 40

<210> SEQ ID NO 830
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 830
attcccagca gcaagggcgg ggggttcaga acccaccgat                                 40

<210> SEQ ID NO 831
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 831
gggggtgtaa cacccgaggg agatggagga tagcgcttgg                                 40

<210> SEQ ID NO 832
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 832
caaagcaggg aggctgatgt agtttccttg ctggaaagaa                                 40

<210> SEQ ID NO 833
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 833
cttccactta gatgagaacg tattttagaa tgttctgaag                                 40

<210> SEQ ID NO 834
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 834
taacagaaat ggggaggaaa gggtatgggg ctcttgagaa                              40

<210> SEQ ID NO 835
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 835
aaacagtgac cctccggtgg cagtcaattg gcctcaggca                              40

<210> SEQ ID NO 836
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 836
gcagaggaat aaggacttcg ggacaattca ctttgaaaag                              40

<210> SEQ ID NO 837
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 837
gacccagtgg aatggtctga gctaagattt gaaggagtgg                              40

<210> SEQ ID NO 838
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 838
tgcacactga tctttcttag ggcattcttc gggaaacagg                              40

<210> SEQ ID NO 839
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 839
ggctcaggat gaacagcaac aggggttggg atgatcactg                              40

<210> SEQ ID NO 840
<211> LENGTH: 40
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 840
gatcatggag atgtgatcta gggaacaaag ccagagaagg                          40

<210> SEQ ID NO 841
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 841
aggcattccc acggtgtgag gtcagattgg gcagggccta                          40

<210> SEQ ID NO 842
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 842
agagccagca cttgctgttc cacacatact agatcagtct                          40

<210> SEQ ID NO 843
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 843
tggacaaccc cctcccacac ccagagctgt ggaaggggag                          40

<210> SEQ ID NO 844
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 844
cacctagatg ctgaccaagg ccctccccat gctgctggag                          40

<210> SEQ ID NO 845
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 845
ataaagcctt cattctccag gaccccgccc ttgccctgtt                          40

<210> SEQ ID NO 846
<211> LENGTH: 40
<212> TYPE: DNA
<213> ORGANISM: Artificial Sequence
<220> FEATURE:

```
<223> OTHER INFORMATION: Description of Artificial Sequence: Synthetic
      probe

<400> SEQUENCE: 846
aggtggtgag tttggggctg gggggcctcc ctgaggagcc                            40

<210> SEQ ID NO 847
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 847
gagagaacca ggtcccacat gctgacacag gtgtccacgg                            40

<210> SEQ ID NO 848
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 848
atccccccaa tctcaccagt gcaccccaca gacaaggcga                            40

<210> SEQ ID NO 849
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 849
aagggcttca gcataagagt cagaacccgc cccccttcct                            40

<210> SEQ ID NO 850
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 850
tgtgggctga agggacgagg ctggggcact gggtgggagg                            40

<210> SEQ ID NO 851
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 851
ttgcaatgtg gaagagtcag gggcacattg tctgggctga                            40

<210> SEQ ID NO 852
<211> LENGTH: 40
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 852
taagtgggag ggagcgggga cctagtgtgg gcatgaggac                                40

<210> SEQ ID NO 853
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 853
ggagcaggga tttggctggg caatggagag aaaggtctga                                40

<210> SEQ ID NO 854
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 854
acacagagat gcccaggaac ttgctcttta gtaaagcagc                                40

<210> SEQ ID NO 855
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 855
tggagagagg tccttgaaag gttttgaacc ccataaagag                                40

<210> SEQ ID NO 856
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 856
tcaggaggca gcccagtgat agggtccaag gaaccagtgg                                40

<210> SEQ ID NO 857
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 857
acagtctact gactttttcct attcagctgt gagcattcaa                               40

<210> SEQ ID NO 858
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 858 ctgtccctg gaccttgaca cctggctccc caaccctgtc                              40

<210> SEQ ID NO 859
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 859
aggaaaccca gattccacca gacacttcct tcttccccc                              40

<210> SEQ ID NO 860
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 860
ggctatctgg cctgagacaa caaatgctgc ctcccaccct                             40

<210> SEQ ID NO 861
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 861
gtctggcact gggactttca gaactcctcc ttccctgact                             40

<210> SEQ ID NO 862
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 862
ttgccccaga cccgtcattc aatggctagc tttttccatg                             40

<210> SEQ ID NO 863
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 863
aaaaacacga gcaccccaa ccacaacggc cagttctctg                              40

<210> SEQ ID NO 864
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 864
ttaaccttgg acatggtaaa ccatccaaaa ccttcctctc                              40

<210> SEQ ID NO 865
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 865
agcaactaaa cctctccact gggcacttat ccttggtttc                              40

<210> SEQ ID NO 866
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 866
gaacctctta ttctcttaga acccacagct gccaccacag                              40

<210> SEQ ID NO 867
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 867
tcccttctcc cagtgtaaga ccccaaatca ctccaaatga                              40

<210> SEQ ID NO 868
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 868 caaccccccaa cccgatgcct gcttcagatg tttcccatgt                             40

<210> SEQ ID NO 869
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 869
cataaacctg gctcctaaag gctaaatatt ttgttggaga                              40

<210> SEQ ID NO 870
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 870
```
ctgctgacct gccctcccag gtcagaatca tcctcatgca    40

<210> SEQ ID NO 871
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 871
tgttctccag acctgtgcac tctatctgtg caacagagat    40

<210> SEQ ID NO 872
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 872
cgtgcagcaa acaatgtgga attccaataa ccccccactc    40

<210> SEQ ID NO 873
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 873
aaatatgagt ctcccaaagt tccctagcat ttcaaaatcc    40

<210> SEQ ID NO 874
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 874
catcataaaa agatcttgtg gtccacagat cctctagccc    40

<210> SEQ ID NO 875
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 875
ctcccaaccc agaatccagc tccacagata cattgctact    40

<210> SEQ ID NO 876
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 876
cactctgaga ccagaaacta gaactttat tcctcatgct                    40

<210> SEQ ID NO 877
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 877
caccagcact caggagattg tgagactccc tgatccctgc                    40

<210> SEQ ID NO 878
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 878
tgcctagatc ctttgcactc caagacccag tgtgccctaa                    40

<210> SEQ ID NO 879
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 879
gggggtgggt acgatccccg attcttcata caaagcctca                    40

<210> SEQ ID NO 880
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 880
ggacaaaggc agaggagaca cgcccaggat gaaacagaaa                    40

<210> SEQ ID NO 881
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 881
tggatgcacc aggccctgta gctcatggag acttcatcta                    40

<210> SEQ ID NO 882
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 882
gggagagcta gcacttgctg ttctgcaatt actagatcac                    40

<210> SEQ ID NO 883
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 883
ggctggacaa ccccctccca cacccagagc tgtggaaggg                    40

<210> SEQ ID NO 884
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 884
tggcacccag aggctgacca aggccctccc catgctgctg                    40

<210> SEQ ID NO 885
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 885
cctataaaac cttcattccc caggactccg cccctgccct                    40

<210> SEQ ID NO 886
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 886
tgcaggtggt aagcttgggg ctggggagcc tcccccagga                    40

<210> SEQ ID NO 887
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 887
aggaagacaa ccgggaccca catggtgaca cagctctccg                    40

<210> SEQ ID NO 888
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 888
caaccatggc ccctctcacc aatccacgtc acggacaggg                    40

<210> SEQ ID NO 889
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 889
tcagcttgac agtcagggct ggctccctct cctgcatccc                           40

<210> SEQ ID NO 890
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 890
tccctgtctg ggctggggtg ctgggttggg ggggaaagag                           40

<210> SEQ ID NO 891
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 891
tgtgggagtg aggactgttg caatatggag gggctggggg                           40

<210> SEQ ID NO 892
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 892
gggagaaagt tctggggtaa gtgggaggga gcggggacct                           40

<210> SEQ ID NO 893
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 893
ttgtggggct caaaacctcc aaggacctct ctcaatgcca                           40

<210> SEQ ID NO 894
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 894
tgcccaaccc tatcccagag accttgatgc ttggcctccc                           40

```
<210> SEQ ID NO 895
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 895 tcttgccota ggatacccag atgccaacca gacacctcct                          40

<210> SEQ ID NO 896
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 896
ttcctagcca ggctatctgg cctgagacaa caaatgggtc                          40

<210> SEQ ID NO 897
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 897
tcttagcccc agactcttca ttcagtggcc cacattttcc                          40

<210> SEQ ID NO 898
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 898
aggaaaaaca tgagcatccc cagccacaac tgccagctct                          40

<210> SEQ ID NO 899
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 899
ccccttcaga gttactgaca aacaggtggg cactgagact                          40

<210> SEQ ID NO 900
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 900
tggaaagtta gcttatttgt ttgcaagtca gtaaaatgtc                          40

<210> SEQ ID NO 901
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 901
gactcaggag tctcatggac tctgccagca ttcacaaaac                           40

<210> SEQ ID NO 902
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 902
atgctgtctg ctaagctgtg agcagtaaaa gcctttgcct                           40

<210> SEQ ID NO 903
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 903 gatttgggggg gggcaaggtg tactaatgtg aacatgaacc                          40

<210> SEQ ID NO 904
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 904
gtgtgcacag catccaccta gactgctctg gtcaccctac                           40

<210> SEQ ID NO 905
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 905
aggattccta atctcaggtt tctcaccagt ggcacaaacc                           40

<210> SEQ ID NO 906
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 906
caaaggctga gcaggtttgc aagttgtccc agtataagat                           40

<210> SEQ ID NO 907
<211> LENGTH: 40
```

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 907
gtcaaggaca atcgatacaa tatgttcctc cagagtaggt                                40

<210> SEQ ID NO 908
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 908
gcaagatgat atctctctca gatccaggct tgcttactgt                                40

<210> SEQ ID NO 909
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 909
tctgtgtgtc ttctgagcaa agacagcaac accttttttt                                40

<210> SEQ ID NO 910
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 910
aacgttgaga ctgtcctgca gacaagggtg gaaggctctg                                40

<210> SEQ ID NO 911
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 911
cataaataag caggatgtga cagaagaagt atttaatggt                                40

<210> SEQ ID NO 912
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 912
gctgccagac acagtcgatc gggacctaga accttggtta                                40

<210> SEQ ID NO 913
<211> LENGTH: 40
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 913
gggatcctga gcgctgcctt attctgggtt tggcagtgga                           40

<210> SEQ ID NO 914
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 914
tcactcaaac ccagaagttc tgatccccag ccatgcccct                           40

<210> SEQ ID NO 915
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 915
agcctcttcc tcctttgaaa ttcaagaggg tggacccact                           40

<210> SEQ ID NO 916
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 916
ggagctggga ccttaccagt ctcctccctc attgacctaa                           40

<210> SEQ ID NO 917
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 917
gaggatatga gattcttagg ccattcccac atcagtacct                           40

<210> SEQ ID NO 918
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 918
tacccagaac tctacccctc aggattccag caccttcttc                           40

<210> SEQ ID NO 919
<211> LENGTH: 40
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 919
gcctctgccc ttcaggggcc aaagagcctt aagccacaaa                    40

<210> SEQ ID NO 920
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 920
atcccattac tatcacccca aaccctggac ctaatggttc                    40

<210> SEQ ID NO 921
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 921
aatgggcaac cctcgatcct cagactcttg aggaatcaag                    40

<210> SEQ ID NO 922
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 922
gataccctca agtggagtaa ggattaggtg gcaagatgga                    40

<210> SEQ ID NO 923
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 923
gtgcttgccc agggcacct tcatggagct agaagggctg                     40

<210> SEQ ID NO 924
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 924
gatgacaccc aaggcctctg gggcatcttt catgctcaga                    40

<210> SEQ ID NO 925
<211> LENGTH: 40
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 925
tgctggccac accctcagag tgtggatgct ggatgatgag                               40

<210> SEQ ID NO 926
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 926
gaggcacgct gcaggatag tcacagcaac atgacgtcat                                40

<210> SEQ ID NO 927
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 927
agaggaggat gtcggcagct ctacggttgg caggtggctg                               40

<210> SEQ ID NO 928
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 928
gacactaggc ctcagcctgg caccatgcag gccactccca                               40

<210> SEQ ID NO 929
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 929
acttttgagt cctggatccc tatgattcca ggctccctgt                               40

<210> SEQ ID NO 930
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 930
ccttgagatt tcatggatgg tgacatatgg ccattctcta                               40

<210> SEQ ID NO 931
<211> LENGTH: 40
<212> TYPE: DNA
<213> ORGANISM: Artificial Sequence
<220> FEATURE:
<223> OTHER INFORMATION: Description of Artificial Sequence: Synthetic

```
            probe

<400> SEQUENCE: 931
aaaacccata agttcaggtc cctgtgccct ccacccagaa                    40

<210> SEQ ID NO 932
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 932
tcgtatctgg gagactcact tgggagagca atagacttgg                    40

<210> SEQ ID NO 933
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 933
tacaagatgt ggtggagata aggctgatgc tggcacagtg                    40

<210> SEQ ID NO 934
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 934
gtacacacca tggtgttcat cagggccctg ggtagtccct                    40

<210> SEQ ID NO 935
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 935
gctgtgacct cacaggagtc cgtgcctcca cccctactc                     40

<210> SEQ ID NO 936
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 936
cgtcgcacca agaaat                                              16

<210> SEQ ID NO 937
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 937
tagacttgcc atacgt                                                        16

<210> SEQ ID NO 938
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 938
aattcttgag accagg                                                        16

<210> SEQ ID NO 939
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 939
atctgcccaa actcca                                                        16

<210> SEQ ID NO 940
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 940
ttcccaagcg tcatct                                                        16

<210> SEQ ID NO 941
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 941
tctatcggac gctgta                                                        16

<210> SEQ ID NO 942
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 942
aaaaaaaaaa atttcttggt gcgacg                                             26

<210> SEQ ID NO 943
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 943
aaaaaaaaaa acgtatggca agtcta                                          26

<210> SEQ ID NO 944
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 944
aaaaaaaaaa cctggtctca agaatt                                          26

<210> SEQ ID NO 945
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 945
aaaaaaaaaa tggagtttgg gcagat                                          26

<210> SEQ ID NO 946
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 946
aaaaaaaaaa agatgacgct tgggaa                                          26

<210> SEQ ID NO 947
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 947
aaaaaaaaaa tacagcgtcc gataga                                          26

<210> SEQ ID NO 948
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 948
atttatagaa accgggggcg aaaaaacgta tggcaagtct a                         41

<210> SEQ ID NO 949
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 949
```

```
cgaacaggag gagcagagag aaaaaacgta tggcaagtct a                    41
```

<210> SEQ ID NO 950
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 950

```
gctggcgacg caaaagaaga aaaaaacgta tggcaagtct a                    41
```

<210> SEQ ID NO 951
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 951

```
catggtgtct gagcgatgtg aaaaaacgta tggcaagtct a                    41
```

<210> SEQ ID NO 952
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 952

```
tacgaccaaa tccgttgact aaaaaacgta tggcaagtct a                    41
```

<210> SEQ ID NO 953
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 953

```
cagagttaaa agcagccctg aaaaaacgta tggcaagtct a                    41
```

<210> SEQ ID NO 954
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 954

```
gggtcattga tggcaacaat aaaaaacgta tggcaagtct a                    41
```

<210> SEQ ID NO 955
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 955
aaccatgtag ttgaggtcaa aaaaaacgta tggcaagtct a                          41

<210> SEQ ID NO 956
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 956
gggtggaatc atattggaac aaaaaacgta tggcaagtct a                          41

<210> SEQ ID NO 957
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 957
ttgacggtgc catggaattt aaaaaacgta tggcaagtct a                          41

<210> SEQ ID NO 958
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 958
cattgatgac aagcttcccg aaaaaacgta tggcaagtct a                          41

<210> SEQ ID NO 959
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 959
tcctggaaga tggtgatggg aaaaaacgta tggcaagtct a                          41

<210> SEQ ID NO 960
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 960
ccacttgatt ttggagggat aaaaaacgta tggcaagtct a                          41

<210> SEQ ID NO 961
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 961
ggactccacg acgtactcag aaaaaacgta tggcaagtct a                          41

<210> SEQ ID NO 962
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 962
ttctccatgg tggtgaagac aaaaaacgta tggcaagtct a                          41

<210> SEQ ID NO 963
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 963
agagatgatg accctttttgg aaaaaacgta tggcaagtct a                         41

<210> SEQ ID NO 964
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 964
gacgaacatg ggggcatcag aaaaaacgta tggcaagtct a                         41

<210> SEQ ID NO 965
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 965
catacttctc atggttcaca aaaaaacgta tggcaagtct a                         41

<210> SEQ ID NO 966
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 966
attgctgatg atcttgaggc aaaaaacgta tggcaagtct a                         41

<210> SEQ ID NO 967
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 967
ctaagcagtt ggtggtgcag aaaaaacgta tggcaagtct a                         41

<210> SEQ ID NO 968
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 968
ccacgatacc aaagttgtca aaaaaacgta tggcaagtct a                    41

<210> SEQ ID NO 969
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 969
tcttctgggt ggcagtgatg aaaaaacgta tggcaagtct a                    41

<210> SEQ ID NO 970
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 970
tagaggcagg gatgatgttc aaaaaacgta tggcaagtct a                    41

<210> SEQ ID NO 971
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 971
tcagctcagg gatgaccttg aaaaaacgta tggcaagtct a                    41

<210> SEQ ID NO 972
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 972
cactgacacg ttggcagtgg aaaaaacgta tggcaagtct a                    41

<210> SEQ ID NO 973
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 973
caggtttttc tagacggcag aaaaaacgta tggcaagtct a                    41

```
<210> SEQ ID NO 974
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 974
caccttcttg atgtcatcat aaaaaacgta tggcaagtct a                   41

<210> SEQ ID NO 975
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 975
gctgttgaag tcagaggaga aaaaaacgta tggcaagtct a                   41

<210> SEQ ID NO 976
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 976
cgtcaaaggt ggaggagtgg aaaaaacgta tggcaagtct a                   41

<210> SEQ ID NO 977
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 977
agtggtcgtt gagggcaatg aaaaaacgta tggcaagtct a                   41

<210> SEQ ID NO 978
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 978
tcataccagg aaatgagctt aaaaaacgta tggcaagtct a                   41

<210> SEQ ID NO 979
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 979
cctgttgctg tagccaaatt aaaaaacgta tggcaagtct a                   41

<210> SEQ ID NO 980
```

```
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 980
tgaggagggg agattcagtg aaaaaacgta tggcaagtct a                           41

<210> SEQ ID NO 981
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 981
ctcttcaagg ggtctacatg aaaaaacgta tggcaagtct a                           41

<210> SEQ ID NO 982
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 982
tacatgacaa ggtgcggctc aaaaaacgta tggcaagtct a                           41

<210> SEQ ID NO 983
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 983
tgagcacagg gtactttatt aaaaaacgta tggcaagtct a                           41

<210> SEQ ID NO 984
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 984
aggagtatga ttgtcaaccc aaaaatggag tttgggcaga t                           41

<210> SEQ ID NO 985
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 985
cctatataag gcgaagcaca aaaatggagt ttgggcagat                             40

<210> SEQ ID NO 986
<211> LENGTH: 41
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 986
gagtgactcg agagagctac aaaaatggag tttgggcaga t                    41

<210> SEQ ID NO 987
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 987
atagtgagca acgtaggctt aaaaatggag tttgggcaga t                    41

<210> SEQ ID NO 988
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 988
ggacatgagt tgggcaattt aaaaatggag tttgggcaga t                    41

<210> SEQ ID NO 989
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 989
gagatcaact cccgaaggaa aaaaatggag tttgggcaga t                    41

<210> SEQ ID NO 990
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 990
aatcttgtcc aaggcatcag aaaaatggag tttgggcaga t                    41

<210> SEQ ID NO 991
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 991
aacttcgaag ggtctgtcag aaaaatggag tttgggcaga t                    41

<210> SEQ ID NO 992
<211> LENGTH: 41
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 992
ggttggggat gatgtcaatt aaaaatggag tttgggcaga t            41

<210> SEQ ID NO 993
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 993
taccaaagtc agggtacgtt aaaaatggag tttgggcaga t            41

<210> SEQ ID NO 994
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 994
tgagatcagc tttggtcatg aaaaatggag tttgggcaga t            41

<210> SEQ ID NO 995
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 995
ttggcaatgg ttcccaaatt aaaaatggag tttgggcaga t            41

<210> SEQ ID NO 996
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 996
ctgaagagcc tccatgaatg aaaaatggag tttgggcaga t            41

<210> SEQ ID NO 997
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 997
ccaccaagta ggcagaataa aaaaatggag tttgggcaga t            41

<210> SEQ ID NO 998
<211> LENGTH: 41
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 998
tgctttgtga tcacaaccac aaaaatggag tttgggcaga t            41

<210> SEQ ID NO 999
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 999
cagaagactc ccaagcatac aaaaatggag tttgggcaga t            41

<210> SEQ ID NO 1000
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1000
agcacgcaca gtgaaggaac aaaaatggag tttgggcaga t            41

<210> SEQ ID NO 1001
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1001
tctaggtact ctgtctgatc aaaaatggag tttgggcaga t            41

<210> SEQ ID NO 1002
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1002
taaagggtga tgggatagcc aaaaatggag tttgggcaga t            41

<210> SEQ ID NO 1003
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1003
tgtttagttc ttcctgatca aaaaatggag tttgggcaga t            41

<210> SEQ ID NO 1004
<211> LENGTH: 41
<212> TYPE: DNA
<213> ORGANISM: Artificial Sequence
<220> FEATURE:

```
<223> OTHER INFORMATION: Description of Artificial Sequence: Synthetic
      probe

<400> SEQUENCE: 1004
agggtttctg gtccaaatag aaaaatggag tttgggcaga t                            41

<210> SEQ ID NO 1005
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1005
tcattagtga ggctcttgta aaaaatggag tttgggcaga t                            41

<210> SEQ ID NO 1006
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1006
aaagtgcttg actgccaagt aaaaatggag tttgggcaga t                            41

<210> SEQ ID NO 1007
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1007
tgaattccaa ctgaccttct aaaaatggag tttgggcaga t                            41

<210> SEQ ID NO 1008
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1008
gagcccgacg aggaataaat aaaaatggag tttgggcaga t                            41

<210> SEQ ID NO 1009
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1009
tgaacacacg gcggacatag aaaaatggag tttgggcaga t                            41

<210> SEQ ID NO 1010
<211> LENGTH: 41
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 1010
atcaactcat cacagctgtc aaaaatggag tttgggcaga t          41

<210> SEQ ID NO 1011
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1011 aagatttgc tctgctggag aaaaatggag tttgggcaga t           41

<210> SEQ ID NO 1012
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1012
agagaagagc tcaaggcact aaaaatggag tttgggcaga t          41

<210> SEQ ID NO 1013
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1013
gtggattcca agcttgagat aaaaatggag tttgggcaga t          41

<210> SEQ ID NO 1014
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1014
agactgggag gtatgatagc aaaaatggag tttgggcaga t          41

<210> SEQ ID NO 1015
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1015
ctctgacaga gatgtcatct aaaaatggag tttgggcaga t          41

<210> SEQ ID NO 1016
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1016
tagatggact tctgtgtctc aaaaatggag tttgggcaga t            41

<210> SEQ ID NO 1017
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1017
gctccacaaa agctgagttg aaaaatggag tttgggcaga t            41

<210> SEQ ID NO 1018
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1018
catatatacc acctcgaagc aaaaatggag tttgggcaga t            41

<210> SEQ ID NO 1019
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1019
acacagtact cgtcaatggg aaaaatggag tttgggcaga t            41

<210> SEQ ID NO 1020
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1020
ttcccatcaa attccttgag aaaaatggag tttgggcaga t            41

<210> SEQ ID NO 1021
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1021
gagattgtca ccttctcaac aaaaatggag tttgggcaga t            41

<210> SEQ ID NO 1022
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1022
tgcagcaagg tgaagacaca aaaaatggag tttgggcaga t        41

<210> SEQ ID NO 1023
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1023 gcttttggc catcatatag aaaaatggag tttgggcaga t          41

<210> SEQ ID NO 1024
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1024
aactgcctta tcattcttgt aaaaatggag tttgggcaga t         41

<210> SEQ ID NO 1025
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1025
atcctcaagg gaaaagccag aaaaatggag tttgggcaga t         41

<210> SEQ ID NO 1026
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1026
tgatcatgcg atagatgcgg aaaaatggag tttgggcaga t         41

<210> SEQ ID NO 1027
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1027
catcaggaac tgcagcattg aaaaatggag tttgggcaga t         41

<210> SEQ ID NO 1028
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1028

```
caagggcaca agttttccaa aaaaatggag tttgggcaga t                   41
```

<210> SEQ ID NO 1029
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1029

```
tactgccttc aacacaagga aaaaatggag tttgggcaga t                   41
```

<210> SEQ ID NO 1030
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1030

```
agagtagaga gggaatgggg aaaaatggag tttgggcaga t                   41
```

<210> SEQ ID NO 1031
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1031

```
tacacaacat ccaatcctgc aaaaatggag tttgggcaga t                   41
```

<210> SEQ ID NO 1032
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1032

```
agatgacgct tgggaa                                               16
```

<210> SEQ ID NO 1033
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1033

```
tcgctctctg ctcctcctgt tc                                        22
```

<210> SEQ ID NO 1034
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1034

```
cgcccaatac gaccaaatcc                                              20

<210> SEQ ID NO 1035
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1035
gtcaacccca ccgtgttctt c                                            21

<210> SEQ ID NO 1036
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1036
tttctgctgt ctttgggacc ttg                                          23

<210> SEQ ID NO 1037
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1037
aaaaaaaaaa                                                         10
```

METHODS FOR FLUORESCENCE IMAGING MICROSCOPY AND NANO-FISH

CROSS-REFERENCE TO RELATED APPLICATIONS

This application is a continuation of U.S. application Ser. No. 16/319,157 filed on Jan. 18, 2019, issued as U.S. Pat. No. 11,353,400, which application is a 371 of international Application No. PCT/US2017/042946 filed on Jul. 19, 2017 which application claims the benefit of U.S. Provisional Application No. 62/364,245, filed Jul. 19, 2016, which application is incorporated herein by reference in its entirety for all purposes.

INCORPORATION BY REFERENCE OF A SEQUENCE LISTING SUBMITTED AS A TEXT FILE

A Sequence Listing is provided herewith as a text file, "48539-712_601_SL.txt," created on Nov. 6, 2020 and having a size of 235,724 bytes. The contents of the text file are incorporated by reference herein in their entirety.

BACKGROUND OF THE INVENTION

Imaging techniques such as fluorescence in situ hybridization (FISH) allows for visualization of DNA or RNA regions, and/or assessment of gene expression, chromosome position, and/or protein localization. In some instances, these imaging methods are limited by small field of view and/or limited resolution. As such, data acquisition from large number of cells requires multiple fields of view and thereby presents challenges in obtaining high throughput and high resolution imaging data. Additionally, for example, existing FISH techniques typically use fluorescent probes that span tens to hundreds of kilobases (kb). This precludes the use of existing FISH techniques for accurate spatial localization of smaller genomic sequences. As such, new FISH techniques are required to detect the localization of probes to small genomic sequences.

SUMMARY OF THE INVENTION

In various aspects, the present disclosure provides a method for detecting a presence of a target nucleic acid sequence in an intact cell, the method comprising: a) providing a nucleic acid sequence comprising the target nucleic acid sequence in the intact cell, wherein the target nucleic acid sequence is less than 2.5 kilobases in length; b) contacting the intact cell with a first plurality of probes, wherein each probe comprises a first detectable label and a probe sequence that binds to a portion of the target nucleic acid sequence; and c) detecting a presence of the first detectable label in the intact cell, wherein the presence of the first detectable label indicates the presence of the target nucleic acid sequence. In some aspects, the detecting is within a period of not more than 48 hours.

In various aspects, a method comprises detecting a target nucleic acid sequence within a period of not more than 48 hours, wherein the target nucleic acid sequence is a non-amplified target nucleic acid sequence. In further aspects, the method comprises contacting the target nucleic acid sequence with a first plurality of probes, wherein each probe comprises a first detectable label and probe sequence that binds to a portion of the target nucleic acid sequence. In still further aspects, the method comprises detecting a presence of the first detectable label on the target nucleic acid sequence, wherein the presence of the first detectable label indicates the presence of the target nucleic acid sequence.

In various aspects, a method for quantifying a target nucleic acid sequence in an intact cell is provided herein, the method comprising: a) providing a nucleic acid sequence comprising the target nucleic acid sequence in the intact cell; b) contacting the intact cell with a first plurality of probes, wherein each probe comprises a first detectable label and a probe sequence that binds to a portion of the target nucleic acid sequence; and c) determining a number of the target nucleic acid sequences present in the intact cell within a period of not more than 48 hours.

In some aspects, the target nucleic acid sequence comprises a nucleic acid sequence of not more than 10 kilobases in length, not more than 8 kilobases in length, not more than 6 kilobases in length, not more than 4 kilobases in length, not more than 3 kilobases in length, not more than 2 kilobases in length, not more than 1.5 kilobases in length, or not more than 1 kilobases in length.

In some aspects, the method further comprises: d) contacting the intact cell with a second detectable label that binds to a portion of a cellular structure, and e) detecting a position of the first detectable label in the intact cell relative to the second detectable label, wherein the position is used to determine a spatial position of the target nucleic acid sequence.

In other aspects, the method further comprises: d) providing the intact cell further comprising a second target nucleic acid sequence; e) contacting the intact cell with a second plurality of probes, wherein each probe comprises a second detectable label and a probe sequence that binds to a portion of the second target nucleic acid sequence, and f) detecting a position of the first detectable label in the intact cell relative to the second detectable label, wherein the position is used to determine the spatial position of the target nucleic acid sequence.

In some aspects, the target nucleic acid sequence comprises an exogenous nucleic acid sequence. In some aspects, the target nucleic acid sequence comprises a nucleic acid sequence encoding somatic rearrangement. In some aspects, the target nucleic acid sequence comprises a nucleic acid sequence encoding a B cell receptor or a T cell receptor.

In some aspects, the method comprises the first plurality of probes bound to the nucleic acid sequence is less than 250 probes, less than 200 probes, less than 150 probes, less than 100 probes, less than 80 probes, less than 60 probes, less than 50 probes, less than 40 probes, less than 30 probes, less than 20 probes, less than 15 probes, less than 10 probes, or less than 8 probes.

In some aspects, the period is not more than 24 hours.

In some aspects, the method further comprises binding at least a portion of the first plurality of probes to the target nucleic acid sequence.

In some aspects, the method further comprises washing the intact cell after contacting the target nucleic acid sequence with the first plurality of probes. In some aspects, the method further comprises optically detecting the first detectable label. In some aspects, the method further comprises optically detecting the second detectable label.

In some aspects, the intact cell is obtained from a tissue. In some aspects, the intact cell is a mammalian or eukaryotic cell. In some aspects, the intact cell is a hematopoietic progenitor cell, a monocyte, a macrophage, a microglia, a neuron, or a T-cell.

In some aspects, the method further comprises introducing the exogenous nucleic acid sequence into the cell. In some aspects, the introducing comprises electroporation, lipofection, transfection, microinjection, viral transduction, or use of a gene gun. In some aspects, the exogenous nucleic acid sequence is integrated into the genome of the cell.

In some aspects, the probe sequence of at least one probe of the first plurality of probes comprises an oligonucleotide sequence. In some aspects, the probe sequence of at least one probe of the first plurality of probes comprises an amino acid sequence. In some aspects, the second plurality of probes bound to the second target nucleic acid sequence is less than 250 probes, less than 200 probes, less than 150 probes, less than 100 probes, less than 80 probes, less than 60 probes, less than 50 probes, less than 40 probes, less than 30 probes, less than 20 probes, less than 15 probes, less than 10 probes, or less than 8 probes. In some aspects, the probe sequence of at least one probe of the second plurality of probes comprises an oligonucleotide sequence. In some aspects, the probe sequence of at least one probe of the second plurality of probes comprises an amino acid sequence.

In various aspects, the present disclosure provides a method for assessing a phenotype of an intact genetically modified cell comprising: a) providing the intact genetically modified cell comprising a target nucleic acid sequence less than 2.5 kilobases in length; b) contacting the intact genetically modified cell with a first plurality of probes, wherein each probe comprises a first detectable label and a probe sequence that binds to a portion of the target nucleic acid sequence; c) detecting a presence of the first detectable label in the intact cell, wherein the presence of the first detectable label indicates the presence of the target nucleic acid sequence; d) determining a phenotype of the intact genetically modified cell; and e) correlating the phenotype of the intact genetically modified cell with the presence of the target nucleic acid sequence. In some aspects, the intact genetically modified cell is a eukaryotic intact genetically modified cell. In some aspects, the phenotype is a product expressed due to a genetic modification in the intact genetically modified cell, a quality of the product expressed due to the genetic modification in the genetically modified cell, or a combination thereof. In some aspects, the phenotype is an increased or decreased expression of the product, an increase or decrease in the quality of the product, or a combination thereof. In some aspects, the method further comprises determining a number or location of genetic modifications in the intact genetically modified cell. In some aspects, the product expressed is a transgene protein, RNA, or a secondary product of the genetic modification. In some aspects, the method further comprises: f) selecting a first intact genetically modified cell comprising a phenotype of interest; g) determining a set of conditions used for a genetic modification of the first intact genetically modified cell; and h) preparing a second genetically modified cell using the set of conditions for genetic modification.

In various aspects, the present disclosure provides an in situ method of determining the localization of a regulatory element, the method comprising: a) contacting a regulatory element with a first set of detection agents; b) photobleaching the first set of detection agents for a first time point at a first wavelength to generate a second set of detection agents capable of generating a light at a second wavelength; c) detecting at least one burst generated by the second set of detection agents to generate a detection profile; and d) based on step c), analyzing the detection profile to determine the localization of the regulatory element. In some aspects, the first set of detection agent is a first set of fluorescently labeled probes.

In some aspects, the method further comprises hybridizing the first set of fluorescently labeled probes to a set of target sites on a regulatory element.

In some aspects, the second set of detection agent is a second set of fluorescently labeled probes. In some aspects, the fluorescent moieties of the first set of fluorescently labeled probes are the same.

In some aspects, the method further comprises a third set of fluorescently labeled probes. In some aspects, the third set of fluorescently labeled probes is photobleached to generate a fourth set of fluorescently labeled probes. In some aspects, the fluorescent moieties of the first set of fluorescently labeled probes are the same as the fluorescent moieties of the third set of fluorescently labeled probes. In some aspects, wherein the fluorescent moieties of the first set of fluorescently labeled probes are different than the fluorescent moieties of the third set of fluorescently labeled probes. In some aspects, wherein the third set of fluorescently labeled probes hybridizes to different target sites of the regulatory element from the first set of fluorescently labeled probes. In some aspects, the third set of fluorescently labeled probes hybridizes to different target sites of a different regulatory element from the first set of fluorescently labeled probes. In some aspects, the fluorescent moieties of the first set of fluorescently labeled probes are different than the fluorescent moieties of the third set of fluorescently labeled probes and the first set of fluorescently labeled probes hybridizes to different target sites from the third set of fluorescently labeled probes.

In some aspects, the method further comprises photobleaching the first set of fluorescently labeled probes for a first time point at a first wavelength and a third wavelength to generate a fourth set of fluorescently labeled probes capable of fluorescence at a fourth wavelength. In some aspects, the first wavelength and the third wavelength is applied simultaneously. In some aspects, the first wavelength and the third wavelength is applied sequentially In some aspects, the first wavelength is at 491 nm light. In some aspects, the third wavelength is at 405 nm light. In some aspects, the fluorescent moiety comprises a fluorescent small molecule. In some aspects, the fluorescent moiety does not comprise a fluorescent protein. In some aspects, the detection profile comprises a chromatic aberration correction. In some aspects, the detection profile comprises less than 5%, 4%, 3%, 2%, 1%, 0.5%, 0.1%, or 0% chromatic aberration. In some aspects, the localization of the regulatory element provides activity state of the regulatory element. In some aspects, the localization of the regulatory element provides interaction state with at least one additional regulatory element. In some aspects, the regulatory element comprises DNA, RNA, polypeptides, or a combination thereof. In some aspects, the regulatory element is DNA. In some aspects, the regulatory element is RNA. In some aspects, the RNA is an enhancer RNA (eRNA). In some aspects, the regulatory element is a DNaseI hypersensitive site (DHS).

In some aspects, the method further comprises: a) hybridizing a first set of fluorescently labeled probes to a set of target sites on a DHS in a cell sample; b) photobleaching the first set of fluorescently labeled probes for a first time point at a first wavelength to generate a second set of fluorescently labeled probes capable of fluorescence at a second wavelength; c) detecting at least one fluorescent burst generated by the second set of fluorescently labeled probes to generate a DHS profile; and d) comparing the DHS profile with a control set of DHS profiles, wherein a correlation between the DHS profile and the control set leads to identification of the cell type. In some aspects, the regulatory element is a polypeptide. In some aspects, the regulatory element comprises chromatin.

In various aspects, a kit is provided by the present disclosure, wherein the kit comprises a probe set and a set of instructions for the method of any of the methods as described herein.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5A shows a schematic of simultaneous labeling and multiplexed imaging of mRNA and protein targets with multicolor QDots via DNA encoding. In general, each molecular target is encoded by target-specific ssDNA-tagged affinity molecule (e.g., an antibody, aptamer, oligonucleotide, etc.). The resulting array of target-bound ssDNA tags can be sequentially or simultaneously labeled by complementary imaging probes, enabling multiplexed imaging of all targets of interest (e.g., via fluorescence microscopy with hyperspectral imaging, HSI). FIG. 5B shows an exemplary multiplexed labeling of GAPDH and HSP90-alpha mRNA and corresponding proteins with QDots. DNA encoding methodology enables ssDNA tagging of mRNA targets via in situ hybridization and protein targets via immunorecognition by antibody-ssDNA bioconjugates. All ssDNA tags are simultaneously converted into distinctive optical signals by hybridization with complementary QDot-ssDNA' probes. Fluorescence microscopy with HSI is employed for cell imaging and unmixing of 4 individual QDot channels. Individual grayscale channels are false-colored and merged into a composite 4-color image. Scale bar, 50 μm.

FIG. 7A shows that amine crosslinking by a homobifunctional reagent BS3 is used for covalent conjugation of 5' amine-terminated ssDNA oligonucleotides and PEG-coated amine-functionalized QDots. ssDNA is activated by an excess BS3, purified by desalting, and reacted with QDots overnight. QDot-ssDNA probes are purified from excess unbound ssDNA by ultrafiltration. Agarose gel electrophoresis in FIG. 7B shows increase in QDot gel motility upon conjugation of negatively-charged ssDNA oligonucleotides, confirming successful preparation of QDot-ssDNA probes.

FIG. 8A shows rabbit anti-mouse IgG is partially reduced by treatment with TCEP to expose sulfhydryl groups for ssDNA conjugation. At the same time, 5' amine-terminated ssDNA oligonucleotides are activated by sulfo-SMCC. Mixing and 4-hour incubation of activated ssDNA with reduced IgG yields hIgG-ssDNA bioconjugates. PAGE analysis of bioconjugation products in FIG. 8B confirms formation of primarily IhgG with one ssDNA along with smaller fractions of IhgG conjugated to two and three ssDNA tags.

FIG. 9 illustrates evaluation of a 6-color QDot panel for protein labeling via DNA encoding. FIG. 9A shows specific staining of β-tubulin via incubation with mouse anti-β-tubulin primary antibody and ssDNA-conjugated rabbit anti-mouse secondary antibody followed by immuno-labeling with anti-rabbit QDot655-2'Ab probes indicates preserved functionality of 2'Ab-ssDNA bioconjugates. Consistent β-tubulin staining achieved via hybridization with complementary QDot-ssDNA probes in FIG. 9B confirms successful preparation of a functional 6-color QDot-ssDNA panel. A lack of non-specific binding in FIG. 9C by QDot-ssDNA probes in control experiments skipping incubation with primary and secondary antibodies corroborates utility of such probes for a highly specific target labeling via DNA encoding. True-color images for target staining (FIG. 9B) vs. control (FIG. 9C) are obtained at consistent exposure time for each QDot color. Scale bar, 50 μm.

FIG. 11A, FIG. 11B, FIG. 11C, FIG. 11D, and FIG. 11E show multiplexed protein labeling via DNA encoding with a panel of 1' antibody-ssDNA bioconjugates. Primary antibodies against HSP90-alpha, GAPDH, Lamin A, and β-tubulin are conjugated to ssDNA tags using Thunder-Link oligo conjugation system. Reducing PAGE shows consistent formation of IgG-ssDNA bioconjugates for all antibodies (FIG. 11A). Conventional 2-step immunofluorescence with unmodified antibodies and QDot565-2'Ab probes shows characteristic staining pattern for the 4 proteins of interest (FIG. 11B). Protein labeling in FIG. 11C with 1'Ab-ssDNA bioconjugates and QDot565-2'Ab probes yields staining patterns consistent with unmodified antibodies in FIG. 11B, confirming preserved antigen-binding functionality of 1'Ab-ssDNA. Single-color staining with 1'Ab-ssDNA bioconjugates and complementary QDot-ssDNA' probes further corroborates successful ssDNA conjugation and preparation of an antibody-ssDNA panel suitable for protein labeling via DNA encoding (FIG. 11D). Multiplexed staining via DNA encoding yields consistent staining patterns for all 4 proteins in respective spectral channels of the same hyperspectral image (FIG. 11E). Individual grayscale channels are false-colored for clarity. Scale bar, 50 µm.

FIG. 22A and FIG. 22B show multi-omics evaluation of GAPDH and HSP90-alpha expression at mRNA and protein levels following transfection with a control (non-targeting) siRNA. To assess an effect of transfection on molecular expression profiles in reference to GAPDH RNAi experiments, cells are reverse transfected with non-targeting control siRNA for (FIG. 22A) 24 Hrs and (FIG. 22B) 48 Hrs. All targets of interest are labeled via a 2+2 encoding procedure to produce a 4-plex staining. Consistent with expected lack of RNAi with control siRNA, GAPDH and HSP90 expression remains constant through 48 Hrs of incubation, as evident from consistent intensity of mRNA and protein labeling. Multiplex images are obtained with HSI, and individual channels are normalized for direct comparison of signal intensity. GAPDH mRNA channel is false-colored green, HSP90 mRNA—red, GAPDH protein—yellow, and HSP90 protein—blue in a composite 4-color image. Scale bar, 50 µm.

FIG. 33 shows the use of Nano-FISH to detect a 1.8 kb nucleic acid sequence. FIG. 33A shows a schematic of the Nano-FISH experiment. FIG. 33B shows the application of the Nano-FISH strategy to detect a 1.8 kb region encompassing the HS2 hypersensitive site of the β-globin locus control region (LCR) in triploid K562 erythroleukemia cells. FIG. 33C shows colocalization of the Nano-FISH signals (~1.8 kb target region) with those from standard BAC-derived probes (conventional DNA-FISH; ~170 kb target region), confirming the specificity of the detected Nano-FISH signal. FIG. 33D shows the efficiency and resolution of detection using Nano-FISH may be tuned according to the number of probes being used. FIG. 33E shows a comparison of the size of detected FISH spots between conventional FISH, pooled HS1-5 probes, and HS2 Nano-FISH. FIG. 33F shows a comparison of the intensity of detected FISH signals between conventional FISH, pooled HS 1-5 probes, and HS2 Nano-FISH. FIG. 33G shows Nano-FISH detected for genomic regions with varying size, such as a genomic region size ranging from about 800 bp to 2.1 kb.

FIG. 34 shows the use of Nano-FISH to perform fine structural analysis of specific genomic loci within the nucleus. FIG. 34A shows the distinct spots produced by Nano-FISH probes targeting specific loci on these chromosomes. To measure the relative localization of the detected loci, the relative radial distance (RRD), a normalized measure of the position of the detected spot with respect to the nuclear centroid, was calculated. FIG. 34B shows a schematic of the relative radial distance. FIG. 34C shows that the chromosome 18 Nano-FISH signals are closer to the nuclear periphery. The distributions were obtained across 2,396 chromosome 18 signals and 3,388 chromosome 19 signals. FIG. 34D shows radial histograms of the two target loci. The differences in the distribution of signals with respect to the nuclear centroid are readily apparent in the histograms.

FIG. 35 shows the use of Nano-FISH for examining the interaction of a gene enhancer with its target gene promoter. FIG. 35A shows two-color Nano-FISH in 786-0 and MCF-7 cells. The normalized inter-spot distance (NID) between these two genomic loci were compared. FIG. 35B shows a schematic of the normalized inter-spot distance. FIG. 35C shows that, on average, the spots are situated closer together in 786-O cells compared to MCF-7 cells.

FIG. 35D shows that, in spite of this, absolute colocalization (NID=0) was actually a rare event in both cell types.

FIG. 36 shows the use of Nano-FISH to detect small genomic structural variations such as small losses or gains of DNA. ZFN-mediated genome editing was used to generate a triploid homozygous deletion of the β-globin locus control region (LCR, ~18 kb) in K562 cells, as shown in FIG. 36A. Cells imbued with this deletion are referred to as ΔLCR. Probes targeting either the HS2 or HS3 hypersensitive sites within the deleted region were utilized to detect loss of LCR in the genome edited cells, as shown in FIG. 36B and FIG. 36C. For the converse scenario, using TALEN-mediated homology directed repair, a sequence encoding for eGFP was inserted into the AAVS1 safe harbor locus on chromosome 19, as shown in FIG. 36D. This exogenously-derived sequenced was readily identified by Nano-FISH, as shown in FIG. 36E and FIG. 36F.

FIG. 37 shows the combination of Nano-FISH and super-resolution microscopy to obtain very fine-scale genome localization. FIG. 37A shows that these closely apposed loci are readily discernible as distinct spots by STED microscopy. Pair-wise measurements of other closely situated genomic segments such as HS1-HS4 (~12 kb) and HS2-HGB2 (~25 kb) were also readily obtained and revealed non-linear compaction of the β-globin locus control region and the surrounding genome which contains its target genes, as shown in FIG. 37B. Importantly, the high-throughput STED microscopy approach enables calculation of the distribution of actual distances between these various loci, as shown in FIG. 37C.

FIG. 38 shows a series of experiments to determine the optimal operating parameters for a Nano-FISH experiment. FIG. 38A shows how the labeling efficiency of the Nano-FISH procedure depends on denaturation temperature. With increasing temperature, the efficiency of Nano-FISH labeling increases, until a plateau is reached at a temperature of 78° C. FIG. 38B shows that the Nano-FISH labeling procedure is repeatable across experiments. FIG. 38C shows Nano-FISH detected for genomic regions with varying size, such as a genomic region size ranging from about 800 bp to 2.1 kb. FIG. 38D shows how the labeling efficiency of the Nano-FISH experiment depends on the number of oligo probes used. The labeling efficiency increases with the number of oligo probes used, attaining a maximum efficiency when 30 oligo probes are utilized. FIG. 38E shows how the detected fluorescence spot size depends on the number of oligo probes. FIG. 38F shows how the intensity of the fluorescence spot size depends on the number of oligo probes.

FIG. 39 shows a comparison of Nano-FISH and conventional FISH. FIG. 39A shows fluorescence images of β-globin lacking the LCR using conventional BAC probes (left panel), a pool of HS1-5 probes (middle panel), and the HS2 Nano-FISH technique (right panel). FIG. 39B shows the size of the probe sets used for the BAC, HS 1-5, and HS2. FIG. 38E shows the intensity of the FISH signals for the BAC, HS1-5, and HS2 experiments. As can be seen, the HS2 Nano-FISH experiment utilizes a significantly smaller nucleic acid sequence than conventional FISH techniques. FIG. 39C shows the labeling efficiency of the BAC, HS 1-5, and HS2 experiments. FIG. 39D shows the size of the FISH spots for the BAC, HS 1-5, and HS2 experiments. FIG. 39E shows the intensity of the FISH signals for the BAC, HS 1-5, and HS2 experiments.

DETAILED DESCRIPTION OF THE INVENTION

Cellular activation and extinction patterns can encode information on cell identity, maturation state, cellular memory, and disease state. Tissues are composites of cells which can have one or more morphologically distinct cell types. In some instances, all of the cells in a tissue are processed simultaneously, yielding compounded information with limited sensitivity for cellular activities and/or rare cell types. Alternative approaches employ disaggregation and sorting of tissue components but in the process can destroy cellular architecture and potentially introduce artifacts such as biological stressors and perturbations.

Figure 1:
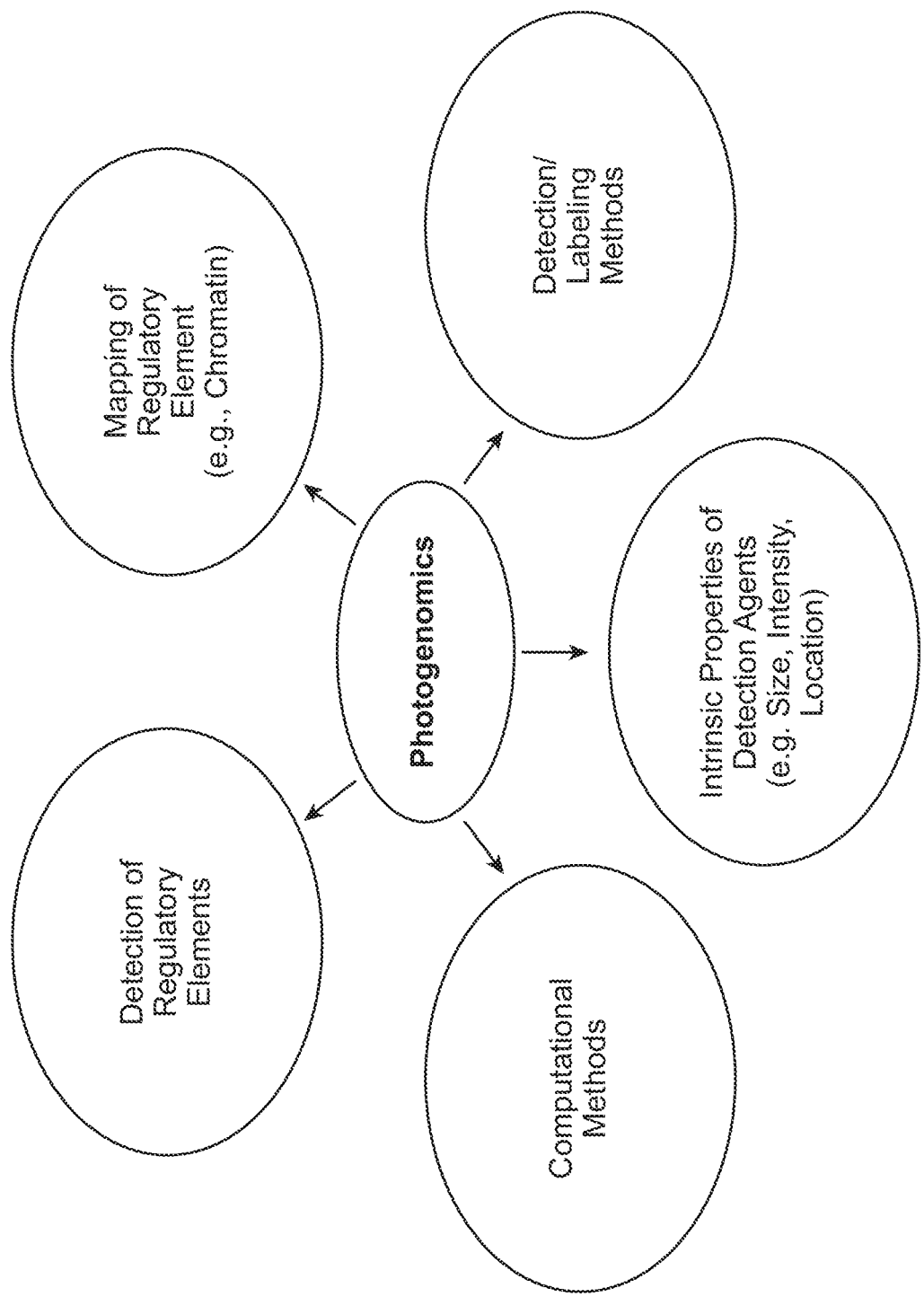
FIG. 1 represents a conceptual illustration of methods described herein.
Figure 2:
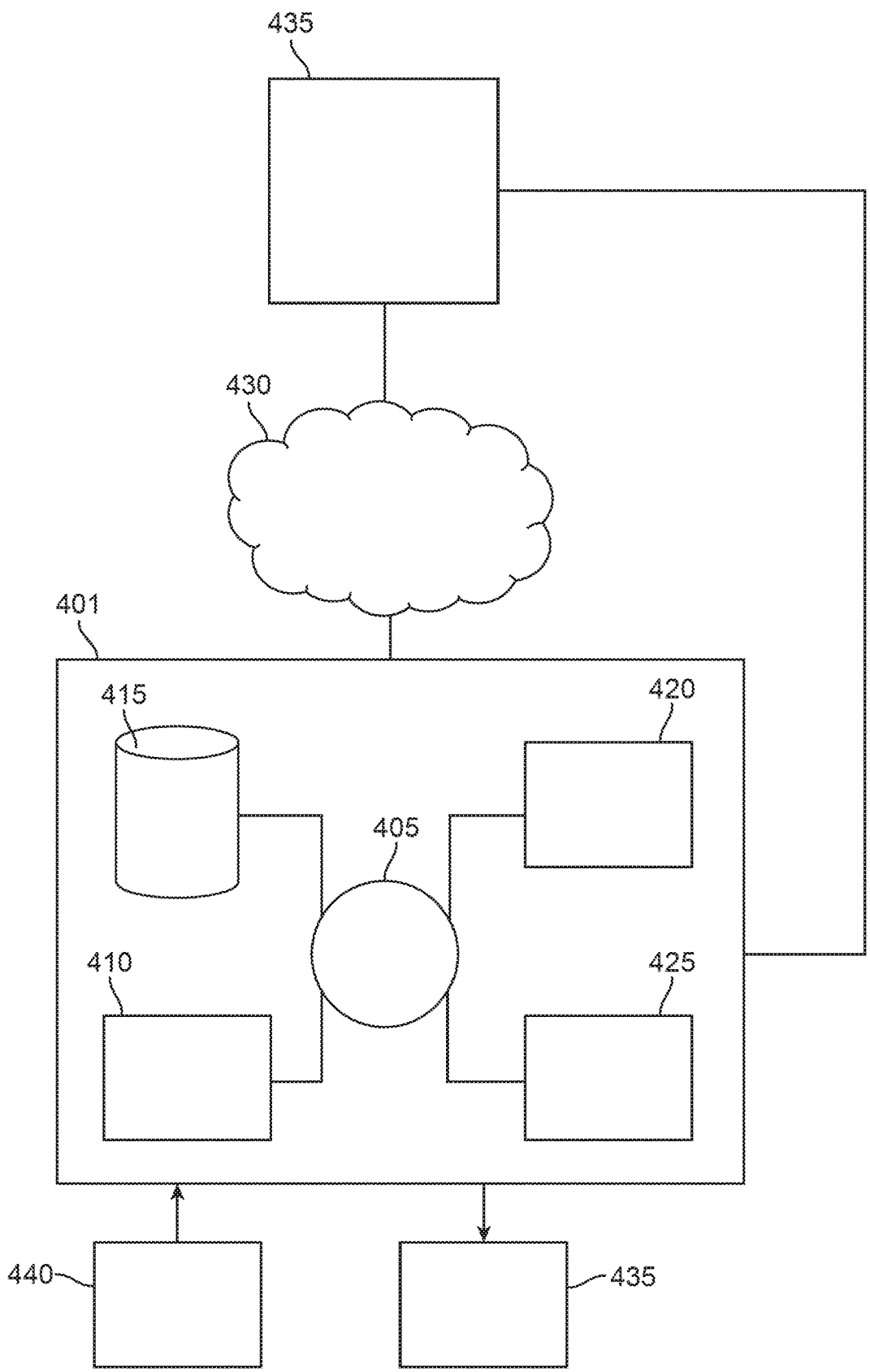
FIG. 2 illustrates a conceptual schematic of an exemplary computer server to be used for processing a method described herein.

Described herein are methods of detecting a cellular regulatory element in situ utilizing a super-resolution microscopy technique to determine the presence, absence, and/or activity of a regulatory element. Also described herein are methods of detecting different types of regulatory elements simultaneously utilizing a heterogeneous set of detection agents, and translating the molecular information from the different types of regulatory elements to determine the activity state of a cell. The activity state of a cell may correlate to a localization, expression level, and/or interaction state of a regulatory element. One or more of the methods described herein may further interpolate 2-dimensional images to generate 3-dimensional maps which enable detection of localization, interaction states, and activity of one or more regulatory elements. Intrinsic properties such as size, intensity, and location of a detection agent further may enable detection of a regulatory element. Described herein are methods of determining the localization of a regulatory element and measuring the activity of a regulatory element. The methods provided herein may avoid the introduction of artifacts such as biological stressors and perturbations or destroys cellular architecture. Exemplary properties associated with the methods described herein are illustrated in FIG. 1.

One or more methods described herein may detect different types of regulatory elements, distinguish between different types of regulatory elements, and/or generate a map of a regulatory element (e.g., chromatin). For example, a regulatory element may be labeled by one or more different types of detection agents. The one or more different types of detection agents may include DNA detection agents, RNA detection agents, protein detection agents, or combinations thereof. The detection agent may comprise a probe portion, which may interact (e.g., hybridize) to a target site within the regulatory element, and optionally comprise a detectable moiety. The detectable moiety may include a fluorophore, such as a fluorescent dye or a quantum dot. The detection agent may be an unlabeled probe which can be further conjugated to an additional labeled probe. Upon labeling, the regulatory element may be detected by stochastic or deterministic super-resolution microscopy method. The stochastic super-resolution microscopy method may be a synthetic aperture optics (SAO) method. The SAO method may generate a detection profile, which can encompass fluorescent signal intensity, size, shape, or localization of the detection agent. Based on the detection profile, the activity state, the localization, expression level, and/or interaction state of the regulatory element may be determined. A map based on the detection profile of the regulatory element may also be generated, and may be correlated to cell type identification (e.g., cancerous cell identification). The regulatory element may be further analyzed in the presence of an exogenous agent or condition, such as a small molecule fragment or a drug, or under an environment such as a change in temperature, pH, nutrient, or a combination thereof. The perturbation of the activity state of the regulatory element in the presence of the exogenous agent or condition may be measured. A report may further be generated and provided to a user, such as a laboratory clinician or health care provider.

The systems and methods disclosed herein also relate to a novel FISH methodology (hereinafter referred to as "Nano-FISH") to reliably label and detect localized small (less than 12 kb in size) DNA segments in cells. In some cases, Nano-FISH utilizes defined pools of synthetic fluorescent dye-labeled oligonucleotides to reliably detect small genomic regions in large numbers of adherent or suspension cells in situ. In some instances, Nano-FISH is conducted utilizing conventional wide-field microscopic imaging. In other embodiments, Nano-FISH is conducted using super-resolution imaging techniques.

In some cases, Nano-FISH is coupled with an automated image informatics pipeline to enable high-throughput detection and 2D and/or 3D spatial localization of small genomic DNA elements in situ in hundreds of, thousands of, or more individual cells per experiment. In some instances, to facilitate rigorous statistical analyses of the resulting large image data sets, a scalable image analysis software suite reliably identifies and quantitatively annotates labeled loci on a single-cell basis.

In some cases, Nano-FISH allows detection of the precise localization of specific regulatory genomic elements in 3D nuclear space, the identification of small-scale structural genomic variations (such as sequence gains or losses), the quantitation of spatial interactions between regulatory elements and their putative target gene(s), or the detection of genomic conformational changes that induce stimulus-dependent gene expression. In some instances, Nano-FISH allows the visualization of the precise localization of a target nucleic acid sequence. The target nucleic acid sequence can be an endogenous nucleic acid sequence, a nucleic acid sequence derived from an exogenous source, or a combination thereof. An exogenous target nucleic acid sequence may be introduced to a cell through electroporation, lipofection, transfection, microinjection, viral transduction, or a gene gun. Non-limiting examples of vector systems that can be used to introduce a target nucleic acid sequence into a cell may include viral vector, episomal vector, naked RNA (recombinant or natural), naked DNA (recombinant or natural), bacterial artificial chromosome (BAC), and RNA/DNA hybrid systems used separately or in combination. Vector systems may be used without additional reagents meant to aid in the incorporation and/or expression of desired mutations. A non-limiting list of reagents meant to aid in the incorporation and/or expression of desired mutations may include Lipofectamine, FuGENE, FuGENE HD, calcium phosphate, HeLaMONSTER, Xtreme Gene. An endogenous nucleic acid sequence may be a gene sequence or fragment thereof. An endogenous nucleic acid sequence may be a sequence in a chromosome. An endogenous nucleic acid sequence may be a nucleic acid sequence resulting from somatic chromosomal rearrangement, such as the nucleic acid sequence of a B cell receptor, T cell receptor, or fragment thereof. In some instances, Nano-FISH allows the detection of the precise localization of exogenous nucleic acids inserted or integrated into a genome. In some embodiments, Nano-FISH allows the detection of the precise localization of exogenous DNA inserted into a genome, as may be inserted by a genetic engineering technique. In some instances, Nano-FISH allows the detection of an episomal nucleic acid sequence.

The systems and methods described herein may be useful in detecting or determining the presence, absence, identity, or quantity of a target nucleic acid sequence in a sample. In particular, the methods, compositions, and systems described herein may be used to efficiently detect, to identify, and to quantify a target nucleic acid sequence that is a short nucleic acid sequences. In some cases, a short nucleic acid sequence that may be detected or quantified using the disclosures of the present application may be from 1 kilobase (kb) in length to about 12 kb in length. A short nucleic acid sequence may be less than 1 kb. A short nucleic acid sequence may be less than 12 kb, less than 11 kb, less than 10 kb, less than 9 kb, less than 8 kb, less than 7 kb, less than 6 kb, less than 5 kb, less than 4 kb, less than 3 kb, less than 2.5 kb, less than 2 kb, less than 1.5 kb, less than 1.2 kb, less than 0.8 kb, or less than 0.5 kb. A short nucleic acid sequence may be from 240 nucleotides to 1 kb in length. A short nucleic acid sequence may be from 360 nucleotides to 1 kb in length. A short nucleic acid sequence may be from 240 nucleotides to 2 kb, 15 nucleotides to 2.5 kb, 240 nucleotides to 3 kb, 15 nucleotides to 4 kb, 240 nucleotides to 5 kb, 15 nucleotides to 6 kb, 240 nucleotides to 7 kb, 240 nucleotides to 8 kb, 240 nucleotides to 9 kb, 15 nucleotides to 10 kb, 240 nucleotides to 11 kb, or 240 nucleotides to 12 kb in length. A short nucleic acid sequence may be from 360 nucleotides to 2 kb, 360 nucleotides to 2.5 kb, 360 nucleotides to 3 kb, 360 nucleotides to 4 kb, 360 nucleotides to 5 kb, 360 nucleotides to 6 kb, 360 nucleotides to 7 kb, 360 nucleotides to 8 kb, 360 nucleotides to 9 kb, 360 nucleotides to 10 kb, 360 nucleotides to 11 kb, or 360 nucleotides to 12 kb in length.

Methods for the detection, identification, and/or quantification of a short nucleic acid sequence of a sample may comprise contacting the short nucleic acid sequence with a probe comprising a detectable label and determining the presence, absence, or quantity of probes bound to the target nucleic acid sequence. Determination of the sequence position of the short nucleic acid sequence relative to other nucleotides or another short nucleic acid sequence (for instance, using a second probe capable of binding to a second target sequence of the nucleic acid) may be a step in the methods described herein. The methods described herein may also comprise determining the spatial position of the short nucleic acid sequence. For example, Nano-FISH may be used to measure the normalized inter-spot distance between a first short nucleic acid sequence encoding an enhancer or portion thereof and a second nucleic acid encoding a promoter of a gene or portion thereof, which may be used to study changes in genome conformation that may be associated with gene function.

The methods described herein may comprise comparing the presence, absence, spatial position, sequence position, or quantity of a short nucleic acid sequence of a sample to a reference value. A non-limiting example of quantifying detection of a short nucleic acid sequence in a cell may comprise quantifying the number of copies of a nucleic acid sequence that has been incorporated into a modified cell (for example, a cell modified by the introduction of a nucleic acid sequence into the cell by genetic editing), which may be used as quality control for modified cells produced by cell engineering strategies.

Also described herein are methods, compositions, and systems useful in characterizing and/or quantifying the presence, absence, position, or identity of a target nucleic acid sequence in a cell or sample derived therefrom relative to a reference nucleic acid sequence in the same cell or sample or relative to a control cell or sample. For example, improvements to the efficiency of detection and to a detection threshold, as described herein, may allow for the detection and characterization of short nucleic acid sequences (for instance, non-repeating nucleic acid sequence insertions) during analysis or validation of cell samples or cell lines.

Additionally, described herein, are methods, compositions, and systems for correlating protein expression with target nucleic acid sequence detection. For example, a target nucleic acid sequence may be associated with the expression of a target protein. Using Nano-FISH, the presence, absence, or quantity of the target nucleic acid sequence may be detected, and a detectable label may be used to detect a target protein expression, which therefore may allow for the correlation between the presence, absence, or quantity of the target nucleic acid sequence and the expression of the target protein.

Types of Regulatory Elements

A regulatory element may be DNA, RNA, a polypeptide, or a combination thereof. A regulatory element may be DNA. A regulatory element may be RNA. A regulatory element may be a polypeptide. A regulatory element may be any combination of DNA, RNA, and/or polypeptide (e.g., protein-protein complexes, protein-DNA/RNA complexes, and the like).

A regulatory element may be DNA. A regulatory element may be a single-stranded DNA regulatory element, a double-stranded DNA regulatory element, or a combination thereof. The DNA regulatory element may be single-stranded. The DNA regulatory element may be double-stranded. The DNA regulatory element may encompass a DNA fragment. The DNA regulatory element may encompass a gene. The DNA regulatory element may encompass a chromosome. The DNA regulatory element may include endogenous DNA regulatory elements (e.g., endogenous genes). The DNA regulatory element may include artificial DNA regulatory elements (e.g., foreign genes introduced into a cell).

A regulatory element may be RNA. A regulatory element may be a single-stranded RNA regulatory element, a double-stranded RNA regulatory element, or a combination thereof. The RNA regulatory element may be single-stranded. The RNA regulatory element may be double-stranded. The RNA regulatory element may include endogenous RNA regulatory elements. The RNA regulatory element may include artificial RNA regulatory elements. The RNA regulatory element may include microRNA (miRNA), transfer RNA (tRNA), ribosomal RNA (rRNA), messenger RNA (mRNA), pre-mRNA, transfer-messenger RNA (tmRNA), heterogeneous nuclear RNA (hnRNA), short interfering RNA (siRNA), or short hairpin RNA (shRNA). The RNA regulatory element may be a RNA fragment. The RNA regulatory element may be an anti-sense RNA.

An RNA regulatory element may be an enhancer RNA (eRNA). An enhancer RNA may be a non-coding RNA molecule transcribed from an enhancer region of a DNA molecule, and may be from about 50 base-pairs (bp) in length to about 3 kilo base pairs in length (e.g., about 100 bp in length, about 200 bp in length, about 500 bp in length, about 1 kb in length, about 1.5 kb in length, about 2 kb in length, or about 2.5 kb in length). An enhancer RNA may be a 1D eRNA or an eRNA that may be unidirectionally transcribed. An enhancer RNA may also be a 2D eRNA or an eRNA that may be bidirectionally transcribed. An eRNA may be polyadenylated. Alternatively, an eRNA may be non-polyadenylated.

A regulatory element may be a DNaseI hypersensitive site (DHS). DHS may be a region of chromatin unoccupied by transcription factors and which is sensitive to cleavage by the DNase I enzyme. The presence of DHS regions within a chromatin may demarcate transcription factory occupancy at a nucleotide resolution. The presence of DHS regions may further correlate with activation of cis-regulatory elements, such as an enhancer, promoter, silencer, insulator, or locus control region. DHS variation may be correlated to variation in gene expression in healthy or diseased cells (e.g., cancerous cells) and/or correlated to phenotypic traits.

A DHS pattern may encode memory of prior cell fate decisions and exposures. For example, upon differentiation, a DHS pattern of a progeny may encode transcription factor occupancy of its parent. Further, a DHS pattern of a cell may encode an environmentally-induced transcription factor occupancy from an earlier time point.

A DHS pattern may encode cellular maturity. An embryonic stem cell may encode a set of DHSs that may be transmitted combinatorially to a differentiated progeny, and this set of DHSs may be decreased with each cycle of differentiation. As such, the set of DHSs may be correlated with time, thereby allowing a DHS pattern to be correlated with cellular maturity.

A DHS pattern may also encode splicing patterns. Protein coding exons may be occupied by transcription factors, which may further be correlated with codon usage patterns and amino acid choice on evolutionary time scales and human fitness. A transcription factory occupancy may further modulate alternative splicing patterns, for example, by imposing sequence constraints at a splice junction. As such, a DHS pattern may encode transcription factor occupancy of one or more exons of interest and may provide additional information on alternative splicing patterns.

A DHS pattern may encode a cell type. For example, within each cell type, about 100,000 to about 250,000 DHSs may be detected. About 5% of the detected DHSs may be located within a transcription start site and the remaining DHSs may be detected at a distal site from the transcription start site. Each cell type may contain a distinct DHS pattern at the distal site and mapping the DHS pattern at the distal site may allow identification of a cell type. An overlap may further be present within two DHS patterns from two different cell types, for example, an overlap of a set of detected DHSs within the two DHS patterns. An overlap may be less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1% of the detected DHSs. The presence of an overlap may not affect the identification of a cell type.

A regulatory element may be a polypeptide. The polypeptide may be a protein or a polypeptide fragment. For example, a regulatory element may be a transcription factor, DNA-binding protein or functional fragment, RNA-binding protein or functional fragment, protein involved in chemical modification (e.g., involved in histone modification), or gene product. A regulatory element may be a transcription factor. A regulatory element may be a DNA or RNA-binding protein or functional fragment. A regulatory element may be a product of a gene transcript. A regulatory element may be a chromatin.

Methods of Detecting a Regulatory Element

Described herein is a method of detecting a regulatory element. The detection may encompass identification of the regulatory element, determining the presence or absence of the regulatory element, and/or determining the activity of the regulatory element. A method of detecting a regulatory element may include contacting a cell sample with a detection agent, binding the detection agent to the regulatory element, and analyzing a detection profile from the detection agent to determine the presence, absence, or activity of the regulatory element.

The method may involve utilizing one or more intrinsic properties associated with a detection agent to aid in detection of the regulatory element. The intrinsic properties may encompass the size of the detection agent, the intensity of the signal, and the location of the detection agent. The size of the detection agent may include the length of the probe and/or the size of the detectable moiety (e.g., the size of a fluorescent dye molecule) may modulate the specificity of interaction with a regulatory element. The intensity of the signal from the detection agent may correlate to the sensitivity of detection. For example, a detection agent with a molar extinction coefficient of about $0.5\text{-}5\times10^6$ $M^{-1}$ $cm^1$ may have a higher intensity signal relative to a detection agent with a molar extinction coefficient outside of the $0.5\text{-}5\times10^6$ $M^{-1}$ $cm^1$ range and may have lower attenuation due to scattering and absorption. Further, a detection agent with a longer excited state lifetime and a large Stoke shift (measured by the distance between the excitation and emission peaks) may further improve the sensitivity of detection. The location of the detection agent may, for example, provide the activity state of a regulatory element. A combination of intrinsic properties of the detection agent may be used to detect a regulatory element of interest.

A detection agent may comprise a detectable moiety that is capable of generating a light, and a probe portion that is capable of hybridizing to a target site on a regulatory element. As described herein, a detection agent may include a DNA probe portion, an RNA probe portion, a polypeptide probe portion, or a combination thereof. Sometimes, a DNA or RNA probe portion may be between about 10 and about 100 nucleotides in length, between about 15 and about 100 nucleotides in length, between about 20 and about 100 nucleotides in length, between about 20 and about 80 nucleotides in length, between about 20 and about 60 nucleotides in length, between about 25 and about 55 nucleotides in length, between about 30 and about 50 nucleotides in length, between about 15 and about 80 nucleotides in length, between about 15 and about 60 nucleotides in length, between about 20 and about 40 nucleotides in length, or between about 20 and about 30 nucleotides in length. Sometimes, a DNA or RNA probe portion may be about 10, about 15, about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60, about 65, about 70, about 80, about 90, about 100, or more nucleotides in length. A DNA or RNA probe portion may be a TALEN probe, ZFN probe, or a CRISPR probe. A DNA or RNA probe portion may be a padlock probe. A polypeptide probe may comprise a DNA-binding protein, a RNA-binding protein, a protein involved in the transcription/translation process, a protein that detects the transcription/translation process, a protein that may detect an open or relaxed portion of a chromatin, or a protein interacting partner of a product of a regulatory element (e.g., an antibody or binding fragment thereof).

A detection agent may comprise a DNA or RNA probe portion which may be between about 10 and about 100 nucleotides in length, between about 15 and about 100 nucleotides in length, between about 20 and about 100 nucleotides in length, between about 20 and about 80 nucleotides in length, between about 20 and about 60 nucleotides in length, between about 25 and about 55 nucleotides in length, between about 30 and about 50 nucleotides in length, between about 15 and about 80 nucleotides in length, between about 15 and about 60 nucleotides in length, between about 20 and about 40 nucleotides in length, or between about 20 and about 30 nucleotides in length. A detection agent may comprise a DNA or RNA probe portion which may be about 10, about 15, about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60, about 65, about 70, about 80, about 90, about 100, or more nucleotides in length.

A detection agent may comprise a DNA or RNA probe selected from a TALEN probe, a ZFN probe, or a CRISPR probe.

A set of detection agents may be used to detect a regulatory element. The set of detection agents may comprise about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, or more detection agents. Each of the detection agents within the set of detection agents may recognize and interact with a distinct region of a regulatory element. Sometimes, about 1, about 2, about 3, about 4, about 5, about 6, about 7, about 8, about 9, about 10, about 11, about 12, about 13, about 14, about 15, about 16, about 17, about 18, about 19, about 20, or more detection agents may be used for detection of a regulatory element. About 1 or more detection agents may be used for detection of a regulatory element. About 2 or more detection agents may be used for detection of a regulatory element. About 3 or more detection agents may be used for detection of a regulatory element. About 4 or more detection agents may be used for detection of a regulatory element. About 5 or more detection agents as used for detection of a regulatory element. About 6 or more detection agents may be used for detection of a regulatory element. About 7 or more detection agents may be used for detection of a regulatory element. About 8 or more detection agents may be used for detection of a regulatory element. About 9 or more detection agents may be used for detection of a regulatory element. About 10 or more detection agents may be used for detection of a regulatory element. About 11 or more detection agents may be used for detection of a regulatory element. About 12 or more detection agents may be used for detection of a regulatory element. About 13 or more detection agents may be used for detection of a regulatory element. About 14 or more detection agents may be used for detection of a regulatory element. About 15 or more detection agents may be used for detection of a regulatory element. About 20 or more detection agents may be used for detection of a regulatory element.

A detection agent may comprise a polypeptide probe selected from a DNA-binding protein, a RNA-binding protein, a protein involved in the transcription/translation process, a protein that detects the transcription/translation process, a protein that may detect an open or relaxed portion of a chromatin, or a protein interacting partner of a product of a regulatory element (e.g., an antibody or binding fragment thereof).

A detectable moiety that is capable of generating a light may be directly conjugated or bound to a probe portion. A detectable moiety may be indirectly conjugated or bound to a probe portion by a conjugating moiety. As described herein, a detectable moiety may be a small molecule (e.g., a dye) which may be directly conjugated or bound to a probe portion. A detectable moiety may be a fluorescently labeled protein or molecule which may be attached to a conjugating moiety (e.g., a hapten group, an azido group, an alkyne group) of a probe.

A profile or a detection profile or signature may include the signal intensity, signal location, or size of the signal of the detection agent. The profile or the detection profile may comprise about 100 image frames, about 500 frames, about 1000 frames, about 2000 frames, about 5000 frames, about 10,000 frames, about 20,000 frames, about 30,000 frames, about 40,000 frames, about 50,000 frames, or more frames. Analysis of the profile or the detection profile may determine the activity of the regulatory element. The degree of activation may also be determined from the analysis of the profile or detection profile. Analysis of the profile or the detection profile may further determine the optical isolation and localization of the detection agents, which may correlate to the localization of the regulatory element.

In additional cases, a detection agent may comprise a polypeptide probe selected from a DNA-binding protein, a RNA-binding protein, a protein involved in the transcription/translation process or detects the transcription/translation process, a protein that may detect an open or relaxed portion of a chromatin, or a protein interacting partner of a product of a regulatory element (e.g., an antibody or binding fragment thereof).

Sometimes, a detectable moiety that is capable of generating a light is directly conjugated or bound to a probe portion. Other times, a detectable moiety is indirectly conjugated or bound to a probe portion by a conjugating moiety. As described elsewhere herein, a detectable moiety may be a small molecule (e.g., a dye) which may be directly conjugated or bound to a probe portion. Alternatively, a detectable moiety may be a fluorescently labeled protein or molecule which may be attached to a conjugating moiety (e.g., a hapten group, an azido group, an alkyne group) of a probe.

In some instances, a profile or a detection profile or signature may include the signal intensity, signal location, or size of the signal of the detection agent. Sometimes, the profile or the detection profile may comprise about 100 frames, 500 frames, 1000 frames, 2000 frames, 5000 frames, 10,000 frames, 20,000 frames, 30,000 frames, 40,000 frames, 50,000 frames or more images. Analysis of the profile or the detection profile may determine the activity of the regulatory element. In some cases, the degree of activation may also be determined from the analysis of the profile or detection profile. In additional cases, analysis of the profile or the detection profile may further determine the optical isolation and localization of the detection agents, which may correlate to the localization of the regulatory element.

Detection of DNA and/or RNA Regulatory Elements

A regulatory element may be DNA. Described herein is a method of detecting a DNA regulatory element, which may include contacting a cell sample with a detection agent, binding the detection agent to the DNA regulatory element, and analyzing a profile from the detection agent to determine the presence, absence, or activity of the DNA regulatory element.

A regulatory element may be RNA. Described herein is a method of detecting a RNA regulatory element, which may include contacting a cell sample with a detection agent, binding the detection agent to the RNA regulatory element, and analyzing a profile from the detection agent to determine the presence, absence, or activity of the RNA regulatory element.

A regulatory element may be an enhancer RNA (eRNA). The presence of an eRNA may correlate to an activated regulatory element. For example, the production of an eRNA may correlate to the transcription of a target gene. As such, the detection of an eRNA element may indicate that a target gene downstream of the eRNA element may be activated.

Provided herein is a method of detecting an eRNA regulatory element, which may include contacting a cell sample with a detection agent, binding the detection agent to the eRNA regulatory element, and analyzing a profile from the detection agent to determine the presence, absence, or activity of the eRNA regulatory element. Described herein is an in situ method of detecting an activated regulatory DNA site, which may include incubating a sample with a set of detection agents (e.g., fluorescently-labeled probes), hybridizing the set of detection agents to at least one enhancer RNA (eRNA), and analyzing a profile (e.g., a fluorescent profile) from the set of detection agents to determine the presence of an eRNA, in which the presence of eRNA correlates to an activated regulatory DNA site.

Detection of a DNaseI Hypersensitive Site, Generation of a DNaseI Hypersensitive Site Map, and Determination of a Cell Type Based on a DNaseI Hypersensitive Site Profile A regulatory element may be a DNaseI hypersensitive site (DHS). A DNaseI hypersensitive site may be an inactivated DNaseI hypersensitive site. A DNaseI hypersensitive site may be an activated DNaseI hypersensitive site. Described herein is a method of detecting a DHS, which may include contacting a cell sample with a detection agent, binding the detection agent to the DHS, and analyzing a profile from the detection agent to determine the presence, absence, or activity of the DHS.

The DHS may be an active DHS and may further contain a single stranded DNA region. The single stranded DNA region may be detected by S1 nuclease. A method of detecting a DHS may further be extended to detect the presence of a single stranded DNA region within a DHS. Such a method, for example, may comprise contacting a cell sample with a detection agent, binding the detection agent to a single stranded region of a DHS, and analyzing a profile from the detection agent to determine the presence or absence of the single stranded region within a DHS.

Also described herein is a method of determining the activity level of a regulatory element, which may include incubating a cell sample with a set of detection agents (e.g., fluorescently labeled probes), in which each detection agent hybridizes to a DHS, measuring a signature (e.g., a fluorescent signature) from the set of detection agents, and based on the signature, determining a DHS profile, and comparing the DHS profile with a control, in which a correlation with the control indicates the activity level of the regulatory element in the cell sample. The signature (e.g., the fluorescent signature) may further correlate to a signal intensity (or a peak height). A set of signal intensities may be compiled into a DHS profile and compared with a control to generate a second DHS profile which comprises a set of relative signal intensities (or relative peak heights). The set of relative signal intensities may correlate to the activity level of a regulatory element.

Also described herein is a method of generating a DHS map, which may provide information on cell-to-cell variation in gene expression, memory of early developmental fate decisions which establish lineage hierarchies, quantitation of embryonic stem cell DHS sites which decreases with cell passage, and presence of oncogenic elements.

The location of a set of DHS sites may be correlated to a cell type. For example, the location of about 1, about 5, about 10, about 15, about 20, about 25, about 30, about 35, about 40, about 45, about 50, about 55, about 60, or more DHS sites may be correlated to a cell type. The location of about 1, about 5, about 10, about 15, about 20, about 25, about 30, about 35, about 40, about 45, about 50, about 55, about 60, or more DHS may be used to determine a cell type. The cell may be a normal cell or a cancerous cell. DHS variation may be used to determine the presence of cancerous cells in a sample. A method of determining a cell type (e.g., a cancerous cell) may include incubating a cell sample with a set of detection agents (e.g., fluorescently labeled probes), in which each detection agent hybridizes to a DHS, measuring a signature (e.g., a fluorescent signature) from the set of detection agents, and based on the signature, determining a DHS profile, and comparing the DHS profile with a control, in which a correlation with the control indicates the cell type of the sample.

A DHS site may be visualized through a terminal deoxynucleotidyl transferase (TdT) dUTP Nick-End labeling (TUNEL) assay. A TUNEL assay may utilize a terminal deoxynucleotidyl transferase (TdT) which may catalyze the addition of a dUTP at the site of a nick or strand break. A fluorescent moiety may further be conjugated to dUTP. A TUNEL assay may be utilized for visualization of a plurality of DHSs present in a cell. A TUNEL assay may be an assay as described in EXAMPLE 2.

The sequence of a DHS site may be detected in situ, by utilizing an in situ sequencing methodology. For example, the two ends of a padlock probe may be hybridized to a target regulatory element sequence and the two ends may be further ligated together by a ligase (e.g., T4 ligase) when bound to the target sequence. An amplification (e.g., a rolling circle amplification or RCA) may be performed utilizing a polymerase (e.g., #29 polymerase), which may result in a single stranded DNA comprising at least about 1, at least about 2, at least about 3, at least about 4, at least about 5, at least about 6, at least about 7, at least about 8, at least about 9, at least about 10, or more tandem copies of the target sequence. The amplified product at least about be sequenced by ligation in situ using partition sequencing compatible primers and labeled probes (e.g., fluorescently labeled probes). For example, each target sequence within the amplified product may bind to a primer and probe set resulting in a bright spot detectable by, e.g., an immunofluorescence microscopy. The labeled probe (e.g., the fluorescent label on the probe) may identify the nucleotide at the ligation site, thereby allowing the color detected to define the nucleotide at the respective ligation position. Sometimes, at least 1, at least 2, at least 3, at least 4, at least 5, at least 6, at least 7, at least 8, at least 9, at least 10, at least 15, at least 20, or more rounds of ligation and detection may occur for detection of a DHS site.

A control as used herein may refer to a DHS profile generated from a regulatory element those activity level is known. A control may also refer to a DHS profile generated from an inactivated regulatory element. A control may further refer to a DHS profile generated from an activated or inactivated regulatory element from a specific cell type. For example, the cell type may be an epithelial cell, connective tissue cell, muscle cell, or nerve cell type. The cell may be a cell derived from heart, lung, kidney, stomach, intestines, liver, pancreas, brain, esophagus, and the like. The cell type may be a hormone-secreting cell, such as a pituitary cell, a gut and respiratory tract cell, thyroid gland cell, adrenal gland cell, Leydig cell of testes, *Theca interna* cell of ovarian follicle, Juxtaglomerular cell, *Macula densa* cell, Peripolar cell, or Mesangial cell type. The cell may be a blood cell or a blood progenitor cell. The cell may be an immune system cell, e.g., monocytes, dendritic cell, neutrophile granulocyte, eosinophil granulocyte, basophil granulocyte, hybridoma cell, mast cell, helper T cell, suppressor T cell, cytotoxic T cell, Natural Killer T cell, B cell, or natural killer cell.

Detection and Mapping of a Chromatin

A regulatory element may also be a chromatin. Provided herein is a method of detecting a chromatin, which may include contacting a cell sample with a detection agent, binding the detection agent to the chromatin, and analyzing a profile from the detection agent to determine the activity state of the chromatin. The activity level of a chromatin may be determined based on the presence or activity level of a nucleic acid of interest or the presence or absence of a chromatin associated protein. The activity level of a chromatin may be determined based on DHS locations. The one or more DHS locations on a chromatin may be used to map chromatin activity state. For example, one or more DHSs may be localized in a region and the surrounding chromatin may be decompacted and readily visualized relative to an inactive chromatin state when a DHS is not present. The one or more DHSs within a localized region may further form a localized DHS set and a plurality of localized DHS sets may further provide a global map or pattern of chromatin activity (e.g., an activity pattern).

Also included herein is a method of generating a chromatin map based on the pattern of DNaseI hypersensitive sites, RNA regulatory elements (e.g., eRNA), chromatin associated proteins or gene products, or a combination thereof. The method of generating a chromatin map may be based on the pattern of DNaseI hypersensitive sites. The method may comprise generating a 3-dimensional map from a detection profile (or a 2-dimensional detection profile). A chromatin map may provide information on the compaction of chromatin, the spatial structure, spacing of regulatory elements, and localization of the regulatory elements to globally map chromatin structure and accessibility.

A chromatin map for a cell type may also be generated, in which each cell type comprises a different chromatin pattern. Each cell type may be associated with at least one unique marker. The at least one unique marker (or fiduciary marker) may be a genomic sequence. The at least one unique marker (or fiduciary marker) may be DHS. A cell type may comprise about 5, about 10, about 15, about 20, about 25, about 30, about 35, about 40, about 45, about 50, about 60, or more unique markers (or fiduciary markers). The cell type may be an epithelia cell, a connective tissue cell, a muscle cell, a nerve cell, a hormone-secreting cell, a blood cell, an immune system cell, or a stem cell type. The cell type may be a cancerous cell type.

A chromatin profile (e.g., based on DHSs) in the presence of an exogenous agent or condition may also be generated. The method may comprise incubating a cell sample with a set of fluorescently labeled probes specific to target sites (e.g., target DHSs) on a chromatin in the presence of an exogenous agent or condition; measuring a fluorescent signature of the set of fluorescently labeled probes; based on the fluorescent signature, generating a fluorescent profile of the chromatin; and comparing the fluorescent profile with a second fluorescent profile of a chromatin obtained from an equivalent sample incubated with an equivalent set of fluorescently labeled probes in the absence of the exogenous agent or condition, wherein a difference between the two sets of fluorescent profiles indicates a change in the chromatin density (e.g., changes in the presences or activation of DHSs) induced by the exogenous agent or condition. The exogenous agent or condition may comprise a small molecule or a drug. The exogenous agent may be a small molecule, such as a steroid. The exogenous agent or condition may comprise an environmental factor, such as a change in pH, temperature, nutrient, or a combination thereof.

Methods of Determining the Localization of a Regulatory Element

Also described herein is a method for determining the localization of a regulatory element. The localization of a regulatory element may provide an activity state of the regulatory element. The localization of a regulatory element may also provide an interaction state with at least one additional regulatory element. For example, the localization of a first regulatory element with respect to a second regulatory element may provide spatial coordinate and distance information between the two regulatory elements, and v further provide information regarding whether the two regulatory elements may interact with each other. The activity state of a regulatory element may include, for example, a transcription or translation initiation event, a translocation event, or an interaction event with one or more additional regulatory elements. The regulatory element may comprise DNA, RNA, polypeptides, or a combination thereof. The regulatory element may be DNA. The regulatory element may be RNA. The regulatory element may be an enhancer RNA (eRNA). The regulatory element may be a DNaseI hypersensitive site (DHS). The DHS may be an inactive DHS or an active DHS. The regulatory element may be a polypeptide. The regulatory element may be chromatin.

The localization of a regulatory element may include contacting a regulatory element with a first set of detection agents, photobleaching the first set of detection agents for a first time point at a first wavelength to generate a second set of detection agents capable of generating a light at a second wavelength, detecting at least one burst generated by the second set of detection agents to generate a detection profile of the second set of detection agents, and analyzing the detection profile to determine the localization of the regulatory element.

A detection agent may comprise a detectable moiety that is capable of generating a light, and a probe portion that is capable of hybridizing to a target site on a regulatory element. Each detection agent within the first set of detection agents may have the same or a different detectable moiety. Each detection agent within the first set of detection agents may have the same detectable moiety. A detectable moiety may comprise a small molecule (e.g., a fluorescent dye). A detectable moiety may comprise a fluorescently labeled polypeptide, a fluorescently labeled nucleic acid probe, and/or a fluorescently labeled polypeptide complex.

Upon photobleaching, a second set of detection agents may be generated from the first set of detection agents, in which the second set may include detection agents that are capable of generating a burst of light detectable at a second wavelength. For example, bleaching of the set of detection agents may lead to about 50%, about 60%, about 70%, about 80%, about 90%, or more detection agents within the set to enter into an "OFF-state". An "OFF-state" may be a dark state in which the detectable moiety crosses from the singlet excited or ON state to the triplet state or OFF-state in which detection of light (e.g., fluorescence) may be low (e.g., less than 10%, less than 5%, less than 1%, or less than 0.5% of the light may be detected). The remainder of the detection agents that have not entered into the OFF-state may generate bursts of lights, or to cycle between a singlet excited state (or ON-state) and a singlet ground state. As such, bleaching of the set of detection agents may generate about 40%, about 30%, about 20%, about 10%, about 5%, or less detection agents within the set that may generate bursts of lights. The bursts of lights may be detected stochastically, at a single burst level in which each burst of light correlates to a single detection agent.

A single wavelength may be used for photobleaching a set of detection agents. At least two wavelengths may be used for photobleaching a set of detection agents. A wavelength at 491 nm may be used. A wavelength at 405 nm may be used in combination with the wavelength at 491 nm. The two wavelengths may be applied simultaneously to photobleach a set of detection agents. Alternatively, the two wavelengths may be applied sequentially to photobleach a set of detection agents.

The time for photobleaching a set of detection agents may be from about 10 seconds to about 4 hours. The time may be from about 30 seconds to about 3.5 hours, from about one minute to about 3 hours, from about 5 minutes to about 2 hours, from about 10 minutes to about 1 hours, from about one minutes to about 1 hour, from about 5 minutes to about 1 hour, or from about 30 minutes to about 2 hours. The time may be at least 10 seconds, at least 20 seconds, at least 30 seconds, at least 40 seconds, at least 50 seconds, at least 1 minute, at least 2 minutes, at least 3 minutes, at least 4 minutes, at least 5 minutes, at least 10 minutes, at least 15 minutes, at least 20 minutes, at least 30 minutes, at least 45 minutes, at least 1 hour, at least 1.5 hours, at least 2 hours, at least 2.5 hours, at least 3 hours, at least 3.5 hours, at least 4 hours, or more.

The concentration of the detection agents may be from about 5 nM to about 1 µM. The concentration of the detection agent may be from about 5 nM to about 900 nM, from about 10 nM to about 800 nM, from about 15 nM to about 700 nM, from about 20 nM to about 500 nM, from about 10 nM to about 500 nM, from about 10 nM to about 400 nM, from about 10 nM to about 300 nM, from about 10 nM to about 200 nM, from about 10 nM to about 100 nM, from about 50 nM to about 500 nM, from about 50 nM to about 400 nM, from about 50 nM to about 300 nM, from about 50 nM to about 200 nM, from about 100 nM to about 500 nM, from about 100 nM to about 300 nM, or from about 100 nM to about 200 nM. The concentration of the detection agents may be about 10 nM, about 15 nM, about 20 nM, about 30 nM, about 40 nM, about 50 nM, about 60 nM, about 70 nM, about 80 nM, about 90 nM, about 100 nM, about 150 nM, about 200 nM, about 250 nM, about 300 nM, about 400 nM, about 500 nM, about 600 nM, about 700 nM, about 800 nM, about 900 nM, or more.

The burst of lights from the set of detection agents may generate a detection profile. The detection profile may comprise about 100 image frames, about 500 frames, about 1000 frames, about 2000 frames, about 5000 frames, about 10,000 frames, about 20,000 frames, about 30,000 frames, about 40,000 frames, about 50,000 frames, or more. The detection profile may also include the signal intensity, signal location, or size of the signal. Analysis of the detection profile may determine the optical isolation and localization of the detection agents, which may correlate to the localization of the regulatory element.

The detection profile may comprise a chromatic aberration correction. The detection profile may comprise less than 5%, less than 4%, less than 3%, less than 2%, less than 1%, less than 0.5%, less than 0.1%, or 0% chromatic aberration. The detection profile may comprise less than 5% chromatic aberration. The detection profile may comprise less than 4% chromatic aberration. The detection profile may comprise less than 3% chromatic aberration. The detection profile may comprise less than 2% chromatic aberration. The detection profile may comprise less than 1% chromatic aberration. The detection profile may comprise less than 0.5% chromatic aberration. The detection profile may comprise less than 0.1% chromatic aberration. The detection profile may comprise 0% chromatic aberration.

More than one regulatory element may be detected at the same time. At least 2, at least 3, at least 4, at least 5, at least 6, at least 7, at least 8, at least 9, at least 10, at least 15, at least 20, or more regulatory elements may be detected at the same time. Each of the regulatory elements may be detected by a set of detection agents. The detectable moiety between the different set of detection agents may be the same. For example, two different sets of detection agents may be used to detect two different regulatory elements and the detectable moieties from the two sets of detection agents may be the same. As such, at least 2, at least 3, at least 4, at least 5, at least 6, at least 7, at least 8, at least 9, at least 10, at least 15, at least 20, or more regulatory elements may be detected at the same time at the same wavelength. Sometimes, the detectable moiety between the different set of detection agents may also be different. For example, two different sets of detection agents may be used to detect two different regulatory elements and the detectable moiety from one set of detection agents may be detected at a different wavelength from the detectable moiety of the second set of detection agents. As such, at least 2, at least 3, at least 4, at least 5, at least 6, at least 7, at least 8, at least 9, at least 10, at least 15, at least 20, or more regulatory elements may be detected at the same time in which each of the regulatory elements may be detected at a different wavelength. The regulatory element may comprise DNA, RNA, polypeptides, or a combination thereof.

Methods of Measuring the Activity of a Regulatory Element

Also described herein is a method of measuring the activity of a target regulatory element. The method may include detection of a regulatory element and one or more products of the regulatory element. One or more products of the regulatory element may also include intermediate products or elements. The method may comprise contacting a cell sample with a first set and a second set of detection agents, in which the first set of detection agents interact with a target regulatory element within the cell and the second set of detection agents interact with at least one product of the target regulatory element, and analyzing a detection profile from the first set and the second set of detection agents, in which the presence or the absence of the at least one product indicates the activity of the target regulatory element.

As discussed herein, a detection agent may comprise a detectable moiety that is capable of generating a light, and a probe portion that is capable of hybridizing to a target site on a regulatory element. Each detection agent within the first set of detection agents may have the same or a different detectable moiety. Each detection agent within the first set of detection agents may have the same detectable moiety. A detectable moiety may comprise a small molecule (e.g., a fluorescent dye). A detectable moiety may comprise a fluorescently labeled polypeptide, a fluorescently labeled nucleic acid probe, and/or a fluorescently labeled polypeptide complex.

The method may also allow photobleaching of the first set and the second set of detection agents, thereby generating a subset of detection agents capable of generating a burst of light. A detection profile may be generated from the detection of a set of light bursts, in which the presence or the absence of the at least one product may indicate the activity of the target regulatory element.

The regulatory element may comprise DNA, RNA, polypeptides, or a combination thereof. The regulatory element may be DNA. The regulatory element may be RNA. The regulatory element may be an enhancer RNA (eRNA). The presence of an eRNA may correlate with target gene transcription that is downstream of eRNA. The regulatory element may be a DNaseI hypersensitive site (DHS). The DHS may be an activated DHS. The pattern of the DHS on a chromatin may correlate to the activity of the chromatin. The regulatory element may be a polypeptide, e.g., a transcription factor, a DNA or RNA-binding protein or binding fragment thereof, or a polypeptide that is involved in chemical modification. The regulatory element may be chromatin.

Target Nucleic Acid Sequence

A target nucleic acid sequence may be a nucleic acid sequence of interest or may encode a DNA, RNA, or protein of interest or a portion thereof. A DNA, RNA, or protein of interest may be a DNA, RNA, or protein produced by a cell or contained within a cell. A target nucleic acid sequence may be incorporated into a structure of a cell. A target nucleic acid sequence may also be associated with a cell. For example, a target nucleic acid sequence may be in contact with the exterior of a cell. A target nucleic acid sequence may be unassociated with a structure of a cell. For example, a target nucleic acid sequence may be a circulating nucleic acid sequence. A target nucleic acid sequence or a portion thereof may be artificially constructed or modified. A target nucleic acid sequence may be a natural biological product. A target nucleic acid sequence may be a short nucleic acid sequence. A target nucleic acid sequence may be a nucleic acid sequence that is from a source that is exogenous to a cell. A target nucleic acid sequence may be an endogenous nucleic acid sequence. A target nucleic acid sequence may be a nucleic acid sequence that comprises a combination of an endogenous nucleic acid sequence and a nucleic acid sequence from a source that is exogenous to a cell. A target nucleic acid sequence may be a chromosomal nucleic acid sequence or fragment thereof. A target nucleic acid sequence may be an episomal nucleic sequence or fragment thereof. A target nucleic acid sequence may be a sequence resulting from somatic rearrangement or somatic hypermutation, such as a nucleic acid sequence from a T cell receptor, B cell receptor, or fragment thereof.

A nucleic acid of a cell or sample, which may comprise the target nucleic acid sequence, may comprise a deoxyribonucleic acid (DNA) or a ribonucleic acid (RNA), or a combination thereof. A nucleic acid may be a chromosome, an oligonucleotide, a plasmid, an artificial chromosome, or a fragment or portion thereof. A nucleic acid may comprise genomic DNA, episomal DNA, complementary DNA, mitochondrial DNA, recombinant DNA, cell-free DNA (cfDNA), messenger RNA (mRNA), pre-mRNA, microRNA (miRNA), transfer RNA (tRNA), transfer messenger RNA (tmRNA), ribosomal RNA (rRNA), heterogeneous nuclear RNA (hnRNA), short interfering RNA (siRNA), anti-sense RNA, or short hairpin RNA (shRNA). A nucleic acid may be single-stranded, double-stranded, or a combination thereof.

A target nucleic acid sequence may comprise a naturally occurring nucleic acid sequence, an artificially constructed nucleic acid sequence (such as an artificially synthesized nucleic acid sequence), or a modified nucleic acid sequence (such as a naturally occurring nucleic acid sequence that has been altered or modified through a natural or artificial process).

A naturally occurring nucleic acid sequence may comprise a nucleic acid sequence present in a cellular sample. A naturally occurring nucleic acid sequence may comprise a nucleic acid sequence present in an unfixed cell. A naturally occurring nucleic acid sequence may comprise a nucleic acid sequence derived from a cellular sample.

A naturally occurring nucleic acid sequence may comprise a nucleic acid sequence present in an acellular sample. A naturally occurring nucleic acid sequence may comprise a nucleic acid sequence derived from an acellular sample. For example, a nucleic acid sequence may be a cell-free DNA sequence present in a bodily fluid (such as a sample of cerebrospinal fluid).

A nucleic acid may comprise a target nucleic acid sequence that is not endogenous to the source (exogenous) from which it was taken or in which it is analyzed.

A nucleic acid may be an artificially synthesized oligonucleotide.

A nucleic acid sequence may comprise one or more modifications. A modification to a nucleic acid sequence may be an insertion, a deletion, or a substitution. A nucleic acid sequence modification comprising an insertion may comprise transformation, transduction, or transfection of a sample. Modification of a nucleic acid sequence may be an artificial modification, resulting from, for instance, genetic engineering or intentional nucleic acid sequence modification during nucleic acid fabrication. A nucleic acid sequence may be the result of somatic rearrangement.

A modification to a nucleic acid sequence comprising an insertion, deletion or substitution may comprise a difference between the nucleic acid sequence and a reference sequence. A reference sequence may be a nucleic acid sequence in a database, an artificial nucleic acid, a nucleic acid sequence of the same cell, a nucleic acid sequence of a cell from the tissue, a nucleic acid sequence from a different tissue of the same subject, or a nucleic acid sequence from a subject of a different species.

A modification to a nucleic acid sequence may comprise a difference in 1 nucleotide (a single nucleotide polymorphism, SNP), at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 25 nucleotides, at least 50 nucleotides, at least 100 nucleotides, at least 250 nucleotides, at least 500 nucleotides, at least 1,000 nucleotides, from 1 to 1,000 nucleotides, from 1 to 500 nucleotides, from 1 to 250 nucleotides, from 1 to 100 nucleotides, from 1 to 50 nucleotides, from 1 to 25 nucleotides, from 1 to 10 nucleotides, from 1 to 9 nucleotides, from 1 to 8 nucleotides, from 1 to 7 nucleotides, from 1 to 6 nucleotides, from 1 to 5 nucleotides, from 1 to 4 nucleotides, from 1 to 3 nucleotides, or from 1 to 2 nucleotides. Modification to a nucleic acid sequence comprising a difference in a plurality of nucleotides may comprise differences in two or more adjacent nucleotides or nucleotide sequences relative to a reference nucleic acid sequence. Modifications to a nucleic acid sequence comprising a difference in a plurality of nucleotides may also comprise differences in two or more non-adjacent nucleotides or nucleotide sequences (such as two or more modifications to the nucleic acid sequence that are separated by at least one nucleotide) relative to a reference nucleic acid sequence.

A target sequence may be assayed in situ or it may be isolated and/or purified from a cellular or acellular sample. For example, a target sequence comprising a nucleic acid may comprise a portion (a region) of genomic DNA located in situ in the nucleus of a fixed (intact) cell. A target sequence may comprise a nucleic acid sequence that is isolated from a sample (such as an aliquot of cerebrospinal fluid).

Detection Agents

Detection agents may be utilized to detect nucleic acid sequence of interest. A detection agent may comprise a probe portion. The probe portion may include a probe, or a combination of probes. The probe portion may comprise a nucleic acid molecule, a polypeptide, or a combination thereof. The detection agents may further comprise a detectable moiety. The detectable moiety may comprise a fluorophore. A fluorophore may be a molecule that may absorb light at a first wavelength and transmit or emit light at a second wavelength. The fluorophore may be a small molecule (such as a dye) or a fluorescent polypeptide. The detectable moiety may be a fluorescent small molecule (such as a dye). The detectable moiety may not contain a fluorescent polypeptide. The detection agent may further comprise a conjugating moiety. The conjugating moiety may allow attachment of the detection agent to a nucleic acid sequence of interest. The detection agent may comprise a probe that is synthesized with direct dye incorporation at the 3' end.

Figure 24:
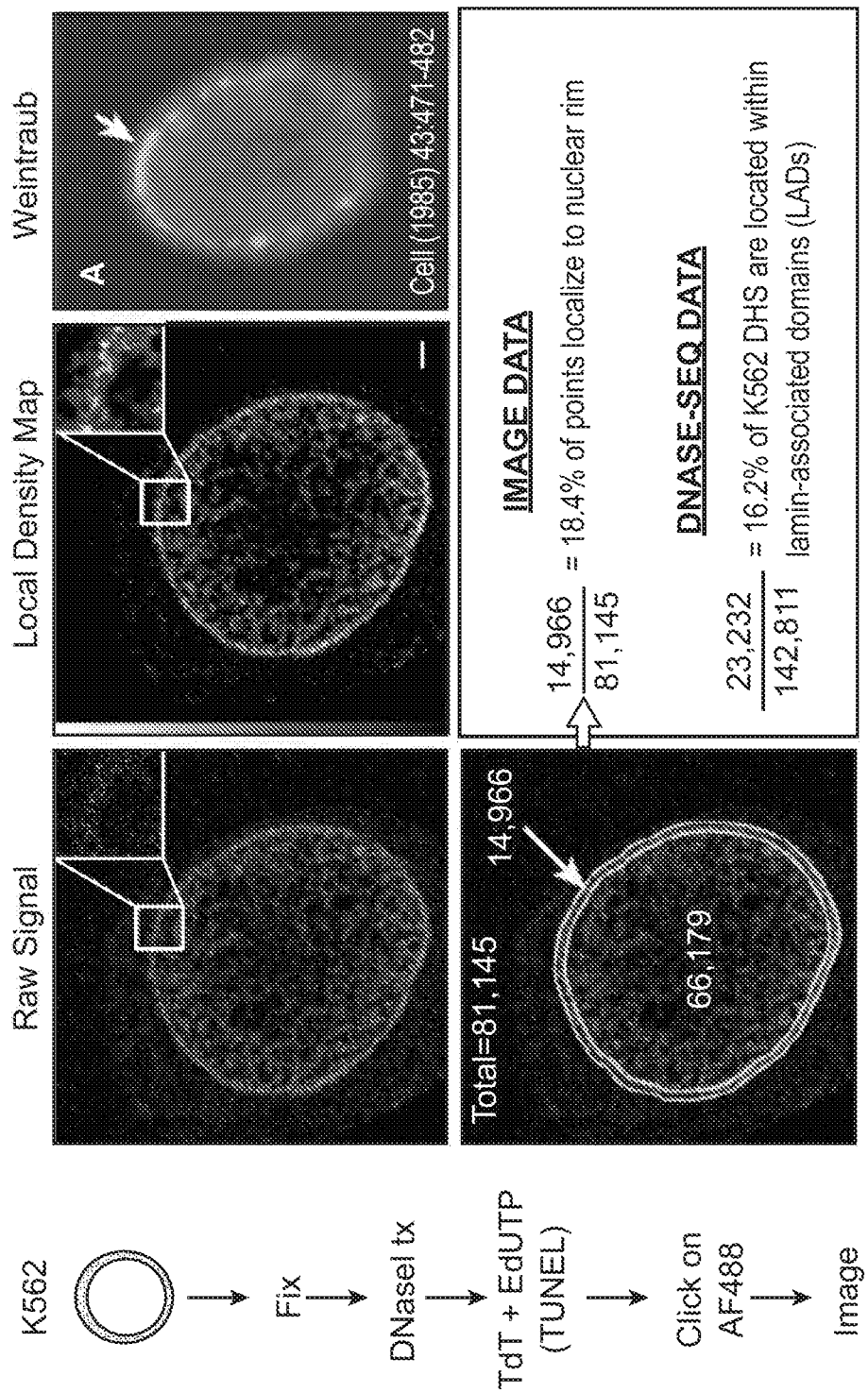
FIG. 24 shows a schematic of a detection agent comprising a probe, a detectable moiety, and a conjugating moiety.
Figure 25:
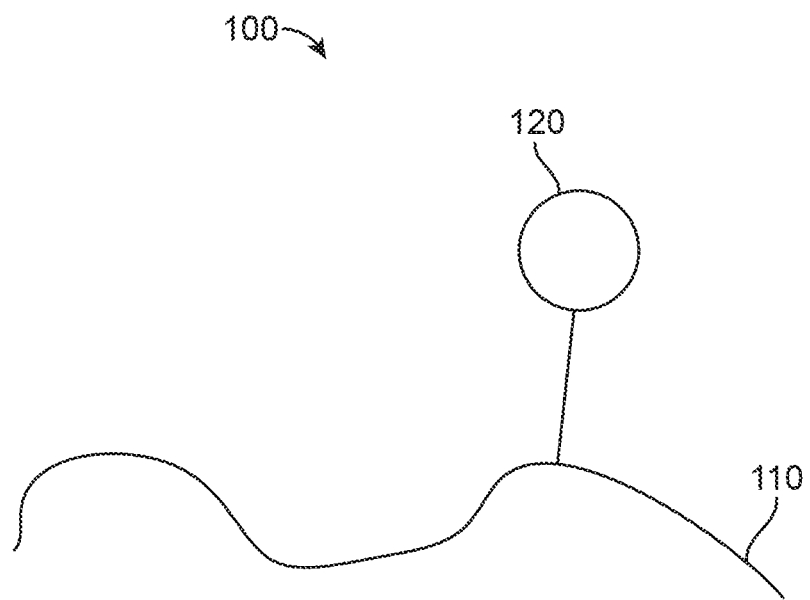
FIG. 25 shows a flowchart for a method of detecting a nucleic acid sequence.

FIG. 24 shows a schematic of a detection agent 100 for use with a Nano-FISH procedure. The detection agent may comprise a probe portion 110, as described herein. The detection agent may comprise a detectable moiety 120, as described herein. The detection agent may comprise a conjugating moiety 130, as described herein.

Probes

A detection agent may comprise a probe portion. A probe portion may comprise a probe or a combination of probes. A probe may be a nucleic acid probe, a polypeptide probe, or a combination thereof. A probe portion may be an unconjugated probe that does not contain a detectable moiety. A probe portion may be a conjugated probe which comprises a single probe with a detectable moiety, or two or more probes in which at least one probe may be an unconjugated probe bound to at least a second probe which comprises a detectable moiety.

A probe may be a nucleic acid probe. The nucleic acid probe may be a DNA probe, a RNA probe, or a combination thereof. The nucleic acid probe may be a DNA probe. The nucleic acid probe may be a RNA probe. The nucleic acid probe may be a double stranded nucleic acid probe, a single stranded nucleic acid probe, or may contain single-stranded and/or double stranded portions. The nucleic acid probe may further comprise overhangs on one or both termini, may further comprises blunt ends on one or both termini, or may further form a hairpin.

The nucleic acid probe may be at least 10, at least 15, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, at least 80, at least 90, at least 100, or more nucleotides in length. The nucleic acid probe may be about 10, about 15, about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60, about 65, about 70, about 80, about 90, or about 100 nucleotides in length. The nucleic acid probe may be about 20 nucleotides in length. The nucleic acid probe may be about 21 nucleotides in length. The nucleic acid probe may be about 22 nucleotides in length. The nucleic acid probe may be about 23 nucleotides in length. The nucleic acid probe may be about 24 nucleotides in length. The nucleic acid probe may be about 25 nucleotides in length. The nucleic acid probe may be about 26 nucleotides in length. The nucleic acid probe may be about 27 nucleotides in length. The nucleic acid probe may be about 28 nucleotides in length. The nucleic acid probe may be about 29 nucleotides in length. The nucleic acid probe may be about 30 nucleotides in length. The nucleic acid probe may be about 31 nucleotides in length. The nucleic acid probe may be about 32 nucleotides in length. The nucleic acid probe may be about 33 nucleotides in length. The nucleic acid probe may be about 34 nucleotides in length. The nucleic acid probe may be about 35 nucleotides in length. The nucleic acid probe may be about 36 nucleotides in length. The nucleic acid probe may be about 37 nucleotides in length. The nucleic acid probe may be about 38 nucleotides in length. The nucleic acid probe may be about 39 nucleotides in length. The nucleic acid probe may be about 40 nucleotides in length. The nucleic acid probe may be about 45 nucleotides in length. The nucleic acid probe may be about 50 nucleotides in length. The nucleic acid probe may be about 55 nucleotides in length. The nucleic acid probe may be about 60 nucleotides in length.

Table 1 lists exemplary probe nucleotide sequences according to the present disclosure.

TABLE 1

Exemplary Probe Nucleotide Sequences

| SEQ ID NO | Nucleotide Sequence |
| --- | --- |
| SEQ ID NO: 1 | TTTCCCTTGCTCTTCATGATTTTAACAACATGATGGATTT |
| SEQ ID NO: 2 | CCCTGCCCCCCATTAACTCACATCCTGAATTTTATGTTTA |
| SEQ ID NO: 3 | GCACTTCATCATCGTCTTTGAAGTCCCCTTCTTGTCCTCC |
| SEQ ID NO: 4 | TATGATGAACACCATGCACCACATGCAGGTTCTGGTGAAG |
| SEQ ID NO: 5 | GATACAAAAGAATATTGGTATGTATGTTGCACAGACTCAT |
| SEQ ID NO: 6 | CCTATTTCCCCCACACAGCCTTCCCACATTGGCCAACCCT |
| SEQ ID NO: 7 | TACAAAGGGCTTCTCTGGCCAGAGAGAGCCGGTGTCTGCT |
| SEQ ID NO: 8 | TGGGGGGGTTAATGGAGTTATGGACTGGGATGGGCAGCCT |
| SEQ ID NO: 9 | ACCTACCTAGGGAACTCTTTCTCCCTGGCACTAGGCTAGT |
| SEQ ID NO: 10 | ACTGACTGAGCTGACCTCCAGTACAGGGCCTGAGGCCACT |
| SEQ ID NO: 11 | CTGGGAGCTAAATAGAAGCAAATATCCCCAGGCCTGGGTG |
| SEQ ID NO: 12 | ATGCGTCAAGCAACTACACTCCCACAGTAAACTGGGAACC |
| SEQ ID NO: 13 | CAGCTCCTTGGCAGCCTAGGCTCTAGCTCAACATCTGCTT |
| SEQ ID NO: 14 | TGCTGGAGTCGCACCAACCTGGCTCTGCCTATCTCCAGCA |
| SEQ ID NO: 15 | CTCTGTAGGCTGCACAACGTGGAACAGATGAAAGGAACCA |
| SEQ ID NO: 16 | TGGGGTAAATTATAATCATGAAATTCCGTCAAGCTTGAAT |

TABLE 1-continued

Exemplary Probe Nucleotide Sequences

| SEQ ID NO | Nucleotide Sequence |
|---|---|
| SEQ ID NO: 17 | AACATATTTAATATGGCATATTCAAATGACAGAAAGTACG |
| SEQ ID NO: 18 | CTTTATTCTTGCTAATGTTGACTCCTTAGCAAAGATAATT |
| SEQ ID NO: 19 | TGATCTTTGCTAAACTCTTCAGGAATAAATGAACATTTCC |
| SEQ ID NO: 20 | TTTTCAAGCAGTTAAGAAGCAAGAATTAATGACTCGAATA |
| SEQ ID NO: 21 | ATGAGAGTGTTGACTGATGAAGGGCTCCTATACGCGGGTT |
| SEQ ID NO: 22 | TCTTTCCCATCTGTTTCCCGGCCCCTACCAGAAATAAGTG |
| SEQ ID NO: 23 | ATGAACCTCCCTCGCTCCAAGACCAGAGCTCCTAGGAAGT |
| SEQ ID NO: 24 | TCTTTATTTTATTGGCCACAATTGAACATAGGTATAATTT |
| SEQ ID NO: 25 | CAGAAGCAAGCCCTGATCAAGGAAACCATTCACACTTGAT |
| SEQ ID NO: 26 | GTGGCTTTTGCTCAAAGTGAGGACGTTATCAGCTCTGCCC |
| SEQ ID NO: 27 | CTTTAAACAAAAACTAAAGGCGTAAGGAAAGATAACTACT |
| SEQ ID NO: 28 | CAGTTGCCACACTTTTTTTCACTGCTAAAGTTCGTAATGA |
| SEQ ID NO: 29 | GGCAATCAGAAGTATTTTGGTTGCTTCTAGGTCAGAATGA |
| SEQ ID NO: 30 | GGCAGCAAACTTGTTTAGGTATGATTCATCATTGTCTGCT |
| SEQ ID NO: 31 | CTACAAAACAATGAGTCTGATTACGACCCACAGAAATGAA |
| SEQ ID NO: 32 | CCTCCCACAGACCCAAACATGCTGCTGCAAATGTCTCACT |
| SEQ ID NO: 33 | GGACAAGCACACACATCGCTGGGAAGATCTGCAAGCCTCC |
| SEQ ID NO: 34 | TAAACCTGGATAACAAGAACACTGTTTCCACTGCGCTAGT |
| SEQ ID NO: 35 | TCATCACGATGACAATGGACAAGCCATATCCCTAACAGGG |
| SEQ ID NO: 36 | TTTCCATGACACCAGGACCGTAAAGCACCTTTTACACCGT |
| SEQ ID NO: 37 | AATTGGGATGTGCAAAACCTCTTAACTTGTAGCACCAAGT |
| SEQ ID NO: 38 | TCTTGTGTTATTCGCCTGCATTGAAATCCCATCCCAATCC |
| SEQ ID NO: 39 | TGAGTGATCTCTTTGCTGATCATAAACATATTCCTCCATC |
| SEQ ID NO: 40 | TGCATTCATTACTAAATACACAGGGCATAGCACATAGTAA |
| SEQ ID NO: 41 | CTTCAATGTTGCCAGGAAAATCCTTGCAGGAATCACACCC |
| SEQ ID NO: 42 | ATTTTTTTCTAAAGCTTTAGGAAATACACACGTTTCCCCT |
| SEQ ID NO: 43 | AGAGTAATCTTCAACAATCCTTGGTCTAAACACACACAAG |
| SEQ ID NO: 44 | CCCAGGGACCCACGCCAAGCTCACCGCACCTTCCACCAAA |
| SEQ ID NO: 45 | AGCTCCTGTACTAGCTGGTGGGGTGTGGAGCACACAGCCC |
| SEQ ID NO: 46 | TCACACAGGGAAAGTGAGGCTTGGTGGTTGATTTGAGCAA |
| SEQ ID NO: 47 | CCTTCCAACAGCCGTGTGAGACAAGAGGTCTTATCCTCTT |
| SEQ ID NO: 48 | ACAAGGGTCACTGAGCACATGCCATGTGTTGGGCACAGTG |
| SEQ ID NO: 49 | GTCTCCTAAGTCTCATTCTTTTCTTAGGATTCTTCAGATC |
| SEQ ID NO: 50 | TCCGCCTAAGTAAAACATAAAATTACTTAAGCTGCGTAAA |
| SEQ ID NO: 51 | CATTTTGACCTGATTATCTTTGTCTATAAGTCTTAAGCCA |
| SEQ ID NO: 52 | CCGGTTCCTCCACCCTCACTGCCCCAACAACTGAAAGAAG |
| SEQ ID NO: 53 | ACAGTGTGTTGAAAGAATCCATAACTCTTTCTTTCCAGCC |
| SEQ ID NO: 54 | GAAGTTTCATCTTTATCAAAATCTCCATTCCCAGGCGGAC |

TABLE 1-continued

Exemplary Probe Nucleotide Sequences

| SEQ ID NO | Nucleotide Sequence |
|---|---|
| SEQ ID NO: 55 | AAGTCCATTTTTTTAAGCTTTGCGCTTCAGCTCCAGAACA |
| SEQ ID NO: 56 | TCTTCGTTATGAATACAAATAGGAAAACAATCAGACCCAA |
| SEQ ID NO: 57 | TCCTCGGGGCATTCTAGAACCGTAGCAGACCTGCTTACAT |
| SEQ ID NO: 58 | TCCTTATGTGGGAAAATAAAGAGGATAGACAGATTTGATT |
| SEQ ID NO: 59 | AGCTGCGAGTCCCTAACAGACTTCCAGGACAGCTGAAAAA |
| SEQ ID NO: 60 | AGGACAAGGGAGAGACGCCCACCCGCCTCTGTCAGGGATA |
| SEQ ID NO: 61 | AATCCATGAGGGTGACATACACATCCTTACTGTTCCCACA |
| SEQ ID NO: 62 | ACTTCCTTCCCTGAGATGCCCATCCTTTGATTCTGGGATT |
| SEQ ID NO: 63 | GCTCCCGGATAAATTAATTACCGTGACCCTGAGCTGCTTC |
| SEQ ID NO: 64 | TAGACTAAGAGAATCTAATTTGTGGCAAAGATCTTGAGTG |
| SEQ ID NO: 65 | TGAAGGATGACTAAGAGCTTCCCTATAAACCCCATACTGG |
| SEQ ID NO: 66 | AGCCAGGACTATAGAGTTTCAGAAAAGGGAGAAAATTCTA |
| SEQ ID NO: 67 | TGCTGCTAATTTAAGTTTCTGGCAAGTCAAAATAAATCTC |
| SEQ ID NO: 68 | CGAAAACCATCAATTAACTAGAATGATCAGGAAATTGCGT |
| SEQ ID NO: 69 | TTTATTTAGTCCCCAGGGTGTATGAAGTGCTCTTCCAGGC |
| SEQ ID NO: 70 | GGTCCTTCTTGGTACCGATATTGCCATATTGGCTGGACAT |
| SEQ ID NO: 71 | TGGCTTGGTAGGATGCACTCACATGGGCTGTAGTAATACT |
| SEQ ID NO: 72 | TATCACCAGCATAACTTGTGGTTCTTCAGCCAGTAATTTC |
| SEQ ID NO: 73 | GAACAACTGGGTATCTACAGGCAAAGAAATGAACCTTGAC |
| SEQ ID NO: 74 | TAGGTACTGTTGTGTCCCTATATATTTGACTTGGTAATAA |
| SEQ ID NO: 75 | TATGTGAACATCGGTGAATATCATAATTTATTATGCAAAC |
| SEQ ID NO: 76 | AGCTGAACACTCTTTGTGGTCCTCTTGAAGCCTAGAATTA |
| SEQ ID NO: 77 | CCCCACCTCACTGCCCCCCAGTTCTGACTCACGGTGTCCC |
| SEQ ID NO: 78 | ACTCCCATCACCTGGCCAGCTTGGCTGTCCCCTGACCCAC |
| SEQ ID NO: 79 | GGCTGCCCAGCTGCCCAGCAGCAAAACTGCATAGGAACTC |
| SEQ ID NO: 80 | GCCCAGGACGCCAAGTGTCACCACCCTCTCCCCAGGCAGG |
| SEQ ID NO: 81 | CACAAGGTCAGCTCCACCCGTGGGTCAGTGTGCCCCAGAT |
| SEQ ID NO: 82 | GGAGACAAAACGGGCACCCAGCCCAGTCATGCCCGTGCCT |
| SEQ ID NO: 83 | CTGAAATCAGTCAGCAGTTTCGGTGAGTCTGCAGCTGACA |
| SEQ ID NO: 84 | CGCCACATTTGGGGCTGGGAGAGATGTCACAGGGGCTGAC |
| SEQ ID NO: 85 | CACATGTTCTCTGCATAGGTTTTTAAGCAGCCAGCAGCTG |
| SEQ ID NO: 86 | TTTAAAATGAAAACCCACACTTCCAAAATAGCACTTGAGT |
| SEQ ID NO: 87 | AACATGTTTGTGTAATTAAGCATTTTAAAATCATAACCAT |
| SEQ ID NO: 88 | TGCTTATCTGTGCTTTTTATGTTCCACCCCCCACCACCA |
| SEQ ID NO: 89 | ATTAATAATAATTCTGTGTTTATGGGGATTGCAGATACAT |
| SEQ ID NO: 90 | CCAGCTTTGTGTCTTCATGACCCAACTGGAGTAAGAATGG |
| SEQ ID NO: 91 | AAAGACCTCATTTGCAGCATGGTTAGCAGTGTCAAACATT |
| SEQ ID NO: 92 | TCTCGTAGCACTGGCTGCAGCCGGCCTGTGTGTGCCCACC |

TABLE 1-continued

Exemplary Probe Nucleotide Sequences

| SEQ ID NO | Nucleotide Sequence |
|---|---|
| SEQ ID NO: 93 | GCCTTCATCCTGAACGGCTGACCAGCGGAAACAAAAGATC |
| SEQ ID NO: 94 | ATGGCCAGATAACAGTGTTTAGACATGTCTTTGATGTTTT |
| SEQ ID NO: 95 | CCCTGACTGTGTAAGGGGTCTCTCTCCATGGGGAATAGAG |
| SEQ ID NO: 96 | CTGAGCTTAGCTTCTACTGTGCTGTTAATTTCAGGCAAGA |
| SEQ ID NO: 97 | AGATCAATAATATTTGCATTAGCTACTTACATCAGTCTCT |
| SEQ ID NO: 98 | TAATTGCAGAAAACTTATAAAGCATGGAAGAATACAAAAC |
| SEQ ID NO: 99 | AAACAAATTCCTCTACCTGGACATGACTGTTGTTAGCATT |
| SEQ ID NO: 100 | GGGAGATTCTTCATATCCTTTTAATGTAGATATGCACATT |
| SEQ ID NO: 101 | ACAAAAAAGGCTATCATATTGTACATATAACTTTGCTGTA |
| SEQ ID NO: 102 | TCTGCTAGGAACCTGTACCCATGTCATTACTGTAAGCATT |
| SEQ ID NO: 103 | ACTACTCAAATTTTAGTATCTGCAGATATCAGATATCCTT |
| SEQ ID NO: 104 | TGAAATGGTATTGTTGCCCTTTCTGATTAGTAAAGTATAC |
| SEQ ID NO: 105 | TTATAATCTAGCAAGGTTAGAGATCATGGATCACTTTCAG |
| SEQ ID NO: 106 | ACAGCTTGCCTCCGATAAGCCAGAATTCCAGAGCTTCTGG |
| SEQ ID NO: 107 | TCAATCAACCTGATAGCTTAGGGGATAAACTAATTTGAAG |
| SEQ ID NO: 108 | GATCATGAAGGATGAAAGAATTTCACCAATATTATAATAA |
| SEQ ID NO: 109 | TTTAGCCATCTGTATCAATGAGCAGATATAAGCTTTACAC |
| SEQ ID NO: 110 | AGGGGTAGATTATTTATGCTGCCCATTTTTAGACCATAAA |
| SEQ ID NO: 111 | CACTACCATTTCACAATTCGCACTTTCTTTCTTTGTCCTT |
| SEQ ID NO: 112 | GCTCCATCAAATCATAAAGGACCCACTTCAAATGCCATCA |
| SEQ ID NO: 113 | TCCTACTTTCAGGAACTTCTTTCTCCAAACGTCTTCTGCC |
| SEQ ID NO: 114 | AATTCTATTTTTCTTCAACGTACTTTAGGCTTGTAATGT |
| SEQ ID NO: 115 | TAAGATGCAAATAGTAAGCCTGAGCCCTTCTGTCTAACTT |
| SEQ ID NO: 116 | CTGTGTTTCAGAATAAAATACCAACTCTACTACTCTCATC |
| SEQ ID NO: 117 | GAAACCATGTTTATCTCAGGTTTACAAATCTCCACTTGTC |
| SEQ ID NO: 118 | CTTTGGAAAAGTAATCAGGTTTAGAGGAGCTCATGAGAGC |
| SEQ ID NO: 119 | GCTGAATCCCCAACTCCCAATTGGCTCCATTTGTGGGGA |
| SEQ ID NO: 120 | GGTGTTATGAACTTAACGCTTGTGTCTCCAGAAAATTCAC |
| SEQ ID NO: 121 | AGTTAATGCACGTTAATAAGCAAGAGTTTAGTTTAATGTG |
| SEQ ID NO: 122 | TAATTGAGAAGGCAGATTCACTGGAGTTCTTATATAATTG |
| SEQ ID NO: 123 | CACGGTCAGATGAAAATATAGTGTGAAGAATTTGTATAAC |
| SEQ ID NO: 124 | CACAAGTCAGCATCAGCGTGTCATGTCTCAGCAGCAGAAC |
| SEQ ID NO: 125 | GGAGGTGGGACTTAGGTGAAGGAAATGAGCCAGCAGAAG |
| SEQ ID NO: 126 | GTCACAGCATTTCAAGGAGGAGACCTCATTGTAAGCTTCT |
| SEQ ID NO: 127 | AAAGAGGTGAAATTAATCCCATACCCTTAAGTCTACAGAC |
| SEQ ID NO: 128 | CTTTACTAAGGAACTTTTCATTTTAAGTGTTGACGCATGC |
| SEQ ID NO: 129 | CAGGTTTTCTTTCCACGGTAACTACAATGAAGTGATCCT |
| SEQ ID NO: 130 | GCTCTACAGGGAGGTTGAGGTGTTAGAGATCAGAGCAGGA |

TABLE 1-continued

Exemplary Probe Nucleotide Sequences

| SEQ ID NO | Nucleotide Sequence |
|---|---|
| SEQ ID NO: 131 | TACTATTTCCAACGGCATCTGGCTTTTCTCAGCCCTTGTG |
| SEQ ID NO: 132 | AAGGTTTAGGCAGGGATAGCCATTCTATTTTATTAGGGC |
| SEQ ID NO: 133 | AGGGGCTCAACGAAGAAAAAGTGTTCCAAGCTTTAGGAAG |
| SEQ ID NO: 134 | GGGCTGAACCCCCTTCCCTGGATTGCAGCACAGCAGCGAG |
| SEQ ID NO: 135 | CTGACGTCATAATCTACCAAGGTCATGGATCGAGTTCAGA |
| SEQ ID NO: 136 | GAAGGTAGAGCTCTCCTCCAATAAGCCAGATTTCCAGAGT |
| SEQ ID NO: 137 | CACCAATATTATTATAATTCCTATCAACCTGATAGGTTAG |
| SEQ ID NO: 138 | AGATATAAGCCTTACACAGGATTATGAAGTCTGAAAGGAT |
| SEQ ID NO: 139 | ACATGTATCTTTCTGGTCTTTTAGCCGCCTAACACTTTGA |
| SEQ ID NO: 140 | CAAAGAACAAGTGCAATATGTGCAGCTTTGTTGCGCAGGT |
| SEQ ID NO: 141 | TATTATTATGTGAGTAACTGGAAGATACTGATAAGTTGAC |
| SEQ ID NO: 142 | TAAAAATCTTTCTCACCCATCCTTAGATTGAGAGAAGTCA |
| SEQ ID NO: 143 | TTGGGTTCACCTCAGTCTCTATAATCTGTACCAGCATACC |
| SEQ ID NO: 144 | CACACCCATCTCACAGATCCCTATCTTAAAGAGACCCTA |
| SEQ ID NO: 145 | ATGGAACCCAACCAGACTCTCAGATATGGCCAAAGATCTA |
| SEQ ID NO: 146 | GACACCAGTCTCTGACACATTCTTAAAGGTCAGGCTCTAC |
| SEQ ID NO: 147 | AGAGATTCAAAAGATTCACTTGTTTAGGCCTTAGCGGGCT |
| SEQ ID NO: 148 | TCCTTAGTCTGAGGAGGAGCAATTAAGATTCACTTGTTTA |
| SEQ ID NO: 149 | TAAATGGGGAAGTTGTTTGAAAACAGGAGGGATCCTAGAT |
| SEQ ID NO: 150 | GGGTTTATACATGACTTTTAGAACACTGCCTTGGTTTTTG |
| SEQ ID NO: 151 | AACTCTTAAAAGATATTGCCTCAAAAGCATAAGAGGAAAT |
| SEQ ID NO: 152 | AAATCGAGGAATAAGACAGTTATGGATAAGGAGAAATCAA |
| SEQ ID NO: 153 | TCAGTTAGGATTTAATCAATGTCAGAAGCAATGATATAGG |
| SEQ ID NO: 154 | CTTGAAAACACTTGAAATTGCTTGTGTAAAGAAACAGTTT |
| SEQ ID NO: 155 | ATAATCTTCAGAGGAAAGTTTTATTCTCTGACTTATTTAA |
| SEQ ID NO: 156 | AGATTCCTTCTGTCATTTTGCCTCTGTTCGAATACTTTCT |
| SEQ ID NO: 157 | ATTTCAGCTTCTAAACTTTATTTGGCAATGCCTTCCCATG |
| SEQ ID NO: 158 | GCAGGAGTTTGTTTTCTTCTGCTTCAGAGCTTTGAATTTA |
| SEQ ID NO: 159 | ACATATCAACGGCACTGGTTCTTTATCTAACTCTCTGGCA |
| SEQ ID NO: 160 | TTATGCTTCCCTGAAACAATACCACCTGCTATTCTCCACT |
| SEQ ID NO: 161 | TTCTCACTCCCTACCACTGAGGACAAGTTTATGTCCTTAG |
| SEQ ID NO: 162 | TTAGAGATTATGTCATTACCAGAGTTAAAATTCTATAATG |
| SEQ ID NO: 163 | GGTCATTCTTAGAATAGTAATCCAGCCAATAGTACAGGTT |
| SEQ ID NO: 164 | CAGGCAATAAGGGCTTTTTAAGCAAAACAGTTGTGATAAA |
| SEQ ID NO: 165 | ATGATGGGCACTGAAGGTTAAAACTTGAGTCTGTCAACTT |
| SEQ ID NO: 166 | AACTCATAAATATCCCATTTTCCGCTGAAATATAGCTTTA |
| SEQ ID NO: 167 | CCTGGTTTCTTTGACCTTTTGGGACCTTGAGTAAGTAAAG |
| SEQ ID NO: 168 | CTTCATTTATTTTCATGATTAAAATTCTAAGAAATTCTTG |

TABLE 1-continued

Exemplary Probe Nucleotide Sequences

| SEQ ID NO | Nucleotide Sequence |
| --- | --- |
| SEQ ID NO: 169 | TTTTTAATTAAATTGCATTGCCTAATGTATTTATGAACTA |
| SEQ ID NO: 170 | CATAGAAATAAAACAATACTCTGAAGTAGTTCAGAATGTG |
| SEQ ID NO: 171 | CAATTTATATAAAGAGTTAATTCAAATGAGACTATTTTAA |
| SEQ ID NO: 172 | AGGGCTTTGAATCTTATGTCTAGAAATTTTGAAAAACCTC |
| SEQ ID NO: 173 | TATATGCTAAGATTCCACCTCTAGTGCTAGAACTGAGAAG |
| SEQ ID NO: 174 | TGACTTGGTGATCTTTTTTAAATTCTGAAACAACAGCAAC |
| SEQ ID NO: 175 | AGCTAAGGACTTTTTCTTGCCTATGCATGCTATCTTCAGT |
| SEQ ID NO: 176 | TGATTATTTAGTATTGAAACTATAACATAGTATGTTTCCT |
| SEQ ID NO: 177 | AAAAAATGTGTATTTCTCTGGAGAAGGTTAAAACTGAGGA |
| SEQ ID NO: 178 | CAAGTGAGCAAGGCTTAAATGGAAGAAGCAATGATCTCGT |
| SEQ ID NO: 179 | CCACCTTCATTAACGAGATCATCCATCATGAGGAAATATG |
| SEQ ID NO: 180 | ACCAGGCCCCTCTGTTTTGTGTCACTAAGGGTGAGGATG |
| SEQ ID NO: 181 | ATGATTTTTCCCTCCCCCGGGCTTCTTTTAGCCATCAATA |
| SEQ ID NO: 182 | TAGCCCCACAGGAGTTTGTTCTGAAAGTAAACTTCCACAA |
| SEQ ID NO: 183 | AAGCTTATTGAGGCTAAGGCATCTGTGAAGGAAAGAAACA |
| SEQ ID NO: 184 | CTCTAAACCACTATGCTGCTAGAGCCTCTTTTCTGTACTC |
| SEQ ID NO: 185 | CTCATTCAGACACTAGTGTCACCAGTCTCCTCATATACCT |
| SEQ ID NO: 186 | TATTTTCTTCTTCTTGCTGGTTTAGTCATGTTTTCTGGGA |
| SEQ ID NO: 187 | GGCAAACCCATTATTTTTTTCTTTAGACTTGGGATGGTGA |
| SEQ ID NO: 188 | TGGGCAGCGTCAGAAACTGTGTGTGGATATAGATAAGAGC |
| SEQ ID NO: 189 | GACTATGCTGAGCTGTGATGAGGGAGGGGCCTAGCTAAAG |
| SEQ ID NO: 190 | TGAGAGTCAGAATGCTCCTGCTATTGCCTTCTCAGTCCCC |
| SEQ ID NO: 191 | TTGGTTTCTACACAAGTAGATACATAGAAAAGGCTATAGG |
| SEQ ID NO: 192 | TGTTTGAGAGTCCTGCATGATTAGTTGCTCAGAAATGCCC |
| SEQ ID NO: 193 | TTACAAATATGTGATTATCATCAAAACGTGAGGGCTAAAG |
| SEQ ID NO: 194 | CAGATAACTTGCAAGTCCTAGGATACCAGGAAAATAAATT |
| SEQ ID NO: 195 | AGCATTATGTCTGTCTGTCATTGTTTTTCATCCTCTTGTA |
| SEQ ID NO: 196 | TTCACAGTTACCCACACAGGTGAACCCTTTTAGCTCTCCT |
| SEQ ID NO: 197 | GAATGTTTCTTTCCTCTCAGGATCAGAGTTGCCTACATCT |
| SEQ ID NO: 198 | AATGCACCAAGACTGGCCTGAGATGTATCCTTAAGATGAG |
| SEQ ID NO: 199 | TCCCAGTAGCACCCCAAGTCAGATCTGACCCCGTATGTGA |
| SEQ ID NO: 200 | GTGTCCTCTAACAGCACAGGCCTTTTGCCACCTAGCTGTC |
| SEQ ID NO: 201 | GGCAAACAAGGTTTGTTTTCTTTTCCTGTTTTCATGCCTT |
| SEQ ID NO: 202 | TTCCATATCCTTGTTTCATATTAATACATGTGTATAGATC |
| SEQ ID NO: 203 | AAATCTATACACATGTATTAATAAAGCCTGATTCTGCCGC |
| SEQ ID NO: 204 | AGGTATAGAGGCCACCTGCAAGATAAATATTTGATTCACA |
| SEQ ID NO: 205 | CTAATCATTCTATGGCAATTGATAACAACAAATATATATA |
| SEQ ID NO: 206 | ATAATATATTCTAGAATATGTCACATTCTGTCTCAGGCAT |

TABLE 1-continued

Exemplary Probe Nucleotide Sequences

| SEQ ID NO | Nucleotide Sequence |
|---|---|
| SEQ ID NO: 207 | TTTCTTTATGATGCCGTTTGAGGTGGAGTTTTAGTCAGGT |
| SEQ ID NO: 208 | AGCTTCTCCTTTTTTTGCCATCTGCCCTGTAAGCATCCT |
| SEQ ID NO: 209 | GGGACCCAGATAGGAGTCATCACTCTAGGCTGAGAACATC |
| SEQ ID NO: 210 | CACACACCCTAAGCCTCAGCATGACTCATCATGACTCAGC |
| SEQ ID NO: 211 | CTGTGCTTGAGCCAGAAGGTTTGCTTAGAAGGTTACACAG |
| SEQ ID NO: 212 | AACTGCTCATGCTTGGACTATGGGAGGTCACTAATGGAGA |
| SEQ ID NO: 213 | CAGAAATGTAACAGGAACTAAGGAAAAACTGAAGCTTATT |
| SEQ ID NO: 214 | CAGAGATGAGGATGCTGGAAGGGATAGAGGGAGCTGAGCT |
| SEQ ID NO: 215 | AAAAGTATAGTAATCATTCAGCAAATGGTTTTGAAGCACC |
| SEQ ID NO: 216 | GTATCTTATTCCCCACAAGAGTCCAAGTAAAAAATAACAG |
| SEQ ID NO: 217 | GAAAAGAATGTTTCTCTCACTGTGGATTATTTTAGAGAGT |
| SEQ ID NO: 218 | AATGGTCAAGATTTTTTAAAAATTAAGAAAACATAAGTT |
| SEQ ID NO: 219 | CTTGAGAAATGAAAATTTATTTTTTTGTTGGAGGATACCC |
| SEQ ID NO: 220 | TCTATCTCCCATCAGGGCAAGCTGTAAGGAACTGGCTAAG |
| SEQ ID NO: 221 | AGTGAGACAGAGTGACTTAGTCTTAGAGGCCCCACTGGTA |
| SEQ ID NO: 222 | GATGAGAAGGCACCTTCATCACTCATCACAGTCAGCTCTG |
| SEQ ID NO: 223 | TCTCCTCTCTCCTTTCTCATCAGAAATTTCATAAGTCTAC |
| SEQ ID NO: 224 | GTCAGGCAGATCACATAAGAAAAGAGGATGCCAGTTAAGG |
| SEQ ID NO: 225 | GTTGCTGTTAGACAATTTCATCTGTGCCCTGCTTAGGAGC |
| SEQ ID NO: 226 | TCTTTAATGAAAGCTAAGCTTTCATTAAAAAAAGTCTAAC |
| SEQ ID NO: 227 | TGCATTCGACTTTGACTGCAGCAGCTGGTTAGAAGGTTCT |
| SEQ ID NO: 228 | GAGGAGGGTCCCAGCCCATTGCTAAATTAACATCAGGCTC |
| SEQ ID NO: 229 | ACTGGCAGTATATCTCTAACAGTGGTTGATGCTATCTTCT |
| SEQ ID NO: 230 | CTTGCCTGCTACATTGAGACCACTGACCCATACATAGGAA |
| SEQ ID NO: 231 | ATAGCTCTGTCCTGAACTGTTAGGCCACTGGTCCAGAGAG |
| SEQ ID NO: 232 | CATCTCCTTTGATCCTCATAATAACCCTATGAGATAGACA |
| SEQ ID NO: 233 | TATTACTCTTACTTTATAGATGATGATCCTGAAAACATAG |
| SEQ ID NO: 234 | CAAGGCACTTGCCCCTAGCTGGGGTATAGGGGAGCAGTC |
| SEQ ID NO: 235 | GTAGTAGTAGAATGAAAAATGCTGCTATGCTGTGCCTCCC |
| SEQ ID NO: 236 | CTTTCCCATGTCTGCCCTCTACTCATGGTCTATCTCTCCT |
| SEQ ID NO: 237 | CCTGGGAGTCATGGACTCCACCCAGCACCACCAACCTGAC |
| SEQ ID NO: 238 | CCACCTATCTGAGCCTGCCAGCCTATAACCCATCTGGGCC |
| SEQ ID NO: 239 | TAGCTGGTGGCCAGCCCTGACCCCACCCCACCCTCCCTGG |
| SEQ ID NO: 240 | TCTGATAGACACATCTGGCACACCAGCTCGCAAAGTCACC |
| SEQ ID NO: 241 | GGGTCTTGTGTTTGCTGAGTCAAAATTCCTTGAAATCCAA |
| SEQ ID NO: 242 | TTAGAGACTCCTGCTCCCAAATTTACAGTCATAGACTTCT |
| SEQ ID NO: 243 | GGCTGTCTCCTTTATCCACAGAATGATTCCTTTGCTTCAT |
| SEQ ID NO: 244 | CCATCCATCTGATCCTCCTCATCAGTGCAGCACAGGGCCC |

TABLE 1-continued

Exemplary Probe Nucleotide Sequences

| SEQ ID NO | Nucleotide Sequence |
|---|---|
| SEQ ID NO: 245 | GCAGTAGCTGCAGAGTCTCACATAGGTCTGGCACTGCCTC |
| SEQ ID NO: 246 | ATGTCCGACCTTAGGCAAATGCTTGACTCTTCTGAGCTCA |
| SEQ ID NO: 247 | TGTCATGGCAAAATAAAGATAATAATAGTGTTTTTTTATG |
| SEQ ID NO: 248 | TAGCGTGAGGATGGAAAACAATAGCAAAATTGATTAGACT |
| SEQ ID NO: 249 | AAGGTCTCAACAAATAGTAGTAGATTTTATCGTCCATTAA |
| SEQ ID NO: 250 | TCCCTCTCCTCTCTTACTCATCCCATCACGTATGCCTCTT |
| SEQ ID NO: 251 | TTCCCTTACCTATAATAAGAGTTATTCCTCTTATTATATT |
| SEQ ID NO: 252 | TTATAGTGATTCTGGATATTAAAGTGGGAATGAGGGGCAG |
| SEQ ID NO: 253 | CTAACGAAGAAGATGTTTCTCAAAGAAGCCATTCTCCCCA |
| SEQ ID NO: 254 | GATCATCTCAGCAGGGTTCAGGAAGATAAAGGAGGATCAA |
| SEQ ID NO: 255 | TGTTGAGGTGGGAGGACCGCTTGAGCCTGGGAAGTGCAAG |
| SEQ ID NO: 256 | AGTGAGCCGAGATTTTGCCACTACACTCCCATTTGGGTGA |
| SEQ ID NO: 257 | GTGAGACCCTTTCTCAAAAACAAACTAATTAAAAAACCCT |
| SEQ ID NO: 258 | TTTACAGATGAAGAAACTGAGTCATACAACTACTAAGAGA |
| SEQ ID NO: 259 | GAGTCACTAATCACTCAGGTGGTCTGGCTCCAGCATCTGT |
| SEQ ID NO: 260 | TTAATCTCTGCTCTATACTGCCCAAGACTTTTATAAAGTC |
| SEQ ID NO: 261 | GTTGAGTCACTGAAATGAGTTATTGGGATGGCTGTGTGGG |
| SEQ ID NO: 262 | GTGCTAAGTTCTTTCCTAAAGGTATGTGAGAATACAAAGG |
| SEQ ID NO: 263 | AAGCATCCTCCTTTTTACACACGTGAACTAGTGCATGCAA |
| SEQ ID NO: 264 | GACACTCAGTGGGCCTGGGTGAAGGTGAGAATTTTATTGC |
| SEQ ID NO: 265 | TGAGAGCCTCTGGGGACATCTTGCCAGTCAATGAGTCTCA |
| SEQ ID NO: 266 | CAATTTCCTTCTCAGTCTTGGAGTAACAGAAGCTCATGCA |
| SEQ ID NO: 267 | ATAAACGGAAATTTTGTATTGAAATGAGAGCCATTGGAAA |
| SEQ ID NO: 268 | TTACTCCAGACTCCTACTTATAAAAAGAGAAACTGAGGCT |
| SEQ ID NO: 269 | GAAGGGTGGGGACTTTCTCAGTATGACATGGAAATGATCA |
| SEQ ID NO: 270 | TGGATTCAAAGCTCCTGACTTTCTGTCTAGTGTATGTGCA |
| SEQ ID NO: 271 | GCCCCTTTTCCTCTAACTGAAAGAAGGAAAAAAAAATGGA |
| SEQ ID NO: 272 | AAAATATTCTACATAGTTTCCATGTCACAGCCAGGGCTGG |
| SEQ ID NO: 273 | TCTCCTGTTATTTCTTTTAAAATAAATATATCATTTAAAT |
| SEQ ID NO: 274 | AAATAAGCAAACCCTGCTCGGGAATGGGAGGGAGAGTCTC |
| SEQ ID NO: 275 | GTCCACCCCTTCTCGGCCCTGGCTCTGCAGATAGTGCTAT |
| SEQ ID NO: 276 | GCCCTGACAGAGCCCTGCCCATTGCTGGGCCTTGGAGTGA |
| SEQ ID NO: 277 | GCCTAGTAGAGAGGCAGGGCAAGCCATCTCATAGCTGCTG |
| SEQ ID NO: 278 | GGAGAGAGAAAAGGGCTCATTGTCTATAAACTCAGGTCAT |
| SEQ ID NO: 279 | ATTCTTATTCTCACACTAAGAAAAAGAATGAGATGTCTAC |
| SEQ ID NO: 280 | ACCCTGCGTCCCCTCTTGTGTACTGGGGTCCCCAAGAGCT |
| SEQ ID NO: 281 | AAAAGTGATGGCAAAGTCATTGCGCTAGATGCCATCCCAT |
| SEQ ID NO: 282 | TATAAACCTGCATTTGTCTCCACACACCAGTCATGGACAA |

TABLE 1-continued

Exemplary Probe Nucleotide Sequences

| SEQ ID NO | Nucleotide Sequence |
|---|---|
| SEQ ID NO: 283 | CCTCCTCCCAGGTCCACGTGCTTGTCTTTGTATAATACTC |
| SEQ ID NO: 284 | AATTTCGGAAAATGTATTCTTTCAATCTTGTTCTGTTATT |
| SEQ ID NO: 285 | TTTCAATGGCTTAGTAGAAAAAGTACATACTTGTTTTCCC |
| SEQ ID NO: 286 | ATTGACAATAGACAATTTCACATCAATGTCTATATGGGTC |
| SEQ ID NO: 287 | TGTTTGCTGTGTTTGCAAAAACTCACAATAACTTTATATT |
| SEQ ID NO: 288 | CTACTCTAAGAAAGTTACAACATGGTGAATACAAGAGAAA |
| SEQ ID NO: 289 | TTACAAGTCCAGAAAATAAAAGTTATCATCTTGAGGCCTC |
| SEQ ID NO: 290 | TTCTAGGAATAATATCAATATTACAAAATTAATCTAACAA |
| SEQ ID NO: 291 | GAACAGCAATGAGATAATGTGTACAAAGTACCCAGACCTA |
| SEQ ID NO: 292 | GTAGAGCATCAAGGAAGCGCATTGCGGAGCAGTTTTTTGT |
| SEQ ID NO: 293 | TTGTTTTTGTATTCTGTTTCGTGAGGCAAGGTTTCACTCT |
| SEQ ID NO: 294 | TCCAGGCTGGAGTGCAGTGGCAAGATCATGTCTCACTGCA |
| SEQ ID NO: 295 | TGACCTCCTGAGCTCAAGGGATCCTCCCATTTCGGCCTCC |
| SEQ ID NO: 296 | TAGCTGGGACTACAGGTGTACATCACATGCCTGGCTAATT |
| SEQ ID NO: 297 | TTTTTTTTTTAAGTAGAGACGAGGTCTTGCTATGTTGTCC |
| SEQ ID NO: 298 | TAATATCAAACTCTTGAGCTCAAGCAGTCCTCCCACTTCT |
| SEQ ID NO: 299 | TGGAGGTATCCAGTATGAAATTTAGATAATACCTGCCTTC |
| SEQ ID NO: 300 | GTTGAAATTAGAACTTAATGATATAATGCATCAATGAACT |
| SEQ ID NO: 301 | ATAGTTCCTAGCACAAAGTAAGAATCCTTTCAATGTGTGT |
| SEQ ID NO: 302 | GTGTATGTATTTATCTGTTATTAATAGGAATCTTATGGGC |
| SEQ ID NO: 303 | TCTCACTTAATCCTTATTAATAACTATGAAGCAGGTATTT |
| SEQ ID NO: 304 | GAGTTTTCCAAGTGAGTTAAGTATAGCTTGTAATACTTAA |
| SEQ ID NO: 305 | ATATCCACAGGTTACATAGCTAGTATATAACTGAGAAATA |
| SEQ ID NO: 306 | TATTTATATTATAAAACATTCTAACAATACAGATGTATAT |
| SEQ ID NO: 307 | TAAAAAACTGAAAGGGCTCATGCAACCCTACCTTCTCAAT |
| SEQ ID NO: 308 | CTTCTTCACTTAGAAAAAACCAGCCTTAGCTGTCTGCTAT |
| SEQ ID NO: 309 | CCTTTCAAAATATACTTCTGAGAAATGAGAGAGAGAAATG |
| SEQ ID NO: 310 | GGGTAGAAGGAAGGAAGATAGGGTAAGAGACAGGGAAGGA |
| SEQ ID NO: 311 | TGGGGAAAGAAATTAAATTATTCTTTTCTCTGTCTCTTGA |
| SEQ ID NO: 312 | GCTCTTTCCATTACATTGAATCAAAGGTAATGTTGCCATT |
| SEQ ID NO: 313 | GACTCTTGAAATAAAGAAAGACCGATGTATGAAATAATTT |
| SEQ ID NO: 314 | AGTCTATGGCATTTTCAAAATGCAAGGTGATGTCTTACTA |
| SEQ ID NO: 315 | GCCTTTGCTTTATTATTAGAAATGGGGAAGTGAGTATAGA |
| SEQ ID NO: 316 | TTATCAGGAGATATATTAGGAAAAAGGGAAACTGGAGAAA |
| SEQ ID NO: 317 | GAGGAGTATCCAGATGTCCTGTCCCTGTAAGGTGGGGCA |
| SEQ ID NO: 318 | CCTTCAATCAAAAGGGCTCCTTAACAACTTCCTTGCTTGG |
| SEQ ID NO: 319 | CCACCATCTTGGACCATTAGCTCCACAGGTATCTTCTTCC |
| SEQ ID NO: 320 | AGTGGTCATAACAGCAGCTTCAGCTACCTCTCTAAAGAGT |

TABLE 1-continued

Exemplary Probe Nucleotide Sequences

| SEQ ID NO | Nucleotide Sequence |
| --- | --- |
| SEQ ID NO: 321 | CCAGATATAGGTCAGGAAATATAATCCACTAATAAAAAGA |
| SEQ ID NO: 322 | CATTTTGACTGTAGTTGTTTGTTTTTTGTCATTGTGACTA |
| SEQ ID NO: 323 | TAACATTCTCACTCTTTCATCAGTAATCACTCAGGTTATT |
| SEQ ID NO: 324 | GACCAACAGACTGTGGGAAAAATCAGAGAAGGAGGCATCC |
| SEQ ID NO: 325 | GCTTACTAGCCTAAACTGAAATTGCTATAGCAGAGTGAAC |
| SEQ ID NO: 326 | AGGTTTACAGATATTTTCCACAAAGAGTAAAAGGATTGAA |
| SEQ ID NO: 327 | TCTCCAGATCAATGCATAGGAAATAATAATGGACCATAAA |
| SEQ ID NO: 328 | ATATTATGACGAACAACATTAGGATAAGTCCATATCAATT |
| SEQ ID NO: 329 | ATCCAGTCATAAGCACAGACTACGTGAAGCACGTCCAAGT |
| SEQ ID NO: 330 | GCAGGAGAAATGAGAGGAGCAAGAAAGAGGAGCCATTTGA |
| SEQ ID NO: 331 | GAATAGCAGAAAAAGGAAAGGCAAGTCATATTAACAAATG |
| SEQ ID NO: 332 | TCATGCCAACAGTACAGATAACTCTGCTAATAAAGGTAGA |
| SEQ ID NO: 333 | TAATACAGGTAGTAGCAGATATCTACATAGTAGTTAAAGG |
| SEQ ID NO: 334 | GGCCATCAGTACAGAAGATTCCATAAAGGAGAACCTAAAG |
| SEQ ID NO: 335 | AGAATAATTTGTCAGAAGCTTAAAAGCTGAACTCTGAGGC |
| SEQ ID NO: 336 | AACTACAATATCCTTTTGACTGTGGAAAGGGTGGTGAAAG |
| SEQ ID NO: 337 | GTTCAAGGACATTTGAGCCAACATAGAGAGGAACATTGGC |
| SEQ ID NO: 338 | TGAGGGATATCTGTCCTGATGTTGTCCAGGATGGTGATGA |
| SEQ ID NO: 339 | CATATAAATAACGTAGAGAAAACAGGAGGGGATAGAGATC |
| SEQ ID NO: 340 | CAAAGAGGCATCAAAGATAGGGATGTTTGTAAGGATGAAA |
| SEQ ID NO: 341 | CTGTTCTTCTCTGAGTAGCCAAGCTCAGCTTGGTTCAAGC |
| SEQ ID NO: 342 | CATACTGTGGATCTGTAGCAAATTCCCCCTGAAAACCCAG |
| SEQ ID NO: 343 | TCTGACCCTCACATTCAAGTTCTGAGGAAGGGCCACTGCC |
| SEQ ID NO: 344 | GCCTTGAGATACCTGGTCCTTATTCCTTGGACTTTGGCAA |
| SEQ ID NO: 345 | ATAGGGCTTGTTTTAGGGAGAAACCTGTTCTCCAAACTCT |
| SEQ ID NO: 346 | CTGGTGTCCATACTCTGAATGGGAAGAATGATGGGATTAC |
| SEQ ID NO: 347 | AGCAGGAGAGGATCAACCCCATACTCTGAATCTAAGAGAA |
| SEQ ID NO: 348 | TCAGATCCCTGGATGCAAGCCAGGTCTGGAACCATAGGCA |
| SEQ ID NO: 349 | CTCCTCCCTACCACCTTTAGCCATAAGGAAACATGGAATG |
| SEQ ID NO: 350 | GACACAAACCTGGGCCTTTCAATGCTATAACCTTTCTTGA |
| SEQ ID NO: 351 | CTACCTGACTTCTGAGTCAGGATTTATAAGCCTTGTTACT |
| SEQ ID NO: 352 | TGAACCAACAAGCATCGAAGCAATAATGAGACTGCCCGCA |
| SEQ ID NO: 353 | GAAAAGCAATAATCCATTTTTCATGGTATCTCATATGATA |
| SEQ ID NO: 354 | TAACACTTATCTCTCTGAACTTTGGGCTTTTAATATAGGA |
| SEQ ID NO: 355 | TTTTCTGACTGTCTAATCTTTCTGATCTATCCTGGATGGC |
| SEQ ID NO: 356 | ATCTTCATCGAATTTGGGTGTTTCTTTCTAAAAGTCCTTT |
| SEQ ID NO: 357 | GAAATTACAAATGCTAAAGCAAACCCAAACAGGCAGGAAT |
| SEQ ID NO: 358 | ATTAGGCATCTTACAGTTTTTAGAATCCTGCATAGAACTT |

TABLE 1-continued

Exemplary Probe Nucleotide Sequences

| SEQ ID NO | Nucleotide Sequence |
| --- | --- |
| SEQ ID NO: 359 | TACAATATTTGACTCTTCAGGTTAAACATATGTCATAAAT |
| SEQ ID NO: 360 | AACATTCAGTGAAGTGAAGGGCCTACTTTACTTAACAAGA |
| SEQ ID NO: 361 | TCTTTTCCTATCAGTGGTTTACAAGCCTTGTTTATATTTT |
| SEQ ID NO: 362 | TATTTTTGTTCTGAGAATATAGATTTAGATACATAATGGA |
| SEQ ID NO: 363 | CAAAATCTAACACAAAATCTAGTAGAATCATTTGCTTACA |
| SEQ ID NO: 364 | AGAATTTATGACTTGTGATATCCAAGTCATTCCTGGATAA |
| SEQ ID NO: 365 | TTACACTAGAAAATAGCCACAGGCTTCCTGCAAGGCAGCC |
| SEQ ID NO: 366 | AGTTTGAACACTTGTTATGGTCTATTCTCTCATTCTTTAC |
| SEQ ID NO: 367 | ACTTCGTGAGAGATGAGGCAGAGGTACACTACGAAAGCAA |
| SEQ ID NO: 368 | TCTTGAGAATGAGCCTCAGCCCTGGCTCAAACTCACCTGC |
| SEQ ID NO: 369 | AATAGGATGTCTGTGCTCCAAGTTGCCAGAGAGAGAGATT |
| SEQ ID NO: 370 | ATTAAAGATCCCTCCTGCTTAATTAACATTCACAAGTAAC |
| SEQ ID NO: 371 | ACTTAAAGTAGCGATACCCTTTCACCCTGTCCTAATCACA |
| SEQ ID NO: 372 | TCTCAGGTGTTAACTTTATAGTGAGGACTTTCCTGCCATA |
| SEQ ID NO: 373 | ATAGTTTCATATAAATGGGTTCCTCATCATCTATGGGTAC |
| SEQ ID NO: 374 | GGTATTTACATTTGCCATTCCCTATGCCCTAAATATTTAA |
| SEQ ID NO: 375 | TATTGATATTCCTTGAAAATTCTAAGCATCTTACATCTTT |
| SEQ ID NO: 376 | CTTTTATTCTCCCCTTCACCGAATCTCATCCTACATTGGC |
| SEQ ID NO: 377 | TAGTGTCCCAAATTTTATAATTTAGGACTTCTATGATCTC |
| SEQ ID NO: 378 | ATATGGTCACCTCTTTGTTCAAAGTCTTCTGATAGTTTCC |
| SEQ ID NO: 379 | ACAATCTTCCTGCTTCTACCACTGCCCCACTACAATTTCT |
| SEQ ID NO: 380 | AGTCACTGTCACCACCACCTAAATTATAGCTGTTGACTCA |
| SEQ ID NO: 381 | CTGACCCCTTGCCTTCACCTCCAATGCTACCACTCTGGTC |
| SEQ ID NO: 382 | AGAAAATCCTGTTGGTTTTCGTGAAAGGATGTTTTCAGA |
| SEQ ID NO: 383 | ACATATACTCACAGCCAGAAATTAGCATGCACTAGAGTGT |
| SEQ ID NO: 384 | ACCCAAAGACTCACTTTGCCTAGCTTCAAAATCCTTACTC |
| SEQ ID NO: 385 | TGAGGTAGAGACTGTGATGAACAAACACCTTGACAAAATT |
| SEQ ID NO: 386 | TCCATATCCACCCACCCAGCTTTCCAATTTTAAAGCCAAT |
| SEQ ID NO: 387 | AAGGTATGATGTGTAGACAAGCTCCAGAGATGGTTTCTCA |
| SEQ ID NO: 388 | CTCTGGTCAGCATCCAAGAAATACTTGATGTCACTTTGGC |
| SEQ ID NO: 389 | AACTGTGAACTTCCTTCAGCTAGAGGGGCCTGGCTCAGAA |
| SEQ ID NO: 390 | TGATTGTTCTCTGACTTATCTACCATTTTCCCTCCTTAAA |
| SEQ ID NO: 391 | AAACAAACCCATCAAATTCCCTGACCGAACAGAATTCTG |
| SEQ ID NO: 392 | CAGAGGTCACAGCCTAAACATCAAATTCCTTGAGGTGCGG |
| SEQ ID NO: 393 | GAAGGCAGGTGTGGCTCTGCAGTGTGATTGGGTACTTGCA |
| SEQ ID NO: 394 | CATGGAGGAAAAACTCATCAGGGATGGAGGCACGCCTCTA |
| SEQ ID NO: 395 | AGCTTGTTAAATTGAATTCTATCCTTCTTATTCAATTCTA |
| SEQ ID NO: 396 | CATAGTTGTCAGCACAATGCCTAGGCTATAGGAAGTACTC |

TABLE 1-continued

Exemplary Probe Nucleotide Sequences

| SEQ ID NO | Nucleotide Sequence |
| --- | --- |
| SEQ ID NO: 397 | GCAGATATAGCTTGATGGCCCCATGCTTGGTTTAACATCC |
| SEQ ID NO: 398 | CTAAATAACTAGAATACTCTTTATTTTTTCGTATCATGAA |
| SEQ ID NO: 399 | AGTGTTTAAAGGGTGATATCAGACTAAACTTGAAATATGT |
| SEQ ID NO: 400 | GGATGGGTCTAGAAAGACTAGCATTGTTTTAGGTTGAGTG |
| SEQ ID NO: 401 | TGCTGCCAACATTAACAGTCAAGAAATACCTCCGAATAAC |
| SEQ ID NO: 402 | TATTGTGAGAGGTCTGAATAGTGTTGTAAAATAAGCTGAA |
| SEQ ID NO: 403 | TTACAACATGATGGCTTGTTGTCTAAATATCTCCTAGGGA |
| SEQ ID NO: 404 | CTAAGTAGAAGGGTACTTTCACAGGAACAGAGAGCAAAAG |
| SEQ ID NO: 405 | GTCTTGTATTGCCCAGTGACATGCACACTGGTCAAAGTA |
| SEQ ID NO: 406 | CCCTATGTCTTCCCTGATGGGCTAGAGTTCCTCTTTCTCA |
| SEQ ID NO: 407 | AAAGTTTCCCCAAATTTTACCAATGCAAGCCATTTCTCCA |
| SEQ ID NO: 408 | AACTGCAGATTCTCTGCATCTCCCTTTGCCGGGTCTGACA |
| SEQ ID NO: 409 | TAGTGCTGTGGTGCTGTGATAGGTACACAAGAAATGAGAA |
| SEQ ID NO: 410 | TAACTAGCGTCAAGAACTGAGGGCCCTAAACTATGCTAGG |
| SEQ ID NO: 411 | CATTGGCTCCGTCTTCATCCTGCAGTGACCTCAGTGCCTC |
| SEQ ID NO: 412 | TGTTTATGTGTTATAGTGTTCATTTACTCTTCTGGTCTAA |
| SEQ ID NO: 413 | CCTTTGACCCCTTGGTCAAGCTGCAACTTTGGTTAAAGGG |
| SEQ ID NO: 414 | TTCTCTTGGGTTACAGAGATTGTCATATGACAAATTATAA |
| SEQ ID NO: 415 | TGGAAGTTGTGGTCCAAGCCACAGTTGCAGACCATACTTC |
| SEQ ID NO: 416 | CTGCCCTGTGGCCCTTGCTTCTTACTTTTACTTCTTGTCG |
| SEQ ID NO: 417 | AACTCAGATATTGTGGATGCGAGAAATTAGAAGTAGATAT |
| SEQ ID NO: 418 | TACAGAACCACCAAGTAGTAAGGCTAGGATGTAGACCCAG |
| SEQ ID NO: 419 | TGAGCTCTCCTACTGTCTACATTACATGAGCTCTTATTAA |
| SEQ ID NO: 420 | AAGCTAATAAGTAGACAATTAGTAATTAGAAGTCAGATGG |
| SEQ ID NO: 421 | AGCCCAATGTACTTGTAGTGTAGATCAACTTATTGAAAGC |
| SEQ ID NO: 422 | CCAATACTCAGAAGTAGATTATTACCTCATTTATTGATGA |
| SEQ ID NO: 423 | GCTAGAATCAAATTTAAGTTTATCATATGAGGCCGGGCAC |
| SEQ ID NO: 424 | TAATACTAATGATAAGTAACACCTCTTGAGTACTTAGTAT |
| SEQ ID NO: 425 | ATGGTAATTCTGTGAGATATGTATTATTGAACATACTATA |
| SEQ ID NO: 426 | TGAAAGAGAAGTGGGAATTAATACTTACTGAAATCTTTCT |
| SEQ ID NO: 427 | GAGAGACACGAGGAAATAGTGTAGATTTAGGCTGGAGGTA |
| SEQ ID NO: 428 | GTTGAGAGGGAAACAAGATGGTGAAGGGACTAGAAACCAC |
| SEQ ID NO: 429 | CAAGGTTCTGAACATGAGAAATTTTTAGGAATCTGCACAG |
| SEQ ID NO: 430 | TGCCATCTAAAAAAATCTGACTTCACTGGAAACATGGAAG |
| SEQ ID NO: 431 | GGGATCCTCTCTTAAGTGTTTCCTGCTGGAATCTCCTCAC |
| SEQ ID NO: 432 | GTTTCCTTCATGTGACAGGGAGCCTCCTGCCCCGAACTTC |
| SEQ ID NO: 433 | TTGGATAAGAGTAGGGAAGAACCTAGAGCCTACGCTGAGC |
| SEQ ID NO: 434 | ATCTGGGGCTTTGTGAAGACTGGCTTAAAATCAGAAGCCC |

TABLE 1-continued

Exemplary Probe Nucleotide Sequences

| SEQ ID NO | Nucleotide Sequence |
|---|---|
| SEQ ID NO: 435 | ACCGCAATGCTTCCTGCCCATTCAGGGCTCCAGCATGTAG |
| SEQ ID NO: 436 | TATGGGAAGCAGGGTATGAAAGAGCTCTGAATGAAATGG |
| SEQ ID NO: 437 | GGTTGCATGAATCAGATTATCAACAGAAATGTTGAGACAA |
| SEQ ID NO: 438 | AATGCAGGCCTAGGCATGACTGAAGGCTCTCTCATAATTC |
| SEQ ID NO: 439 | TAACGTTTTCTTGTCTGCTACCCCATCATATGCACAACAA |
| SEQ ID NO: 440 | TTAATTCCCAAACTCATATAGCTCTGAGAAAGTCTATGCT |
| SEQ ID NO: 441 | CCCTATAGGGGATTTCTACCCTGAGCAAAAGGCTGGTCTT |
| SEQ ID NO: 442 | TCCTCACCATATAGAAAGCTTTTAACCCATCATTGAATAA |
| SEQ ID NO: 443 | TAAGCTGTCTAGCAAAAGCAAGGGCTTGGAAAATCTGTGA |
| SEQ ID NO: 444 | AGGATTAGAAGATTCTTCTGTGTGTAAGAATTTCATAAAC |
| SEQ ID NO: 445 | ATTATCTTCTGGAATAGGGAATCAAGTTATATTATGTAAC |
| SEQ ID NO: 446 | CTCTCTGGTTGACTGTTAGAGTTCTGGCACTTGTCACTAT |
| SEQ ID NO: 447 | TCTTCAGTTAGATGGTTAACTTTGTGAAGTTGAAAACTGT |
| SEQ ID NO: 448 | CTACACCATGTGGAGAAGGGGTGGTGGTTTTGATTGCTGC |
| SEQ ID NO: 449 | ACTTTCCTAACCTGAGCCTAACATCCCTGACATCAGGAAA |
| SEQ ID NO: 450 | TACACTTTATTCGTCTGTGTCCTGCTCTGGGATGATAGTC |
| SEQ ID NO: 451 | TACTCTTTGCATTCCACTGTTTTTCCTAAGTGACTAAAAA |
| SEQ ID NO: 452 | AAAGGCCTCCCAGGCCAAGTTATCCATTCAGAAAGCATTT |
| SEQ ID NO: 453 | TATTGACATGTACTTCTTGGCAGTCTGTATGCTGGATGCT |
| SEQ ID NO: 454 | TTTGGTCCTAATTATGTCTTTGCTCACTATCCAATAAATA |
| SEQ ID NO: 455 | GTTAAAAAAACTACCTCTCAACTTGCTCAAGCATACACTC |
| SEQ ID NO: 456 | TAATTAGTGCTTTGCATAATTAATCATATTTAATACTCTT |
| SEQ ID NO: 457 | ACTAGTGTTCTGTACTTTATGCCCATTCATCTTTAACTGT |
| SEQ ID NO: 458 | GTATTTTTGTTTAACTGCAATCATTCTTGCTGCAGGTGA |
| SEQ ID NO: 459 | GCAGTGACTTATAAATGCTAACTACTCTAGAAATGTTTGC |
| SEQ ID NO: 460 | TTATAAGCATGATTACAGGAGTTTTAACAGGCTCATAAGA |
| SEQ ID NO: 461 | AGTATCCCTCAAGTAGTGTCAGGAATTAGTCATTTAAATA |
| SEQ ID NO: 462 | AGTCACCCATTTGGTATATTAAAGATGTGTTGTCTACTGT |
| SEQ ID NO: 463 | TGGTCATAAAACATTGAATTCTAATCTCCCTCTCAACCCT |
| SEQ ID NO: 464 | ACAGTTGAAAAGACCTAAGCTTGTGCCTGATTTAAGCCTT |
| SEQ ID NO: 465 | CAACTACAGGGCCTTGAACTGCACACTTTCAGTCCGGTCC |
| SEQ ID NO: 466 | GTGGTTCTTTGAAGAGACTTCCACCTGGGAACAGTTAAAC |
| SEQ ID NO: 467 | TGGAGGAAATATTTATCCCCAGGTAGTTCCCTTTTTGCAC |
| SEQ ID NO: 468 | GCCTGGTGCTTTTGGTAGGGGAGCTTGCACTTTCCCCCTT |
| SEQ ID NO: 469 | TCTCATTTCTTTGAGAACTTCAGGGAAAATAGACAAGGAC |
| SEQ ID NO: 470 | CAAACTTTTCAAGCCTTCTCTAATCTTAAAGGTAAACAAG |
| SEQ ID NO: 471 | TCAACAAAGGAGAAAAGTTTGTTGGCCTCCAAAGGCACAG |
| SEQ ID NO: 472 | GATGCAACAGACCTTGGAAGCATACAGGAGAGCTGAACTT |

TABLE 1-continued

Exemplary Probe Nucleotide Sequences

| SEQ ID NO | Nucleotide Sequence |
|---|---|
| SEQ ID NO: 473 | CATCTGAGATCCCAGCTTCTAAGACCTTCAATTCTCACTC |
| SEQ ID NO: 474 | TATCTTAACAGTGAGTGAACAGGAAATCTCCTCTTTTCCC |
| SEQ ID NO: 475 | AACTCATGCTTTGTAGATGACTAGATCAAAAAATTTCAGC |
| SEQ ID NO: 476 | TCAAAGGAAGTCAAAAGATGTGAAAAACAATTTCTGACCC |
| SEQ ID NO: 477 | TGCCTTCACTTAAGTAATCAATTCCTAGGTTATATTCTGA |
| SEQ ID NO: 478 | CCCTACCTTGTTCAAAATGTTCCTGTCCAGACCAAAGTAC |
| SEQ ID NO: 479 | GCACTTACAAATTATACTACGCTCTATACTTTTTGTTTAA |
| SEQ ID NO: 480 | CTTTAGTTTCATTTCAAACAATCCATACACACACAGCCCT |
| SEQ ID NO: 481 | TAGGGACCACAGGGTTAAGGGGGCAGTAGAATTATACTCC |
| SEQ ID NO: 482 | CTCACAATTAAGCTAAGCAGCTAAGAGTCTTGCAGGGTAG |
| SEQ ID NO: 483 | GTTGAAAGACAGAGAGGATGGGGTGCTATGCCCCAAATCA |
| SEQ ID NO: 484 | GCTTGTCTAATTTTATATATCACCCTACTGAACATGACCC |
| SEQ ID NO: 485 | AATATTGTACACGTACACCAAAGCATCATGTTGTACCCCA |
| SEQ ID NO: 486 | TGTGAAGTGGTGGATTTGTTAATTAGCCTTATTTAACCAT |
| SEQ ID NO: 487 | TGACACATATGACATTTTAACTATGTTCCAGATTTTTGAA |
| SEQ ID NO: 488 | GCAAGGAATCATTCAATGTTTTCTAAATCTATTACTGCAT |
| SEQ ID NO: 489 | CATTTTCATAGGTTTTCCTCGATTGATCATTATTCATGAT |
| SEQ ID NO: 490 | AAAGTGATCAAGATATTTTTAGTTCAGGCTCCAAAATTTT |
| SEQ ID NO: 491 | CTTTACAGGCCGAGAAAAATGAATCTGAATTCCTGACCTC |
| SEQ ID NO: 492 | TCCACTCAAGGCCTACATTCTGCTATAATGCAATTTCAAG |
| SEQ ID NO: 493 | AACTGCTTAAAATTAATGGCACAAGTCATGTTTTTGATGT |
| SEQ ID NO: 494 | CTGACTGTGACGTAGCAATAAAGAAACCCACGTTTCATAT |
| SEQ ID NO: 495 | CTGGCCCACTGCTTGGAGGAGAGCACTCAGGACCATGAAC |
| SEQ ID NO: 496 | TTCTGAAATGATAAAGTCAATCACAGGAAGGCACCTGGAC |
| SEQ ID NO: 497 | ATCATTCTCTTTCCCTTCCTCTATGTGGCAGAAAGTAAAA |
| SEQ ID NO: 498 | GGAGATAATAATGTGTTACTCCCTAAGGCAGAGTGCCCTT |
| SEQ ID NO: 499 | CAATTAACTTGGCCATGTGACTGGTTGTGACTAAAATAAT |
| SEQ ID NO: 500 | CACTAAATCAATATACTTCTCAACAATTTCCAACAGCCCT |
| SEQ ID NO: 501 | CTAGGCTCCTGAGTTTGCTGGGGATGCGAAGAACCCTTAT |
| SEQ ID NO: 502 | CCGAGGACCCCGCACTCGGAGCCGCCAGCCGGCCCCACCG |
| SEQ ID NO: 503 | TTGGAAGCACAGGGTGTGGGATAATGCTAATTACTAGTGA |
| SEQ ID NO: 504 | GTTCAGTATGCCTTTGATTTTACAATAATATTCCTGTTAT |
| SEQ ID NO: 505 | AGATTCCATGAAGTATTACAGCATTTGGTAGTCTTTTTGC |
| SEQ ID NO: 506 | TATTTGCTCTGAAATAAGACATAATTTGGGGTGAGAAAGC |
| SEQ ID NO: 507 | ACTCATGATATTTGGCTCTAGAATACATGCTCTGAATCAT |
| SEQ ID NO: 508 | TCCAAGATGAAGTGGCTACTAACTGACAGAGGGCATAATT |
| SEQ ID NO: 509 | TATTCACAGTAACTCTGTGCCTCAAGTACTATTGTAATAC |
| SEQ ID NO: 510 | ACATCCTCAATCTACACACTAGGATAGTATAAAAGTAATA |

TABLE 1-continued

Exemplary Probe Nucleotide Sequences

| SEQ ID NO | Nucleotide Sequence |
| --- | --- |
| SEQ ID NO: 511 | GTCTACCCATATGTGACCTTCATGTCTTTGCTCTAAGCCC |
| SEQ ID NO: 512 | CGTGTAATCCTTGACAATGTCATCTCATCTATTTATTCCC |
| SEQ ID NO: 513 | TCTGAAAGAGACTAACCTTCCCTCGCTTTGCAGAGAAAGA |
| SEQ ID NO: 514 | ATGCATGGATTCTCTTGAAAAAATGTTTCTGCCATGATGT |
| SEQ ID NO: 515 | TAGTTGAAGACCTACTGTGTTCAGGGCCGTGAGCCAGGGC |
| SEQ ID NO: 516 | CAACGTGGAGAGCTGTCCTGGCACCATTTCTTCCTGCTGT |
| SEQ ID NO: 517 | ATCCTCAAAGGAGCCTGGCTTGGGCTAACAAGGAAGAACT |
| SEQ ID NO: 518 | TGCCTGGGACCCTGCCCCAAGCAAAGTAATAATCTGAATG |
| SEQ ID NO: 519 | CTGGTGTGTCCAGTGTGATCCCTGCACCCATGCCCGGAGC |
| SEQ ID NO: 520 | CTGCCCCCTGCAGCAGGGAAGGGGCTCTGGAAGGGTCTGA |
| SEQ ID NO: 521 | TAGCTGCTGCCCCACTATGCACCATCGCTTATCTGTTCTT |
| SEQ ID NO: 522 | GAAACCCGAAAAATGTCCTGGTCCTCTTCTTAAGTCTGGG |
| SEQ ID NO: 523 | GCTGAGAACATGACTCTGCTTGGCGTTCCATTTAATTGAC |
| SEQ ID NO: 524 | GAGAGGGTGTGCATTTGAAGTATAGATTTGTTAAACATAG |
| SEQ ID NO: 525 | CATCAGGCAAAAATACTTCGATGGGACTGTGTTCTTTCAG |
| SEQ ID NO: 526 | TCTAAAGTGATGTAATGTTGCCACGGAAATTCTAATCCCT |
| SEQ ID NO: 527 | CGTGCAGAACCAGCTCTGTCTTCCCAGACACTGTCGCTTT |
| SEQ ID NO: 528 | ACCCCTGAGCACCTCAGTGTCCGTGACTGTGGAGCGGAGG |
| SEQ ID NO: 529 | CTGCCTGGGACACGTACGGCTGCCCAGTGATCCTGAGCGC |
| SEQ ID NO: 530 | CACAGCCGGATGGTGTGGGAGCTGGCACTGCCGGGGCTCC |
| SEQ ID NO: 531 | CGTCTTGGCAGAGGCTCCCTGTCATCAAGGACCTGAGGTT |
| SEQ ID NO: 532 | GACCCCACAAAGATGAGCGGGTCCCCTTCCCAATTTTCGG |
| SEQ ID NO: 533 | TCAGGAAGCCGGTGCTCAGCAAACTTATCTGAAGCTCTTG |
| SEQ ID NO: 534 | GAGGCTGCAGAGGAACATCGTTTGGTCAAATGTGAAATGT |
| SEQ ID NO: 535 | CTAGCTTCTAGAAAGTGCTGCCAATTTGGGGACCAAGGGA |
| SEQ ID NO: 536 | GGAAACACTTCTTTTTCCCTTGACAAAGGACATCCTCTGC |
| SEQ ID NO: 537 | GCATGTGCATAAACACTCGTGTGTGTGTCCTTTTATCCCA |
| SEQ ID NO: 538 | CCAAATCTCTATACATGTCCATAGAGAGAGGCAGACGTAT |
| SEQ ID NO: 539 | GGGTTGAAGACAAGGGGCTCAGAGCTTGCTTTTTATACAC |
| SEQ ID NO: 540 | AGATTCATCTTCATGGCAGGACTTCAGGCAAGAGAGGCCC |
| SEQ ID NO: 541 | CTCACCCCTTAGCAGGACCCTGACGGAACTGGGTACAGGC |
| SEQ ID NO: 542 | GGTTGGGAGACAATGGGTGGCCCCTCGGTGTGGTGTCCTC |
| SEQ ID NO: 543 | AGAGTCTAGAGGGCCCGTGGGGACGGGAGTCCTGGGAACC |
| SEQ ID NO: 544 | GCGGCATGTCCGGCTTCACCCTGCCCAGAATCACAGCCTC |
| SEQ ID NO: 545 | ATGGTTAAAAAATTCTCCTACTTAAGACTCCCAGACCCCT |
| SEQ ID NO: 546 | GGGTTGAAGACAAGGGGCTCAGAGCTTGCTTTTTATACAC |
| SEQ ID NO: 547 | AGATTCATCTTCATGGCAGGACTTCAGGCAAGAGAGGCCC |
| SEQ ID NO: 548 | CTCACCCCTTAGCAGGACCCTGACGGAACTGGGTACAGGC |

TABLE 1-continued

Exemplary Probe Nucleotide Sequences

| SEQ ID NO | Nucleotide Sequence |
|---|---|
| SEQ ID NO: 549 | GGTTGGGAGACAATGGGTGGCCCCTCGGTGTGGTGTCCTC |
| SEQ ID NO: 550 | AGAGTCTAGAGGGCCCGTGGGACGGGAGTCCTGGGAACC |
| SEQ ID NO: 551 | GCGGCATGTCCGGCTTCACCCTGCCCAGAATCACAGCCTC |
| SEQ ID NO: 552 | TGAGATTCCAGGGCTGGTTCCACAACGGCCGGCATCGGCC |
| SEQ ID NO: 553 | CTGAGTCACTAACAAAGCTCAGGCCTGACCACAGGACATT |
| SEQ ID NO: 554 | GGCTGGCCTACCTGCCACGGGGCCAGGGCTGGGTGCTTTC |
| SEQ ID NO: 555 | GGGCTCTGGACGCTGGAGGCCTGAGGCTGCACCCCAGGTT |
| SEQ ID NO: 556 | ACAGTGGCCACTCACCCACTGGGCCCACATCCCCACAGGC |
| SEQ ID NO: 557 | ACTCTGCCAGCCTTTGATGCCTCGCTGAGACAGAGGGTCT |
| SEQ ID NO: 558 | AGCCGGGGCTCTGGCCCCATCCAGGGGCTCCCCCAGCAGC |
| SEQ ID NO: 559 | CCTTGGAAGTCAGTCAGCAGGTCAGGACACAGTTCAGCCC |
| SEQ ID NO: 560 | TTACATGCAGTTGGTCTTCTCCTGTGAATGGGGAAACTGA |
| SEQ ID NO: 561 | CTGCATCACAGAACAGCTGCATTTCTAATGTCAGGCTTCT |
| SEQ ID NO: 562 | CAGCCTGGGAGGCTTGTCAACCTCCTTTGACAAGCACGCC |
| SEQ ID NO: 563 | AGAAACTGGGGCTCCAGGGCATGGAGGCTGCCTGTGGCCA |
| SEQ ID NO: 564 | TCCCGGCCTGGAGGAAGTCTTATTAGCCTCATTTCATGGA |
| SEQ ID NO: 565 | TCCTGCCAGCCCCTCACGCTCACGAATTCAGTCCCAGGG |
| SEQ ID NO: 566 | AATTCTAAAGGTGAAGGGACGTCTACACCCCCAACAAAAC |
| SEQ ID NO: 567 | GGAAATATTAGTCCCCTCTGCCTGGGACAAGACCACCGAA |
| SEQ ID NO: 568 | AAACACACCTCTGAATGGAAAGCTGAGAAACAGTGATCTC |
| SEQ ID NO: 569 | ACTGCACCCCCTCCCTTCCCGTGCCGGCAATTTAACCGGG |
| SEQ ID NO: 570 | TGCCTTCCTACCTTGACCAGTCGGTCCTTGCGGGGGTCCC |
| SEQ ID NO: 571 | ATTTCCTTCATCTTGTCCTTCTAGCCTGGAGACTCTTCGG |
| SEQ ID NO: 572 | AATGCCCGAAAATTCCAGCAGCAGCCCAAGATGGTGGCCA |
| SEQ ID NO: 573 | CGTTGCAAATGCCCAAGGGGGTAACCCTAAAAGTTAAAGG |
| SEQ ID NO: 574 | ACACAACCCCTGTGCAAGTTTCATTCCGGCGCACAGGGGC |
| SEQ ID NO: 575 | TGCAAGAACTAATTTAGCATGCAAGGACGGGGAGGACCGG |
| SEQ ID NO: 576 | GCCACGAGGGCACCCACGGGCGGACAGACGGCCAAAGAAT |
| SEQ ID NO: 577 | ACCCCATATCCAAGCCGGCAGAATGGGCGCATTTCCAAGA |
| SEQ ID NO: 578 | GCCTGGGGAGACCACGAGAAGGGGTGACTGGGGCGCGGCG |
| SEQ ID NO: 579 | CTGCAGTAGGGGACAACTAGGAAGGCCGGCAGGCCACACG |
| SEQ ID NO: 580 | GAGTGGGTCCCCCGGGATTTAGGGGGTGAGGTGGAGGTGG |
| SEQ ID NO: 581 | TCCCCGCCAGGGAAGAGGGGTGCAGGGGGCCCCGTCCGCC |
| SEQ ID NO: 582 | TGAGGCGCCGCGCCTGCCCTGCGGCGGAGTTGCCCCTGTA |
| SEQ ID NO: 583 | AAACGCCGGGAGCAGCGAGGGGCAGAGCCCAAAAGCCATC |
| SEQ ID NO: 584 | TTGTTAAGCAAAGATCAAAGCCCGGCAGAGAATGGGAGCG |
| SEQ ID NO: 585 | CAACTTCAACAAAACTCCCCTGTAGTCCGTGTGACGTTAC |
| SEQ ID NO: 586 | CTGCTACTGCGCCGACAGCCCTCTGGAGGCTCCAGGACTT |

TABLE 1-continued

Exemplary Probe Nucleotide Sequences

| SEQ ID NO | Nucleotide Sequence |
|---|---|
| SEQ ID NO: 587 | GCTCTTCTGCCCCTCGCCGGAGCGTGCGGACTCTGCTGCT |
| SEQ ID NO: 588 | TCCGCGCTCGGCTCTCGCTTCTGCTGCCCCGCGCTCCCTC |
| SEQ ID NO: 589 | TTTCCACTTCGCAGCACAGGAGCTGGTGTTCCATGGCTGG |
| SEQ ID NO: 590 | GGTCGTTGAGGAGGTTGGCATCGGGGTACGCGCGGCGGAT |
| SEQ ID NO: 591 | TGTCCTACTTCAAATGTGTGCAGAAGGAGGTCCTGCCGTC |
| SEQ ID NO: 592 | TCGGGCGGCTCTCTTAAGACTTCCCTGCAACTTGTTGCCC |
| SEQ ID NO: 593 | ACCCACGTTTCTTTGCTACTCACCCCCCTCCCTTCTCTCC |
| SEQ ID NO: 594 | CTAGAACTTTGAAGTTTGCCGTGGTGTTTCTAGGGATCCG |
| SEQ ID NO: 595 | AGAAGGGGTCCGGAGGGGTGCCTTCGGGAGAAGCCAGT |
| SEQ ID NO: 596 | CAGGGGCACCCCAATGGGCCCGAGGGTGCGGGCTGGCAGG |
| SEQ ID NO: 597 | GGGTGCGCTTTGTGTCCCCGCCTGCGCCCCAGCCCGGCT |
| SEQ ID NO: 598 | GCCTCAGCGGCCGGGAGCCGCCAACTCCGGGGGGAGGGGG |
| SEQ ID NO: 599 | AAAGTGCAGTAATACCCTTGATCAGAGTTGATGACTTGAA |
| SEQ ID NO: 600 | GAGAGAAATAAAGTAGTTGCTCTATTTGTAAATTGAAAAG |
| SEQ ID NO: 601 | GGTAGCAGTGATTGCTGTATATTTGTGAAAAGGAGGCAAG |
| SEQ ID NO: 602 | TGCTGATAATGGAAGTGCAGTGGGTTAGCTTTGTTTCCAT |
| SEQ ID NO: 603 | CCGTTCTACCGTGACTAGTATGGAATTGTGGGAACCAGAA |
| SEQ ID NO: 604 | TTAACATCAGTGTCAACTGCAGTGTTGTTTCTGAGTAATA |
| SEQ ID NO: 605 | CATAACTCCATGCTCTCAAACCAATCACTCCTTCATTCAT |
| SEQ ID NO: 606 | TTCTCCTATGCTGCACCAGAAAGGGTTTTGTGGGTTATCA |
| SEQ ID NO: 607 | ATCGTTCAGCATCTTTAGGAAATATCCAGAGACTGCATTG |
| SEQ ID NO: 608 | TTTATTAAGAGCAAAAAAAGCCTGTTTCGTTAGCCAGTCA |
| SEQ ID NO: 609 | TTGTTCATATGCCTAACTTAATAAATTCTTCATACAGAAA |
| SEQ ID NO: 610 | ATAACTTTTAAACCCAAACACCTAGAGATTTCATTATGTA |
| SEQ ID NO: 611 | TTCTTACCATTAAGTCTTCCAAATGATAATTTATTATAAA |
| SEQ ID NO: 612 | TATGTAAGGACAACTTCATTATATGCTTGAAGAAATTGTT |
| SEQ ID NO: 613 | AATCTTAAAAGTGACACTAGTCACATTCCACACGGTTAAA |
| SEQ ID NO: 614 | ATTTTGAAAACTATTCCTTTATCTGGAATGAATGTAAACC |
| SEQ ID NO: 615 | TTGCATTAAGGGCACCAGAAACTTATAGAAAACCAAAAAG |
| SEQ ID NO: 616 | TAAAAGACAGTGAACTGAACAGTAATTAACATTACATCCA |
| SEQ ID NO: 617 | CAAAAAACTGTGTTTATCATATACCAAACATTTTCAAGTT |
| SEQ ID NO: 618 | TCTCAGGATATTTTGTTCTCTGACACAAATACACCAGTCA |
| SEQ ID NO: 619 | TAGCTTTACATCTCAGAATGAATCAATGTGGGGGCAGAAA |
| SEQ ID NO: 620 | AGACCTATATACCTATAGTGCCTAATAGACAATAAGCCAC |
| SEQ ID NO: 621 | TCTCTCCCCTGCCTAGACTAAGGTAAGTGGGTCTTACCTT |
| SEQ ID NO: 622 | CATCCTGCTTTTAAAACCCTTAGTGCTCAGCGGCTTGTCT |
| SEQ ID NO: 623 | AGCTTATAAACTTCAGAGTAATGTAGCACAAATGTCTGTC |
| SEQ ID NO: 624 | AACTTGAAATAAAACTTTAAACGTTGATTGATTCTTTCCC |

TABLE 1-continued

Exemplary Probe Nucleotide Sequences

| SEQ ID NO | Nucleotide Sequence |
|---|---|
| SEQ ID NO: 625 | GACAGGCTTAGAGTCCATAACAAACAATCTTAGCTGGAAA |
| SEQ ID NO: 626 | TGCTCAACAACACTTGTGGAAGAGCAGGGCAAGCTATTTC |
| SEQ ID NO: 627 | TTACAACATCACTGTAGACATTACTTTTACCCACAGTGCC |
| SEQ ID NO: 628 | ATCCTAGTTGTATATACTTCTTGGATAAAGTATCTTCGTA |
| SEQ ID NO: 629 | ATTTTTGGGGAGTGCCATTCCTGCAGGTCTTGAAGACAGG |
| SEQ ID NO: 630 | CACACAGCCAATGAAACTGACAGAGCCAATGCAACCAAAA |
| SEQ ID NO: 631 | ACGACTTCAATCAAGAGAAACAGGCAGGTCAGAGTGTGAA |
| SEQ ID NO: 632 | CTGGTTATCAGGGTTCATAGCACATAGGTTTGACAACCAC |
| SEQ ID NO: 633 | TTTATTATTCAGCTGGGTAAGCCAAGTGACAGTCTTCCCC |
| SEQ ID NO: 634 | GTTTTATTCTAGGAATCAACTGCTTTCTAAAAATGTCTAA |
| SEQ ID NO: 635 | TTTACTGATGGTACTTATTCCCCCAATTATTGATTATTGA |
| SEQ ID NO: 636 | GCATTTAGGAATATTCAATATTGATACTAAGGTCATCTTT |
| SEQ ID NO: 637 | TACTCTGTAATGTAGTAATCTTTATGAAGAAATAAATTTG |
| SEQ ID NO: 638 | ATTTTGAAAAAATGTTTCACTGCATTTTACTATACAAGCT |
| SEQ ID NO: 639 | ACCACACATTCATCAAAAAATACCTCAAAGAAAATTCTGC |
| SEQ ID NO: 640 | GTTGTCACAATAAACTCAGTACTGAGTAAAATATCACAAA |
| SEQ ID NO: 641 | GAGTATATATTGTATTACTTACCTGATGCGCAAAGACCCA |
| SEQ ID NO: 642 | AAAATGACAGCAACATAGGTGCCACCTGAGGTCCACATCT |
| SEQ ID NO: 643 | TGGAGAGAGTGGGGTTAATCTGTTACTACACTTTGCTACT |
| SEQ ID NO: 644 | ATTTCCATCATTTTGTCTTTCAGTAAGCATGTACGAAGTA |
| SEQ ID NO: 645 | GAGATGAAGATGGTACATCAGTAGGGAGCCCCTCTACTGG |
| SEQ ID NO: 646 | TCTAATTCATCAAAGTATTCTGGGTTGATTCCAGGTACGT |
| SEQ ID NO: 647 | ACAAACTCGTTTTGTACAGAGAGGAAAATATTAAAACACC |
| SEQ ID NO: 648 | ATGTTAATTATAAACACTGTTATAAGTTTTACAAATGTAA |
| SEQ ID NO: 649 | TCCACTGGCAGAGAGAATATATGTTTCCATTACGGTCCCA |
| SEQ ID NO: 650 | TCAAAGGTTTTCTATCACGTTTTCTATTATTTACTCACAT |
| SEQ ID NO: 651 | AAAAACAAGAGTCACACAACCTATGCTCCACAATATCTGC |
| SEQ ID NO: 652 | ATAGGTTATTCTACAATCGACACCAACTATCAGCGGCTTT |
| SEQ ID NO: 653 | ATTGAATTAAATGATGGCTTGATTATCCAGGAATCAGCCA |
| SEQ ID NO: 654 | CTTACCATAACAGAGTAATCTCTAGCTTATTCCAAGGATA |
| SEQ ID NO: 655 | ACCTAAAATTTAACTAGAATCACTTTTCAATGAAGCTGCT |
| SEQ ID NO: 656 | TAAACTAAGAGCCTTTGATCTTGCCTTATTCTGATAAAAT |
| SEQ ID NO: 657 | AAATAATAATTCACAAGGAAATCCTTATTGTTTATTTAAA |
| SEQ ID NO: 658 | GTAATATGTAGGTTAAACAGAAATGTTGGTTGAATCATGT |
| SEQ ID NO: 659 | TGCAGACACTAATCAAACCAAACAGGGCCAATTAAAATTG |
| SEQ ID NO: 660 | TAAAGTGCAATGGGACAGAGCAACTTCATTTTCACAAACA |
| SEQ ID NO: 661 | TAATCTAATTGCCAGAAATGCTTGCCCATTGCAATGGGAG |
| SEQ ID NO: 662 | AGTTGACAATGACTGCTTAGTTTAGGGTTTTGAAGTAAAC |

TABLE 1-continued

Exemplary Probe Nucleotide Sequences

| SEQ ID NO | Nucleotide Sequence |
|---|---|
| SEQ ID NO: 663 | CAGATGGCAGGTATTCTGTGAATTAACACTGATGCTTCTG |
| SEQ ID NO: 664 | AGTCAAGTTCAGAAATGATCTGTTATGACCCCATGAAACG |
| SEQ ID NO: 665 | GGGATGCTCTGATACATCATTCAGTAAAATGATAGAAAAA |
| SEQ ID NO: 666 | TAGCTGTATTGCTTGATAGCTTCATAGCTTGATAACCATT |
| SEQ ID NO: 667 | TTTTAGCAGGGAATTAACACAGGTATATAAATGAAGAAAA |
| SEQ ID NO: 668 | TTGATTGTTTATGAAGCTGAGATTGTTTACTGGTTTCGAG |
| SEQ ID NO: 669 | TCTGTGTTTTTATGTTTGGGAACATGAGGGAATCAGTTCT |
| SEQ ID NO: 670 | TTCTTAAGCTTTCATTTTTCCAGTGGTGAATGTAGAGAGA |
| SEQ ID NO: 671 | ACGGTAACTGAATAAACTTAAGAACTGAGGTAAAGTTTTC |
| SEQ ID NO: 672 | TCAATATGTAAAATTGATCAATTCAGACACCTTTATATGG |
| SEQ ID NO: 673 | TGTCTCTTTCATGCTGTAAATAGAGCATTGCATGAAAGAT |
| SEQ ID NO: 674 | TTCATAGCACAGTTTATAAACCTAAGAAAGCAAAGATGAA |
| SEQ ID NO: 675 | AACCAAGCAGGATTCTATGACTAAAAAAGTGTATTTGTAT |
| SEQ ID NO: 676 | AGATAGAGAATTTCAAAGAAACCATCTTTATCAGCTGCAC |
| SEQ ID NO: 677 | CCAAGAATGAAAAGATGCACTAATTCGACTGAAAGCCAAG |
| SEQ ID NO: 678 | TCATAGTTGAGACATATAACAACCATAAAGGTCCGCATAT |
| SEQ ID NO: 679 | AGGAAAGGGTGGAAAGGCAAGCAGCGGGGAGTGTTGGCTG |
| SEQ ID NO: 680 | CTATAAATTGACCTATCCTGTAAAAAAGGATGTCACAGCA |
| SEQ ID NO: 681 | ACAATTGACCTAAGACTGTAAATTGTAAATTGACTATAAA |
| SEQ ID NO: 682 | GCAAGACTGGGTATACTATTAATAGGAAAAAATGAACTTC |
| SEQ ID NO: 683 | ATTGCTTTGATATTGATTGAATCACAGAGAAAATCCTAAG |
| SEQ ID NO: 684 | TAGATTATGCTGGCAAATCTCAGTGATCAGAGAATTATAT |
| SEQ ID NO: 685 | ATTCAGAAATGGAATAGGAAGATATTTATGTGCCATCCTG |
| SEQ ID NO: 686 | GTTTGAATTATTATTCAAACAGTGTATGTTTGTTTGTACT |
| SEQ ID NO: 687 | AATGCAACAGAGACAGGTATTTATAGCATCTGTTTTCCAT |
| SEQ ID NO: 688 | TTTAATATCCAAATATGTATGGACACATACAATTGTACAT |
| SEQ ID NO: 689 | ACGTCTACCGTCATTTTCGTAATTATTCGGTTTCCCTGTC |
| SEQ ID NO: 690 | GGAGCGCTCCTGCGCGCCTTGTTCGTTAGGATTTATTTTT |
| SEQ ID NO: 691 | GGTGGCTCCCTAATGCCTGCTCGTTTCAGGTCTCAGCTCT |
| SEQ ID NO: 692 | CCTTAGTGTGTTGAGGACGCTGCAGAAGGTACAGAGGAGA |
| SEQ ID NO: 693 | GACCAGATGGTAGGACAGTCATTCTCCTCTGCGTCTCCGC |
| SEQ ID NO: 694 | CGTGAGGCATGGAGTTTTTGTCCTGCCCCTGCCTGGTTAG |
| SEQ ID NO: 695 | TTTAAGTCTCTGGCACCGTGCATAGCAGAATTGGTTGGGA |
| SEQ ID NO: 696 | TCTTTCTCCAAGTGCCTCTATGTTGGCACATCTCTGAAAT |
| SEQ ID NO: 697 | TGCGTCCCGGCCAGGTAAGCAGCTTCCCTCTCAGCTGCCT |
| SEQ ID NO: 698 | GGGTGTATGTAGCTGGCAGAAGTGGGACTTGGTCGCAACC |
| SEQ ID NO: 699 | CGTGGCGAGTGGGCGGTAGCTGCTCGTAGAGCGTGTGAAA |
| SEQ ID NO: 700 | GTTGGCCCTAAAAGTTATCATTCATGCTAGTTTGACCAAT |

TABLE 1-continued

Exemplary Probe Nucleotide Sequences

| SEQ ID NO | Nucleotide Sequence |
|---|---|
| SEQ ID NO: 701 | AAGTGGGAGGAGCTGGGCAAGAAAGTCCACCCCTTTTTCT |
| SEQ ID NO: 702 | GCCGAGCCGAAGTCATCTGCCAATCAAAACAGCCACAGGG |
| SEQ ID NO: 703 | CGCGTACCTAATGGGAGACAGACAGGTGCCTTTAAAGCGG |
| SEQ ID NO: 704 | TGGGGAAAGCGGAGGAAGGCATGGAGTGTGGGCGTTAGGG |
| SEQ ID NO: 705 | GCATATTCTGCCTTGAAGTCATTGGTTGGTCCTGGAAGTG |
| SEQ ID NO: 706 | AATTGGTCTGGGGGAGGAGCTACGACAGTCCAGGGGCGGG |
| SEQ ID NO: 707 | GTGTCGTGCTGATTGGATGTATCCGCCCCCCTCTCTTAAA |
| SEQ ID NO: 708 | CAACACGCCAGCGCGAGGACCCGAACGTCAATCAAGAGAC |
| SEQ ID NO: 709 | GCGTTCGATTGGCCTCCCGCGCAGGCTGCTAGGATTGGCT |
| SEQ ID NO: 710 | CCCTGCCCCCTTTCGCGGATTGGGTGATCGCTCCAAGGCG |
| SEQ ID NO: 711 | CTGACCCTTGGAGGCTTTCTATTGGTTCCTGGCAGGGATG |
| SEQ ID NO: 712 | TCCCGAATATAGGCCAGTCATTGCTCCTGCTGAACGTCGC |
| SEQ ID NO: 713 | CCCCTCCTCTCTTCTCGTCTCTGGCGCCGACCCGCCCCCG |
| SEQ ID NO: 714 | GCTCAAGGGAGGCCGCGGCGTCTGCCGATGGCTCCGCGGA |
| SEQ ID NO: 715 | TGGGGGAGTGGGCCCGGGGTTGTTCTGACGACGGGGGTCG |
| SEQ ID NO: 716 | CCCGGGCGCTATCGCGATAGCGGCGCGAAGCGGAAGTGGG |
| SEQ ID NO: 717 | CGGGGGAGGCGAGCGCCCGCCGCCTTTTTCTCGCGCCCCG |
| SEQ ID NO: 718 | CACAGGAGCTGGCGCCGCCGCTGAGGAGCGTATCGCGACA |
| SEQ ID NO: 719 | GTTGCCGACTCGCGCTCTCGGCTTCTGCTCCGGGCTTCT |
| SEQ ID NO: 720 | ACTCGGAGCTCGGATCCCAGTGTGGACCTGGACTCGAATC |
| SEQ ID NO: 721 | GGCTCCTCCTTGTTCCGAGCCCGAAGGCCCGCCCCTTCAC |
| SEQ ID NO: 722 | CTTTCCGGAGCCCGTCTGTTCCCCTTCGGGTCCAAAGCTT |
| SEQ ID NO: 723 | GACCCCGCCTCATTCCTCACGGCGAGCTCCAGACCCCGCC |
| SEQ ID NO: 724 | AGAACTCAAGCTCCCGATTGTGCCCGAAGGAACCCGAAGG |
| SEQ ID NO: 725 | ACTATTGCCGAAGTGAGCCGAAGTTTGTGGCCCCGCTTCC |
| SEQ ID NO: 726 | ACATGTGGCTCCGCCCACACTGGCCTCAGCTCTCCGTTCT |
| SEQ ID NO: 727 | ACAGTGACCCTAAGGACTCGACTACCTCCGAAGAAAGCCG |
| SEQ ID NO: 728 | CTTGTACCCAACTATCTACGAAGTAAACCGAAGCTTGTGG |
| SEQ ID NO: 729 | TATCTGGCGAACCTGTTGACTCCGCCTATCATCCTAGCGT |
| SEQ ID NO: 730 | GGCAAGTCGCTTTCGCCCCGCCCCCTTGTAAATACTCATG |
| SEQ ID NO: 731 | CTCCTCTACTTGGGAACTTGAGGATCGTCACCCTGGCCCG |
| SEQ ID NO: 732 | TTGGCTCCGCCCCACTGAGCGCACCTCCCTCTGCCGCTTC |
| SEQ ID NO: 733 | TCCTTGCTCCACCCCCTCATGCCGACACCCTCGTCAACTT |
| SEQ ID NO: 734 | TCCACCGATAGAACCAGCGAGTCACCTCATAAACAGTAAT |
| SEQ ID NO: 735 | CGCTCAGTCCGCCTCCTTGCCTCCCTTCAGAATGTCCCAC |
| SEQ ID NO: 736 | GCCGTCCACTCTCCGCTCGGGCGGGCTCACCCCAATTGGG |
| SEQ ID NO: 737 | CGACCGAACCCCACAGCCGAAAGCCCCGCCCCCTGGACAC |
| SEQ ID NO: 738 | CTCCGAGCGCCAGCGCACCCCAGTTGGGGAGTTCCCGCCC |

TABLE 1-continued

Exemplary Probe Nucleotide Sequences

| SEQ ID NO | Nucleotide Sequence |
| --- | --- |
| SEQ ID NO: 739 | AGCCCCGCCTCCTCCCGGACGCAATAGGTTCGGCGTTCGG |
| SEQ ID NO: 740 | AGCAATTTGACGTTCGGGTGTTCTCGGCTCGGCCGAATCC |
| SEQ ID NO: 741 | TGCCCCCTCCCGAGCACAGGAAGTTCGGCGTTCGGGCGTC |
| SEQ ID NO: 742 | TTTCGGACCTCCTCGCTCTCAGACTCCCACAGTACAAAAC |
| SEQ ID NO: 743 | CGAGCCTTCGCTCCTCCTCTTTCCGAACGACTGTGATTCG |
| SEQ ID NO: 744 | GAGGCTAAGGCACCGCCGAGGCCACACCCTCTTCCGGACG |
| SEQ ID NO: 745 | GCGTCCCCCTTCGGGTGTTCCCGTCAGCGGTCAGAAGCTC |
| SEQ ID NO: 746 | CCTTACAAAGGTCCATTTTGGCACCACCCTCTTGCAAAGT |
| SEQ ID NO: 747 | GGAGCGTGAAAAACAAACCTCCGCAAGCGCGGCGACACGC |
| SEQ ID NO: 748 | ACCCGCTCTGTGCCCGCACTGCCGTACCTACCATTGCGCC |
| SEQ ID NO: 749 | GGTCCTCAGCATCTGCATATGTAGCCCCTCCCGCTGGTCA |
| SEQ ID NO: 750 | CCCAACCCCTACCCCCAATCCATCTTAGAGCTGATTCTCT |
| SEQ ID NO: 751 | ACTCCAGTGATTCTTCCTTATGCTAGGGACTCGAGGACCC |
| SEQ ID NO: 752 | GAGAATTGAGAAGTCAGTGTGGGAGGGGATGTCCCAGTAC |
| SEQ ID NO: 753 | TTTCTGGTTCGCGTTGGCTGCATTGTGGAGCTGAGGGATG |
| SEQ ID NO: 754 | TAGCTTCTTAATCTCCTTCTTTAGGTCAGCCTCATACTTT |
| SEQ ID NO: 755 | TTCTCCCTGGGACCCAGCAGTCCACTCTCCCAGTTCCCTC |
| SEQ ID NO: 756 | AAAGTCAGACCTCAGGACCCAGGAACTGGGGCCCACAGCT |
| SEQ ID NO: 757 | TCTTGATTTGGTCCCTCAGCCGCTGCAGATGGGAAAAGCA |
| SEQ ID NO: 758 | TAAGCTGCCTCTTGTCCTTGATCTCGTTGGACGCTACCCA |
| SEQ ID NO: 759 | GGCTCTGGGCTCCTACCGTCTCAATGAGCTTGCGGTTGTC |
| SEQ ID NO: 760 | TGAGGACCTCTGGGGTCTGGCCGCTCTGCCTCCGCCCCTT |
| SEQ ID NO: 761 | CTGCCTCTTCACTTCCCTTAGGTGCAGAAACCTTACTTCT |
| SEQ ID NO: 762 | CGACCTGAGCCTCGTGACCCTACTTTCTGAGCTCTGAGTC |
| SEQ ID NO: 763 | TCAAAGGTGGGAAAGGAGCTGACTAAGGGCCAGCAGACAC |
| SEQ ID NO: 764 | CCGTTCCATTTGCTGTAGAGAGTGCAGTTGGCAGGGGGGC |
| SEQ ID NO: 765 | GCTGTAAGCTTTGGTTTTGGTCTCTCGTTCCACAACTTTG |
| SEQ ID NO: 766 | CCAACTCACCGTGAGCCACTGGCCAACCTCTTCCTTCTCC |
| SEQ ID NO: 767 | CCAGGGCTCAGGATCCTCAGAGTTCACCTCCTCTTCTCTA |
| SEQ ID NO: 768 | GTCCACCTGCATGTTGAGCGTGTCGATGGTATTCTAGGGG |
| SEQ ID NO: 769 | GCGTGTCTGCACTGACAGTGACTCCACTTCACTCTCAAAC |
| SEQ ID NO: 770 | TGTCGGGTCTCCCTCACTCACATCCTTGTCGCCCTTCTTC |
| SEQ ID NO: 771 | CTGCTGGCCAGCCCATTCCCATGCCCATCCCCATCCCAAA |
| SEQ ID NO: 772 | GAATCCAGGCCCCAACTCCCAGGAGCATAAATGACTGGCC |
| SEQ ID NO: 773 | TCTCAAATCCCTAATCCCGGCTGTTGGCCCTGTCCGCCTG |
| SEQ ID NO: 774 | CCTGCCCCACGCGTGCAGCTGCTAAGCCCTCCCAATCCTG |
| SEQ ID NO: 775 | CCCAGACACCCAGGGGACCCTGAGATTCTGTCTGACCTCC |
| SEQ ID NO: 776 | CTTCCCCCAAGTCGCTCCTCTTCACAAAGGCCCCACGGTC |

TABLE 1-continued

Exemplary Probe Nucleotide Sequences

| SEQ ID NO | Nucleotide Sequence |
| --- | --- |
| SEQ ID NO: 777 | CCTCTGGGTGCCAGGAGGCCTCTTGCCATGGGTGTCCTTC |
| SEQ ID NO: 778 | CTGCCTTGTCTCTACCCACTGTGCTCTCCCTAGGACCAGG |
| SEQ ID NO: 779 | GGCGAGGGGAGGTCCTGCAGCTGCTCGCGTGGGCTGCCC |
| SEQ ID NO: 780 | TGCGCTCGATCTCATCCTTCAGTTCGTAGCCCACCTGGGG |
| SEQ ID NO: 781 | TCACCTGCTTCACAGGCGGCGGCTCCTGCCACTTGTCGAA |
| SEQ ID NO: 782 | CTCGCTTCTTCCGCTGTCCATCCAGGGGCGCAGGCAGCGG |
| SEQ ID NO: 783 | CCCATGCCTACCGGACCCCAGGGCCCCTCACCTGCGGCC |
| SEQ ID NO: 784 | AGTCGGCTGGGAGGAGGACGCCGGCTTCTCCCCTCCATGA |
| SEQ ID NO: 785 | ATCTTGCGGTACCTGGGGACGGGTGGGTGGGCGGCGCCAG |
| SEQ ID NO: 786 | TTGGCCTGCTTCCGGATCTCCGTCAGCCCCAGCCGCTCCT |
| SEQ ID NO: 787 | GGAGGGCGCTCTGGGAGTCTGACCTCTCCGAAGCTCATAC |
| SEQ ID NO: 788 | AGGAGGCAGAGGGCGGTGGCGGCTGGCTGGCTGTGGGGTT |
| SEQ ID NO: 789 | AGACATGAGCCAGGGCCACAGGACGAGAGGAGGGCGGTG |
| SEQ ID NO: 790 | CCAAGGGCCGCGAGGGTCGCTTTGGGGCTGAATGGATGGA |
| SEQ ID NO: 791 | GATGGGAAGCCGCGGGGGCTCTAAGCAGCGGAGACACAGG |
| SEQ ID NO: 792 | GGAGCCTCTGGGCAGGGAGGAACCGGCCAAGGAGCCCGGG |
| SEQ ID NO: 793 | GGCGGGGCCCAGGGACGGGGCGGCCGTGCAGCAGGGCACT |
| SEQ ID NO: 794 | CTGCAGGACCAAGGGGATGACGCTGGGATAACAGAGGAGA |
| SEQ ID NO: 795 | CAGAACAGGTTTAATAGGATGAGGTGGCCTCTGAGTTCGG |
| SEQ ID NO: 796 | CCATTCCTTCCTTACTCGTGTGGGTCGGGGGATGTCAGGA |
| SEQ ID NO: 797 | GGCCCGGTCCCAGCACTGCTCTGTGAGCTCAGAGTTGGGA |
| SEQ ID NO: 798 | TGGGGGCCCACACACGCGGGGGATGCCGGGGAGCCTGAGA |
| SEQ ID NO: 799 | CACGGGCACCTGCTCCGGTACCCACTCGGCCCGGCTGAGG |
| SEQ ID NO: 800 | CTCCACCAGCCGGAAGCCCAGCGGTCACCAGCCGGCCGGT |
| SEQ ID NO: 801 | AGGCGTCCTCCTCGATCTAGGGGGAAGAGGAGGCGCCCTG |
| SEQ ID NO: 802 | ACTTGCCCAGGTGGCCCAGGCTGAATCCCAGGTCCTCCTG |
| SEQ ID NO: 803 | TGGCCTCGTTTACCTGTGTCTGCCGCACACGCCCACTGCC |
| SEQ ID NO: 804 | GTCTGGCCCATACCTGCAGCGTCTTGGAGATCCTGGCCTT |
| SEQ ID NO: 805 | GCTCCCCCCACCTTGTGTCCCTCGGTCCCCAGCCCCACCT |
| SEQ ID NO: 806 | TGCAGGGTCCGCTGTGGGAGGACAGGGAGGCTGCGATCT |
| SEQ ID NO: 807 | TCGCGGATGGTGGACTTCCCGCCATATACGACGCTCTGCT |
| SEQ ID NO: 808 | AGTGGGGTGAAGGCCACGCTGGAGGCCGTGCCCGAGGAGC |
| SEQ ID NO: 809 | CGGCTGCTGAGCCTAACCACCTCCTGGGCTTCTTTCCAGC |
| SEQ ID NO: 810 | GCTCATGGTATCCCTACCGCAGGCAATCTGTGGACAGCAC |
| SEQ ID NO: 811 | CTGAATGTCACCTGAAGGGTCACAGAAGCTACTCACAGGG |
| SEQ ID NO: 812 | TTAAGTGTTCTCAATATGAGATTAGCTGGAGCCGCCTAAT |
| SEQ ID NO: 813 | GAAGATCCATCTGTTGGAAGCCAGAGGACTAGTGGGAAAC |
| SEQ ID NO: 814 | CCCCCACAGGGATCTGACACACAACTTAGGTTGTCAGCCA |

TABLE 1-continued

Exemplary Probe Nucleotide Sequences

| SEQ ID NO | Nucleotide Sequence |
|---|---|
| SEQ ID NO: 815 | GCCCAGCTTCCCAAGTCCTGCCTGGACACCGCCCCATGGA |
| SEQ ID NO: 816 | AATCACCTTCATGCTTAAAACACTCACACTGATTTCCAGC |
| SEQ ID NO: 817 | CCTCTTGGGGACCTGGGTGACCTTACTCACCCTCATGGCT |
| SEQ ID NO: 818 | GTTGCTGTGGACAGGCTTGGAGCCGTTTTTGGCTGGAGAC |
| SEQ ID NO: 819 | GGAGGGGTAGGTGGGCGGCACAGCTGGGGACTGAGGGTGC |
| SEQ ID NO: 820 | GCCAGGAGTGGTGCTCAAGGCAGAGGCAGCAGGCGGGGGG |
| SEQ ID NO: 821 | CAGGGCACTTGGGGGTGCTGCGGGGGCGGGGACCCCATTG |
| SEQ ID NO: 822 | GGTGCCCGAGTTGTGGCTGGGAGCTGGACTGGCCTTGGGG |
| SEQ ID NO: 823 | CTGCTTGCCAGCCCCTCCACCGGCACTGCTGTTACTACTG |
| SEQ ID NO: 824 | GCCCCCCACCCCGCTGCCTCCTCACTCACTGGTGGCGCCA |
| SEQ ID NO: 825 | CGGGCTGTCTGCCACAACTGAGCTGTAACCTGGGAACAAA |
| SEQ ID NO: 826 | GCTGGCATTGTTGCCCCCACTGCTGCTCAAAGCCACCTCT |
| SEQ ID NO: 827 | AGGTGGGTTGTGGGGGCCGGAAGGGGGGCCCAAGGCCTGG |
| SEQ ID NO: 828 | TCCCAACCCTGCCGATGGCCGAGACACTCACGAGGTGCTG |
| SEQ ID NO: 829 | GGGGGTGAGGCGCCTGCGCCTCTCTGTTTCAAAAGGCTGC |
| SEQ ID NO: 830 | ATTCCCAGCAGCAAGGGCGGGGGGTTCAGAACCCACCGAT |
| SEQ ID NO: 831 | GGGGGTGTAACACCCGAGGGAGATGGAGGATAGCGCTTGG |
| SEQ ID NO: 832 | CAAAGCAGGGAGGCTGATGTAGTTTCCTTGCTGGAAAGAA |
| SEQ ID NO: 833 | CTTCCACTTAGATGAGAACGTATTTTAGAATGTTCTGAAG |
| SEQ ID NO: 834 | TAACAGAAATGGGGAGGAAAGGGTATGGGGCTCTTGAGAA |
| SEQ ID NO: 835 | AAACAGTGACCCTCCGGTGGCAGTCAATTGGCCTCAGGCA |
| SEQ ID NO: 836 | GCAGAGGAATAAGGACTTCGGGACAATTCACTTTGAAAAG |
| SEQ ID NO: 837 | GACCCAGTGGAATGGTCTGAGCTAAGATTTGAAGGAGTGG |
| SEQ ID NO: 838 | TGCACACTGATCTTTCTTAGGGCATTCTTCGGGAAACAGG |
| SEQ ID NO: 839 | GGCTCAGGATGAACAGCAACAGGGGTTGGGATGATCACTG |
| SEQ ID NO: 840 | GATCATGGAGATGTGATCTAGGGAACAAAGCCAGAGAAGG |
| SEQ ID NO: 841 | AGGCATTCCCACGGTGTGAGGTCAGATTGGGCAGGGCCTA |
| SEQ ID NO: 842 | AGAGCCAGCACTTGCTGTTCCACACATACTAGATCAGTCT |
| SEQ ID NO: 843 | TGGACAACCCCCTCCCACACCCAGAGCTGTGGAAGGGGAG |
| SEQ ID NO: 844 | CACCTAGATGCTGACCAAGGCCCTCCCCATGCTGCTGGAG |
| SEQ ID NO: 845 | ATAAAGCCTTCATTCTCCAGGACCCCGCCCTTGCCCTGTT |
| SEQ ID NO: 846 | AGGTGGTGAGTTTGGGGCTGGGGGGCCTCCCTGAGGAGCC |
| SEQ ID NO: 847 | GAGAGAACCAGGTCCCACATGCTGACACAGGTGTCCACGG |
| SEQ ID NO: 848 | ATCCCCCCAATCTCACCAGTGCACCCCACAGACAAGGCGA |
| SEQ ID NO: 849 | AAGGGCTTCAGCATAAGAGTCAGAACCCGCCCCCCTTCCT |
| SEQ ID NO: 850 | TGTGGGCTGAAGGGACGAGGCTGGGGCACTGGGTGGGAGG |
| SEQ ID NO: 851 | TTGCAATGTGGAAGAGTCAGGGGCACATTGTCTGGGCTGA |
| SEQ ID NO: 852 | TAAGTGGGAGGGAGCGGGGACCTAGTGTGGGCATGAGGAC |

TABLE 1-continued

Exemplary Probe Nucleotide Sequences

| SEQ ID NO | Nucleotide Sequence |
|---|---|
| SEQ ID NO: 853 | GGAGCAGGGATTTGGCTGGGCAATGGAGAGAAAGGTCTGA |
| SEQ ID NO: 854 | ACACAGAGATGCCCAGGAACTTGCTCTTTAGTAAAGCAGC |
| SEQ ID NO: 855 | TGGAGAGAGGTCCTTGAAAGGTTTTGAACCCCATAAAGAG |
| SEQ ID NO: 856 | TCAGGAGGCAGCCCAGTGATAGGGTCCAAGGAACCAGTGG |
| SEQ ID NO: 857 | ACAGTCTACTGACTTTTCCTATTCAGCTGTGAGCATTCAA |
| SEQ ID NO: 858 | CTGTCCCCTGGACCTTGACACCTGGCTCCCCAACCCTGTC |
| SEQ ID NO: 859 | AGGAAACCCAGATTCCACCAGACACTTCCTTCTTCCCCCC |
| SEQ ID NO: 860 | GGCTATCTGGCCTGAGACAACAAATGCTGCCTCCCACCCT |
| SEQ ID NO: 861 | GTCTGGCACTGGGACTTTCAGAACTCCTCCTTCCCTGACT |
| SEQ ID NO: 862 | TTGCCCCAGACCCGTCATTCAATGGCTAGCTTTTTCCATG |
| SEQ ID NO: 863 | AAAAACACGAGCACCCCCAACCACAACGGCCAGTTCTCTG |
| SEQ ID NO: 864 | TTAACCTTGGACATGGTAAACCATCCAAAACCTTCCTCTC |
| SEQ ID NO: 865 | AGCAACTAAACCTCTCCACTGGGCACTTATCCTTGGTTTC |
| SEQ ID NO: 866 | GAACCTCTTATTCTCTTAGAACCCACAGCTGCCACCACAG |
| SEQ ID NO: 867 | TCCCTTCTCCCAGTGTAAGACCCCAAATCACTCCAAATGA |
| SEQ ID NO: 868 | CAACCCCCAACCCGATGCCTGCTTCAGATGTTTCCCATGT |
| SEQ ID NO: 869 | CATAAACCTGGCTCCTAAAGGCTAAATATTTTGTTGGAGA |
| SEQ ID NO: 870 | CTGCTGACCTGCCCTCCCAGGTCAGAATCATCCTCATGCA |
| SEQ ID NO: 871 | TGTTCTCCAGACCTGTGCACTCTATCTGTGCAACAGAGAT |
| SEQ ID NO: 872 | CGTGCAGCAAACAATGTGGAATTCCAATAACCCCCCACTC |
| SEQ ID NO: 873 | AAATATGAGTCTCCCAAAGTTCCCTAGCATTTCAAAATCC |
| SEQ ID NO: 874 | CATCATAAAAAGATCTTGTGGTCCACAGATCCTCTAGCCC |
| SEQ ID NO: 875 | CTCCCAACCCAGAATCCAGCTCCACAGATACATTGCTACT |
| SEQ ID NO: 876 | CACTCTGAGACCAGAAACTAGAACTTTTATTCCTCATGCT |
| SEQ ID NO: 877 | CACCAGCACTCAGGAGATTGTGAGACTCCCTGATCCCTGC |
| SEQ ID NO: 878 | TGCCTAGATCCTTTGCACTCCAAGACCCAGTGTGCCCTAA |
| SEQ ID NO: 879 | GGGGGTGGGTACGATCCCCGATTCTTCATACAAAGCCTCA |
| SEQ ID NO: 880 | GGACAAAGGCAGAGGAGACACGCCCAGGATGAAACAGAAA |
| SEQ ID NO: 881 | TGGATGCACCAGGCCCTGTAGCTCATGGAGACTTCATCTA |
| SEQ ID NO: 882 | GGGAGAGCTAGCACTTGCTGTTCTGCAATTACTAGATCAC |
| SEQ ID NO: 883 | GGCTGGACAACCCCCTCCCACACCCAGAGCTGTGGAAGGG |
| SEQ ID NO: 884 | TGGCACCCAGAGGCTGACCAAGGCCCTCCCCATGCTGCTG |
| SEQ ID NO: 885 | CCTATAAAACCTTCATTCCCCAGGACTCCGCCCCTGCCCT |
| SEQ ID NO: 886 | TGCAGGTGGTAAGCTTGGGGCTGGGGAGCCTCCCCCAGGA |
| SEQ ID NO: 887 | AGGAAGACAACCGGGACCCACATGGTGACACAGCTCTCCG |
| SEQ ID NO: 888 | CAACCATGGCCCCTCTCACCAATCCACGTCACGGACAGGG |
| SEQ ID NO: 889 | TCAGCTTGACAGTCAGGGCTGGCTCCCTCTCCTGCATCCC |
| SEQ ID NO: 890 | TCCCTGTCTGGGCTGGGGTGCTGGGTTGGGGGGGAAAGAG |

TABLE 1-continued

Exemplary Probe Nucleotide Sequences

| SEQ ID NO | Nucleotide Sequence |
|---|---|
| SEQ ID NO: 891 | TGTGGGAGTGAGGACTGTTGCAATATGGAGGGGCTGGGGG |
| SEQ ID NO: 892 | GGGAGAAAGTTCTGGGGTAAGTGGGAGGGAGCGGGGACCT |
| SEQ ID NO: 893 | TTGTGGGGCTCAAAACCTCCAAGGACCTCTCTCAATGCCA |
| SEQ ID NO: 894 | TGCCCAACCCTATCCCAGAGACCTTGATGCTTGGCCTCCC |
| SEQ ID NO: 895 | TCTTGCCCTAGGATACCCAGATGCCAACCAGACACCTCCT |
| SEQ ID NO: 896 | TTCCTAGCCAGGCTATCTGGCCTGAGACAACAAATGGGTC |
| SEQ ID NO: 897 | TCTTAGCCCCAGACTCTTCATTCAGTGGCCCACATTTTCC |
| SEQ ID NO: 898 | AGGAAAAACATGAGCATCCCCAGCCACAACTGCCAGCTCT |
| SEQ ID NO: 899 | CCCCTTCAGAGTTACTGACAAACAGGTGGGCACTGAGACT |
| SEQ ID NO: 900 | TGGAAAGTTAGCTTATTTGTTTGCAAGTCAGTAAAATGTC |
| SEQ ID NO: 901 | GACTCAGGAGTCTCATGGACTCTGCCAGCATTCACAAAAC |
| SEQ ID NO: 902 | ATGCTGTCTGCTAAGCTGTGAGCAGTAAAAGCCTTTGCCT |
| SEQ ID NO: 903 | GATTTGGGGGGGCAAGGTGTACTAATGTGAACATGAACC |
| SEQ ID NO: 904 | GTGTGCACAGCATCCACCTAGACTGCTCTGGTCACCCTAC |
| SEQ ID NO: 905 | AGGATTCCTAATCTCAGGTTTCTCACCAGTGGCACAAACC |
| SEQ ID NO: 906 | CAAAGGCTGAGCAGGTTTGCAAGTTGTCCCAGTATAAGAT |
| SEQ ID NO: 907 | GTCAAGGACAATCGATACAATATGTTCCTCCAGAGTAGGT |
| SEQ ID NO: 908 | GCAAGATGATATCTCTCAGATCCAGGCTTGCTTACTGT |
| SEQ ID NO: 909 | TCTGTGTGTCTTCTGAGCAAAGACAGCAACACCTTTTTTT |
| SEQ ID NO: 910 | AACGTTGAGACTGTCCTGCAGACAAGGGTGGAAGGCTCTG |
| SEQ ID NO: 911 | CATAAATAAGCAGGATGTGACAGAAGAAGTATTTAATGGT |
| SEQ ID NO: 912 | GCTGCCAGACACAGTCGATCGGGACCTAGAACCTTGGTTA |
| SEQ ID NO: 913 | GGGATCCTGAGCGCTGCCTTATTCTGGGTTTGGCAGTGGA |
| SEQ ID NO: 914 | TCACTCAAACCCAGAAGTTCTGATCCCCAGCCATGCCCCT |
| SEQ ID NO: 915 | AGCCTCTTCCTCCTTTGAAATTCAAGAGGGTGGACCCACT |
| SEQ ID NO: 916 | GGAGCTGGGACCTTACCAGTCTCCTCCCTCATTGACCTAA |
| SEQ ID NO: 917 | GAGGATATGAGATTCTTAGGCCATTCCCACATCAGTACCT |
| SEQ ID NO: 918 | TACCCAGAACTCTACCCCTCAGGATTCCAGCACCTTCTTC |
| SEQ ID NO: 919 | GCCTCTGCCCTTCAGGGGCCAAAGAGCCTTAAGCCACAAA |
| SEQ ID NO: 920 | ATCCCATTACTATCACCCCAAACCCTGGACCTAATGGTTC |
| SEQ ID NO: 921 | AATGGGCAACCCTCGATCCTCAGACTCTTGAGGAATCAAG |
| SEQ ID NO: 922 | GATACCCTCAAGTGGAGTAAGGATTAGGTGGCAAGATGGA |
| SEQ ID NO: 923 | GTGCTTGCCCAGGGGCACCTTCATGGAGCTAGAAGGGCTG |
| SEQ ID NO: 924 | GATGACACCCAAGGCCTCTGGGGCATCTTTCATGCTCAGA |
| SEQ ID NO: 925 | TGCTGGCCACACCCTCAGAGTGTGGATGCTGGATGATGAG |
| SEQ ID NO: 926 | GAGGCACGCTGCAGGGATAGTCACAGCAACATGACGTCAT |
| SEQ ID NO: 927 | AGAGGAGGATGTCGGCAGCTCTACGGTTGGCAGGTGGCTG |
| SEQ ID NO: 928 | GACACTAGGCCTCAGCCTGGCACCATGCAGGCCACTCCCA |

TABLE 1-continued

Exemplary Probe Nucleotide Sequences

| SEQ ID NO | Nucleotide Sequence |
|---|---|
| SEQ ID NO: 929 | ACTTTTGAGTCCTGGATCCCTATGATTCCAGGCTCCCTGT |
| SEQ ID NO: 930 | CCTTGAGATTTCATGGATGGTGACATATGGCCATTCTCTA |
| SEQ ID NO: 931 | AAAACCCATAAGTTCAGGTCCCTGTGCCCTCCACCCAGAA |
| SEQ ID NO: 932 | TCGTATCTGGGAGACTCACTTGGGAGAGCAATAGACTTGG |
| SEQ ID NO: 933 | TACAAGATGTGGTGGAGATAAGGCTGATGCTGGCACAGTG |
| SEQ ID NO: 934 | GTACACACCATGGTGTTCATCAGGGCCCTGGGTAGTCCCT |
| SEQ ID NO: 935 | GCTGTGACCTCACAGGAGTCCGTGCCTCCACCCCCTACTC |

A nucleic acid probe may be a non-labeled probe, or a probe that does not contain a detectable moiety. A non-labeled probe may further interact with a labeled probe (e.g., a labeled nucleic acid probe). A non-labeled probe may hybridize with a labeled nucleic acid probe. A non-labeled probe may also interact with a labeled polypeptide probe. The labeled polypeptide probe may be a protein that recognizes a sequence within the non-labeled probe. A labeled probe may include a nucleic acid portion and a polypeptide tag portion and the polypeptide tag portion may further interact with a molecule comprising a detectable moiety. For example, a non-labeled probe may be a nucleic acid probe comprising a streptavidin which may interact with a biotinylated molecule comprising a detectable moiety.

A nucleic acid probe may have about 95%, about 96%, about 97%, about 98%, about 99%, or about 100% sequence specificity or sequence complementarity to a target site of a regulatory element. The hybridization may be a high stringent hybridization condition.

A nucleic acid probe may hybridize with a genomic sequence that is present in low or single copy numbers (e.g., genomic sequences that are not repetitive elements). As used herein, repetitive element refers to a DNA sequence that is present in many identical or similar copies in the genome. Repetitive elements are not intended to refer to a DNA sequence that is present on each copy of the same chromosome (e.g., a DNA sequence that is present only once, but is found on both copies of chromosome 11, would not be considered a repetitive element, and would be considered a sequence that is present in the genome as one copy). The genome may consist of three broad sequence components: single copy or at least very low copy number DNA (approximately 60% of the human genome); moderately repetitive elements (approximately 30% of the human genome); and highly repetitive elements (approximately 10% of the human genome). For a review, see Human Molecular Genetics, Chapter 7 (1999), John Wiley & Sons, Inc.

A nucleic acid probe may have reduced off-target interaction. For example, "off-target" or "off-target interaction" may refer to an instance in which a nucleic acid probe against a given target hybridizes or interact with another target site (e.g., a different DNA sequence, RNA sequence, or a cellular protein or other moiety).

A nucleic acid probe may further be cross-linked to a target site of a regulatory element. For example, the nucleic acid probe may be cross-linked by a photo-crosslinking means such as UV or by a chemical cross-linking means such as by formaldehyde, or through a reactive group within the nucleic acid probe. Reactive group may include sulfhydryl-reactive linkers such as bismaleimidohexane (BMH), and the like.

A nucleic acid probe may include natural or unnatural nucleotide analogues or bases or a combination thereof. The unnatural nucleotide analogues or bases may comprise modifications at one or more of ribose moiety, phosphate moiety, nucleoside moiety, or a combination thereof. The unnatural nucleotide analogues or bases may comprise 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, locked nucleic acid (LNA), ethylene nucleic acid (ENA), peptide nucleic acid (PNA), 1', 5'-anhydrohexitol nucleic acids (HNA), morpholino, methylphosphonate nucleotides, thiolphosphonate nucleotides, or 2'-fluoro N3-P5'-phosphoramidites. The nucleic acid probes may further comprise one or more abasic sites. The abasic site may further be functionalized with a detectable moiety.

A nucleic acid probe may comprise a Transcription Activator-Like Effector (TALE) sequence. A TALE may comprise a DNA-binding module which includes a variable number of about 33-35 amino acid residue repeats. Each amino acid repeat recognizes one base pair through two adjacent amino acids (such as at amino acid positions 12 and 13 of the repeat). As such, the amino acid repeat may also be referred to as repeat-variable diresidue (RVD).

A TALE probe described herein may comprise between about 1 to about 50 TALE repeat modules. A TALE probe described herein may comprise between about 5 and about 45, between about 8 and about 45, between about 10 and about 40, between about 12 and about 35, between about 15 and about 30, between about 20 and about 30, between about 8 and about 40, between about 8 and about 35, between about 8 and about 30, between about 10 and about 35, between about 10 and about 30, between about 10 and about 25, between about 10 and about 20, or between about 15 and about 25 TAL effector repeat modules.

A TALE probe described herein may comprise about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 45, or about 50 TALE repeat modules. A TALE probe described herein may comprise about 5 TALE repeat modules. A TALE probe described herein may comprise about 10 TALE repeat modules. A TALE probe described herein may comprise about 11 TALE repeat modules. A TALE probe described herein may comprise about 12 TALE repeat modules. A TALE probe described herein may comprise about 13 TALE repeat modules. A TALE probe described herein may comprise about 14 TALE repeat modules. A TALE probe described herein may comprise about 15 TALE repeat modules. A TALE probe described herein may comprise about 16 TALE repeat modules. A TALE probe described herein may comprise about 17 TALE repeat modules. A TALE probe described herein may comprise about 18 TALE repeat modules. A TALE probe described herein may comprise about 19 TALE repeat modules. A TALE probe described herein may comprise about 20 TALE repeat modules. A TALE probe described herein may comprise about 21 TALE repeat modules. A TALE probe described herein may comprise about 22 TALE repeat modules. A TALE probe described herein may comprise about 23 TALE repeat modules. A TALE probe described herein may comprise about 24 TALE repeat modules. A TALE probe described herein may comprise about 25 TALE repeat modules. A TALE probe described herein may comprise about 26 TALE repeat modules. A TALE probe described herein may comprise about 27 TALE repeat modules. A TALE probe described herein may comprise about 28 TALE repeat modules. A TALE probe described herein may comprise about 29 TALE repeat modules. A TALE probe described herein may comprise about 30 TALE repeat modules. A TALE probe described herein may comprise about 35 TALE repeat modules. A TALE probe described herein may comprise about 40 TALE repeat modules. A TALE probe described herein may comprise about 45 TALE repeat modules. A TALE probe described herein may comprise about 50 TALE repeat modules.

A TAL effector repeat module may be a wild-type TALE DNA-binding module or a modified TALE DNA-binding repeat module enhanced for specific recognition of a nucleotide. A TALE probe described herein may comprise one or more wild-type TALE DNA-binding module. A TALE probe described herein may comprise one or more modified TAL effector DNA-binding repeat module enhanced for specific recognition of a nucleotide. A modified TALE DNA-binding repeat module may comprise 1, 2, 3, 4, 5, 6, 7, 8, 9, 10, 15, 20, 25 or more mutations that may enhance the repeat module for specific recognition of a nucleic acid sequence (e.g., a target sequence). In some cases, a modified TALE DNA-binding repeat module is modified at amino acid position 2, 3, 4, 11, 12, 13, 21, 23, 24, 25, 26, 27, 28, 30, 31, 32, 33, 34, or 35. In some cases, a modified TALE DNA-binding repeat module is modified at amino acid positions 12 or 13.

A TALE repeat module may be a repeat module-like domain or RVD-like domain. A RVD-like domain has a sequence different from naturally occurring polynucleotidic repeat module comprising RVD (RVD domain) but have a similar function and/or global structure. Non-limiting examples of RVD-like domains include protein domains selected from Puf RNA binding protein or Ankyrin superfamily.

A TALE repeat module may comprise a RVD domain of Table 1. A TALE probe described herein may comprise one or more RVD domains selected from Table 1. Sometimes, A TALE probe described herein may comprise up to 1, up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, up to 28, up to 29, up to 30, up to 31, up to 32, up to 33, up to 34, up to 35, up to 36, up to 37, up to 38, up to 39, up to 40, up to 45, up to 50, up to 60, up to 70, up to 80, up to 90, or up to 100 RVD domains selected from TABLE 2.

TABLE 2

| RVD | Nucleotide |
|---|---|
| HD | C |
| NG | T |
| NI | A |
| NN | G > A |
| NS | G, A > C > T |
| NH | G |
| N* | T > C >> G, A |
| NP | T > A, C |
| HG | T |
| H* | T |
| IG | T |
| HA | C |
| ND | C |
| NK | G |
| HI | C |
| HN | G > A |
| NT | G > A |
| NA | G |
| SN | G or A |
| SH | G |
| YG | T |
| IS | — |

*Denotes a gap in the repeat sequence corresponding to a lack of an amino acid residue at the second position of the RVD.

An RVD domain may recognize or interact with one nucleotide. An RVD domain may recognize or interact with more than one nucleotides. The efficiency of a RVD domain at recognizing a nucleotide is ranked as "strong", "intermediate" or "weak". The ranking may be according to a ranking described in Streubel et al., "TAL effector RVD specificities and efficiencies," Nature Biotechnology 30(7): 593-595 (2012). The ranking of RVD may be as illustrated in TABLE 3, based on the ranking provided in Streubel et al. Nature Biotechnology 30(7): 593-595 (2012).

TABLE 3

| RVD | Nucleotide | Efficiency |
|---|---|---|
| HD | C | strong |
| NG | T | weak |
| NI | A | weak |
| NN | G > A | Strong (G), intermediate (A) |
| NS | G, A > C > T | intermediate |
| NH | G | intermediate |
| N* | T > C >> G, A | weak |
| NP | T > A, C | intermediate |
| NK | G | weak |
| HN | G > A | intermediate |
| NT | G > A | intermediate |
| SN | G or A | Weak |
| SH | G | Weak |
| IS | — | weak |

*Denotes a gap in the repeat sequence corresponding to a lack of an amino acid residue at the second position of the RVD.

A TALE DNA-binding domain may further comprise a C-terminal truncated TALE DNA-binding repeat module. A C-terminal truncated TALE DNA-binding repeat module may be between about 18 and about 40 residues in length. A C-terminal truncated TALE DNA-binding repeat module may be between about 20 and about 40, between about 22 and about 38, between about 24 and about 35, between about 28 and about 32, between about 25 and about 40, between about 25 and about 38, between about 25 and about 30, between about 28 and about 40, or between about 28 and about 35 residues in length. A C-terminal truncated TALE DNA-binding repeat module may be at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or more residues in length. A C-terminal truncated TALE DNA-binding repeat module may be about 18, about 19, about 20, about 21, about 22, about 23, about 24, about 25, about 26, about 27, about 28, about 29, about 30, about 31, about 32, about 33, about 34, about 35, about 36 about 37, about 38, about 39, or about 40 residues in length. A C-terminal truncated TALE DNA-binding repeat module may be about 18 residues in length. A C-terminal truncated TALE DNA-binding repeat module may be about 19 residues in length. A C-terminal truncated TALE DNA-binding repeat module may be about 20 residues in length. A C-terminal truncated TALE DNA-binding repeat module may be about 21 residues in length. A C-terminal truncated TALE DNA-binding repeat module may be about 22 residues in length. A C-terminal truncated TALE DNA-binding repeat module may be about 23 residues in length. A C-terminal truncated TALE DNA-binding repeat module may be about 24 residues in length. A C-terminal truncated TALE DNA-binding repeat module may be about 25 residues in length. A C-terminal truncated TALE DNA-binding repeat module may be about 26 residues in length. A C-terminal truncated TALE DNA-binding repeat module may be about 27 residues in length. A C-terminal truncated TALE DNA-binding repeat module may be about 28 residues in length. A C-terminal truncated TALE DNA-binding repeat module may be about 29 residues in length. A C-terminal truncated TALE DNA-binding repeat module may be about 30 residues in length. A C-terminal truncated TALE DNA-binding repeat module may be about 31 residues in length. A C-terminal truncated TALE DNA-binding repeat module may be about 32 residues in length. A C-terminal truncated TALE DNA-binding repeat module may be about 33 residues in length. A C-terminal truncated TALE DNA-binding repeat module may be about 34 residues in length. A C-terminal truncated TALE DNA-binding repeat module may be about 35 residues in length. A C-terminal truncated TALE DNA-binding repeat module may be about 36 residues in length. A C-terminal truncated TALE DNA-binding repeat module may be about 37 residues in length. A C-terminal truncated TALE DNA-binding repeat module may be about 38 residues in length. A C-terminal truncated TALE DNA-binding repeat module may be about 39 residues in length. A C-terminal truncated TALE DNA-binding repeat module may be about 40 residues in length. A C-terminal truncated TALE DNA-binding repeat module may be a RVD domain of TABLE 2.

A TALE DNA-binding domain may further comprise an N-terminal cap. An N-terminal cap may be a polypeptide portion flanking the DNA-binding repeat module. An N-terminal cap may be any length and may comprise from about 0 to about 136 amino acid residues in length. An N-terminal cap may be about 5, about 10, about 15, about 20, about 25, about 30, about 35, about 40, about 45, about 50, about 60, about 70, about 80, about 90, about 100, about 110, about 120, or about 130 amino acid residues in length. An N-terminal cap may modulate structural stability of the DNA-binding repeat modules. An N-terminal cap may modulate nonspecific interactions. An N-terminal cap may decrease nonspecific interaction. An N-terminal cap may reduce off-target effect. As used here, off-target effect refers to the interaction of a TALE protein with a sequence that is not the target sequence of interest. An N-terminal cap may further comprise a wild-type N-terminal cap sequence of a TALE protein or may comprise a modified N-terminal cap sequence.

A TALE DNA-binding domain may further comprise a C-terminal cap sequence. A C-terminal cap sequence may be a polypeptide portion flanking the C-terminal truncated TALE DNA-binding repeat module. A C-terminal cap may be any length and may comprise from about 0 to about 278 amino acid residues in length. A C-terminal cap may be about 5, about 10, about 15, about 20, about 25, about 30, about 35, about 40, about 45, about 50, about 60, about 80, about 100, about 150, about 200, or about 250 amino acid residues in length. A C-terminal cap may further comprise a wild-type C-terminal cap sequence of a TALE protein, or may comprise a modified C-terminal cap sequence.

A nuclease domain may be linked to a TALE DNA-binding domain either directly or through a linker. A linker may be between about 1 and about 50 amino acid residues in length. A linker may be from about 5 to about 45, from about 5 to about 40, from about 5 to about 35, from about 5 to about 30, from about 5 to about 25, from about 5 to about 20, from about 5 to about 15, from about 10 to about 40, from about 10 to about 35, from about 10 to about 30, from about 10 to about 25, from about 10 to about 20, from about 12 to about 40, from about 12 to about 35, from about 12 to about 30, from about 12 to about 25, from about 12 to about 20, from about 14 to about 40, from about 14 to about 35, from about 14 to about 30, from about 14 to about 25, from about 14 to about 20, from about 14 to about 16, from about 15 to about 40, from about 15 to about 35, from about 15 to about 30, from about 15 to about 25, from about 15 to about 20, from about 15 to about 18, from about 18 to about 40, from about 18 to about 35, from about 18 to about 30, from about 18 to about 25, from about 18 to about 24, from about 20 to about 40, from about 20 to about 35, from about 20 to about 30, or from about 25 to about 30 amino acid residues in length.

A linker for linking a nuclease domain to a TALE DNA-binding domain may be about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, or about 50 amino acid residues in length. A linker may be about 10 amino acid residues in length. A linker may be about 11 amino acid residues in length. A linker may be about 12 amino acid residues in length. A linker may be about 13 amino acid residues in length. A linker may be about 14 amino acid residues in length. A linker may be about 15 amino acid residues in length. A linker may be about 16 amino acid residues in length. A linker may be about 17 amino acid residues in length. A linker may be about 18 amino acid residues in length. A linker may be about 19 amino acid residues in length. A linker may be about 20 amino acid residues in length. A linker may be about 21 amino acid residues in length. A linker may be about 22 amino acid residues in length. A linker may be about 23 amino acid residues in length. A linker may be about 24 amino acid residues in length. A linker may be about 25 amino acid residues in length. A linker may be about 26 amino acid residues in length. A linker may be about 27 amino acid residues in length. A linker may be about 28 amino acid residues in length. A linker may be about 29 amino acid residues in length. A linker may be about 30 amino acid residues in length.

A TALE probe may be designed to recognize each strand of a double-stranded segment of DNA by engineering the TALE to include a sequence of repeat-variable diresidue subunits that may comprise about 22, about 23, about 24, about 25, about 26, about 27, about 28, about 29, about 30, about 31, about 32, about 33, about 34, about 35, about 36, about 37, about 38, about 39, or about 40 amino acid repeats capable of associating with specific DNA sequences, such that the detectable label of the TALE probe is located at the target nucleic acid sequence.

A nucleic acid probe may be a locked nucleic acid probe (such as a labeled locked nucleic acid probe), a labeled or unlabeled peptide nucleic acid (PNA) probe, a labeled or unlabeled oligonucleotide, an oligopaint, an ECHO probe, a molecular beacon probe, a padlock (or molecular inversion probe), a labeled or unlabeled toe-hold probe, a labeled TALE probe, a labeled ZFN probe, or a labeled CRISPR probe.

A nucleic acid probe may be a labeled or unlabeled locked nucleic acid probe or a labeled or unlabeled peptide nucleic acid probe. Locked nucleic acid probes and peptide nucleic acid probes are known to those of skill in the art and are described in Briones et al., Anal Bioanal Chem (2012) 402:3071-3089.

A nucleic acid probe may be a padlock (or molecular inversion probe). A padlock probe may be hybridized to a target regulatory element sequence in which the two ends may correspond to the target sequence. A padlock probe may be ligated together by a ligase (such as T4 ligase) when bound to the target sequence. An amplification (such as a rolling circle amplification or RCA) may be performed utilizing for example #29 polymerase, which may result in a single stranded DNA comprising multiple tandem copies of the target sequence.

A nucleic acid probe may be an oligopaint as described in U.S. Publication No. 2010/0304994; and in Beliveau, et al., "Versatile design and synthesis platform for visualizing genomes with oligopaint FISH probes," PNAS 109(52): 21301-21306 (2012). Oligopaint may refer to detectably labeled polynucleotides that have sequences complementary to an oligonucleotide sequence (such as a portion of a DNA sequence, like a particular chromosome or sub-chromosomal region of a particular chromosome). Oligopaints may be generated from synthetic probes and arrays that are, optionally, computationally patterned (rather than using natural DNA sequences and/or chromosomes as a template).

A nucleic acid probe may be a labeled or unlabeled toe-hold probe. Toe-hold probes are known to those of skill in the art as described in Zhang et al. Optimizing the Specificity of Nucleic Acid Hybridization, Nature Chemistry 4: 208-214 (2012).

A nucleic acid probe may be a molecular beacon. Molecular beacons may be hairpin shaped molecules with an internally quenched fluorophore whose fluorescence is restored when they bind to a target nucleic acid sequence. Molecular beacons are known to those of skill in the art as described in Guo et al., Anal. Bioanal. Chem. (2012) 402: 3115-3125.

A nucleic acid probe may be an ECHO probe. ECHO probes may be sequence-specific, hybridization-sensitive, quencher-free fluorescent probes for RNA detection, which may be designed using the concept of fluorescence quenching caused by intramolecular excitonic interaction of fluorescent dyes. ECHO probes are known to those of skill in the art as described in Kubota et al., PLoS ONE, Vol. 5, Issue 9, el 3003 (2010); or Okamoto, Chem. Soc. Rev., 2011, 40, 5815-5828, Wang et al., RNA (2012), 18:166-175.

A probe may be a clustered regularly interspaced palindromic repeat (CRISPR) probe. The CRISPR system may use a Cas9 protein to recognize DNA sequences, in which the target specificity may be solely determined by a small guide (sg) RNA and a protospacer adjacent motif (PAM). Upon binding to target DNA, the Cas9-sgRNA complex may generate a DNA double-stranded break. For imaging applications, a Cas9 protein may be replaced with an endonuclease-deactivated Cas9 (dCas9) protein. For example, imaging a cell, such as by fluorescence in situ hybridization (FISH), may be achieved by synthesizing a dCas9 within the cell, synthesizing RNA within the cell to bind genomic DNA and to complex with the dCas9 forming a dCas9/RNA complex, labeling the dCas9/RNA complex, and imaging the labeled dCas9/RNA complex within the live cell bound to genomic DNA. The endonuclease-deactivated Cas9 may be synthesized in vivo by using an integrated construct, a transiently transfected construct, by injection into the cell of a syncitia of nuclei or via electroporation into cells and/or nuclei.

A probe may comprise an endonuclease-deactivated Cas9 (dCas9) protein as described in Chen et al., "Dynamic imaging of genomic loci in living human cells by an optimized CRISPR/Cas system," Cell 155(7): 1479-1491 (2013); or Ma et al, "Multicolor CRISPR labeling of chromosomal loci in human cells," PNAS 112(10): 3002-3007 (2015). The dCas9 protein may be further labeled with a detectable moiety.

The RNA of the Cas9/RNA complex may be synthesized in vivo by using an integrated construct, a transiently transfected construct, by injection into the cell of a syncitia of nuclei or via electroporation into cells and/or nuclei. The Cas9/RNA complex may be labeled by making a fusion protein that includes Cas9 and a reporter, by injection of RNA that has been attached to a reporter into the cell or by a syncitia of nuclei including RNA that has been attached to a reporter, by electroporation into cells or nuclei or by indirect labeling of the RNA by hybridization with a labeled secondary oligonucleotide. The label may be a conditional reporter, based on the binding of Cas9/RNA to the target nucleic acid. The label may be quenched and may then be activated upon the Cas9/RNA complex binding to the target nucleic acid.

A probe may be a transcription activator-like effector nuclease (TALEN) probe. TALENs are engineered restriction enzymes generated by fusing the TALE DNA binding domain to a FokI DNA cleavage domain. A FokI DNA cleavage domain may comprise an endonuclease-deactivated FokI domain. A nucleic acid probe may be a TALEN probe comprising an endonuclease-deactivated FokI domain.

A probe may be a zinc-finger nuclease (ZFN) probe. Similar to TALEN, a zinc-finger nuclease is an engineered restriction enzyme generated by fusing a zinc finger DNA-binding domain to a zinc finger nuclease. A zinc finger nuclease may comprise an endonuclease-deactivated zinc finger nuclease. A nucleic acid probe may be a ZFN probe comprising an endonuclease-deactivated zinc finger nuclease.

A probe disclosed herein may be a polypeptide probe. A polypeptide probe may include a protein or a binding fragment thereof that interacts with a target site (such as a nucleic acid target site or a protein target) of interest. A polypeptide probe may comprise a DNA-binding protein, a RNA-binding protein, a protein involved in the transcription/translation process or detects the transcription/translation process, a protein that may detect an open or relaxed portion of a chromatin, or a protein interacting partner of a product of a regulatory element.

A polypeptide probe may be a DNA-binding protein. The DNA-binding protein may be a transcription factor that modulates the transcription process, polymerases, or histones. A DNA-binding protein may comprise a zinc finger domain, a helix-turn-helix domain, a leucine zipper domain (such as a basic leucine zipper domain), a high mobility group box (HMG-box) domain, and the like. The DNA-binding protein may interact with a nucleic acid region in a sequence specific manner. The DNA-binding protein may interact with a nucleic acid region in a sequence non-specific manner. The DNA-binding protein may interact with single-stranded DNA. The DNA-binding protein may interact with double-stranded DNA. The DNA-binding protein probe may further comprise a detectable moiety.

A polypeptide probe may be a RNA-binding protein. The RNA-binding protein may participate in forming ribunucleoprotein complexes. The RNA-binding protein may modulate post-transcription such as in splicing, polyadenylation, mRNA stabilization, mRNA localization, or in translation. A RNA-binding protein may comprise a RNA recognition motif (RRM), dsRNA binding domain, zinc finger domain, K-Homology domain (KH domain), and the like. The RNA-binding protein may interact with single-stranded RNA. The RNA-binding protein may interact with double-stranded RNA. The RNA-binding protein probe may further comprise a detectable moiety.

A polypeptide probe may be a protein that may detect an open or relaxed portion of a chromatin. The polypeptide probe may be a modified enzyme that lacks cleavage activity. The modified enzyme may be an enzyme that recognizes DNA or RNA (double-stranded or single-stranded). Examples of modified enzymes may be obtained from oxidoreductases, transferases, hydrolases, lyases, isomerases, or ligases. A modified enzyme may be an endonuclease (such as a deactivated restriction endonuclease such as the TALEN or CRISPR probes described herein).

A polypeptide probe may be an antibody or binding fragment thereof. The antibody or binding fragment thereof may be a protein interacting partner of a product of a regulatory element. The antibody or binding fragment thereof may comprise a humanized antibody or binding fragment thereof, murine antibody or binding fragment thereof, chimeric antibody or binding fragment thereof, monoclonal antibody or binding fragment thereof, monovalent Fab', divalent Fab2, F(ab)'3 fragments, single-chain variable fragment (scFv), bis-scFv, (scFv)2, diabody, minibody, nanobody, triabody, tetrabody, disulfide stabilized Fv protein (dsFv), single-domain antibody (sdAb), Ig NAR, camelid antibody or binding fragment thereof, or a chemically modified derivative thereof. The antibody or binding fragment thereof may further comprise a detectable moiety.

Multiple probes may be used together in a probe set to detect a nucleic acid sequence using Nano-FISH. The probe set may be designed for the detection of the target nucleic acid sequence. For exampler, the probe set may be optimized for probes based on GC content, 16mer base matches (for determining bindind specificity of the probe), and their predicted melting temperature when hybrized. The 16mer base matches may have a total of 24 matches to the 16mer database. In some embodiments, probe sets with greater than 100 16-mer database matches may be discarded.

Exemplary probe nucleotide sequences are shown in TABLE 1 for probe sets for different target sequences. Some exemplary probe sequences may be target sequences located in the GREB 1 promoter of chromosome 2, ER iDHS 1 of chromosome 2, ER iDHS2 of chromosome 2, HBG1up of chromosome 11, HBG2 up of chromosome 11, HS 1 of chromosome 11, HS2 of chromosome 11, HS3 of chromosome 11, HS4 of chromosome 11, HS5 of chromosome 11, HS1 Lflank of chromosome 11, HS1 2 flank of chromosome 11, HS2 3 flank of chromosome 11, HS3 4flank of chromosome 11, HS4 5 flank of chromosome 11, HS5 Rflank of chromosome 11, CCND1 SNP of chromosome 11, CCND1 CTL of chromosome 11, the CCND1 promoter of chromosome 11, Chromosome 18 dead1 of chromosome 18, Chromosome 18 dead2 of chromosome 18, Chromosome dead3 of chromosome 18, CNOT promoter of chromosome 19, CNOT inter1 of chromosome 19, CNOT inter2 of chromosome 19, CNOT inter3 of chromosome 19, TSEN promoter of chromosome 19, KLK2 promoter of chromosome 19, KLK3 promoter of chromosome 19, or KLK eRNA of chromosome 19. GREB 1 is gene that may be induced by estrogen stimulation of MCF-7 breast cancer cells. ER iDHS1 and ER iDHS2 are DHS that may be induced by estrogen stimulation of MCF-7 breast cancer cells. HBG1up and HBG2up are hemoglobin genes expressed in K562 erthyro leukemia cells. HS1, HS2, HS3, HS4, and HS5 are hypersensitive sits in the beta-globin locus control region, and HS1 Lflank, HS2 3flank, HS3 4flank, HS4 5flank, HS5 Rflank are sequences in the intervening regions between HS 1-HS5. CCND SNP is an enhancer for the CCND1 gene, CCND1 CTL is a control region adjacent to the CCND1 SNP, and the CCND1 promoter is the promoter region of the CCND1 gene. Chromosome 18 dead1, Chromosome 18 dead 2, and Chromosome 18 dead3 are non-hypersensitive regions of chromosome 18. The CNOT promoter is the promoter (active region) of CNOT. The TSEN promoter is the promoter (active region) of TSEN. The KLK2 promoter is the promoter KLK2. The KLK3 promoter is the promoter of KLK3. KLK eRNA is an enhancer for the KLK2 gene and/or the KLK3 gene, and which may also enhance RNA. For example, a probe set comprising at least nine different Q570 labeled probes selected from the group consisting of SEQ ID NO: 1-SEQ ID NO: 39 may be used to detect the GREB 1 promoter in chromosome 2. A Q570 labeled probe set comprising probes with SEQ ID NO: 7-SEQ ID NO: 35 may be used to detect the GREB 1 promoter in chromosome 2. A probe set comprising at least nine different Q670 labeled probes selected from the group consisting of SEQ ID NO: 40-SEQ ID NO: 72 may be used to detect the ER iDHS 1 in chromosome 2. A probe set comprising at least nine different Q670 labeled probes selected from the group consisting of SEQ ID NO: 73-SEQ ID NO: 104 may be used to detect the ER iDHS 2 in chromosome 2. A probe set comprising at least nine different Q570 labeled probes selected from the group consisting of SEQ ID NO: 105-SEQ ID NO: 134 may be used to detect the HBG1up in chromosome 11. A probe set comprising at least nine different Q570 labeled probes selected from the group consisting of SEQ ID NO: 135-SEQ ID NO: 164 may be used to detect the HBG2up in chromosome 11. A probe set comprising at least nine different Q570/670 labeled probes selected from the group consisting of SEQ ID NO: 165-SEQ ID NO: 194 may be used to detect HS 1 in chromosome 11. A probe set comprising at least nine different Q570/670 labeled probes selected from the group consisting of SEQ ID NO: 195-SEQ ID NO: 224 may be used to detect HS2 in chromosome 11. A probe set comprising at least nine different Q570/670 labeled probes selected from the group consisting of SEQ ID NO: 225-SEQ ID NO: 254 may be used to detect HS3 in chromosome 11. A probe set comprising at least nine different Q670 labeled probes selected from the group consisting of SEQ ID NO: 255-SEQ ID NO: 298 may be used to detect HS4 in chromosome 11. A probe set comprising at least nine different Q570/670 labeled probes selected from the group consisting of SEQ ID NO: 299-SEQ ID NO: 340 may be used to detect HS5 in chromosome 11. A probe set comprising at least nine different Q670 labeled probes selected from the group consisting of SEQ ID NO: 341-SEQ ID NO: 370 may be used to detect HS 1 Lflank in chromosome 11. A probe set comprising at least nine different Q570 labeled probes selected from the group consisting of SEQ ID NO: 371-SEQ ID NO: 400 may be used to detect HS 1 2flank in chromosome 11. A probe set comprising at least nine different Q670 labeled probes selected from the group consisting of SEQ ID NO: 401-SEQ ID NO: 430 may be used to detect HS2 3flank in chromosome 11. A probe set comprising at least nine different Q570 labeled probes selected from the group consisting of SEQ ID NO: 431-SEQ ID NO: 460 may be used to detect HS3 4flank in chromosome 11. A probe set comprising at least nine different Q670 labeled probes selected from the group consisting of SEQ ID NO: 461-SEQ ID NO: 484 may be used to detect HS4 5flank in chromosome 11. A probe set comprising at least nine different Q570 labeled probes selected from the group consisting of SEQ ID NO: 485-SEQ ID NO: 514 may be used to detect HS5 Rflank in chromosome 11. A probe set comprising at least nine different Q570 labeled probes selected from the group consisting of SEQ ID NO: 515-SEQ ID NO: 544 may be used to detect CCND1 SNP in chromosome 11. A probe set comprising at least nine different Q670 labeled probes selected from the group consisting of SEQ ID NO: 545-SEQ ID NO: 564 may be used to detect CCND1 CTL in chromosome 11. A probe set comprising at least nine different Q670 labeled probes selected from the group consisting of SEQ ID NO: 565-SEQ ID NO: 598 may be used to detect the CCND1 promoter in chromosome 11. A probe set comprising at least nine different Q670 labeled probes selected from the group consisting of SEQ ID NO: 599-SEQ ID NO: 628 may be used to detect Chromosome 18 dead1 in chromosome 18. A probe set comprising at least nine different Q670 labeled probes selected from the group consisting of SEQ ID NO: 629-SEQ ID NO: 658 may be used to detect Chromosome 18 dead2 in chromosome 18. A probe set comprising at least nine different Q670 labeled probes selected from the group consisting of SEQ ID NO: 659-SEQ ID NO: 688 may be used to detect Chromosome 18 dead3 in chromosome 18. A probe set comprising at least nine different Q670 labeled probes selected from the group consisting of SEQ ID NO: 689-SEQ ID NO: 718 may be used to detect the CNOT3 promoter in chromosome 19. A probe set comprising at least nine different Q670 labeled probes selected from the group consisting of SEQ ID NO: 719-SEQ ID NO: 748 may be used to detect the TSEN34 promoter in chromosome 19. A probe set comprising at least nine different Q670 labeled probes selected from the group consisting of SEQ ID NO: 749-SEQ ID NO: 778 may be used to detect CNOT3 inter1 in chromosome 19. A probe set comprising at least nine different Q670 labeled probes selected from the group consisting of SEQ ID NO: 779-SEQ ID NO: 808 may be used to detect CNOT3 inter2 in chromosome 19. A probe set comprising at least nine different Q670 labeled probes selected from the group consisting of SEQ ID NO: 809-SEQ ID NO: 838 may be used to detect CNOT3 inter3 in chromosome 19. A probe set comprising at least nine different Q570 labeled probes selected from the group consisting of SEQ ID NO: 839-SEQ ID NO: 868 may be used to detect the KLK2 promoter in chromosome 19. A probe set comprising at least nine different Q570 labeled probes selected from the group consisting of SEQ ID NO: 869-SEQ ID NO: 898 may be used to detect the KLK3 promoter in chromosome 19. A probe set comprising at least nine different Q670 labeled probes selected from the group consisting of SEQ ID NO: 899-SEQ ID NO: 935 may be used to detect KLK eRNA in chromosome 19.

Detectable Moieties

A detecting agent may comprise a detectable moiety. A detectable moiety may be a small molecule (such as a dye) or a macromolecule. A macromolecule may include polypeptides (such as proteins and/or protein fragments), nucleic acids, carbohydrates, lipids, macrocyles, polyphenols, and/or endogenous macromolecule complexes. A detectable moiety may be a small molecule. A detectable moiety may be a macromolecule.

A detectable moiety may include a moiety that is detectable by a colorimetric method or a fluorescent method. For example, a colorimetric method may be an assay which utilizes reagents that undergo a measurable color change in the presence of an analyte (such as an enzyme, an antibody, a compound, a hormone). Exemplary colorimetric method may include enzyme-mediated detection method such as tyramide signal amplification (TSA) which utilizes horseradish peroxidase (HRP) to generate a signal when digested by tyramide substrate and 3,3',5,5'-Tetramethylbenzidine (TMB) which generates a blue color upon oxidation to 3,3'5,5'-tetramethylbenzidine diamine in the presence of a peroxidase enzyme such as HRP. A detectable moiety described herein may include a moiety that is detectable by a colorimetric method.

A detectable moiety may also include a moiety that is detectable by a fluorescent method. Sometimes, the detectable moiety may be a fluorescent moiety. A fluorescent moiety may be a small molecule (such as a dye) or a fluorescently labeled macromolecule. A fluorescently labeled macromolecule may include a fluorescently labeled polypeptide (such as a labeled protein and/or a protein fragment), a fluorescently labeled nucleic acid molecule, a fluorescently labeled carbohydrate, a fluorescently labeled lipid, a fluorescently labeled macrocyle, a fluorescently labeled polyphenol, and/or a fluorescently labeled endogenous macromolecule complex (such as a primary antibody-secondary antibody complex).

A fluorescent small molecule may comprise rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, bilirubin 1-dimethylaminonaphthyl-5-sulfonate, 1-anilino-8-naphthalene sulfonate, 2-p-touidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), 5(6)-

FAM, 5-FAM, Fluorescein dT, 5-TAMRA-cadavarine, 2-aminoacridone, HEX, JOE (NHS Ester), MAX, TET, ROX, TAMRA, TARMA™ (NHS Ester), TEX 615, ATTO™ 488, ATTO™ 532, ATTO™ 550, ATTO™ 565, ATTO™ Rho101, ATTO™ 590, ATTO™ 633, ATTO™ 647N, TYE™ 563, TYE™ 665, or TYE™ 705.

A fluorescent moiety may comprise Cy3, Cy5, Cy5.5, Cy7, Q570, Alexa488, Alexa555, Alexa594, Alexa647, Alexa680, Alexa 750, Alexa 790, Atto488, Atto532, Atto647N, TexasRed, CF610, Propidium iodide, Q670, IRDye700, IRDye800, Indocyanine green, Pacific Blue dye, Pacific Green dye, or Pacific Orange dye.

A fluorescent moiety may comprise a quantum dot (QD). Quantum dots may be a nanoscale seminconducting photoluminescent material, for example, as described in Alivisatos A. P., "Semiconductor clusters, nanocrystals, and quantum dots," Science 271(5251): 933-937 (1996).

Exemplary QDs may include, but are not limited to, CdS quantum dots, CdSe quantum dots, CdSe/CdS core/shell quantum dots, CdSe/ZnS core/shell quantum dots, CdTe quantum dots, PbS quantum dots, and/or PbSe quantum dots. As used herein, CdSe/ZnS may mean that a ZnS shell is coated on a CdSe core surface (a "core-shell" quantum dot). The shell materials of core-shell QDs may have a higher bandgap and passivate the core QDs surfaces, resulting in higher quantum yield and higher stability and wider applications than core QDs.

QDs may absorb a wide spectrum of light, and may be physically tuned with emission bandwidths in various wavelengths. See, e.g., Badolato, et al., Science 208:1158-61 (2005). For example, the emission bandwidth may be in the visible spectrum (from about 350 to about 750 nm), the ultraviolet-visible spectrum (from about 100 nm to about 750 nm), or in the near-infrared spectrum (from about 750 nm to about 2500 nm). QDs that emit energy in the visible range may include, but are not limited to, CdS, CdSe, CdTe, ZnSe, ZnTe, GaP, and GaAs. QDs that emit energy in the blue to near-ultraviolet range include, but are not limited to, ZnS and GaN. QDs that emit energy in the near-infrared range include, but are not limited to, InP, InAs, InSb, PbS, and PbSe.

The radius of a QD may be modulated to manipulate the emission bandwidth. For example, a radius of between about 5 and about 6 nm QD may emit wavelengths resulting in emission colors such as orange or red. A radius of between about 2 and about 3 nm may emit wavelengths resulting in emission colors such as blue or green.

A QD may further form a QD microstructure, which encompasses one or more layers of QD. For example, each quantum dot containing layer may comprise a single type of quantum dot of a specific emission color. For example, each layer may be made of any material suitable for use that (a) allows excitation light to reach the quantum dot and allows fluorescence generated from the quantum dot to pass through the layer(s) for detection and (b) may be combined with a quantum dot to form a layer. Examples of materials that may be used to form layers containing quantum dots include, but are not limited to, inorganic, organic, or polymeric material, each with or without biodegradable properties, and combinations thereof. The layers may comprise silica-based compounds or polymers. Exemplary silica-based layers may include, but are not limited to, those comprising tetramethoxy silane or tetraethylorthosilicate. Exemplary polymer layers may include, but are not limited to, those comprising polystyrene, poly (methyl methacrylate), polyhydroxyalkanoate, polylactide, or co-polymers thereof.

The quantum dot further may comprise a spacer layer which serves as a barrier to prevent interactions between different QD layers, and may be made of any material suitable for use that (a) allows excitation light to reach the quantum dots in the quantum dot containing layer(s) below it and allows fluorescence generated from those quantum dots to pass through it and (b) may segregate the quantum dots in one layer from those in other layers. Examples of materials that may be used to form spacer layers are the same as for the quantum dot containing layers.

The materials used for the quantum dot containing and spacer layers may be the same or different. The same material may be used in the quantum dot containing layers and the spacer layers.

The quantum dot containing layers and the spacer layers within a given QD molecule may be any thickness and may be varied. For example, thicker QD-containing layers may allow for the loading of increased QDs in the shell, resulting in greater fluorescence intensity for that layer than for a thinner layer containing the same concentration of QDs. Thus, varying layer thickness may facilitate preparing QD-containing layer of various intensities, thereby generating spectrally distinct QD bar codes. In various instances, the QD-containing layers may be between 5 nm and 500 nm; 10 nm and 500 nm; 5 nm and 100 nm, and 10 nm and 100 nm. Those of skill in the art will understand that other methods for varying intensity also exist, for example, modifying concentrations of the same QD in one microstructure with a first unique barcode compared to a second QD microstructure with a different fluorescent barcode. The ability to vary the intensities for the same QD color allows for an increased number of distinct and distinguishable microstructures (e.g., spectrally distinct barcodes). The spacer layers may be greater than 10 nm, up to approximately 5 m thick; the spacer layers may be greater than 10 nm, up to approximately 500 nm thick; the space layers may be greater than 10 nm, up to approximately 100 nm thick.

The quantum dot-containing and spacer layers may be arranged in any order. Examples include, but are not limited to, alternating QD-containing layers and spacer layers, or quantum dot containing layers separated by more than one spacer layer. Thus, a "spacer layer" may comprise a single layer, or may comprise two or more such spacer layers.

The QD microstructure may comprise any number of quantum dot containing layers suitable for use with the microstructure. For example, a microstructure described herein may comprise 2, 3, 4, 5, 6, 7, 8, 9, 10, or more quantum dot-containing layers and an appropriate number of spacer layers based on the number of quantum dot-containing layers. Further, the number of quantum dot containing layers in a given microstructure may range from 1 to "m," where "m" is the number of quantum dots that may be used.

A defined intensity level may refer to a known amount of quantum dots in each quantum dot containing layer, resulting in a known amount of fluorescent intensity generated from the QD containing layer upon appropriate stimulation. Since each QD containing layer has a defined intensity level, each microstructure may possess a defined ratio of fluorescence intensities generated from the various QD-containing layers upon stimulation. This defined ratio is referred to herein as a barcode. Thus, each type of microstructure with the same QD layers possesses a similar barcode that may be distinguished from microstructures with different QD layers.

Thus, each quantum dot containing layer may comprise a single type of quantum dot of a specific emission color and the layer is produced to possess a defined intensity level, based on the concentration of the QD in the layer. By varying the intensity levels of QDs ("n") in different microstructures and using a variety of different quantum dots ("m"), the number of different unique barcodes (and thus the number of different unique microstructure populations that may be produced) is approximated by the equation, ($n^m$-1) unique codes. This may provide the ability to generate a large number of different populations of microstructures each with its own unique barcode.

A set of QD-labeled probes may further generate a spectrally distinct barcode. For example, each probe with the set of QD-labeled probes may comprise a QD with a distinct excitation wavelength and the combination of the set may generate a distinct barcode. A set of spectrally distinct QD-labeled probes may be utilized to detect a regulatory element. As such, when detecting two or more regulatory elements, each regulatory element may be spectrally barcoded.

A quantum dot provided herein may include QDot525, QDot 545, QDot 565, QDot 585, QDot 605, or QDot 655. A probe described herein may comprise a quantum dot. A probe described herein may comprise QDot525, QDot 545, QDot 565, QDot 585, QDot 605, or QDot 655. A probe described herein may comprise QDot525. A probe described herein may comprise QDot 545. A probe described herein may comprise QDot 565. A probe described herein may comprise QDot 585. A probe described herein may comprise QDot 605. A probe described herein may comprise QDot 655.

A quantum dot may comprise a quantum dot as described in Han et al., "Quantum-dot-tagged microbeads for multiplexed optical coding of biomolecules," Nat. Biotechnol. 19:631-635 (2001); Gao X., "QD barcodes for biosensing and detection," Conf Proc IEEE Eng Med Biol Soc 2009: 6372-6373 (2009); and Zrazhevskiy, et al., "Multicolor multicycle molecular profiling with quantum dots for single-cell analysis," Nat Protoc 8:1852-1869 (2013).

A QD may further comprise a functional group or attachment moiety. One example of such a QD that has a functional group or attachment moiety is a QD with a carboxylic acid terminated surface, such as those commercially available though, for example, Quantum Dot, Inc., Hayward, CA Conjugating Moiety The probe may include a conjugating moiety. The conjugation moiety may be attached at the 5' terminus, the 3' terminus, or at an internal site. The conjugating moiety may be a nucleotide analog (such as bromodeoxyuridine). The conjugating moiety may be a conjugating functional group. The conjugating functional group may be an azido group or an alkyne group. The probe may further be derivatized through a chemical reaction such as click chemistry. The click chemistry may be a copper(I)-catalyzed [3+2]-Huisgen 1,3-dipolar cyclo-addition of alkynes and azides leading to 1,2,3-triazoles. The click chemistry may be a copper free variant of the above reaction.

The conjugating moiety may comprise a hapten group. A hapten group may include digoxigenin, 2,4-dinitrophenyl, biotin, avidin, or are selected from azoles, nitroaryl compounds, benzofurazans, triterpenes, ureas, thioureas, rotenones, oxazoles, thiazoles, coumarins, cyclolignans, heterobiaryl compounds, azoaryl compounds or benzodiazepines. A hapten group may include biotin.

The probe comprising the conjugating moiety may further be linked to a second probe (such as a nucleic acid probe or a polypeptide probe), a fluorescent moiety (such as a dye such as a quantum dot), a target nucleic acid, or a conjugating partner such as a polymer (such as PEG), a macromolecule (such as a carbohydrate, a lipid, a polypeptide), and the like.

Samples

A sample described herein may be a fresh sample or a fixed sample. The sample may be a fresh sample. The sample may be a fixed sample. The sample may be a live sample. The sample may be subjected to a denaturing condition. The sample may be cryopreserved.

The sample may be a cell sample. The cell sample may be obtained from the cells or tissue of an animal. The animal cell may comprise a cell from an invertebrate, fish, amphibian, reptile, or mammal. The mammalian cell may be obtained from a primate, ape, equine, bovine, porcine, canine, feline, or rodent. The mammal may be a primate, ape, dog, cat, rabbit, ferret, or the like. The rodent may be a mouse, rat, hamster, gerbil, hamster, chinchilla, or guinea pig. The bird cell may be from a canary, parakeet, or parrot. The reptile cell may be from a turtle, lizard, or snake. The fish cell may be from a tropical fish. For example, the fish cell may be from a zebrafish (such as *Danio rerio*). The amphibian cell may be from a frog. An invertebrate cell may be from an insect, arthropod, marine invertebrate, or worm. The worm cell may be from a nematode (such as *Caenorhabditis elegans*). The arthropod cell may be from a tarantula or hermit crab.

The cell sample may be obtained from a mammalian cell. For example, the mammalian cell may be an epithelial cell, connective tissue cell, hormone secreting cell, a nerve cell, a skeletal muscle cell, a blood cell, an immune system cell, or a stem cell. A cell may be a fresh cell, live cell, fixed cell, intact cell, or cell lysate.

Cell samples may be cells derived from a cell line. Exemplary cell lines include, but are not limited to, 293A cell line, 293FT cell line, 293F cell line, 293 H cell line, HEK 293 cell line, CHO DG44 cell line, CHO-S cell line, CHO-K1 cell line, Expi293F™ cell line, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cell line, FreeStyle™ CHO-S cell line, GripTite™ 293 MSR cell line, GS-CHO cell line, HepaRG™ cell line, T-REx™ Jurkat cell line, Per.C6 cell line, T-REx™-293 cell line, T-REx™-CHO cell line, T-REx™-HeLa cell line, NC-HIMT cell line, and PC12 cell line.

The cell sample may be obtained from cells of a primate. The primate may be a human, or a non-human primate. The cell sample may be obtained from a human. For example, the cell sample may comprise cells obtained from blood, urine, stool, saliva, lymph fluid, cerebrospinal fluid, synovial fluid, cystic fluid, ascites, pleural effusion, amniotic fluid, chorionic villus sample, vaginal fluid, interstitial fluid, buccal swab sample, sputum, bronchial lavage, Pap smear sample, or ocular fluid. The cell sample may comprise cells obtained from a blood sample, an aspirate sample, or a smear sample.

The cell sample may be a circulating tumor cell sample. A circulating tumor cell sample may comprise lymphoma cells, fetal cells, apoptotic cells, epithelia cells, endothelial cells, stem cells, progenitor cells, mesenchymal cells, osteoblast cells, osteocytes, hematopoietic stem cells, foam cells, adipose cells, transcervical cells, circulating cardiocytes, circulating fibrocytes, circulating cancer stem cells, circulating myocytes, circulating cells from a kidney, circulating cells from a gastrointestinal tract, circulating cells from a lung, circulating cells from reproductive organs, circulating cells from a central nervous system, circulating hepatic cells, circulating cells from a spleen, circulating cells from a thymus, circulating cells from a thyroid, circulating cells from an endocrine gland, circulating cells from a parathyroid, circulating cells from a pituitary, circulating cells from an adrenal gland, circulating cells from islets of Langerhans, circulating cells from a pancreas, circulating cells from a hypothalamus, circulating cells from prostate tissues, circulating cells from breast tissues, circulating cells from circulating retinal cells, circulating ophthalmic cells, circulating auditory cells, circulating epidermal cells, circulating cells from the urinary tract, or combinations thereof.

A cell sample may be a peripheral blood mononuclear cell sample.

A cell sample may comprise cancerous cells. The cancerous cells may form a cancer which may be a solid tumor or a hematologic malignancy. The cancerous cell sample may comprise cells obtained from a solid tumor. The solid tumor may include a sarcoma or a carcinoma. Exemplary sarcoma cell sample may include, but are not limited to, cell sample obtained from alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, or telangiectatic osteosarcoma.

Exemplary carcinoma cell samples may include, but are not limited to, cell samples obtained from an anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

The cancerous cell sample may comprise cells obtained from a hematologic malignancy. Hematologic malignancy may comprise a leukemia, a lymphoma, a myeloma, a non-Hodgkin's lymphoma, or a Hodgkin's lymphoma. The hematologic malignancy may be a T-cell based hematologic malignancy. The hematologic malignancy may be a B-cell based hematologic malignancy. Exemplary B-cell based hematologic malignancy may include, but are not limited to, chronic lymphocytic leukemia (CLL), small lymphocytic lymphoma (SLL), high risk CLL, a non-CLL/SLL lymphoma, prolymphocytic leukemia (PLL), follicular lymphoma (FL), diffuse large B-cell lymphoma (DLBCL), mantle cell lymphoma (MCL), Waldenström's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. Exemplary T-cell based hematologic malignancy may include, but are not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

A cell sample described herein may comprise a tumor cell line sample. Exemplary tumor cell line sample may include, but are not limited to, cell samples from tumor cell lines such as 600MPE, AU565, BT-20, BT-474, BT-483, BT-549, Evsa-T, Hs578T, MCF-7, MDA-MB-231, SkBr3, T-47D, HeLa, DU145, PC3, LNCaP, A549, H1299, NCI-H460, A2780, SKOV-3/Luc, Neuro2a, RKO, RKO-AS45-1, HT-29, SW1417, SW948, DLD-1, SW480, Capan-1, MC/9, B72.3, B25.2, B6.2, B38.1, DMS 153, SU.86.86, SNU-182, SNU-423, SNU-449, SNU-475, SNU-387, Hs 817.T, LMH, LMH/2A, SNU-398, PLHC-1, HepG2/SF, OCI-Ly1, OCI-Ly2, OCI-Ly3, OCI-Ly4, OCI-Ly6, OCI-Ly7, OCI-Ly10, OCI-Ly18, OCI-Ly19, U2932, DB, HBL-1, RIVA, SUDHL2, TMD8, MEC1, MEC2, 8E5, CCRF-CEM, MOLT-3, TALL-104, AML-193, THP-1, BDCM, HL-60, Jurkat, RPMI 8226, MOLT-4, RS4, K-562, KASUMI-1, Daudi, GA-10, Raji, JeKo-1, NK-92, and Mino.

A cell sample may comprise cells obtained from a biopsy sample, necropsy sample, or autopsy sample.

The cell samples (such as a biopsy sample) may be obtained from an individual by any suitable means of obtaining the sample using well-known and routine clinical methods. Procedures for obtaining tissue samples from an individual are well known. For example, procedures for drawing and processing tissue sample such as from a needle aspiration biopsy are well-known and may be employed to obtain a sample for use in the methods provided. Typically, for collection of such a tissue sample, a thin hollow needle is inserted into a mass such as a tumor mass for sampling of cells that, after being stained, will be examined under a microscope.

A cell may be a eukaryotic cell. A cell may be a yeast cell. A cell may be a plant cell. A cell may be obtained from an agricultural plant.

Detection of a Target Nucleic Acid Sequence

Figure 26:
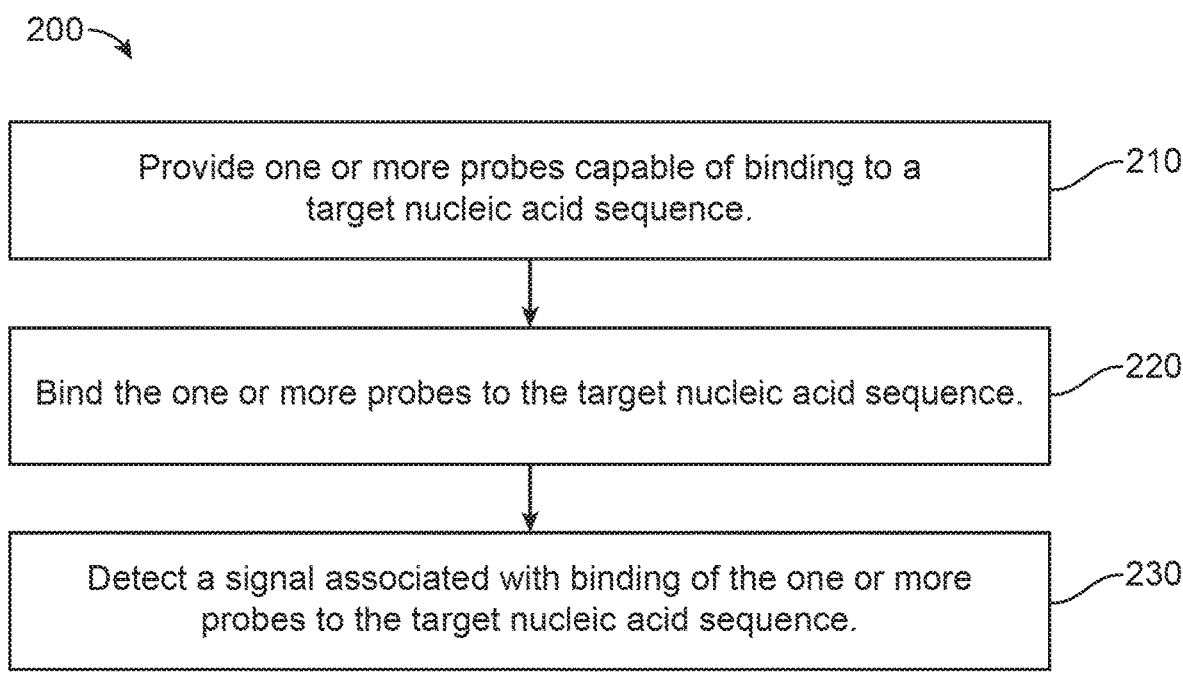
FIG. 26 shows a flowchart for a method of determining the spatial position of a nucleic acid sequence.

FIG. 26 shows a flowchart for a method 200 of detecting a target nucleic acid sequence. The method may comprise an operation 210 of providing one or more probes capable of binding to a target nucleic acid sequence, as described herein. The method may comprise an operation 220 of binding the one or more probes to the target nucleic acid sequence, as described herein. The method may comprise an operation 230 of detecting a signal associated with binding of the one or more probes to the target nucleic acid sequence, as described herein.

The target nucleic acid sequence may be detected in an intact cell. The target nucleic acid sequence may be detected in a fixed cell. The target nucleic sequence may be detected in a lysate or chromatin spread.

A probe may be used to detect a nucleic acid sequence in a sample. For example, a probe comprising a probe sequence capable of binding a nucleic acid sequence (such as a target nucleic acid sequence) and a detectable label (such as a detectable agent) may be used to detect the nucleic acid sequence. A method for detecting a nucleic acid sequence may comprise contacting a nucleic acid sequence with a probe comprising a probe sequence configured to bind at least a portion of the nucleic acid sequence and detecting the probe (such as detecting the detectable label of the probe). The detection of a nucleic acid sequence may comprise binding the probe to the nucleic acid sequence. For example, the detection of a nucleic acid sequence may comprise binding the probe sequence, such as the sequence of an oligonucleotide probe, to a target nucleic acid sequence. In some cases, the detection of a nucleic acid sequence may comprise hybridizing the probe sequence (such as the nucleic acid binding region) of a nucleic acid probe to a target nucleic acid sequence.

A nucleic acid sequence may be contacted with a plurality of probes. A nucleic acid sequence may be contacted with a number of probes ranging from about 1 to about $10^8$ probes, from about 2 to about $10^7$ probes, from about 10 to about $10^6$ probes, from about 100 to about 105 probes, from about 1,000 to about $10^4$ probes, from about 1,000 to about 5,000 probes, from about 1,000 probes to about 50,000 probes, from about 1,000 to about $10^5$ probes, from about 1,000 to about 500,000 probes, from about 1,000 probes to about $10^6$ probes, from about 1,000 probes to about 50 million probes, or from about 1,000 probes to about $10^8$ probes. The probes of the plurality of probes may be the same. A plurality of probes may have sequences such that the probes are tiled across the nucleic acid sequence. Each probe can bind to a target nucleic acid sequence along the nucleic acid sequence. The probes of a plurality may be different. A first probe of the plurality of probes may be different than a second probe of the plurality of probes. The plurality of probes may bind to the nucleic acid sequence with from 0 to 10 nucleotides separating each probe.

A nucleic acid sequence may be washed after it has been contacted with a probe. Washing a nucleic acid sequence after it has been contacted with a probe may reduce background signal for detection of the detectable label of the probe.

A nucleic acid sequence (such as a target nucleic acid sequence) may be contacted by a plurality of probes. A nucleic acid sequence may be contacted with a plurality of types of probes. That is, a method of detection of a nucleic acid sequence (such as a target nucleic acid sequence) may comprise contacting the target nucleic acid sequence with a plurality of sets of probes (such as a plurality of types of probes). A first probe set (such as a first type of probe) may be different from a second probe set (such a second type of probe) in that the first probe type comprises a first probe sequence which is different than the probe sequence of the second probe type. The probe sequence of a first type of probe may be the same as the probe sequence of a second type of probe. A first probe set may comprise a first detectable label and a first probe sequence and a second probe set may comprise a second detectable label and a second probe sequence, wherein the first and second probe sequences are the same and the first and second detectable labels are different. The first and second probe sequences may be different and the first and second detectable labels of a first and second probe set may be the same. The first and second probe sequences of a first and second probe set may be different and the first and second detectable labels of a first and second probe set may be different. A method of detecting a nucleic acid sequence may comprise contacting a nucleic acid sequence with 1, 2, 3, 4, 5, 6, 7, 8, 9, 10, 11, 12, 13, 14, 15, 16, 17, 18, 19, or 20 types of probes.

A first probe sequence may be configured to specifically recognize (such as to bind to or to hybridize with) a first nucleic acid sequence (such as a first target nucleic acid sequence). A second probe sequence may be configured to specifically recognize (such as to bind to or to hybridize with) a second nucleic acid sequence (such as a second target nucleic acid sequence).

A detectable label may be detected with a detector. A detector may detect the signal intensity of the detectable label. A detector may spatially distinguish between two detectable labels. A detector may also distinguish between a first and second detectable label based on the spectral pattern produced by the first and second detectable labels, wherein the first and second detectable label do not produce an identical spectral intensity pattern. For example, a detector may distinguish between a first and second detectable signal, wherein the wavelength of the signal produced by the first detectable label is not the same as the wavelength of the signal produced by the second detectable label. A detector may resolve (such as by spatially distinguishing or spectrally distinguishing) a first and second detectable label that are less than 1 kb apart, less than kb apart, less than kb apart, less than 2 kb apart, less than 2.5 kb apart, less than 3 kb apart, less than 3.5 kb apart, less than 4 kb apart, less than 4.5 kb apart, less than 5 kb apart, less than 5.5 kb apart, less than 6 kb apart, less than 6.5 kb apart, less than 7 kb apart, less than 7.5 kb apart, less than 8 kb apart, less than 8.5 kb apart, less than 9 kb apart, less than 9.5 kb apart, less than 10 kb apart, less than 10.5 kb apart, less than 11 kb apart, less than 11.5 kb apart, less than 12 kb apart, less than 20 kb apart, less than 50 kb apart, or less than 100 kb apart. The detectable label of the probe may be detected optically. For example, a detectable label of a probe may be detected by light microscopy, fluorescence microscopy, or chromatography. Detection of the detectable label of a probe may comprise stimulating the probe or a portion thereof (such as the detectable label) with a source of radiation (such as a light source, such as a laser). Detection of the detectable label of a probe may also comprise an enzymatic reaction.

Detection of the target nucleic acid sequence may be within a period of not more than 48 hours, not more than 36 hours, not more than 24 hours, not more than 23 hours, not more than 22 hours, not more than 21 hours, not more than 20 hours, not more than 19 hours, not more than 18 hours, not more than 17 hours, 1 not more than 6 hours, not more than 15 hours, not more than 14 hours, not more than 13 hours, or not more than 12 hours.

Determining the presence of a genetic modification in a cell using the Nano-FISH method described herein may be useful is assessing the phenotype of the cell resulting from the genetic modification. A method for assessing a phenotype of an intact genetically modified cell may comprise: a) providing the intact genetically modified cell comprising a target nucleic acid sequence less than 2.5 kilobases in length; b) contacting the intact genetically modified cell with a first plurality of probes, wherein each probe comprises a first detectable label and a probe sequence that binds to a portion of the target nucleic acid sequence; c) detecting a presence of the first detectable label in the intact cell, wherein the presence of the first detectable label indicates the presence of the target nucleic acid sequence; d) determining a phenotype of the intact genetically modified cell; and e) correlating the phenotype of the intact genetically modified cell with the presence of the target nucleic acid sequence. The method may further comprise determining a number or location of genetic modifications in the intact genetically modified cell. The method may further comprise f) selecting a first intact genetically modified cell comprising a phenotype of interest; g) determining a set of conditions used for a genetic modification of the first intact genetically modified cell; and h) preparing a second genetically modified cell using the set of conditions for genetic modification. The intact genetically modified cell may be a eukaryotic cell that was genetically modified. The intact genetically modified cell may be a bacteria cell that was genetically modified. The intact genetically modified cell may be a mammalian cell that was genetically modified. The intact genetically modified cell may be any cell as described herein that was genetically modified. The phenotype may be a product expressed as a result of the genetic modification of the cell. The phenotype may be an increased level or decreased level of the product expressed as a result of the genetic modification of the cell. The phenotype may be an increased quality of the product expressed as a result of the genetic modification of the cell. The expressed product may be protein, such as an enzyme. The expressed product may be a transgene protein, RNA, or a secondary product of the genetic modification. For example, if an enzyme is produced as a result of the genetic modification of the cell, a secondary product of the genetic modification is a product of the enzyme.

Determining the number of target nucleic acid sequences in a cell may be useful in determining the phenotype of the cell. Cells with a specific number of target nucleic acid sequences may be tested for increased cellular activity, decreased cellular activity, or toxicity. Increased cellular activity may be increased expression of a protein or a cellular product. Decreased cellular activity may be decreased expression of a protein or a cellular product. Toxicity may be a result of cellular activity that may be too high or too low, resulting in cell death. For example, the contacting a sample of cells with a probe configured to bind to a particular target nucleic acid sequence and then determining the number of target nucleic acid sequences in the cell may be an expedient means of determining whether the number of target nucleic acid sequences may be affecting the cell phenotype or function.

A method of detecting or determining the presence of a nucleic acid sequence may comprise determining the number of probes associated with the nucleic acid sequence. A method of detecting or determining the presence of a nucleic acid sequence may comprise determining the number of probes hybridized to the nucleic acid sequence.

It may also be possible to determine the quantity of target nucleic acid sequences in this manner. Quantification of target nucleic acid sequences in a sample using the methods, compositions, and systems described herein may be useful in determining the number of repeated sequences in a nucleic acid of a sample.

Determining the presence, absence, identity, spatial position or sequence position of a target nucleic acid sequence in a sample may be useful in determining a condition of a patient. For example, contacting a patient sample with a probe configured to bind to a particular nucleic acid sequence may be an expedient means of determining whether the patient has the nucleic acid sequence. Similarly, contacting a patient sample with a plurality of types of probes, each configured to bind to a different nucleic acid sequence, may be an expedient means of screening patients for various genetic or acquired conditions, such as inherited mutations.

Determination of the Spatial Position of a Nucleic Acid Sequence

Figure 27:
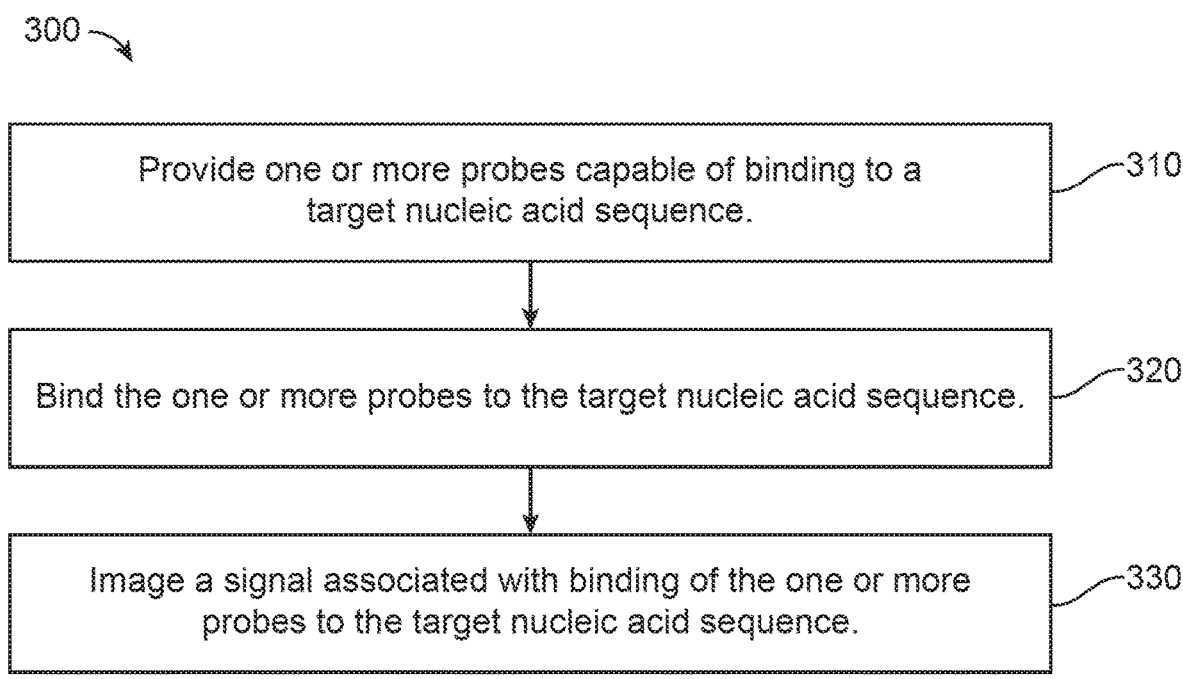
FIG. 27 shows a flowchart for a method of detecting the sequence position of a nucleic acid sequence.

FIG. 27 shows a flowchart for a method 300 of determining the spatial position of a nucleic acid sequence. The method may comprise an operation 310 of providing one or more probes capable of binding to a target nucleic acid sequence, as described herein. The method may comprise an operation 320 of binding the one or more probes to the target nucleic acid sequence, as described herein. The method may comprise an operation 330 of imaging a signal associated with binding of the one or more probes to the target nucleic acid sequence, as described herein.

A method of detecting or determining the presence of a nucleic acid sequence may comprise determining the spatial position of a nucleic acid sequence (such as a target nucleic acid sequence). Determining the spatial position of a nucleic acid sequence may comprise contacting a nucleic acid sequence with a probe, which may comprise a detectable label and a probe sequence configured to bind to the nucleic acid sequence, and detecting the detectable label of the probe.

The spatial position of the nucleic acid sequence may be determined relative to features of the sample (such as features of a cell), structures of the sample (such structures or organelles of the cell), or other nucleic acids by using the same or a different imaging modality to detect the reference features, structures, or nucleic acids. For instance, the spatial position of a nucleic acid sequence in a cell relative to the nucleus of a cell by using a plurality of antibodies with a detectable label to counter-label structures of the cell, such as the cell membrane. A cell line expressing a detectable label (such as a fusion protein with a structural protein expressed by the cell) may be used to determine spatial position of a nucleic acid sequence in a cell.

Data collected from detection of all or a portion of the detectable labels in a sample may be used to form one or more two-dimensional images or a three-dimensional rendering or to make calculations determining or estimating the spatial position of the target nucleic acid sequence.

A first probe comprising a first detectable label and a first probe sequence configured to bind to a nucleic acid sequence (such as a target nucleic acid sequence) may be used as a reference position for a second probe comprising a second detectable label and a second probe sequence configured to bind to a second nucleic acid sequence (such as a second target nucleic acid sequence). For example, a first probe specific to a first target nucleic acid sequence of a nucleic acid with a known or anchored position on the nucleic acid may be used as a reference to determine the spatial position of a second target nucleic acid sequence bound by a second probe prior to or during imaging.

Detection of the Sequence Position of a Nucleic Acid Sequence

Figure 28:
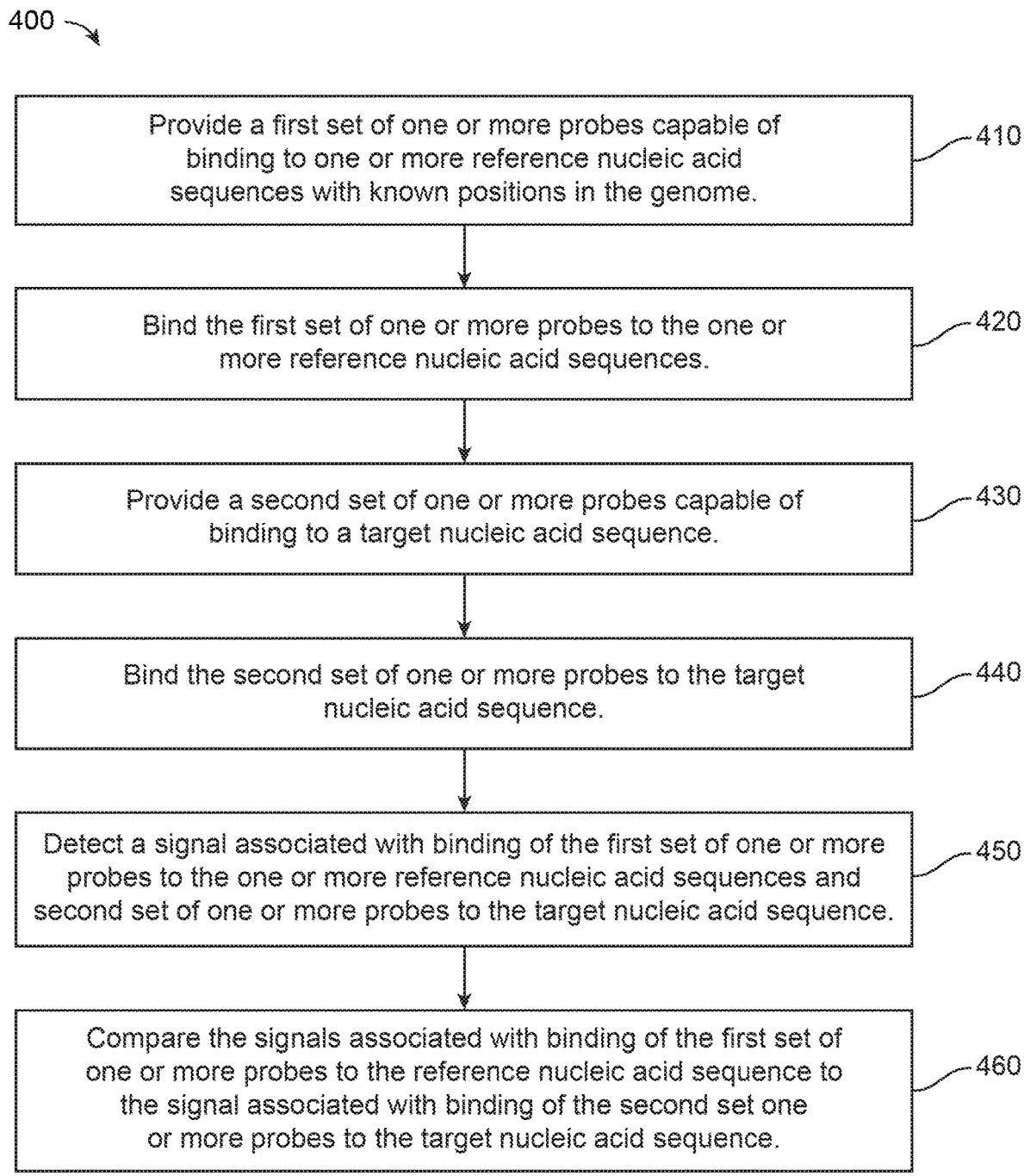
FIG. 28 shows a flowchart for a method of detecting a nucleic acid in a sample relative to a control.

FIG. 28 shows a flowchart for a method 400 of detecting the sequence position of a nucleic acid sequence. The method may comprise an operation 410 of providing a first set of one or more probes capable of binding to one or more reference nucleic acid sequences with known positions in the genome, as described herein. The method may comprise an operation 420 of binding the first set of one or more probes to the one or more reference nucleic acid sequences, as described herein. The method may comprise an operation 430 of providing a second set of one or more probes capable of binding to a target nucleic acid sequence, as described herein. The method may comprise an operation 440 of binding the second set of one or more probes to the target nucleic acid sequence, as described herein. The method may comprise an operation 450 of detecting a signal associated with binding of the first set of one or more probes to the one or more reference nucleic acid sequences and of the second set of one or more probes to the target nucleic acid sequence, as described herein. The method may comprise an operation 460 of comparing the signals associated with binding of the first set of one or more probes to the reference nucleic acid sequences to the signal associated with binding of the second set of one or more probes to the target nucleic acid sequence.

A method of detecting or determining the presence of a nucleic acid sequence may comprise determining the sequence position of a nucleic acid sequence (such as a target nucleic acid sequence). For example, a probe with a probe sequence configured to recognize a first target sequence with a known position in the sequence of a nucleic acid may be used as reference for calculations or estimations of the sequence position of a second target nucleic acid sequence on the nucleic acid. For example, a first probe having a probe sequence configured to recognize a first target sequence with a first known position in the sequence of a nucleic acid and a second probe having a probe sequence configured to recognize a second target nucleic acid sequence with a second known position in the sequence of the nucleic acid may be used as reference points for a third probe configured to recognize a third target nucleic acid sequence with an unknown position in the nucleic acid. The relative sequence position of the third target nucleic acid sequence may be determined or estimated by comparing it to the positions of the first and second target nucleic acid sequences, as indicated by the signals from the first and second probes.

Detection of Nucleic Acid Sequences in a Sample Relative to a Control

Figure 29:
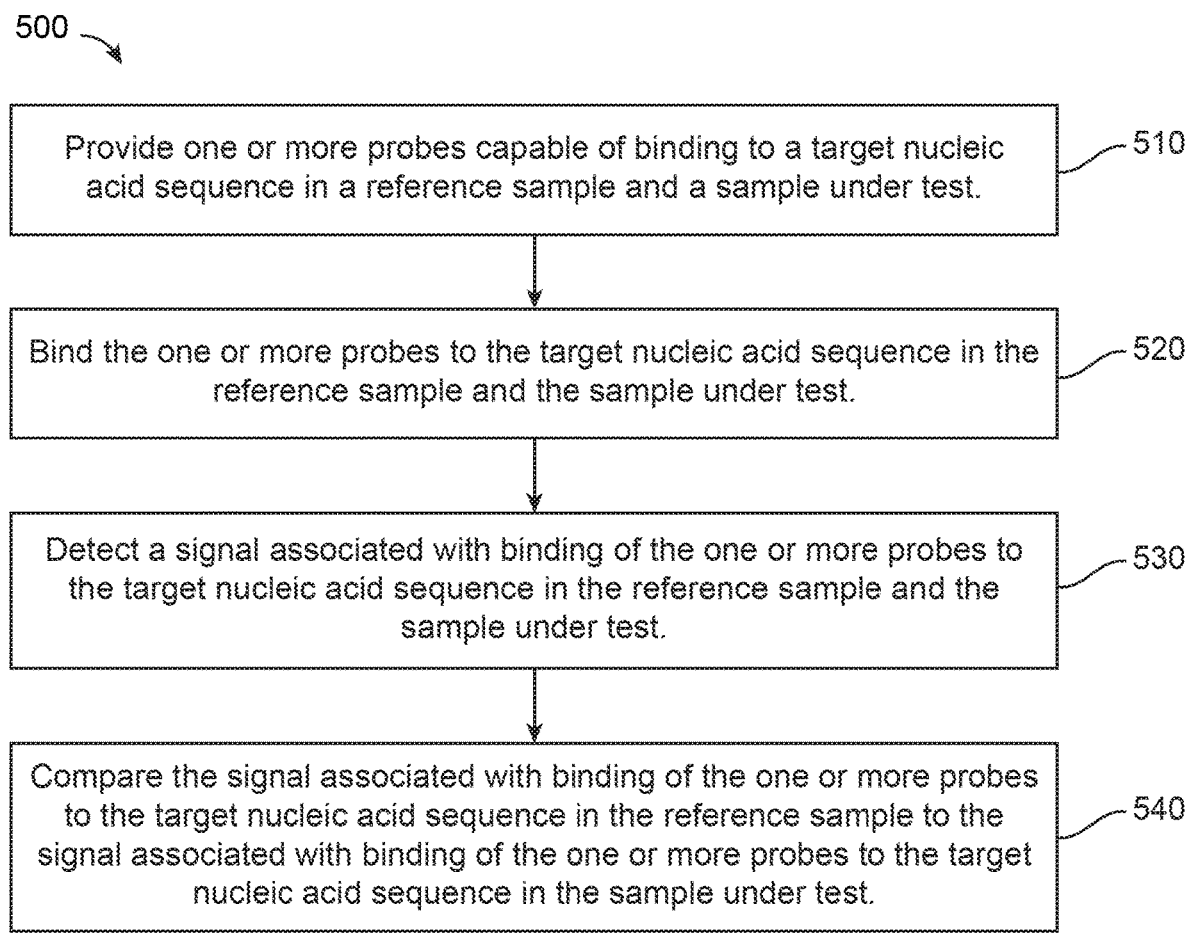
FIG. 29 shows a flowchart for a method of fluorescently detecting a target nucleic acid sequence.

FIG. 29 shows a flowchart for a method 500 of detecting a nucleic acid in a sample relative to a control. The method may comprise an operation 510 of providing a one or more probes capable of binding to a target nucleic acid sequence in a reference sample and a target nucleic acid sequence in a sample under test, as described herein. The method may comprise an operation 520 of binding the one or more probes to the target nucleic acid sequence in the reference sample and the target nucleic acid sequence in the sample under test, as described herein. The method may comprise an operation 530 of detecting a signal associated with binding of the set of one or more probes to the target nucleic acid sequence in the reference sample and the target nucleic acid sequence in the sample being tested, as described herein. The method may comprise an operation 540 of comparing the signal associated with binding of the one or more probes to the target nucleic acid sequence in the reference sample to the signal associated with binding of the one or more probes to the target nucleic acid sequence in the sample under test, as described herein.

Correlation of the Detection of a Target Nucleic Acid Sequence in a Sample with a Target Protein Expression The detection of a target nucleic acid sequence in a cell may be correlated with a target protein expression in the same cell. The method may comprise providing a one or more probes capable of binding to a target nucleic acid sequence in a sample and a target nucleic acid sequence in a sample being tested, as described herein, and further comprise providing one or more detectable labels to detect the target protein expression. The presence, absence, or quantity of the detected target nucleic acid sequence may be correlated to the presence, absence, or quantity of the target protein expression. This information may be used to further investigate the relationship between the target nucleic acid sequence and the target protein, and/or how different treatments may perturb this correlation.

Optical Detection of Nucleic Acid Sequences

Described herein is a method of detecting a nucleic acid sequence. The detection may encompass identification of the nucleic acid sequence, determining the presence or absence of the nucleic acid sequence, and/or determining the activity of the nucleic acid sequence. A method of detecting a nucleic acid sequence may include contacting a cell sample with a detection agent, binding the detection agent to the nucleic acid sequence, and analyzing a detection profile from the detection agent to determine the presence, absence, or activity of the nucleic acid sequence.

The method may involve utilizing one or more intrinsic properties associated with a detection agent to aid in detection of the nucleic acid sequence. The intrinsic properties may encompass the size of the detection agent, the intensity of the signal, and the location of the detection agent. The size of the detection agent may include the length of the probe and/or the size of the detectable moiety (such as the size of a fluorescent dye molecule) may modulate the specificity of interaction with a regulatory element. The intensity of the signal from the detection agent may correlate to the sensitivity of detection. For example, a detection agent with a molar extinction coefficient of about $0.5\text{-}5\times10^6$ $M^{-1}$ $cm^{-1}$ may have a higher intensity signal relative to a detection agent with a molar extinction coefficient outside of the $0.5\text{-}5\times10^6$ $M^{-1}$ $cm^{-1}$ range and may have lower attenuation due to scattering and absorption. Further, a detection agent with a longer excited state lifetime and a large Stoke shift (measured by the distance between the excitation and emission peaks) may further improve the sensitivity of detection. The location of the detection agent may, for example, provide the activity state of a nucleic acid sequence. A combination of intrinsic properties of the detection agent may be used to detect a regulatory element of interest.

A detection agent may comprise a detectable moiety that is capable of generating a light, and a probe portion that is capable of hybridizing to a target site on a nucleic acid sequence. As described herein, a detection agent may include a DNA probe portion, an RNA probe portion, a polypeptide probe portion, or a combination thereof. A DNA or RNA probe portion may be between about 10 and about 100 nucleotides in length, between about 15 and about 100 nucleotides in length, between about 20 and about 100 nucleotides in length, between about 20 and about 80 nucleotides in length, between about 20 and about 60 nucleotides in length, between about 25 and about 55 nucleotides in length, between about 30 and about 50 nucleotides in length, between about 15 and about 80 nucleotides in length, between about 15 and about 60 nucleotides in length, between about 20 and about 40 nucleotides in length, or between about 20 and about 30 nucleotides in length. A DNA or RNA probe portion may be about 10, about 15, about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60, about 65, about 70, about 80, about 90, or about 100 nucleotides in length. A DNA or RNA probe portion may be a TALEN probe, ZFN probe, or a CRISPR probe. A DNA or RNA probe portion may be a padlock probe. A polypeptide probe may comprise a DNA-binding protein, a RNA-binding protein, a protein involved in the transcription/translation process or detects the transcription/translation process, a protein that may detect an open or relaxed portion of a chromatin, or a protein interacting partner of a product of a regulatory element (such as an antibody or binding fragment thereof).

In some instances, a detection agent may comprise a DNA or RNA probe portion which may be between about 10 and about 100 nucleotides in length, between about 15 and about 100 nucleotides in length, between about 20 and about 100 nucleotides in length, between about 20 and about 80 nucleotides in length, between about 20 and about 60 nucleotides in length, between about 25 and about 55 nucleotides in length, between about 30 and about 50 nucleotides in length, between about 15 and about 80 nucleotides in length, between about 15 and about 60 nucleotides in length, between about 20 and about 40 nucleotides in length, or between about 20 and about 30 nucleotides in length. A detection agent may comprise a DNA or RNA probe portion which may be about 10, about 15, about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60, about 65, about 70, about 80, about 90, or about 100 nucleotides in length.

A detection agent may comprise a DNA or RNA probe selected from a TALEN probe, a ZFN probe, or a CRISPR probe.

A set of detection agents may be used to detect a nucleic acid sequence. The set of detection agents may comprise about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, or more detection agents. Each of the detection agents within the set of detection agents may recognize and interact with a distinct region of a nucleic acid sequence. About 1, about 2, about 3, about 4, about 5, about 6, about 7, about 8, about 9, about 10, about 11, about 12, about 13, about 14, about 15, about 16, about 17, about 18, about 19, about 20, or more detection agents may be used for detection of a nucleic acid sequence. About 1 or more detection agents may be used for detection of a nucleic acid sequence. About 2 or more detection agents may be used for detection of a nucleic acid sequence. About 3 or more detection agents may be used for detection of a nucleic acid sequence. About 4 or more detection agents may be used for detection of a nucleic acid sequence. About 5 or more detection agents may be used for detection of a nucleic acid sequence. About 6 or more detection agents may be used for detection of a nucleic acid sequence. About 7 or more detection agents may be used for detection of a nucleic acid sequence. About 8 or more detection agents may be used for detection of a nucleic acid sequence. About 9 or more detection agents may be used for detection of a nucleic acid sequence. About 10 or more detection agents may be used for detection of a nucleic acid sequence. About 11 or more detection agents may be used for detection of a nucleic acid sequence. About 12 or more detection agents may be used for detection of a nucleic acid sequence. About 13 or more detection agents may be used for detection of a nucleic acid sequence. About 14 or more detection agents may be used for detection of a nucleic acid sequence. About 15 or more detection agents may be used for detection of a nucleic acid sequence. About 20 or more detection agents may be used for detection of a nucleic acid sequence.

A detection agent may comprise a polypeptide probe selected from a DNA-binding protein, a RNA-binding protein, a protein involved in the transcription/translation process or detects the transcription/translation process, a protein that may detect an open or relaxed portion of a chromatin, or a protein interacting partner of a product of a regulatory element (such as an antibody or binding fragment thereof).

A detectable moiety that is capable of generating a light may be directly conjugated or bound to a probe portion. A detectable moiety may indirectly conjugated or bound to a probe portion by a conjugating moiety. As described herein, a detectable moiety may be a small molecule (such as a dye) which may be directly conjugated or bound to a probe portion. A detectable moiety may be a fluorescently labeled protein or molecule which may be attached to a conjugating moiety (such as a hapten group, an azido group, an alkyne group) of a probe.

A profile or a detection profile or signature may include the signal intensity, signal location, and/or size of the signal of the detection agent. The profile or the detection profile may comprise about 100 image frames, about 500 frames, about 1000 frames, about 2000 frames, about 5000 frames, about 10,000 frames, about 20,000 frames, about 30,000 frames, about 40,000 frames, about 50,000 frames, or more image frames. Analysis of the profile or the detection profile may determine the activity of the regulatory element. The degree of activation may also be determined from the analysis of the profile or detection profile. Analysis of the profile or the detection profile may further determine the optical isolation and localization of the detection agents, which may correlate to the localization of the nucleic acid sequence.

Figure 30:
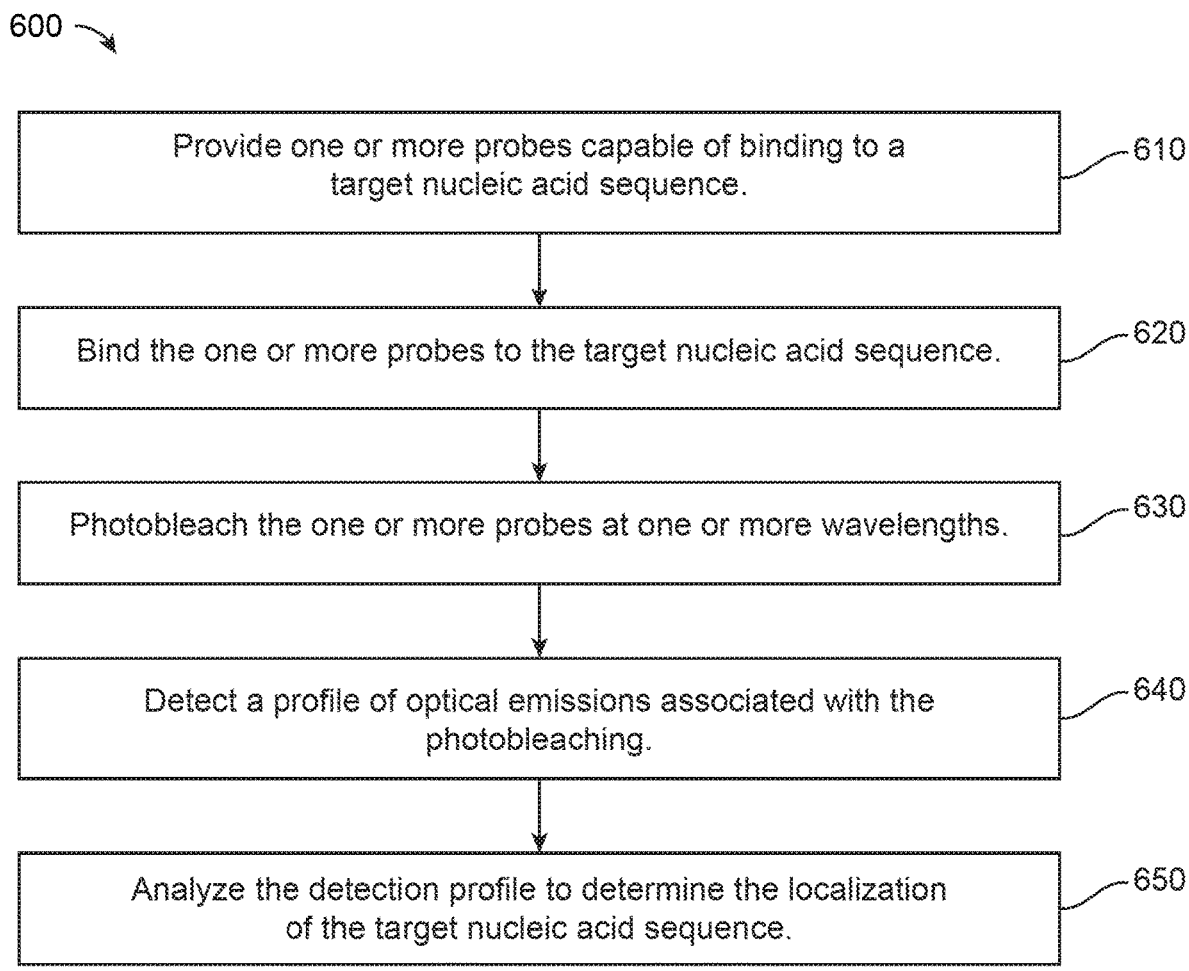
FIG. 30 shows a flowchart for a method of analyzing a fluorescence image of one or more target nucleic acid sequences.

FIG. 30 shows a flowchart for a method 600 of fluorescently detecting a target nucleic acid sequence. The method may comprise an operation 610 of providing a one or more probes capable of binding to a target nucleic acid sequence, as described herein. The method may comprise an operation 620 of binding the one or more probes to the target nucleic acid sequence, as described herein. The method may comprise an operation 630 of photobleaching the one or more probes at one or more wavelengths, as described herein. The method may comprise an operation 640 of detecting a profile of optical emissions associated with the photobleaching, as described herein. The method may comprise an operation 650 of analyzing the detection profile to determine the localization of the target nucleic acid sequence, as described herein.

The localization of a nucleic acid sequence may include contacting a nucleic acid sequence with a first set of detection agents, photobleaching the first set of detection agents for a first time point at a first wavelength to generate a second set of detection agents capable of generating a light at a second wavelength, detecting at least one burst generated by the second set of detection agents to generate a detection profile of the second set of detection agents, and analyzing the detection profile to determine the localization of the nucleic acid sequence.

A detection agent may comprise a detectable moiety that is capable of generating a light, and a probe portion that is capable of hybridizing to a target site on a nucleic acid sequence. Each detection agent within the first set of detection agents may have the same or a different detectable moiety. Each detection agent within the first set of detection agents may have the same detectable moiety. A detectable moiety may comprise a small molecule (such as a fluorescent dye). A detectable moiety may comprise a fluorescently labeled polypeptide, a fluorescently labeled nucleic acid probe, and/or a fluorescently labeled polypeptide complex.

Upon photobleaching, a second set of detection agents may be generated from the first set of detection agents, in which the second set may include detection agents that are capable of generating a burst of light detectable at a second wavelength. For example, bleaching of the set of detection agents may lead to about 50%, about 60%, about 70%, about 80%, about 90%, or more detection agents within the set to enter into an "OFF-state". An "OFF-state" may be a dark state in which the detectable moiety crosses from the singlet excited electronic or ON state to the triplet electronic state or OFF-state in which detection of light (such as fluorescence) may be low (for instance, less than 10%, less than 5%, less than 1%, or less than 0.5% of light may be detected). The remainder of the detection agents that have not entered into the OFF-state may generate bursts of lights, or to cycle between a singlet excited electronic state (or ON-state) and a singlet ground electronic state. As such, bleaching of the set of detection agents may generate about 40%, about 30%, about 20%, about 10%, about 5%, or less detection agents within the set that may generate bursts of lights. The bursts of lights may be detected stochastically, at a single burst level in which each burst of light correlates to a single detection agent.

A single wavelength may be used for photobleaching a set of detection agents. At least two wavelengths may be used for photobleaching a set of detection agents. A wavelength at 491 nm may be used. A wavelength at 405 nm may be used in combination with the wavelength at 491 nm. The two wavelengths may be applied simultaneously to photobleach a set of detection agents. The two wavelengths may be applied sequentially to photobleach a set of detection agents.

The time for photobleaching a set of detection agents may be from about 10 seconds to about 4 hours. The time may be from about 30 seconds to about 3.5 hours, from about one minute to about 3 hours, from about 5 minutes to about 2 hours, from about 10 minutes to about 1 hours, from about one minutes to about 1 hour, from about 5 minutes to about 1 hour, or from about 30 minutes to about 2 hours. The time may be at least 10 seconds, 20 seconds, 30 seconds, 40 seconds, 50 seconds, 1 minute, 2 minutes, 3 minutes, 4 minutes, 5 minutes, 10 minutes, 15 minutes, 20 minutes, 30 minutes, 45 minutes, 1 hour, 1.5 hours, 2 hours, 2.5 hours, 3 hours, 3.5 hours, 4 hours, or more.

The concentration of the detection agents may be from about 5 nM to about 1 µM. The concentration of the detection agent may be from about 5 nM to about 900 nM, from about 10 nM to about 800 nM, from about 15 nM to about 700 nM, from about 20 nM to about 500 nM, from about 10 nM to about 500 nM, from about 10 nM to about 400 nM, from about 10 nM to about 300 nM, from about 10 nM to about 200 nM, from about 10 nM to about 100 nM, from about 50 nM to about 500 nM, from about 50 nM to about 400 nM, from about 50 nM to about 300 nM, from about 50 nM to about 200 nM, from about 100 nM to about 500 nM, from about 100 nM to about 300 nM, or from about 100 nM to about 200 nM. The concentration of the detection agents may be about 10 nM, 15 nM, 20 nM, 30 nM, 40 nM, 50 nM, 60 nM, 70 nM, 80 nM, 90 nM, 100 nM, 150 nM, 200 nM, 250 nM, 300 nM, 400 nM, 500 nM, 600 nM, 700 nM, 800 nM, 900 nM, or more.

The burst of lights from the set of detection agents may generate a detection profile. The detection profile may comprise about 100 image frames, about 500 frames, about 1000 frames, about 2000 frames, about 5000 frames, about 10,000 frames, about 20,000 frames, about 30,000 frames, about 40,000 frames, about 50,000 frames, or more image frames. The detection profile may also include the signal intensity, signal location, or size of the signal. Analysis of the detection profile may determine the optical isolation and localization of the detection agents, which may correlate to the localization of the nucleic acid sequence.

The detection profile may comprise a chromatic aberration correction. The detection profile may comprise less than 5%, 4%, 3%, 2%, 1%, 0.5%, 0.1%, or 0% chromatic aberration. The detection profile may comprise less than 5% chromatic aberration. The detection profile may comprise less than 4% chromatic aberration. The detection profile may comprise less than 3% chromatic aberration. The detection profile may comprise less than 2% chromatic aberration. The detection profile may comprise less than 1% chromatic aberration. The detection profile may comprise less than 0.5% chromatic aberration. The detection profile may comprise less than 0.1% chromatic aberration. The detection profile may comprise 0% chromatic aberration.

More than one nucleic acid sequence may be detected at the same time. Sometimes, at least 2, at least 3, at least 4, at least 5, at least 6, at least 7, at least 8, at least 9, at least 10, at least 15, at least 20, or more nucleic acid sequence may be detected at the same time. Each of the nucleic acid sequences may be detected by a set of detection agents. The detectable moiety between the different set of detection agents may be the same. For example, two different sets of detection agents may be used to detect two different nucleic acid sequences and the detectable moieties from the two sets of detection agents may be the same. As such, at least 2, at least 3, at least 4, at least 5, at least 6, at least 7, at least 8, at least 9, at least 10, at least 15, at least 20, or more nucleic acid sequences may be detected at the same time at the same wavelength. The detectable moiety between the different set of detection agents may also be different. For example, two different sets of detection agents may be used to detect two different nucleic acid sequences and the detectable moiety from one set of detection agents may be detected at a different wavelength from the detectable moiety of the second set of detection agents. As such, at least 2, at least 3, at least 4, at least 5, at least 6, at least 7, at least 8, at least 9, at least 10, at least 15, at least 20, or more nucleic acid sequences may be detected at the same time in which each of the nucleic acid sequences may be detected at a different wavelength. The nucleic acid sequence may comprise DNA, RNA, polypeptides, or a combination thereof.

The activity of a target nucleic acid sequence may be measuring utilizing the methods described herein. The methods may include detection of a nucleic acid sequence and one or more products of the nucleic acid sequence. One or more products of the nucleic acid sequence may also include intermediate products or elements. The method may comprise contacting a cell sample with a first set and a second set of detection agents, in which the first set of detection agents interact with a target nucleic acid sequence within the cell and the second set of detection agents interact with at least one product of the target nucleic acid sequence, and analyze a detection profile from the first set and the second set of detection agents, in which the presence or the absence of the at least one product indicates the activity of the target nucleic acid sequence.

As described herein, a detection agent may comprise a detectable moiety that is capable of generating a light, and a probe portion that is capable of hybridizing to a target site on a nucleic acid sequence. Each detection agent within the first set of detection agents may have the same or a different detectable moiety. Each detection agent within the first set of detection agents may have the same detectable moiety. A detectable moiety may comprise a small molecule (such as a fluorescent dye). A detectable moiety may comprise a fluorescently labeled polypeptide, a fluorescently labeled nucleic acid probe, and/or a fluorescently labeled polypeptide complex.

The method may also allow photobleaching of the first set and the second set of detection agents, whereby generating a subset of detection agents capable of generating a burst of light. A detection profile may be generated from the detection of a set of light bursts, in which the presence or the absence of the at least one product may indicate the activity of the target nucleic acid sequence.

The nucleic acid sequence may comprise DNA, RNA, polypeptides, or a combination thereof. The nucleic acid sequence may be DNA. The nucleic acid sequence may be RNA. The nucleic acid sequence may be an enhancer RNA (eRNA). The presence of an eRNA may correlate with target gene transcription that is downstream of eRNA. The nucleic acid sequence may be a DNaseI hypersensitive site (DHS). The DHS may be an activated DHS. The pattern of the DHS on a chromatin may correlate to the activity of the chromatin. The nucleic acid sequence may be a polypeptide, such as a transcription factor, a DNA or RNA-binding protein or binding fragment thereof, or a polypeptide that is involved in chemical modification. The nucleic acid sequence may be chromatin.

Epifluorescence Imaging

One or more far-field or near-field fluorescence techniques may be utilized for the detection, localization, activity determination, and mapping of one or more nucleic acid sequences described herein. A microscopy method may be a high magnification oil immersion microscopy method. In such a method, wide-field and/or confocal fluorescent microscopes may achieve sub-cellular resolution.

Super-Resolution Imaging

A microscopy method may utilize a super-resolution microscopy, which allows images to be taken with a higher resolution than the diffraction limit. A super-resolution microscopy method may utilize a deterministic super-resolution microscopy method, which utilizes a fluorophore's nonlinear response to excitation to enhance resolution. Exemplary deterministic super-resolution methods may include stimulated emission depletion (STED), ground state depletion (GSD), reversible saturable optical linear fluorescence transitions (RESOLFT), and/or saturated structured illumination microscopy (SSIM). A super-resolution microscopy method may also include a stochastic super-resolution microscopy method, which utilizes a complex temporal behavior of a fluorophore, to enhance resolution. Exemplary stochastic super-resolution method may include super-resolution optical fluctuation imaging (SOFI), all single-molecular localization method (SMLM) such as spectral precision determination microscopy (SPDM), SPDMphymod, photo-activated localization microscopy (PALM), fluorescence photo-activated localization microscopy (FPALM), stochastic optical reconstruction microscopy (STORM), and dSTROM.

A microscopy method may be a single-molecular localization method (SMLM). A microscopy method may be a spectral precision determination microscopy (SPDM) method. A SPDM method may rely on stochastic burst or blinking of fluorophores and subsequent temporal integration of signals to achieve lateral resolution at, for example, between about 10 nm and about 100 nm.

A microscopy method may be a spatially modulated illumination (SMI) method. A SMI method may utilize phased lasers and interference patterns to illuminate specimens and increase resolution by measuring the signal in fringes of the resulting Moire patterns.

A microscopy method may be a synthetic aperture optics (SAO) method. A SAO method may utilize a low magnification, low numerical aperture (NA) lens to achieve large field of view and depth of field, without sacrificing spatial resolution. For example, an SAO method may comprise illuminating the detection agent-labeled target (such as a target nucleic acid sequence) with a predetermined number (N) of selective excitation patterns, where the number (N) of selective excitation patterns is determined based upon the detection agent's physical characteristics corresponding to spatial frequency content (such as the size, shape, and/or spacing of the detection agents on the imaging target) from the illuminated target, optically imaging the illuminated target at a resolution insufficient to resolve the objects on the target, and processing optical images of the illuminated target using information on the selective excitation patterns to obtain a final image of the illuminated target at a resolution sufficient to resolve the objects on the target. The number (N) of selective excitation patterns may correspond to the number of k-space sampling points in a k-space sampling space in a frequency domain, with the extent of the k-space sampling space being substantially proportional to an inverse of a minimum distance ($\Delta x$) between the objects that is to be resolved by SAO, and with the inverse of the k-space sampling interval between the k-space sampling points being less than a width (w) of a detected area captured by a pixel of a system for said optical imaging. The number (N) may include a function of various parameters of the imaging system (such as a magnification of the objective lens, numerical aperture of the objective lens, wavelength of the light emitted from the imaging target, and/or effective pixel size of the pixel sensitive area of the image detector, etc.).

A SAO method may analyze a set of detection agent profiles from at least 100, at least 200, at least 250, at least 500, at least 1000, or more cells imaged simultaneously within one field of view utilizing an imaging instrument. The one field of view may be a single wide field of view allowing image capture of at least 100, at least 200, at least 250, at least 500, at least 1000, or more cells. The single wide field of view may be about 0.70 mm by about 0.70 mm field of view. The SAO imaging instrument may enable a resolution of about 0.25 µm with a 20×/0.45 NA lens. The SAO imaging instrument may enable a depth of field of about 2.72 µm with a 20×/0.45 NA lens. The imaging instrument may enable a working distance of about 7 mm with a 20×/0.45 NA lens. The imaging instrument may enable a z-stack of 1 with a 20×/0.45 NA lens. The SAO method may further integrate and interpolate 3-dimensional images from 2-dimensional images.

The SAO imaging instrument may be an SAO instrument as described in U.S. Publication No. 2011/0228073 (Lightspeed Genomics, Inc).

Analysis of Fluorescence Images

Figure 31:
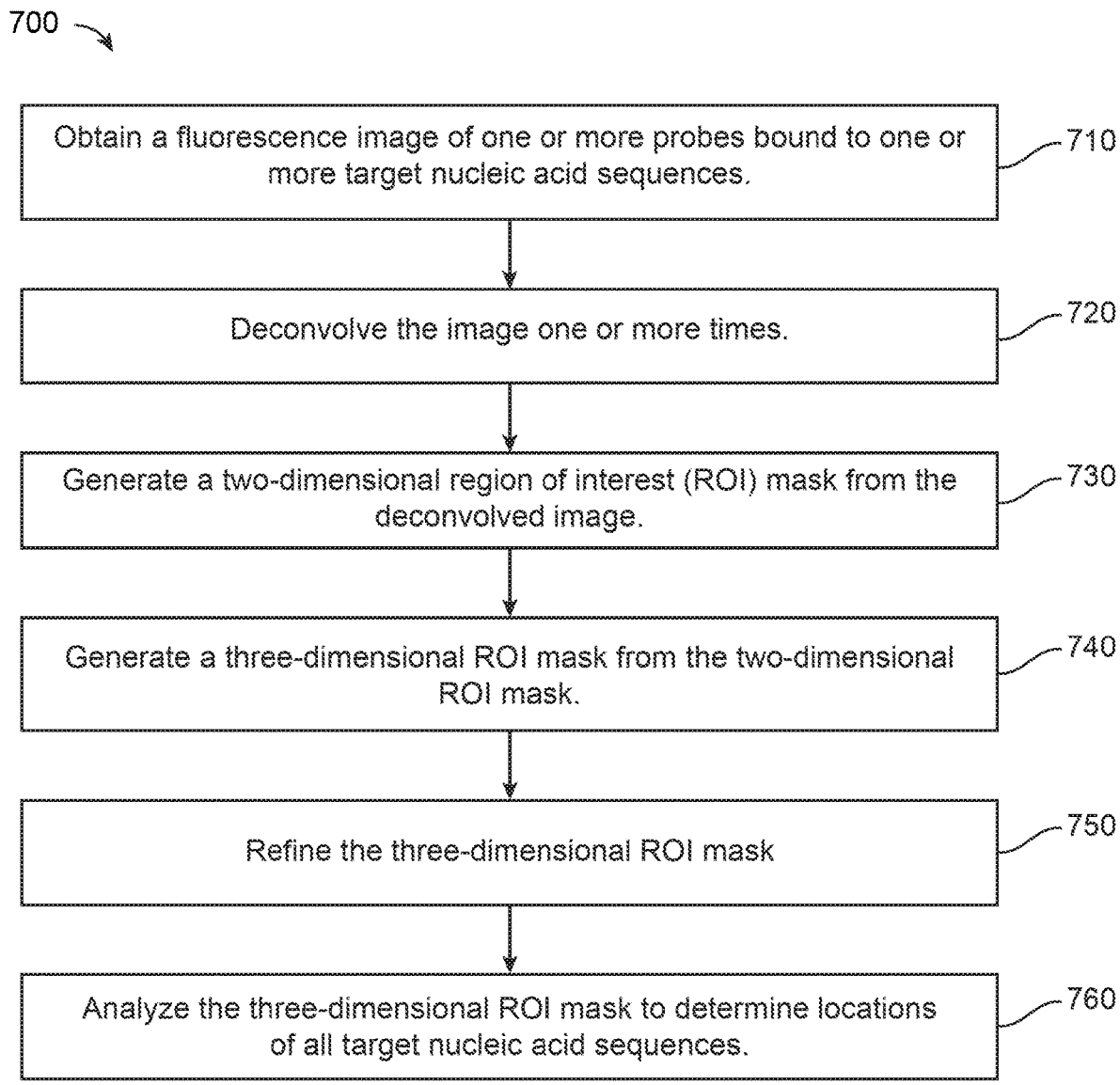
FIG. 31 shows a flowchart for a method of analyzing a fluorescence image of one or more target nucleic acid sequences.
Figure 32:
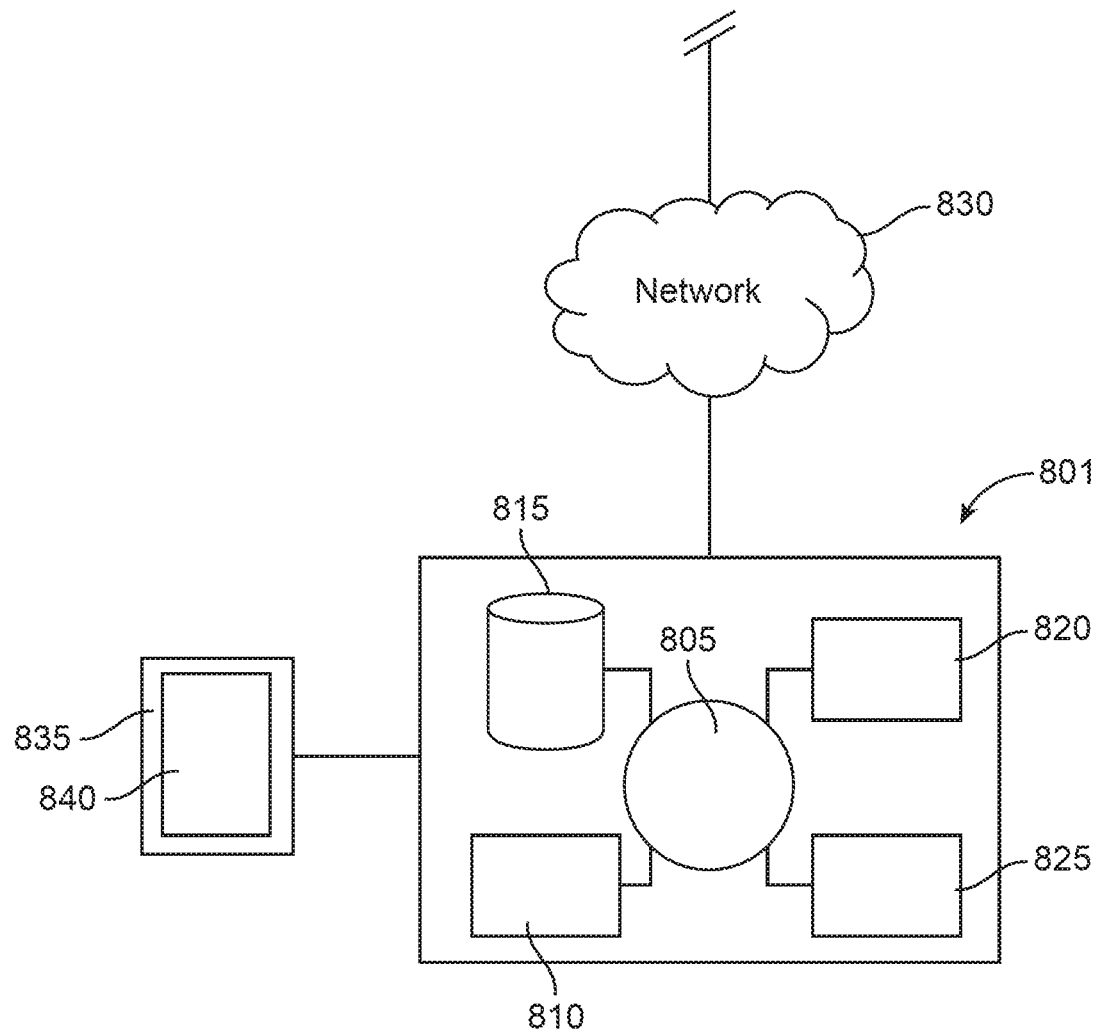
FIG. 32 illustrates a conceptual schematic of an exemplary computer server to be used for processing one or more methods described herein.

FIG. 31 shows a flowchart for a method 700 of analyzing a fluorescence image of one or more target nucleic acid sequences. The method may comprise an operation 710 of obtaining a fluorescence image of one or more probes bound to one or more target nucleic acid sequences, as described herein. The method may comprise an operation 720 of deconvolving the image one or more times, as described herein. The method may comprise an operation 730 of generating a two-dimensional region of interest (ROI) mask from the deconvolved image, as described herein. The method may comprise an operation 740 of generating a three-dimensional ROI mask from the two-dimensional ROI mask, as described herein. The method may comprise an operation 750 of refining the three-dimensional ROI mask, as described herein. The method may comprise an operation 760 of analyzing the three-dimensional ROI mask to determine the locations of all target nucleic acid sequences, as described herein.

Images obtained using the systems and methods described herein may be subjected to an image analysis method. The images may be obtained using the epifluorescence imaging systems and methods described herein. The image may be obtained using the super-resolution imaging systems and methods described herein. The image analysis method may allow a quantitative morphometric analysis to be conducted on regions of interest (ROIs) within the images.

The image analysis method may comprise a deconvolution of the image. The image analysis method may comprise an iterative deconvolution of the image. The image analysis method may comprise 1, 2, 3, 4, 5, 6, 7, 8, 9, or 10 iterations of deconvolving the image. The image analysis method may comprise more than 1, more than 2, more than 3, more than 4, more than 5, more than 6, more than 7, more than 8, more than 9, or more than 10 iterations of deconvolving the image. The deconvolution procedure may reduce out-of-focus blur in the epifluorescence images or super-resolution images, enhancing the signal-to-noise ratio (SNR) within ROIs.

The image analysis method may further comprise an identification of the ROIs. The ROIs may be identified using an automated detection method.

The image analysis method may further comprise segmentation of the ROIs. This may allow the rapid delineation of ROIs within the epifluorescence or super-resolution images. The segmentation of ROIs may comprise utilizing a maximum intensity projection image to generate a two-dimensional ROI mask. The two-dimensional ROI mask may act as a template for an initial three-dimensional mask. For instance, the initial three-dimensional mask may be generated by projecting the two-dimensional ROI mask into a third spatial dimension. The projection may be a weighted projection. The initial three-dimensional mask may be further refined to obtain a refined three-dimensional ROI mask. Refinement of the initial three-dimensional mask may be achieved utilizing adaptive thresholding and/or region growing methods. Refinement of the initial three-dimensional mask may be achieved by iteratively applying adaptive thresholding and/or region growing methods. The iterative procedure may result in a final three-dimensional ROI mask. The final three-dimensional ROI mask may comprise information regarding the locations of all FISH-labeled nucleic acid sequences within each cell in a sample.

The image analysis method may be implemented in an automated manner, such as using the digital processing devices described herein.

Digital Processing Device

The systems, apparatus, and methods described herein may include a digital processing device, or use of the same. The digital processing device may include one or more hardware central processing units (CPU) that carry out the device's functions. The digital processing device may further comprise an operating system configured to perform executable instructions. In some instances, the digital processing device is optionally connected to a computer network, is optionally connected to the Internet such that it accesses the World Wide Web, or is optionally connected to a cloud computing infrastructure. In other instances, the digital processing device is optionally connected to an intranet. In other instances, the digital processing device is optionally connected to a data storage device.

In accordance with the description herein, suitable digital processing devices may include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers may include those with booklet, slate, and convertible configurations, known to those of skill in the art.

The digital processing device may include an operating system configured to perform executable instructions. The operating system may be, for example, software, including programs and data, which may manage the device's hardware and provides services for execution of applications. Those of skill in the art will recognize that suitable server operating systems may include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some cases, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku©, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some instances, the device may include a storage and/or memory device. The storage and/or memory device may be one or more physical apparatuses used to store data or programs on a temporary or permanent basis. In some instances, the device is volatile memory and requires power to maintain stored information. In other instances, the device is non-volatile memory and retains stored information when the digital processing device is not powered. In still other instances, the non-volatile memory comprises flash memory. The non-volatile memory may comprise dynamic random-access memory (DRAM). The non-volatile memory may comprise ferroelectric random access memory (FRAM). The non-volatile memory may comprise phase-change random access memory (PRAM). The device may be a storage device including, by way of non-limiting examples, CD-ROMs, DVDs, flash memory devices, magnetic disk drives, magnetic tapes drives, optical disk drives, and cloud computing based storage. The storage and/or memory device may also be a combination of devices such as those disclosed herein.

The digital processing device may include a display to send visual information to a user. The display may be a cathode ray tube (CRT). The display may be a liquid crystal display (LCD). Alternatively, the display may be a thin film transistor liquid crystal display (TFT-LCD). The display may further be an organic light emitting diode (OLED) display. In various cases, on OLED display is a passive-matrix OLED (PMOLED) or active-matrix OLED (AMOLED) display. The display may be a plasma display. The display may be a video projector. The display may be a combination of devices such as those disclosed herein.

The digital processing device may also include an input device to receive information from a user. For example, the input device may be a keyboard. The input device may be a pointing device including, by way of non-limiting examples, a mouse, trackball, track pad, joystick, game controller, or stylus. The input device may be a touch screen or a multi-touch screen. The input device may be a microphone to capture voice or other sound input. The input device may be a video camera or other sensor to capture motion or visual input. Alternatively, the input device may be a Kinect™, Leap Motion™, or the like. In further aspects, the input device may be a combination of devices such as those disclosed herein.

Non-Transitory Computer Readable Storage Medium

In some instances, the systems, apparatus, and methods disclosed herein may include one or more non-transitory computer readable storage media encoded with a program including instructions executable by the operating system of an optionally networked digital processing device. In further instances, a computer readable storage medium is a tangible component of a digital processing device. In still further instances, a computer readable storage medium is optionally removable from a digital processing device. A computer readable storage medium may include, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

The systems, apparatus, and methods disclosed herein may include at least one computer program, or use of the same. A computer program includes a sequence of instructions, executable in the digital processing device's CPU, written to perform a specified task. In some embodiments, computer readable instructions are implemented as program modules, such as functions, objects, Application Programming Interfaces (APIs), data structures, and the like, that perform particular tasks or implement particular abstract data types. In light of the disclosure provided herein, those of skill in the art will recognize that a computer program, in certain embodiments, is written in various versions of various languages.

The functionality of the computer readable instructions may be combined or distributed as desired in various environments. A computer program may comprise one sequence of instructions. A computer program may comprise a plurality of sequences of instructions. In some instances, a computer program is provided from one location. In other instances, a computer program is provided from a plurality of locations. In additional cases, a computer program includes one or more software modules. Sometimes, a computer program may include, in part or in whole, one or more web applications, one or more mobile applications, one or more standalone applications, one or more web browser plug-ins, extensions, add-ins, or add-ons, or combinations thereof.

Web Application

A computer program may include a web application. In light of the disclosure provided herein, those of skill in the art will recognize that a web application, in various aspects, utilizes one or more software frameworks and one or more database systems. In some cases, a web application is created upon a software framework such as Microsoft® .NET or Ruby on Rails (RoR). In some cases, a web application utilizes one or more database systems including, by way of non-limiting examples, relational, non-relational, object oriented, associative, and XML database systems. Sometimes, suitable relational database systems may include, by way of non-limiting examples, Microsoft® SQL Server, mySQL™, and Oracle®. Those of skill in the art will also recognize that a web application, in various instances, is written in one or more versions of one or more languages. A web application may be written in one or more markup languages, presentation definition languages, client-side scripting languages, server-side coding languages, database query languages, or combinations thereof. A web application may be written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). A web application may be written to some extent in a client-side scripting language such as Asynchronous Javascript and XML (AJAX), Flash® Actionscript, Javascript, or Silverlight®. A web application may be written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. Sometimes, a web application may be written to some extent in a database query language such as Structured Query Language (SQL). Other times, a web application may integrate enterprise server products such as IBM® Lotus Domino®. In some instances, a web application includes a media player element. In various further instances, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

A computer program may include a mobile application provided to a mobile digital processing device. In some cases, the mobile application is provided to a mobile digital processing device at the time it is manufactured. In other cases, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

A computer program may include a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. A computer program may include one or more executable complied applications.

Web Browser Plug-In

The computer program may include a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™ PHP, Python™, and VB .NET, or combinations thereof.

Web browsers (also called Internet browsers) may be software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

The systems and methods disclosed herein may include software, server, and/or database modules, or use of the same. In view of the disclosure provided herein, software modules may be created by techniques known to those of skill in the art using machines, software, and languages known to the art. The software modules disclosed herein may be implemented in a multitude of ways. A software module may comprise a file, a section of code, a programming object, a programming structure, or combinations thereof. A software module may comprise a plurality of files, a plurality of sections of code, a plurality of programming objects, a plurality of programming structures, or combinations thereof. In various aspects, the one or more software modules comprise, by way of non-limiting examples, a web application, a mobile application, and a standalone application. In some instances, software modules are in one computer program or application. In other instances, software modules are in more than one computer program or application. In some cases, software modules are hosted on one machine. In other cases, software modules are hosted on more than one machine. Sometimes, software modules may be hosted on cloud computing platforms. Other times, software modules may be hosted on one or more machines in one location. In additional cases, software modules are hosted on one or more machines in more than one location.

Databases

The methods, apparatus, and systems disclosed herein may include one or more databases, or use of the same. In view of the disclosure provided herein, those of skill in the art will recognize that many databases are suitable for storage and retrieval of analytical information described elsewhere herein. In various aspects described herein, suitable databases may include, by way of non-limiting examples, relational databases, non-relational databases, object oriented databases, object databases, entity-relationship model databases, associative databases, and XML databases. A database may be internet-based. A database may be web-based. A database may be cloud computing-based. Alternatively, a database may be based on one or more local computer storage devices.

Services

Methods and systems described herein may further be performed as a service. For example, a service provider may obtain a sample that a customer wishes to analyze. The service provider may then encodes the sample to be analyzed by any of the methods described herein, performs the analysis and provides a report to the customer. The customer may also perform the analysis and provides the results to the service provider for decoding. In some instances, the service provider then provides the decoded results to the customer.

In other instances, the customer may receive encoded analysis of the samples from the provider and decodes the results by interacting with softwares installed locally (at the customer's location) or remotely (e.g. on a server reachable through a network). Sometimes, the softwares may generate a report and transmit the report to the costumer. Exemplary customers include clinical laboratories, hospitals, industrial manufacturers and the like. Sometimes, a customer or party may be any suitable customer or party with a need or desire to use the methods provided herein.

Server

The methods provided herein may be processed on a server or a computer server, as shown in FIG. 13). The server 801 may include a central processing unit (CPU, also "processor") 805 which may be a single core processor, a multi core processor, or plurality of processors for parallel processing. A processor used as part of a control assembly may be a microprocessor. The server 801 may also include memory 810 (e.g. random access memory, read-only memory, flash memory); electronic storage unit 815 (e.g. hard disk); communications interface 820 (e.g. network adaptor) for communicating with one or more other systems; and peripheral devices 825 which includes cache, other memory, data storage, and/or electronic display adaptors. The memory 810, storage unit 815, interface 820, and peripheral devices 825 may be in communication with the processor 805 through a communications bus (solid lines), such as a motherboard. The storage unit 815 may be a data storage unit for storing data. The server 801 may be operatively coupled to a computer network ("network") 830 with the aid of the communications interface 820. A processor with the aid of additional hardware may also be operatively coupled to a network. The network 830 may be the Internet, an intranet and/or an extranet, an intranet and/or extranet that is in communication with the Internet, a telecommunication or data network. The network 830 with the aid of the server 801, may implement a peer-to-peer network, which may enable devices coupled to the server 801 to behave as a client or a server. The server may be capable of transmitting and receiving computer-readable instructions (e.g., device/system operation protocols or parameters) or data (e.g., sensor measurements, raw data obtained from detecting metabolites, analysis of raw data obtained from detecting metabolites, interpretation of raw data obtained from detecting metabolites, etc.) via electronic signals transported through the network 830. Moreover, a network may be used, for example, to transmit or receive data across an international border.

The server 801 may be in communication with one or more output devices 835 such as a display or printer, and/or with one or more input devices 840 such as, for example, a keyboard, mouse, or joystick. The display may be a touch screen display, in which case it functions as both a display device and an input device. Different and/or additional input devices may be present such an enunciator, a speaker, or a microphone. The server may use any one of a variety of operating systems, such as for example, any one of several versions of Windows®, or of MacOS®, or of Unix®, or of Linux®.

The storage unit 815 may store files or data associated with the operation of a device, systems or methods described herein.

The server may communicate with one or more remote computer systems through the network 830. The one or more remote computer systems may include, for example, personal computers, laptops, tablets, telephones, Smart phones, or personal digital assistants.

A control assembly may include a single server 801. In other situations, the system may include multiple servers in communication with one another through an intranet, extranet and/or the Internet.

The server 801 may be adapted to store device operation parameters, protocols, methods described herein, and other information of potential relevance. Such information may be stored on the storage unit 815 or the server 801 and such data is transmitted through a network.

Kits

A composition described herein may be supplied in the form of a kit. A composition may be a probe set designed for a target nucleic acid sequence. The kits of the present disclosure may further comprise instructions regarding the method of using the probe set to detect the target nucleic acid sequence.

In some embodiments, a kit comprises the compositions and methods for detecting a target nucleic acid sequence (to perform a Nano-FISH assay). The compostions and methods may be for fast detection of the target nucleic acid sequence, e.g., in about 24 hours or less, or in about 48 hours or less. The compostions and methods may be for detection of the target nucleic acid sequence, wherein the target nucleic acid sequence is a short nucleic acid sequence, e.g., less than 2 kb, less than 1.5 kb, or less than 0.5 kb. The compostions and methods may be for detecting and quantifying the target nucleic acid sequence in a cell or in a population of cells. In some embodiments, a kit may further comprise components useful in using the kit components and instructions on how to prepare the components for detection of a target nucleic acid sequence. In some embodiments, the kit may further comprise software needed for detection of the target nucleic acid sequence.

The components of the kit may be in dry or liquid form. If they are in dry form, the kit may include a solution to solubilize the dried material. The kit may also include transfer factor in liquid or dry form. In some embodiments, if the transfer factor is in dry form, the kit includes a solution to solubilize the transfer factor. The kit may also include containers for mixing and preparing the components. The kits as described herein also may include a means for containing compositions of the present disclosure in close confinement for commercial sale and distribution.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts may be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

EXAMPLES

These examples are provided for illustrative purposes only and not to limit the scope of the claims provided herein.

Example 1

DNase Treatment and TUNEL Assay

A TUNEL assay as described below may be used to label DNaseI cut sites on a global cell. For example, all of the DNaseI cut sites within a cell's nucleus may be labeled.

Cells were prepared for a 2-color SPDM for DNA density and DNase I sensitivity (TUNEL) assay.

An adherent cell line, A549 (lung adenocarcinoma), was used for these experiments. They were plated overnight on uncoated 18 mm (#1 thickness) coverslips. Cells were deliberately plated sparsely to be ~20% confluent on the day of the assay.

For all coverslips, cells were fixed with 4% formaldehyde in PBS for 10 minutes at room temperature, and then equilibrated in buffer A at room temperature for 15 minutes. The cells were permeabilized with 0.1% NP-40 in buffer A for 10 minutes at room temperature.

The DNaseI assay was performed with 80 U/ml DNaseI for 3 minutes at 37° C. Cells were then post fixed in 4% formaldehyde in buffer A for 10 minutes at room temperature. The coverslips were permeabilized for 20 minutes with buffer A with 0.25% TX-100, and washed twice with distilled water and were equilibrated with 100 µl of TdT reaction buffer for 10 minutes at room temperature. The terminal deoxynucleotide transferase (TdT) reaction with EdUTP-alkyne (100 µl per coverslip) was performed for 1 hour at 37° C. At the end of the TdT reaction, the coverslips were washed twice with 3% BSA/PBS. The ClickIT reaction was then performed for 2 coverslips to add Alexafluor647 to incorporated EdUTP-alkyne. This reaction was performed for 30 minutes at room temperature, in the dark. The other coverslips were kept in 3% BSA/PBS at room temperature. The coverslips were washed once with 3% BSA/PBS before being stained with Vybrant Violet staining and imaged by a SMLM method.

Figure 3A:
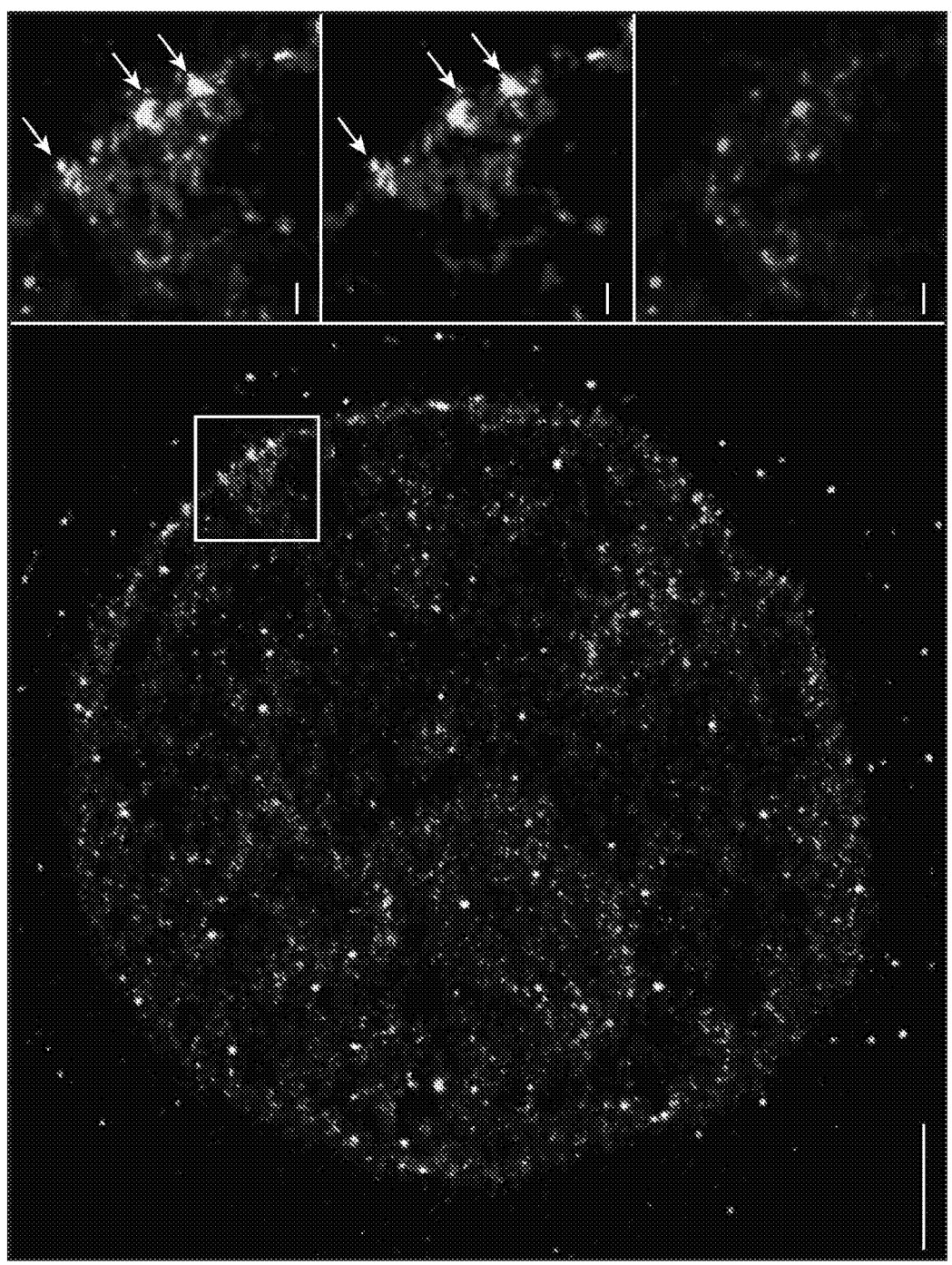
FIG. 3A shows a two color SPDM image (experimental) of chromatin (blue) with DNA sensitive element sites (red), showing anti-colocalization of the DNA sensitive element sites with chromatin. Scale bars: 1000 nm, inserts: 100 nm. The bottom right panel shows chromatin (blue), the middle right panel shows DNA sensitive element sites (red), and the top right panel shows the overlay and the anti-colocalization of the DNA sensitive element with chromatin.
Figure 3B:
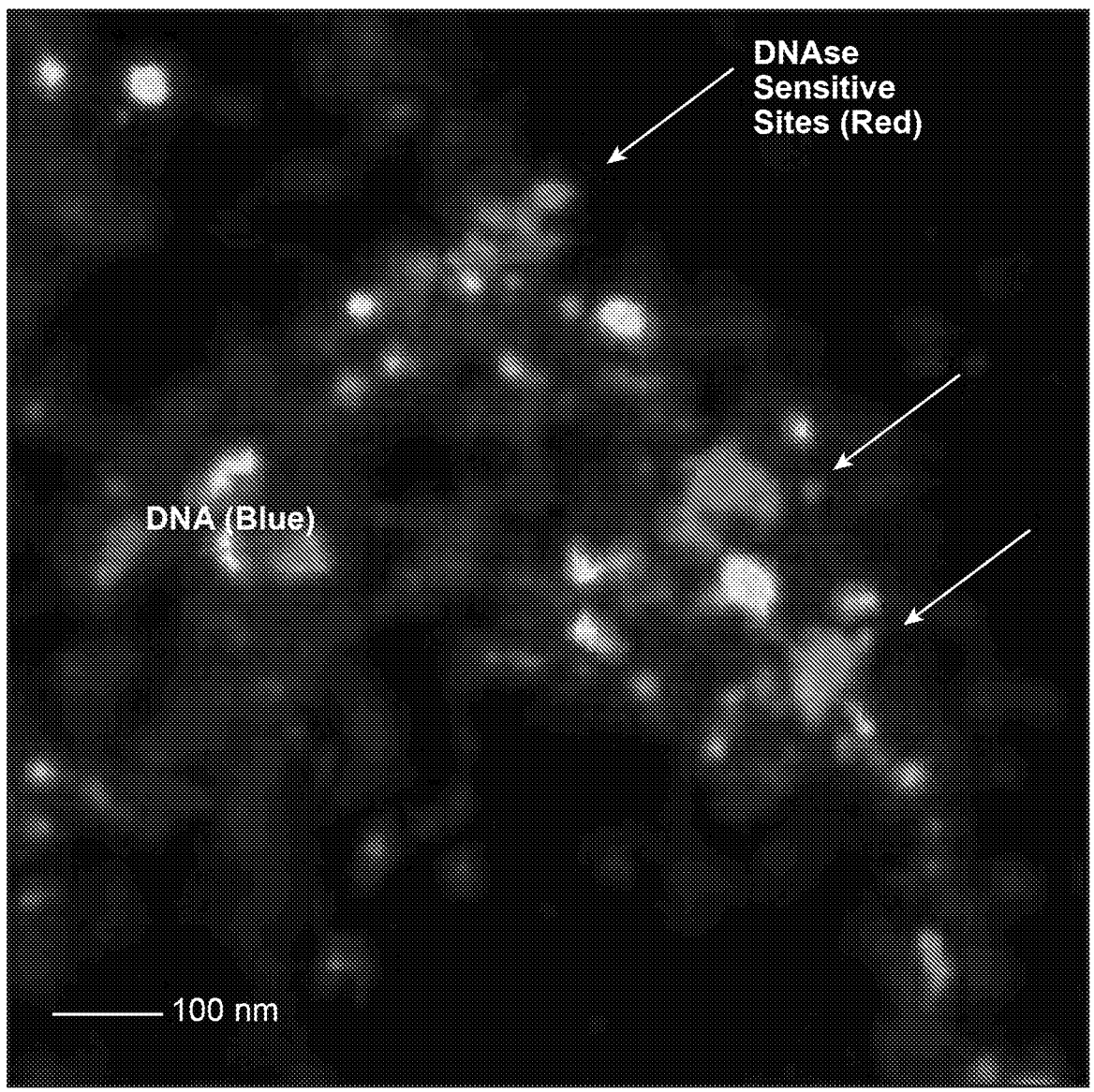
FIG. 3B is the inset of FIG. 3A.

FIG. 3A shows a two color SPDM image (experimental) of chromatin (blue) with a DNA sensitive element (red), showing anti-colocalisation of the DNA sensitive element with chromatin. Scale bars: 1000 nm, inserts: 100 nm. FIG. 3B is the inset of FIG. 3A.

Figure 4A:
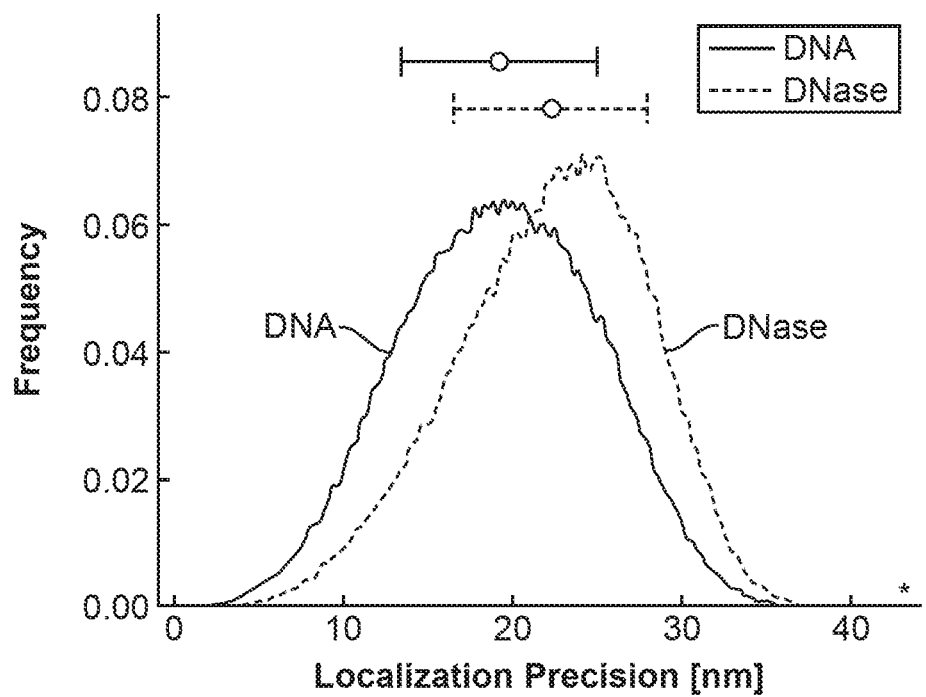
FIG. 4A and FIG. 4B illustrate the localization precision and nearest neighbor distances for DNA and DNase sensitive elements.
Figure 4B:
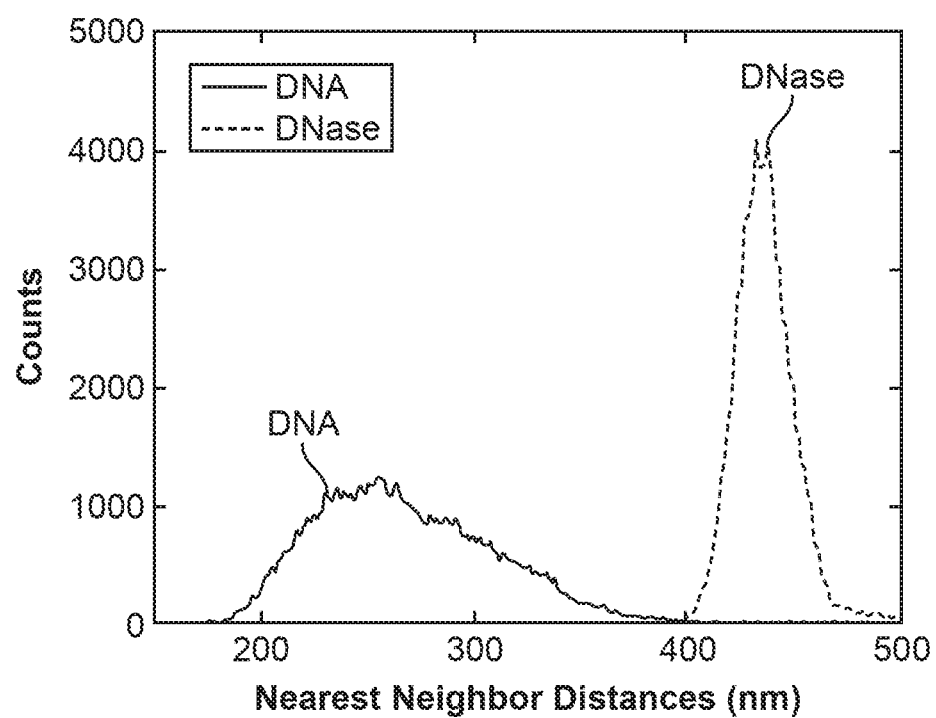

FIG. 4 illustrates the localization precision and nearest neighbor distances for DNA and DNase sensitive elements.

Example 2

DNA Encoding of Molecular Targets on a Multi-Omics Imaging Platform

Integration of imaging data across different molecular target types may provide in-depth insights into cell physiology and pathology. A multi-omics imaging platform may be utilized which enables simultaneous visualization of multiple molecular targets irrespective of target type and imaging probes used. The multi-omics imaging platform comprise (i) decoupling of target binding and labeling steps, (ii) translation of heterogeneous molecular information into an intermediate standardized molecular code amenable to read-out via imaging probes, and (iii) employing encoding capacity and self-assembly capabilities of DNA bonding. Specifically, molecular targets of interest are first encoded with unique ssDNA tags via binding by ssDNA-conjugated target-recognition moieties under optimized conditions favoring specific target binding. Individual ssDNA tags are then converted into detectable signals via sequence-specific hybridization with complementary ssDNA'-conjugated imaging probes under probe-optimized conditions. As such, molecular target uniqueness, localization, abundance, and specimen morphology information are preserved through all steps of labeling procedure, producing comprehensive molecular signatures of a physiological or pathological process.

Methods

Oligonucleotide probe design. Sequences for 6 ssDNA/ssDNA' encoding pairs were selected from a random pool. Selection criteria were: continuous 16 bp complementarity, balanced nucleotide composition, lack of stable secondary structures at room temperature, lack of substantial cross-hybridization between mismatch pairs. See Table 1 for a complete list of ssDNA/ssDNA' encoding pairs.

Sequences for human GAPDH mRNA (NM_002046.5) and HSP90-alpha mRNA (NM_001271969.1) were obtained from NCBI. Sets of mRNA ISH probes were designed using Stellaris RNA FISH Probe Designer (Biosearch Technologies). Probe sets contained 36 unique probes for GAPDH mRNA and 48 probes for HSP90-alpha mRNA. Each probe featured 5' terminal 20 nt-long region complementary to mRNA, a spacer (either AAAAA for smaller 41 nt probes or AAAA-dsSpacer-AAAA for longer 60 nt probes), and a 16 nt-long QDot binding tag. ISH probe strand of the dsSpacer was 5'-TTCCCAAGCGTCATCT-3' (SEQ ID NO:), pre-hybridized with a complementary 5'-AGATGACGCTTGGGAA-3' ssDNA at 1:1 molar ratio to form a 16 bp dsDNA spacer prior to specimen labeling. See Supplementary Tables 2-3 for a complete list of ISH probes. All oligonucleotides were purchased from IDT DNA.

Antibody-ssDNA conjugation. Purified primary and secondary antibodies in PBS were purchased from Sigma-Aldrich. Amine-terminated HPLC purified ssDNA tags were purchased from IDT DNA (see Table 1, sequences 1B-6B). Covalent antibody-ssDNA bioconjugation was achieved either a) via maleimide-mediated amine-sulfhydryl cross-linking or b) using Thunder-Link oligo conjugation system (Innova Biosciences).

For maleimide-mediated crosslinking, IgG was partially reduced by TCEP to expose free sulfhydryl groups, while 5' amine-terminated ssDNA oligonucleotides were activated by sulfo-SMCC (Thermo Scientific). IgG was diluted to 1 mg/mL in 100 µL PBS with 10 mM EDTA, mixed with 0.5 mM TCEP, and incubated for 30 min at 37° C. At the same time, ssDNA was diluted to 40 µM in 100 µL PBS, mixed with 10 mM sulfo-SMCC, and incubated for 30 min at RT. Reduced IgG and activated ssDNA were then purified by 3 rounds of desalting in Zeba desalting spin columns (Thermo Scientific) pre-washed with PBS/10 mM EDTA, mixed, and reacted for 4 Hrs at RT. Finally, unreacted sulfhydryl groups were capped by addition of 1 mM sulfo-SMCC pre-quenched by excess glycine. Antibody-ssDNA bioconjugates were purified by ultrafiltration for at least 6 times with Amicon Ultra 50 KDa MWCO centrifugal filter (Millipore) and stored in PBS solution at 4° C.

For antibody-ssDNA conjugation with Thunder-Link oligo conjugation system, IgG was diluted to 1 mg/mL in 100 µL PBS, activated by the Antibody Activation Reagent for 1 Hr at RT, and purified using desalting column. At the same time, 5' amine-terminated ssDNA oligonucleotides were diluted to 80 µM in 100 µL PBS, activated by the Oligo Activation Reagent for 1 Hr at RT, and desalted. Activated IgG and ssDNA were mixed at a volume ratio of 2:1 (200 μL IgG+100 μL ssDNA+100 μL wash buffer), reacted overnight at RT, and stored at 4° C. For optimization studies, following IgG:ssDNA volume ratios were tested: 50+50, 50+30, 50+20, and 50+10.

QDot-ssDNA conjugation. Amine-functionalized PEG-coated QDots (Qdot ITK amino (PEG) quantum dots, Invitrogen) with emission peaks centered at 525, 545, 565, 585, 605, and 655 nm were used for the preparation of QDot-ssDNA probes. Amine-terminated HPLC purified 16 nt-long ssDNA tags were purchased from IDT DNA (see Table 1, sequences 1A-6A). Oligonucleotides were activated with bifunctional cross-linker BS3 (Bis[sulfosuccinimidyl] suberate, Thermo Scientific), followed by covalent conjugation with QDots. 100 μL 40 μM ssDNA solution in PBS was mixed with 500 molar excess of BS3 and incubated for 30 minutes at room temperature. Excess crosslinker was removed by 3 rounds of desalting in Zeba desalting spin columns (Thermo Scientific) pre-washed with PBS. Activated ssDNA was then mixed with 25 μL 8 μM stock QDot solution. The reaction was incubated overnight at room temperature and purified by ultrafiltration for at least 6 times with Amicon Ultra 100 KDa MWCO centrifugal filter (Millipore). Purified QDot-ssDNA probes were stored in PBS solution at 4° C.

Agarose gel electrophoresis was used for characterization of QDot-ssDNA probes. Procedure was performed on a 2% agarose gel in 1×TBE at 90V for 2 Hrs.

Cell culture and processing. Human cervical cancer cell line HeLa (ATCC) was used as a model specimen for evaluation of the multi-omics imaging via DNA encoding. Cells were grown in glass-bottom 24-well plates (Greiner Bio-One) in a humidified atmosphere at 37° C. with 5% $CO_2$ to a density of 80-90% using MEM culture medium with L-glutamine (Gibco) supplemented with 10% fetal bovine serum (Gibco). Prior to labeling, cells were rinsed with PBS, fixed with 4% formaldehyde in PBS for 5 min at room temperature followed by 15 min at 4° C., permeabilized with ice-cold 0.5% detergent Triton™ X-100 (Thermo Scientific) in PBS for 15 min at 4° C., and washed with PBS. For mRNA imaging, cells were immediately processed for in situ hybridization to minimize degradation of mRNA prior to labeling. For protein imaging only, fixed cells could be stored in PBS with 0.03% sodium azide at 4° C. for several days.

Encoding via immunorecognition. Encoding of protein targets in formalin-fixed cells was performed via incubation with antibody-ssDNA bioconjugates. Prior to labeling, cells were blocked by 2% BSA (from 10% BSA/PBS solution, Thermo Scientific), 0.5% Western blot blocking reagent (from 10% solution, Roche), 0.1% low MW dextran sulfate (9-20 kDa MW, Sigma-Aldrich), 0.1 mg/mL shredded salmon sperm DNA (Invitrogen), and 1×PBS for 30 min at RT. Antibodies were used at a final concentration of 5 μg/mL diluted in 2% BSA, 0.1% dextran sulfate, 0.1 mg/mL shredded salmon sperm DNA, and 1×PBS and incubated with cells for 1-2 Hrs at RT. Following labeling, cells were washed with PBS.

For reference studies, cell labeling with unmodified antibodies was performed in a similar fashion.

Encoding via in situ hybridization (ISH). Encoding of mRNA targets was performed via hybridization with ssDNA-tagged mRNA ISH probes. Cells were equilibrated with 10% formamide (Thermo Scientific), 2 mM RVC (New England BioLabs), 2×SSC (Invitrogen) buffer for 30 min at RT and then incubated with 400 μL/well 250 nM mix of mRNA ISH probes in 1% dextran sulfate (>500 kDa MW, Sigma-Aldrich), 1 mg/mL tRNA (from E. coli, Roche), 10% formamide, 2 mM RVC, 2×SSC hybridization buffer for 4 Hrs (or overnight) at 37° C. Following hybridization, cells were washed with warm 10% formamide, 2×SSC buffer for 30 min at 37° C., two changes of 1×PBS for 10 min at RT, and blocked by 2% BSA, 0.5% Western blot blocking reagent, 0.1% low MW dextran sulfate, 0.1 mg/mL shredded salmon sperm DNA, 1×PBS for 30 min at RT.

Encoding for multi-omics studies. Encoding of protein and mRNA targets on the same specimen was performed by combining immunorecognition and in situ hybridization procedures. First, cells were hybridized with ssDNA-tagged mRNA ISH probes as described above. Following hybridization and washing, cells were blocked, incubated with antibody-ssDNA bioconjugates for 1-2 Hrs at RT, and washed with PBS.

Specimen labeling with QDot probes. Following encoding of targets with ssDNA tags, cells were simultaneously labeled with complementary QDot-ssDNA' probes. QDots were used at a final concentration of 5 nM in 2% BSA, 0.1% low MW dextran sulfate, 0.1 mg/mL shredded salmon sperm DNA, 1×PBS and incubated with cells for 2-4 Hrs at RT. Following staining cells were washed with PBS. Optionally, nuclei could be counter-stained by a 5-min incubation with DAPI.

For reference immunofluorescence studies, cell staining with QDots functionalized with secondary Ab fragments (Qdot goat F(ab')2 anti-mouse or anti-rabbit IgG conjugates (H+L), Invitrogen) was performed in a similar fashion.

RNAi. Knock-down of GAPDH expression was done via cell transfection with GAPDH siRNA (Ambion). For forward transfection, cells were grown in a glass-bottom 24-well plate overnight and then treated with 500 μl/well culture medium containing 25 nM GAPDH siRNA and 0.5 μl/well DharmaFECT-2 transfection reagent (Dharmacon) for 24 Hrs. For reverse transfection, cells were grown in a 10 cm TC-treated dish, trypsinized, mixed in suspension with culture medium containing 25 nM GAPDH siRNA and 0.5 μl/well DharmaFECT-2 transfection reagent, seeded into a glass-bottom 24-well plate at 500 μl/well cell suspension, and incubated for 24 or 48 Hrs. Following transfection, cells were processed for staining. Triplicate samples were also prepared for RT-PCR analysis.

RT-PCR analysis. Total RNA was isolated from cell pellets using TRIzol reagent (Invitrogen) according to the manufacturer's protocol. Two hundred nanograms of RNA was converted to cDNA using random hexamer primer and MultiScribe Reverse Transcriptase Reagent (Applied Biosystems). One hundred nanograms of cDNA was amplified by the Real-Time PCR using SensiFAST™ Real-Time PCR Kits (Bioline, UK) on Chromo4 Real-Time PCR detection system (Bio-Rad). The primers used for GAPDH amplification were 5'-TCGCTCTCTGCTCCTCCTGTTC-3' (forward primer) and 5'-CGCCCAATACGACCAAATCC-3' (reverse primer). Cyclophilin A (PPIA) was used as an internal control, and the primers were 5'-GTCAACCC-CACCGTGTTCTTC-3' (forward primer) and 5'-TTTCTGCTGTCTTTGGGACCTTG-3' (reverse primer). To confirm the PCR specificity, PCR products were subjected to a melting-curve analysis. The comparative threshold ($C_t$) method was used to calculate the relative mRNA amount of the treated sample in comparison to control samples. Mean value from triplicate samples was reported.

Imaging and signal analysis. IX-71 inverted fluorescence microscope (Olympus) equipped with a true-color CCD (QColor5, Olympus) and a hyperspectral imaging camera (Nuance, 420-720 nm spectral range, CRI, now PerkinElmer) was used for cell imaging. Low-magnification images were obtained with ×20 dry objective (NA 0.75, Olympus) and high-magnification with ×40 (NA 1.30, Olympus) and ×100 (NA 1.40, Olympus) oil-immersion objectives. Wide UV filter cube (330-385 nm band-pass excitation, 420 nm long-pass emission, Olympus) was used for imaging of all QDot probes, while Rhodamine LP cube (530-560 nm band-pass excitation, 572 nm long-pass emission, Chroma) was used for Alexa Fluor 555 detection. All images were acquired with cells attached to the coverslip bottom of the well and immersed in PBS without use of anti-fading reagents.

Nuance image analysis software was used to unmix the obtained multispectral images based on the reference spectra of each QDot component along with an extra channel for background fluorescence. In a false-color composite image, brightness and contrast of each channel was automatically adjusted for best visual representation and clear depiction of relative target distribution, unless noted otherwise. For direct comparison of QDot staining intensity individual QDot channels were normalized.

Figure 5A:
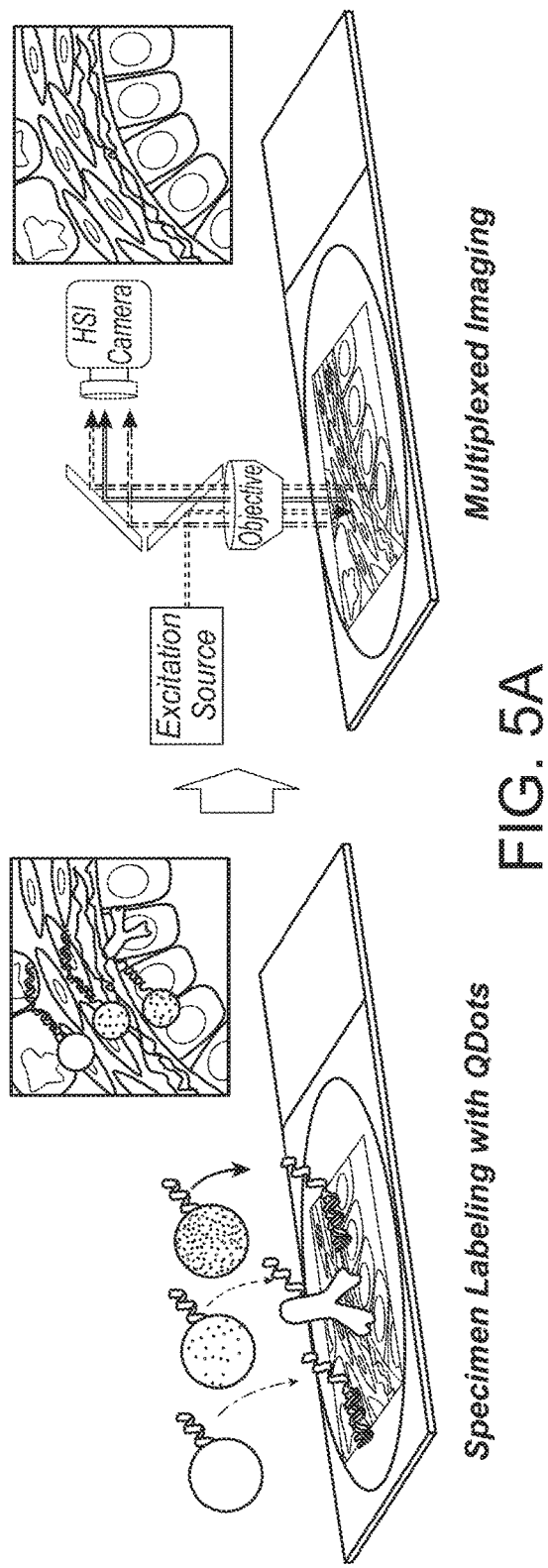
FIG. 5A and FIG. 5B illustrate multi-omics imaging via encoding of molecular information with ssDNA tags.
Figure 5B:
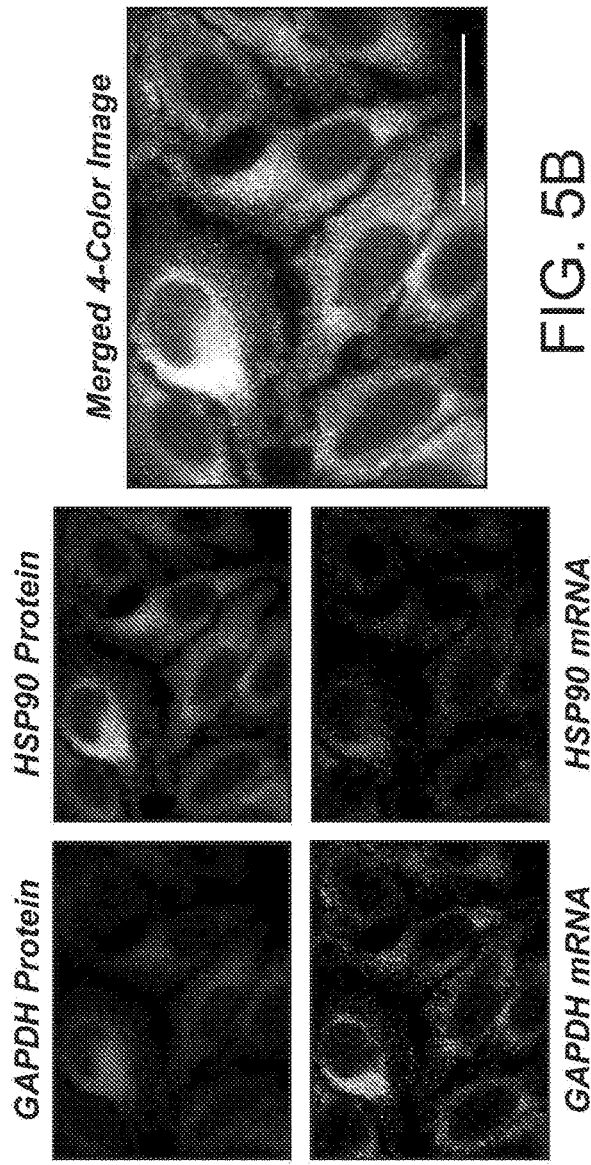
Figure 6:
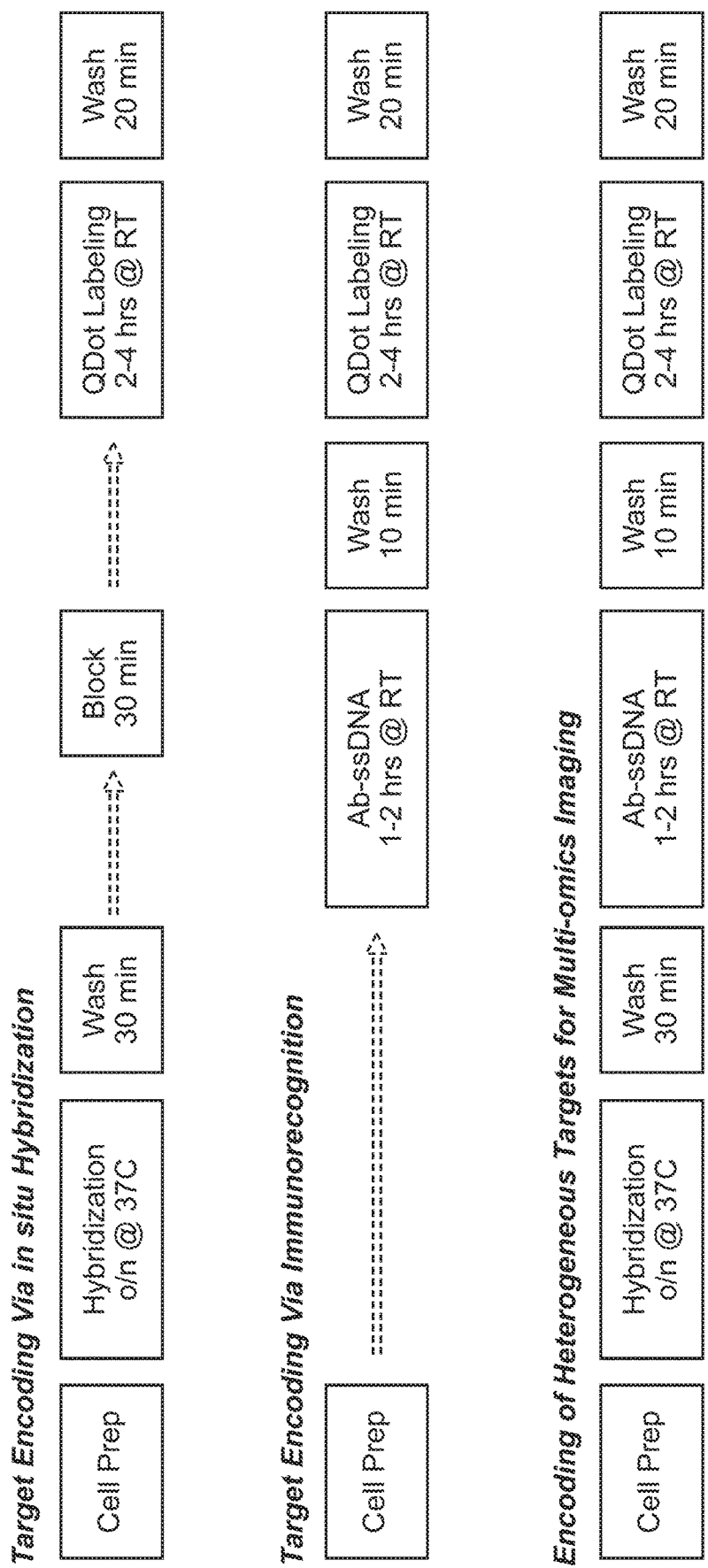
FIG. 6 shows a workflow for target encoding and labeling via in situ hybridization, immunorecognition, and multi-omics procedures. DNA encoding methodology allows for labeling of different types of targets (mRNA and proteins in this proof-of-concept study) under conditions optimized for selective target binding in separate steps. As a result, all targets are converted into a uniform array of intermediate ssDNA tags, which are then simultaneously labeled by complementary QDot-ssDNA' probes for multiplexed imaging.

DNA Encoding for Multi-Omic Imaging Studies. To demonstrate the DNA encoding for multi-omics imaging studies concurrent analysis of single-cell molecular expression profiles at mRNA and protein levels were performed. Fluorescent quantum dot probes (QDots) in combination with fluorescence microscopy and hyperspectral imaging (HSI) were employed for simultaneous visualization of all ssDNA tags following separate encoding of mRNA and protein targets (FIG. 5A). For example, GAPDH and HSP90-alpha mRNA molecules and their respective product proteins can be readily labeled by 4-color QDots to highlight relative intracellular distribution and abundance of the two target types at a single-cell level (FIG. 5B). Unlike direct labeling procedures performed at a single incubation condition fixed for all targets and probes, DNA encoding enables tuning of conditions to favor recognition of individual target types and hybridization with detection probes in separate steps, offering great flexibility in choice of specimens, targets, and imaging systems (FIG. 6).

Figure 7A:
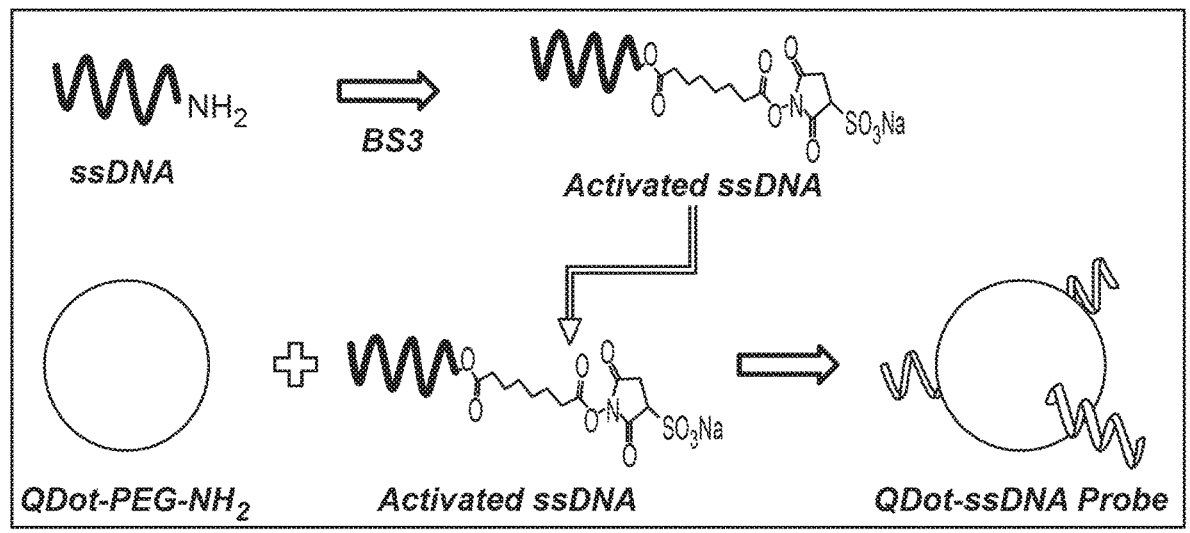
FIG. 7A and FIG. 7B illustrate a schematic and characterization of QDot-ssDNA probe preparation.
Figure 7B:
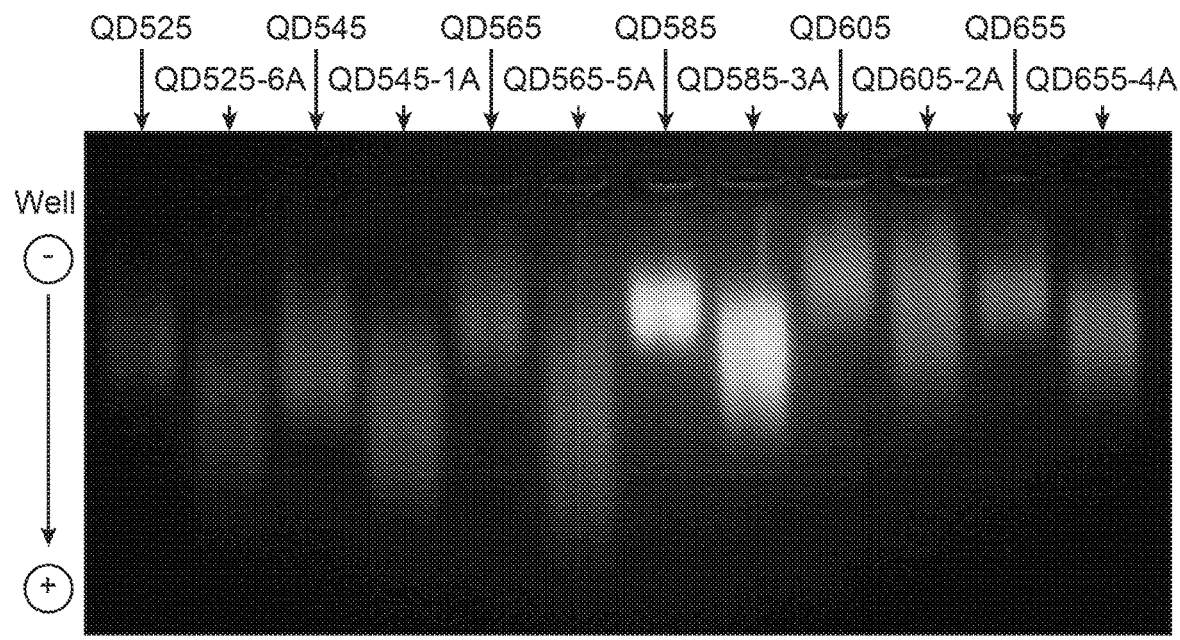
Figure 8A:
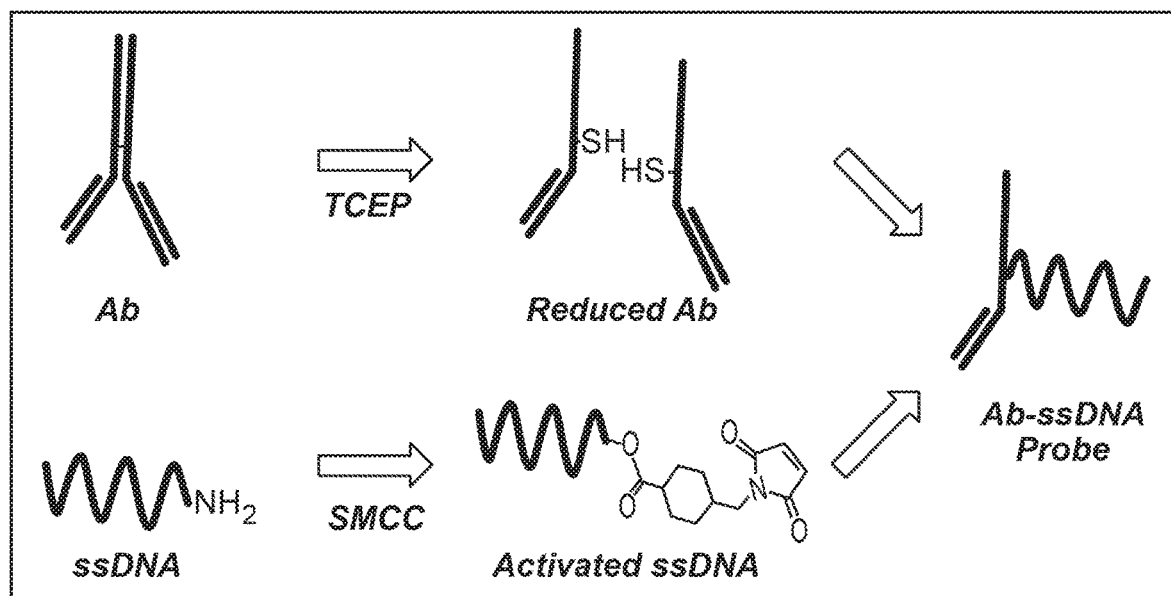
FIG. 8A and FIG. 8B show a schematic and characterization of antibody-ssDNA bioconjugate preparation via maleimide-mediated crosslinking.
Figure 8B:
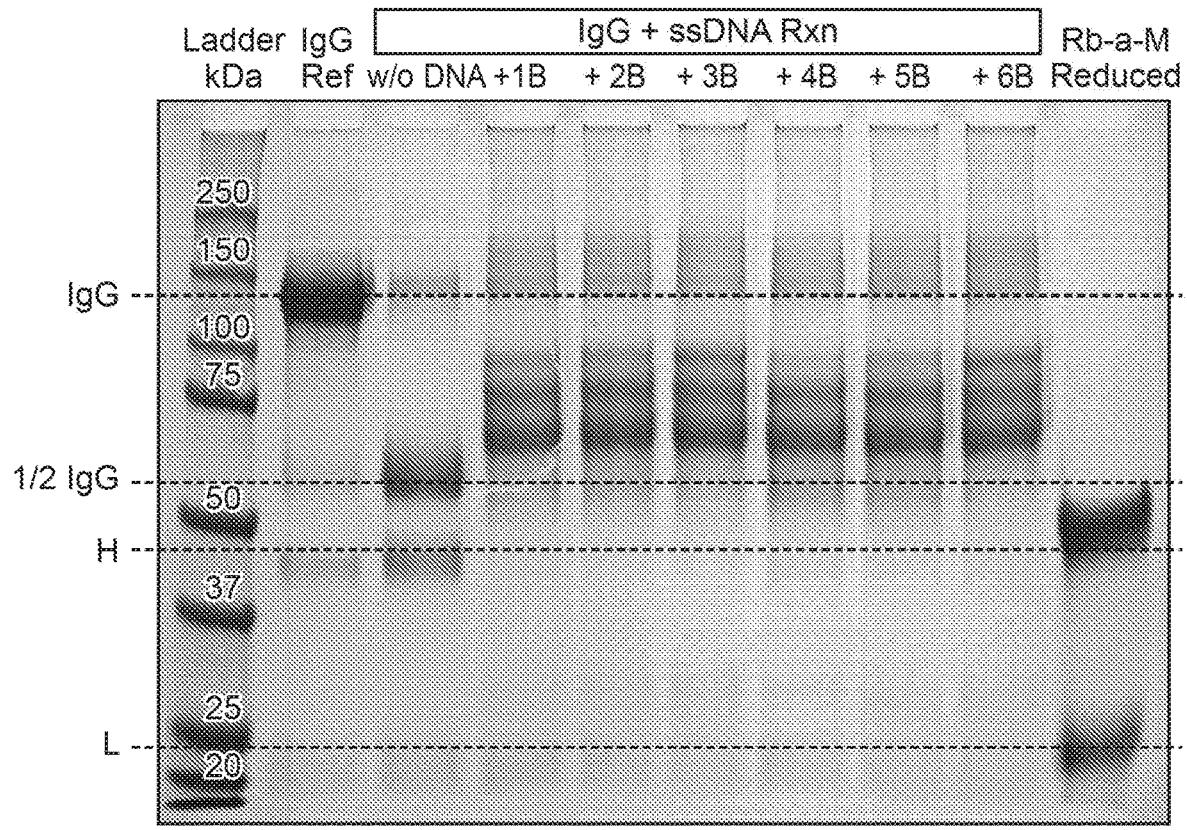

QDot-based Multi-Omics Imaging Platform. To implement and systematically characterize the model QDot-based multi-omics imaging platform, a set of 6 unique 16 bp ssDNA/ssDNA' linkers was developed for encoding of up to 6 different molecular targets (Table 1) along with a library of complementary 6-color QDot-ssDNA probes (FIG. 7A and FIG. 7B) and a control set of 6 secondary antibody-ssDNA (2'Ab-ssDNA) bioconjugates (FIG. 8A and FIG. 8B). Indirect labeling of β-tubulin in HeLa cells via a 3-step procedure involving incubation with unmodified primary antibodies, 2'Ab-ssDNA bioconjugates, and complementary QDot-ssDNA' probes demonstrated preserved antigen-recognition functionality of ssDNA-modified antibodies and high specificity of QDot staining via DNA hybridization (FIG. 9).

Figure 10A:
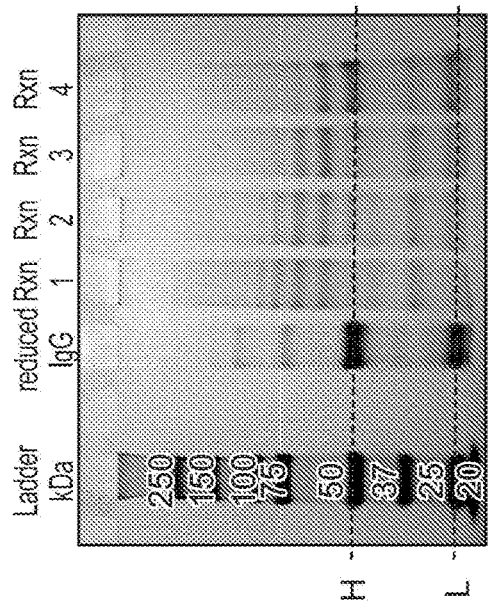
FIG. 10A, FIG. 10B, and FIG. 10C show schematic and characterization of antibody-ssDNA bioconjugate preparation with Thunder-Link oligo conjugation system. A 2-step amine crosslinking strategy as illustrated in FIG. 10A is employed for preparation of covalent antibody-ssDNA bioconjugates with intact IgG. Antibody and 5' amine-terminated ssDNA are simultaneously activated by respective activation reagents, purified via desalting, and reacted overnight, producing IgG with varying number of ssDNA tags attached. A reducing PAGE analysis in FIG. 10B highlights presence of multiple higher-MW bands corresponding to heavy and light chains conjugated to varying number of ssDNA tags. In 4 reaction conditions performed with goat anti-rabbit secondary antibodies, relative volume ratios of activated IgG to ssDNA are 1) 50+50, 2) 50+30, 3) 50+20, and 4) 50+10. As expected, increasing amount of ssDNA in the reaction leads to more ssDNA tags being conjugated to each IgG molecule. Staining of Lamin A in FIG. 10C via incubation with rabbit anti-Lamin A primary antibody and goat anti-rabbit 2'Ab-ssDNA bioconjugates followed by labeling with QDot605-ssDNA' probes confirms preserved specificity of ssDNA-tagged antibodies and successful antibody-ssDNA bioconjugation. At the same time, increasing non-specific binding by 2'Ab-ssDNA bioconjugates can be observed with increasing number of ssDNA tags per IgG in a control experiment skipping incubation with primary antibody. Thus, a volume ratio of Ab:ssDNA=2:1 in Thunder-Link reaction is considered optimal. All true-color images are obtained at consistent exposure for direct comparison of staining intensity. Scale bar, 250 µm.
Figure 10B:
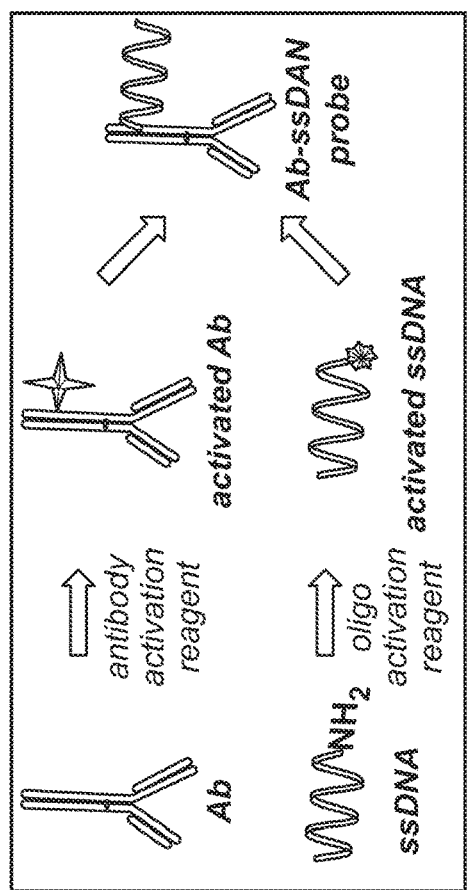
Figure 10C:
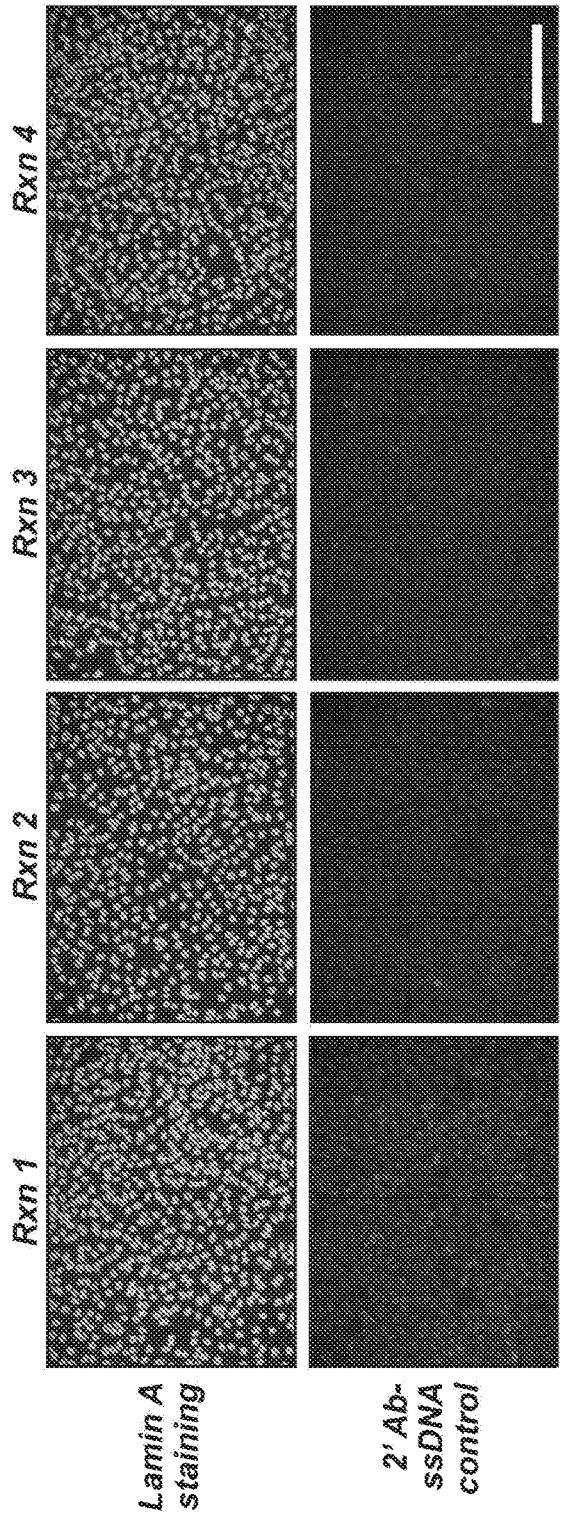

Multiplex Protein Immuno-labeling. Multiplexed protein immuno-labeling was realized through preparation of a library of primary antibody-ssDNA (1'Ab-ssDNA) bioconjugates (FIG. 10A, FIG. 10B, and FIG. 10C; and FIG. 11A, FIG. 11B, FIG. 11C, FIG. 11D, and FIG. 11E). Characterization of such bioconjugates with PAGE and cell staining confirmed preserved stability and antigen-binding functionality of antibodies, specificity of target staining with QDots in a 2-step procedure, and consistent target identification with different QDot colors in a multiplexed imaging format (FIG. 11A, FIG. 11B, FIG. 11C, FIG. 11D, and FIG. 11E). Nuclear envelope protein Lamin A, microtubule β-tubulin, and cytoplasmic proteins HSP90-alpha and GAPDH were labeled as model target molecules with distinct characteristic intracellular localization.

Figure 12:
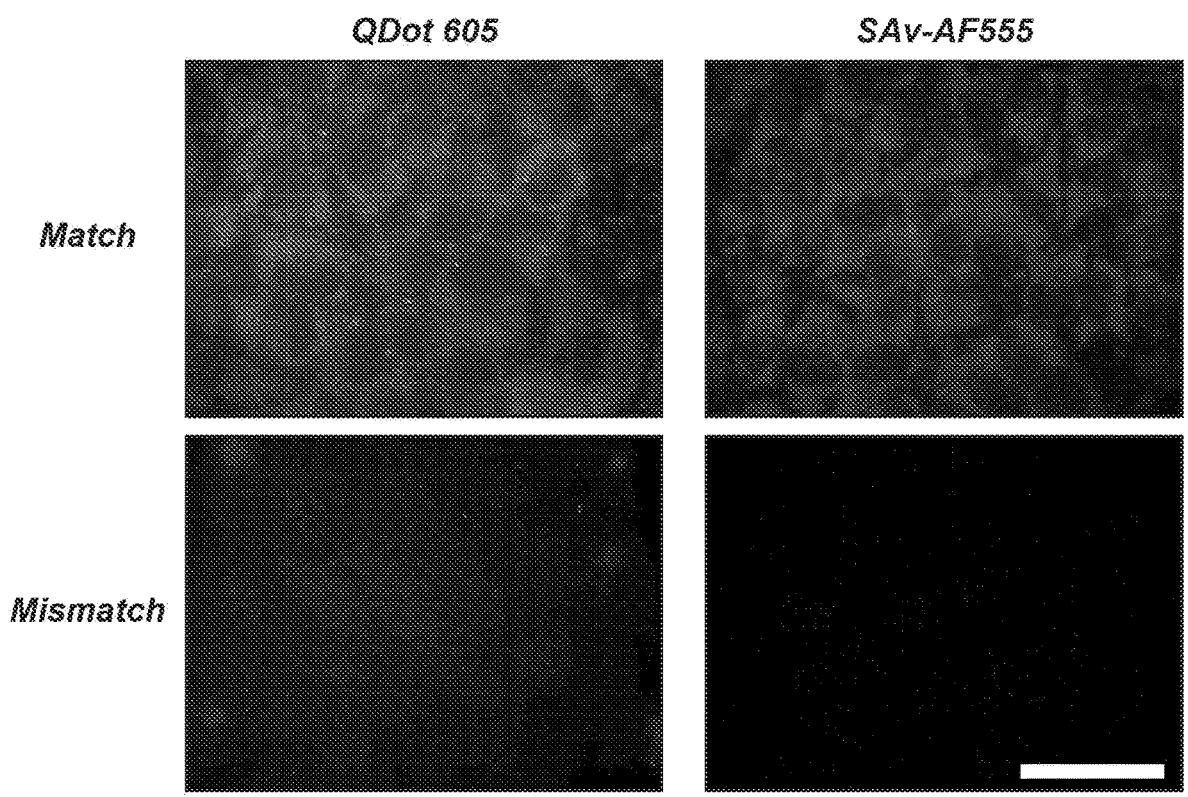
FIG. 12 shows characterization of mRNA labeling intensity and specificity via DNA encoding. GAPDH mRNA is labeled via indirect FISH procedure with 41 nt FISH probe set (see TABLE 5) followed by staining with QDot605-ssDNA (left panels) or AlexaFluor555-labeled streptavidin-ssDNA (right panels) probes. Consistent characteristic punctuate staining pattern is observed with both complementary imaging probes (top row). At the same time, non-complementary probes (bottom row) fail to hybridize to mRNA ISH probes, confirming staining specificity of the DNA encoding methodology. "Match" and "mismatch" true-color images are obtained at consistent exposure for direct comparison of staining intensity. Scale bar, 50 µm.
Figure 13A:
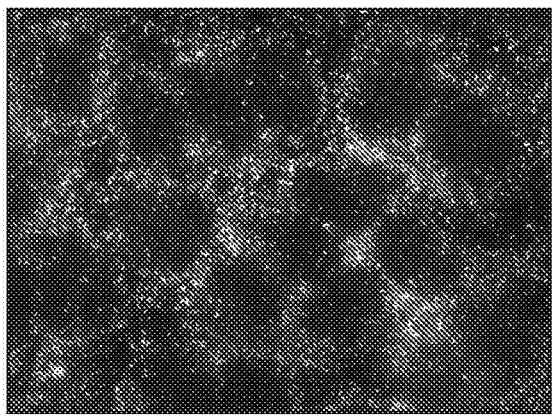
FIG. 13A, FIG. 13B, FIG. 13C, and FIG. 13D illustrates the effect of dsDNA spacer in ISH probe on mRNA labeling intensity. Physical separation of mRNA-recognition and QDot-binding portions of 41 nt ssDNA ISH probes with a 16 bp dsDNA spacer prevents formation of secondary structures, promotes hybridization to target mRNA, and reduces steric hindrance to QDot binding. As a result, a substantial increase in mRNA staining intensity can be realized with such probes (FIG. 13A) in comparison to 41 nt ssDNA FISH probes (FIG. 13B). At the same time, longer 60 nt ssDNA probes without pre-hybridized dsDNA spacers experience greater degree of secondary structure formation, which interferes with mRNA and QDot binding and fails to produce robust mRNA staining (FIG. 13C) above non-specific QDot binding levels (FIG. 13D). All images are obtained with HSI and normalized for direct comparison of signal intensity. Scale bar, 50 µm.
Figure 13B:
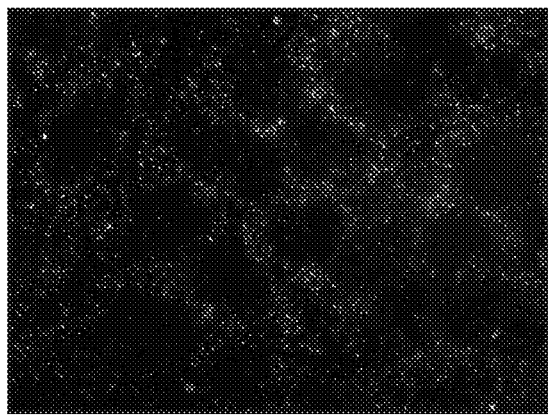
Figure 13C:
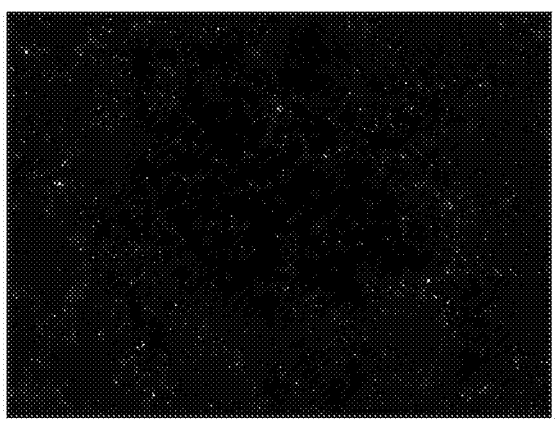
Figure 13D:
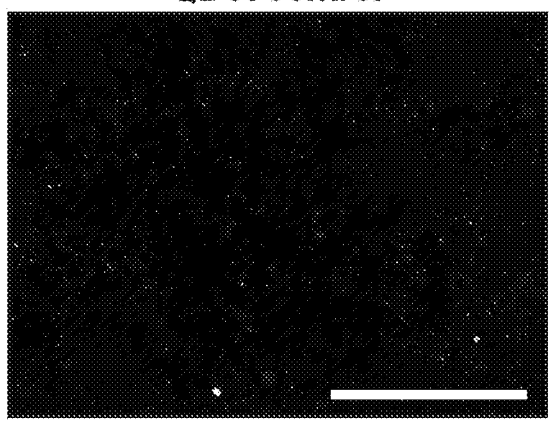

Labeling of model GAPDH and HSP90-alpha mRNA molecules via an indirect in situ hybridization (ISH) procedure was done with modified mRNA ISH oligonucleotide probes featuring 5' 20 nt mRNA-recognition portion and a 3' 16 nt QDot-binding tag separated by a single-stranded AAAAA spacer (Tables 2 and 3). Hybridization of oligonucleotide probes under optimized ISH conditions yielded labeling of each mRNA molecule with multiple ssDNA tags (up to 36 for GAPDH and 48 for HSP90-alpha), producing distinct spots upon staining with complementary QDot-ssDNA probes consistent with results achieved with conventional mRNA ISH protocols (FIG. 12). In some instances, non-complementary QDot-ssDNA probes failed to hybridize to exposed ssDNA tags, producing minimal non-specific staining background. To explore effects of potential secondary structure formation in 41 nt ssDNA oligonucleotides as well as steric hindrance experienced by QDots approaching tightly spaced ssDNA tags, an alternative mRNA ISH probe set was designed with each probe containing a 16 bp dsDNA spacer between 5' mRNA-recognition and 3' QDot-binding portions. Indeed, physical separation of functional ssDNA portions improved mRNA staining intensity in comparison to linear 41 nt ssDNA oligonucleotides (FIG. 13A, FIG. 13B, FIG. 13C, and FIG. 13D), offering one strategy for enhancing per-spot signal intensity and improving signal-to-noise ratio.

Figure 14:
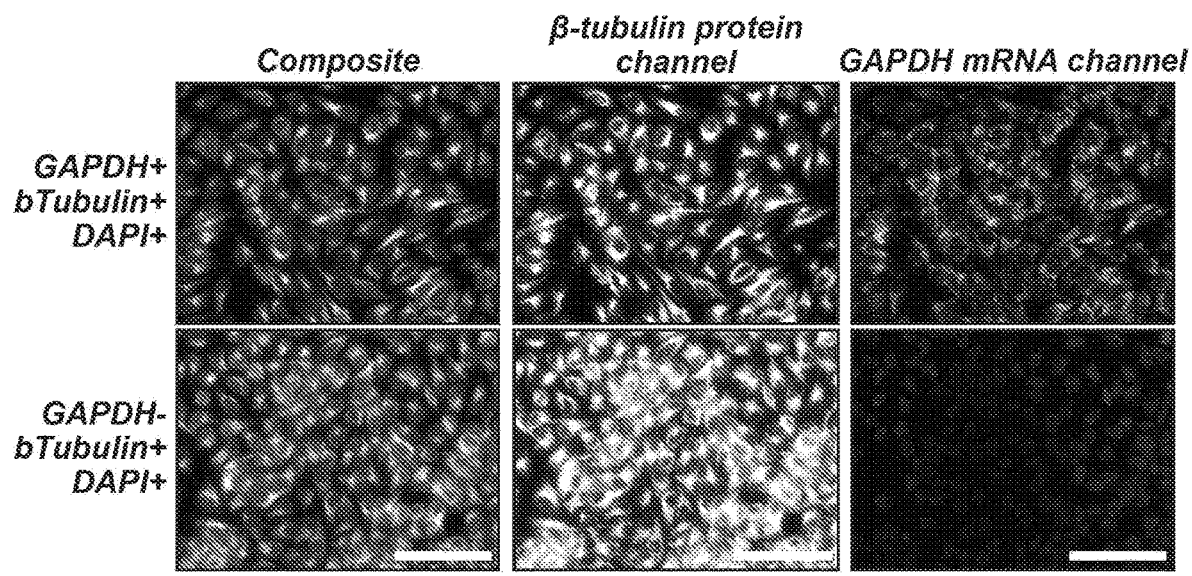
FIG. 14 shows multi-omics QDot staining via DNA encoding. Protein and mRNA targets are encoded with ssDNA tags in separate steps, each using conditions optimal for binding of a specific target type. Consequently, DNA sequence code is converted into an optical signal by hybridization with complementary QDot-ssDNA probes. Specifically, GAPDH mRNA is labeled with a 41 nt ISH probe set followed by labeling of β-tubulin with Ab-ssDNA bioconjugates. Finally, both ssDNA tags are simultaneously hybridized with respective QDot-ssDNA' probes. Clear microtubule staining pattern of β-tubulin (false-colored green) and punctuate pattern of GAPDH mRNA (false-colored red) are observed in dual-labeled specimen (top row), whereas only β-tubulin staining is present in a control specimen that was not hybridized with GAPDH FISH probe set (bottom row). Nuclei are counter-stained with DAPI (false-colored blue). Scale bar, 100 µm.

Separation of target-recognition and QDot-labeling events via an intermediate DNA encoding enabled straightforward implementation of a model multi-omics imaging protocol, with both mRNA and protein targets being robustly labeled by respective QDot probes and accurately identified through hyperspectral imaging and analysis (FIG. 14), corroborating broad applicability of the DNA encoding strategy for simultaneous detection and imaging of various types of targets within the same specimen.

Figure 15:
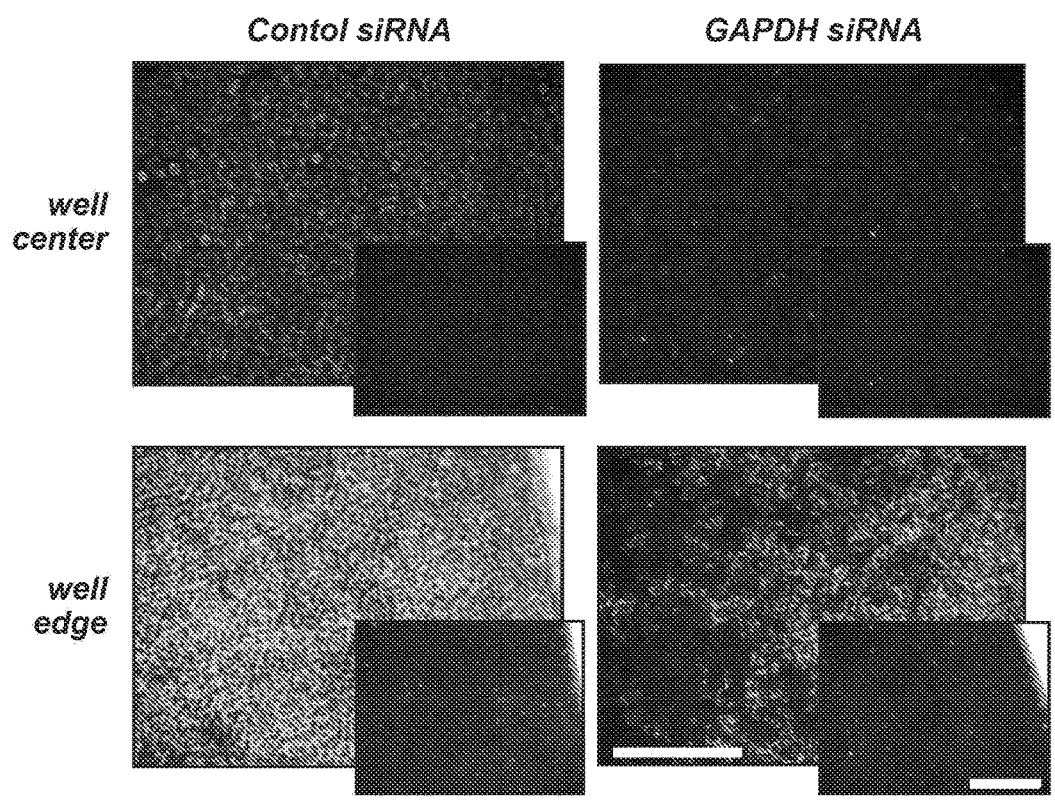
FIG. 15 illustrates the heterogeneity in GAPDH RNAi following forward transfection with siRNA. Cells are seeded into a 24-well plate, allowed to attach, grown overnight, and then transfected with GAPDH siRNA (or non-targeting control siRNA) for 24 Hrs. GAPDH mRNA is encoded via in situ hybridization with mRNA ISH probes and then labeled with QDot605-ssDNA' probes. Imaging of different areas within the well highlights heterogeneity in GAPDH knock-down, likely resulting from heterogeneity in cell transfection with siRNA. Specifically, complete GAPDH mRNA degradation is observed throughout cells in the well center (top right panel), whereas cells at the crowded well edge still express regular levels of GAPDH mRNA (bottom right panel) consistent with GAPDH expression in cells transfected with control siRNA (left panels). Substantial number of non-transfected cells might explain an average silencing efficiency of 78% determined by RT-PCR. Insets: control experiments showing lack of QDot non-specific binding in the absence of complementary ssDNA probes. All images are obtained with true-color camera at the same exposure time for direct comparison of signal intensity. Scale bar, 250 µm.
Figure 16:
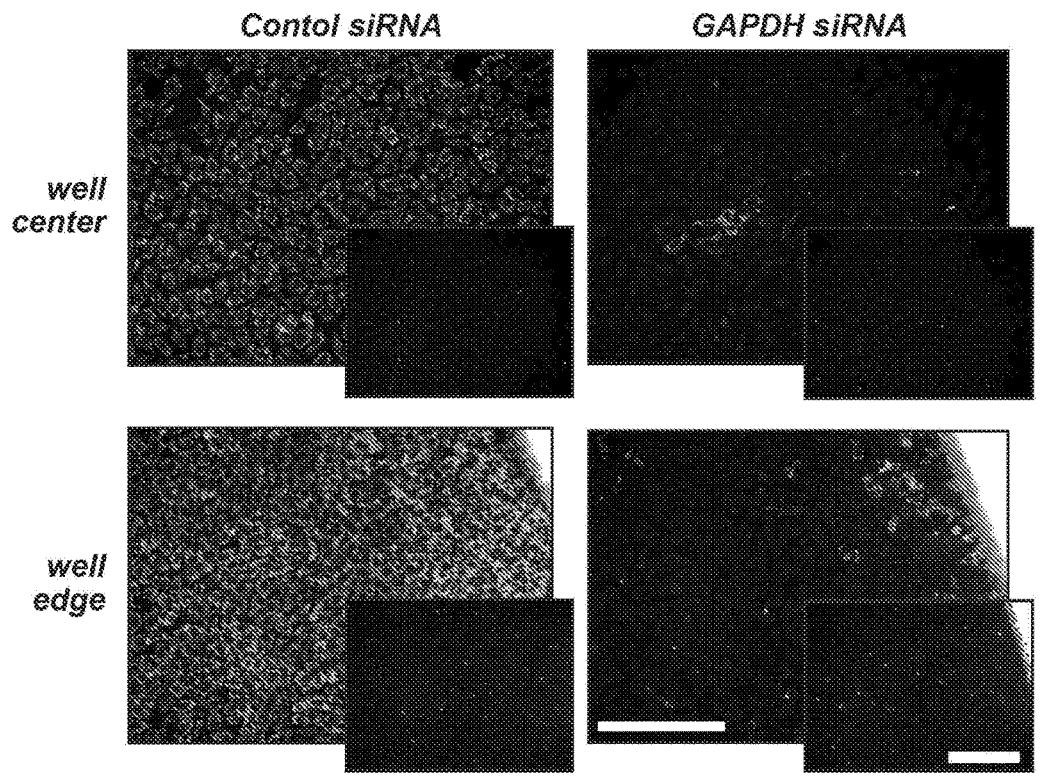
FIG. 16 illustrates the heterogeneity in GAPDH RNAi following reverse transfection with siRNA. Cells are mixed with GAPDH siRNA (or non-targeting control siRNA) in suspension and then seeded to 24-well plate for transfection and growth for 24 Hrs. GAPDH mRNA is encoded via in situ hybridization with mRNA ISH probes and then labeled with QDot605-ssDNA' probes. As evident from imaging of different areas within the well, reverse transfection achieves a more uniform transfection and GAPDH knock-down compared to forward transfection (see FIG. 12). Complete GAPDH mRNA degradation is observed throughout majority of cells, with only occasional colonies with full GAPDH expression forming from non-transfected cells, which is consistent with an improved average silencing efficiency of 95% determined by RT-PCR. Insets: control experiments showing lack of QDot non-specific binding in the absence of complementary ssDNA probes. All images are obtained with true-color camera at the same exposure time for direct comparison of signal intensity. Scale bar, 250 µm.
Figure 17:
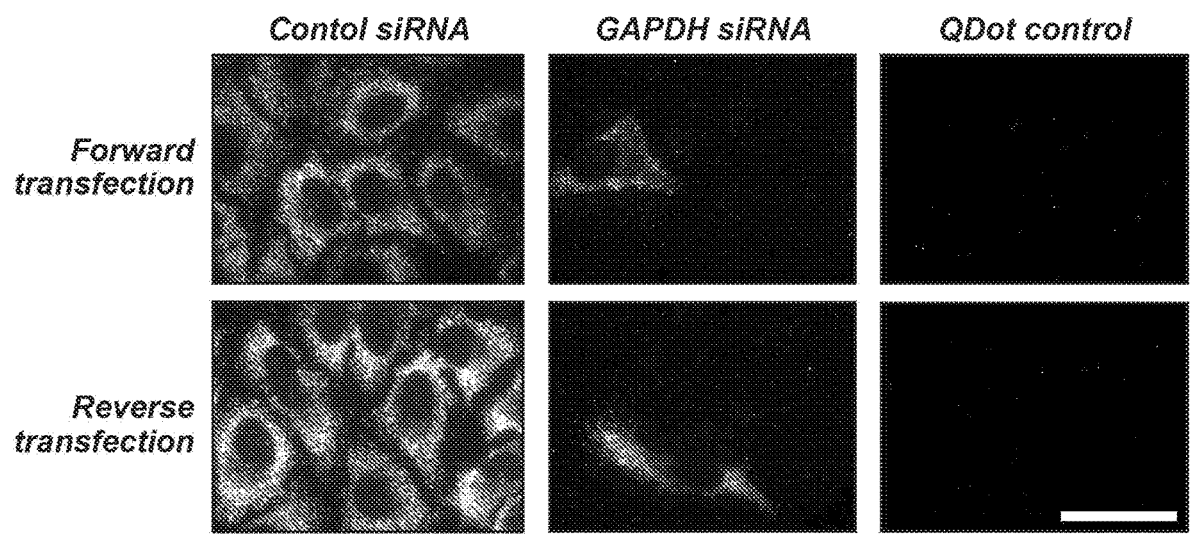
FIG. 17 shows the comparison of RNAi effect on GAPDH mRNA expression following forward vs. reverse transfection with siRNA. Both transfection methods have no effect on GAPDH expression when non-targeting control siRNA is used (left panels) and yield efficient GAPDH knock-down with GAPDH-targeting siRNA (middle panels), as evident from the lack of mRNA staining above non-specific QDot background (right panels). At the same time, small fraction of cells fails to get transfected and, as a result, expresses normal levels of GAPDH mRNA consistent with control experiments. This observation corroborates and all-on/all-off effect of RNAi regardless of transfection method used. All images are obtained with HSI and normalized for direct comparison of signal intensity. Scale bar, 50 µm.

Multi-omics imaging platform was then applied to study gene knock-down via RNAi at a single-cell level. HeLa cells were transfected with GAPDH-targeting siRNA (as well as non-targeting siRNA for control) for 24 Hrs, and GAPDH mRNA abundance was assessed with RT-PCR and QDot-based imaging. In some cases, bulk GAPDH mRNA measurement by RT-PCR indicated silencing efficiency of 78% with forward transfection and 95% with reverse transfection. At the same time, imaging revealed heterogeneity in RNAi, likely resulting from heterogeneous cell transfection with siRNA throughout different regions of cell culture. For example, forward transfection failed to achieve efficient GAPDH mRNA degradation in dense cell populations, yielding areas of completely silenced cells along with patches of cells with normal GAPDH mRNA expression levels (FIG. 15). In contrast, reverse transfection achieved a more uniform cell transfection in suspension, producing a greater proportion of silenced cells with only a few wild-type clones (FIG. 16). Direct comparison of mRNA imaging results obtained from forward vs. reverse transfection further corroborated complete mRNA degradation upon successful transfection with either method along with unperturbed GAPDH mRNA levels in non-transfected cells (FIG. 17), suggesting an all-on/all-off mode of GAPDH RNAi and attributing incomplete silencing observed with bulk RT-PCR analysis to heterogeneity in siRNA transfection.

Figure 18:
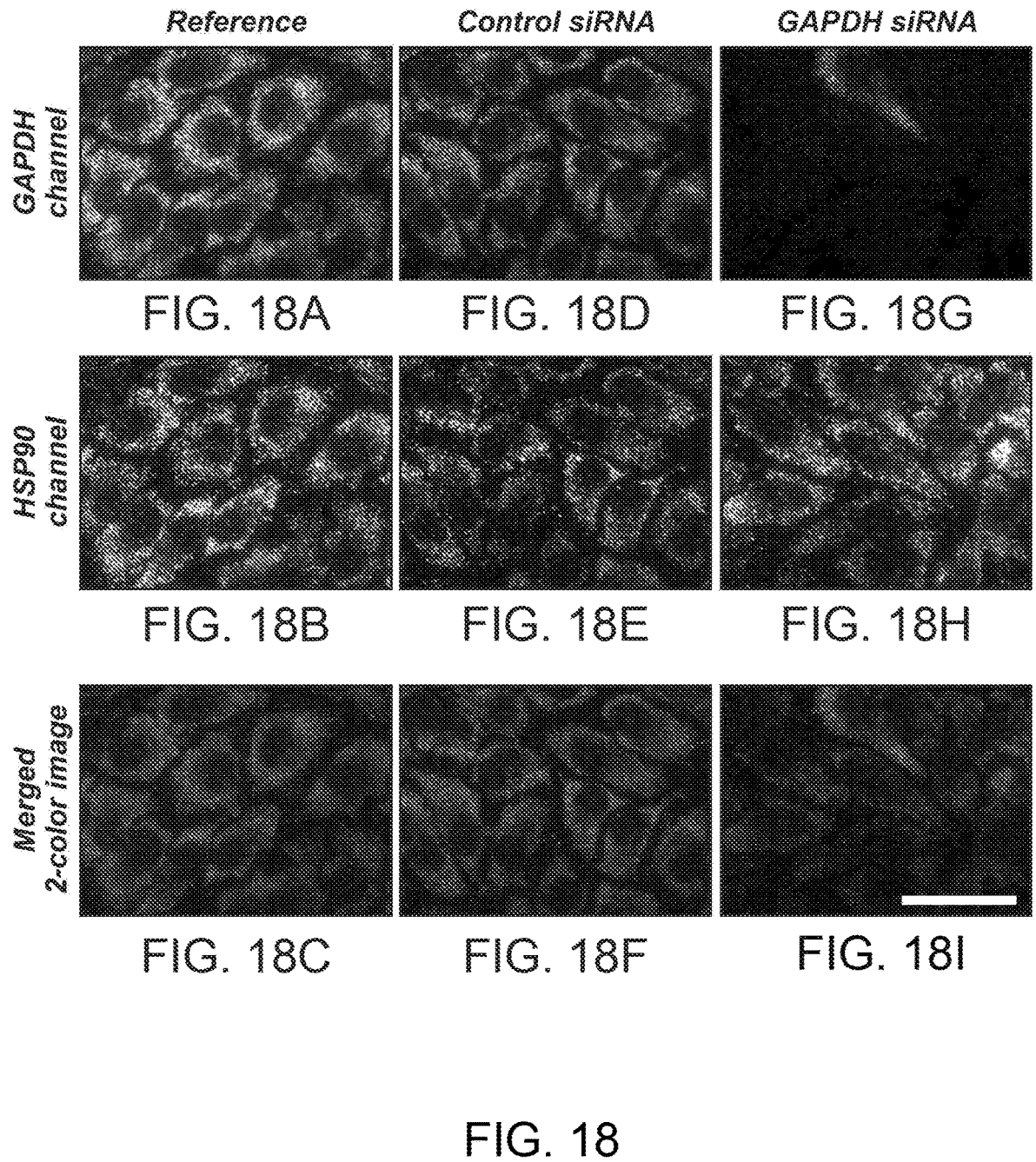
FIG. 18 shows assessment of heterogeneity in cell transfection with siRNA. Dual-labeling of GAPDH and HSP90-alpha mRNA with QDots enables direct visualization of siRNA transfection effect at a single-cell level. Cells are either grown under regular culture conditions (FIG. 18A, FIG. 18B, and FIG. 18C), transfected with control non-targeting siRNA (FIG. 18D, FIG. 18E, and FIG. 18F), or transfected with GAPDH-targeting siRNA (FIG. 18G, FIG. 18H, and FIG. 18I). After a 24-hour treatment with GAPDH siRNA, the majority of cells had completely degraded GAPDH mRNA, as evident from the lack of GAPDH mRNA staining (FIG. 18G). At the same time, HSP90-alpha mRNA not targeted by RNAi machinery remained unperturbed (FIG. 18H). Interestingly, a single cell in the field of view failed to transfect with GAPDH siRNA (FIG. 18G, FIG. 18H, and FIG. 18I), expressing regular levels of GAPDH mRNA consistent with cells treated with control siRNA (FIG. 18D, FIG. 18E, and FIG. 18F) and reference cells not transfected with siRNA (FIG. 18A, FIG. 18B, and FIG. 18C), suggesting an all-on/all-off effect of RNAi. Dual-color images were obtained with hyperspectral imaging (HIS) and were unmixed in QDot channels. Panels for individual channels (FIG. 18A, FIG. 18B, FIG. 18D, FIG. 18E, FIG. 18G, and FIG. 18H) were normalized for direct comparison of signal intensity. In merged 2-color images (FIG. 18C, FIG. 18F, and FIG. 18I) The GAPDH channel was false-colored green and the HSP90-alpha channel was false-colored red. Scale bar, 50 µm.

Selectivity of GAPDH RNAi was confirmed by performing dual-target imaging of GAPDH mRNA and HSP90-alpha mRNA. Target-selective siRNA should trigger degradation of only its complementary target mRNA, having no immediate effect on non-targeted mRNA molecules. This was indeed observed with GAPDH RNAi studies (FIG. 18). Indirect dual-target ISH produced robust staining of both mRNA species in reference HeLa cells grown in culture medium. Similarly, cell transfection with non-targeting control siRNA failed to produce any effect on mRNA expression. Transfection with GAPDH-targeting siRNA, however, triggered rapid degradation of GAPDH mRNA within 24 Hrs post-transfection, while leaving non-targeted HSP90-alpha mRNA intact. A single non-transfected cell within the field of view features intact expression of both GAPDH and HSP90 mRNA, consistent with discussion above.

Figure 19:
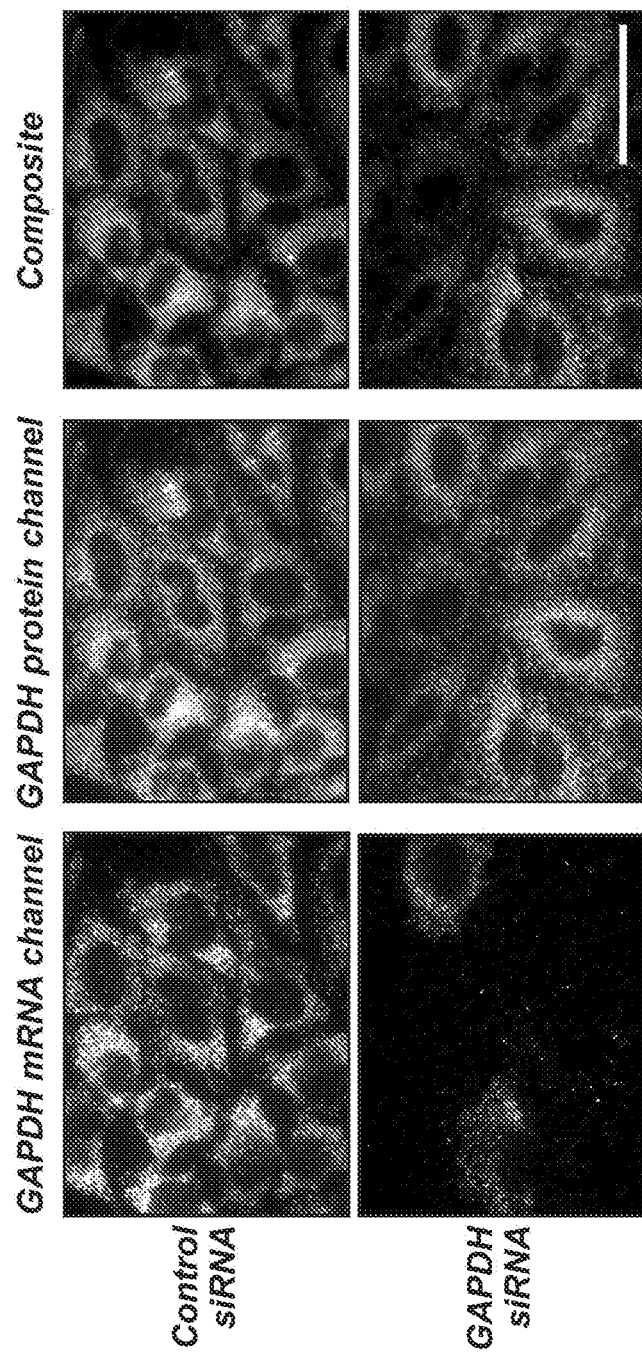
FIG. 19 shows assessment of GAPDH RNAi heterogeneity at mRNA and protein levels with multi-omics imaging. Dual labeling of GAPDH mRNA and protein 24 Hrs post-transfection with GAPDH-targeting siRNA highlights heterogeneity in mRNA expression levels (bottom left panel) along with the lack of RNAi effect on the protein level (bottom middle panel) at this time point. Transfection with non-targeting control siRNA (top row) fails to affect GAPDH expression, yielding uniform mRNA and protein staining throughout all cells. Dual-color images are obtained with HSI, and individual channels are normalized for direct comparison of signal intensity. GAPDH mRNA channel is false-colored red and GAPDH protein channel is false-colored green in a composite 2-color image. Scale bar, 50 µm.
Figure 20A:
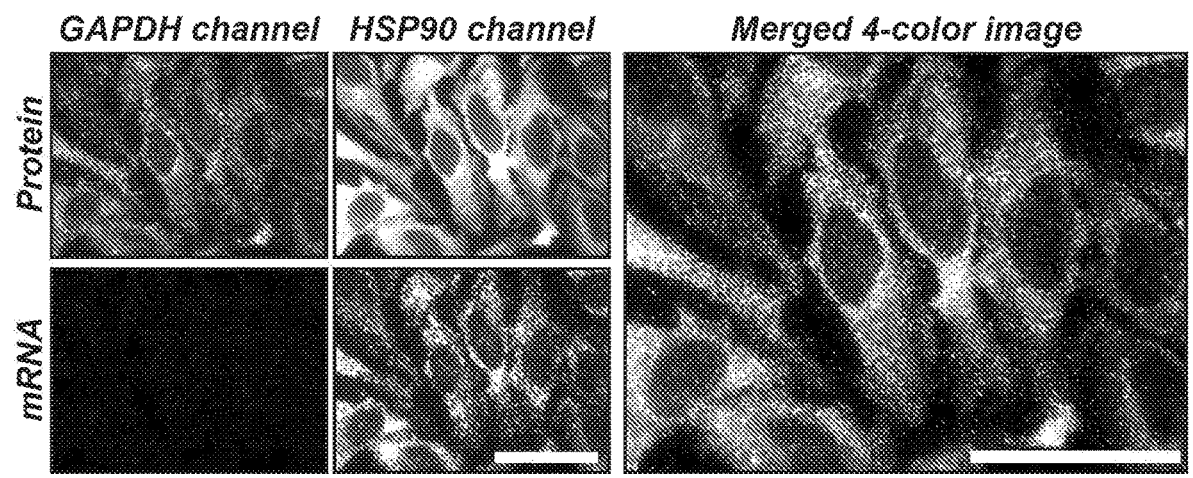
FIG. 20A and FIG. 20B show assessment of disparity in RNAi kinetics at mRNA and protein levels. HeLa cells are transfected with GAPDH siRNA for (FIG. 20A) 24 hours and (FIG. 20B) 48 hours. GAPDH and HSP90-alpha mRNA along with corresponding proteins are simultaneously assessed with QDot-based multi-omics imaging methodology. Consistent with mRNA-only analysis, multi-omics imaging highlights complete and selective degradation of GAPDH mRNA 24 hours post-transfection, whereas GAPDH protein level remains nearly unperturbed (FIG. 20A). Lagging mRNA knock-down, 48 hours post-transfection selective degradation of GAPDH protein can be observed (FIG. 20B). All grayscale images are normalized to HSP90 protein channel for direct comparison of staining intensities. In a merged 4-color image GAPDH protein channel is false-colored yellow, HSP90-alpha protein—blue, GAPDH mRNA—green, and HSP90-alpha mRNA—red. Scale bar, 50 µm.
Figure 20B:
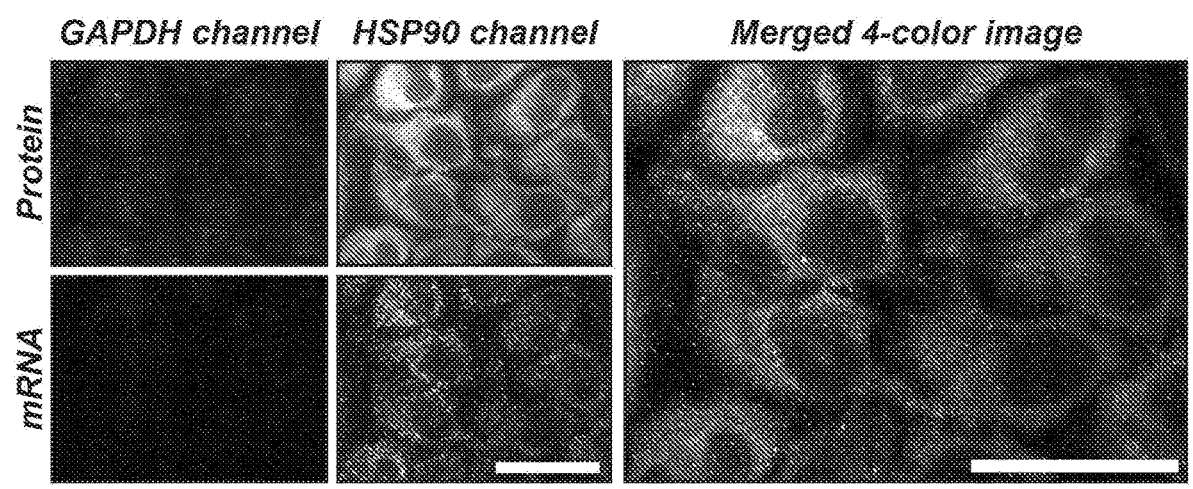
Figure 21A:
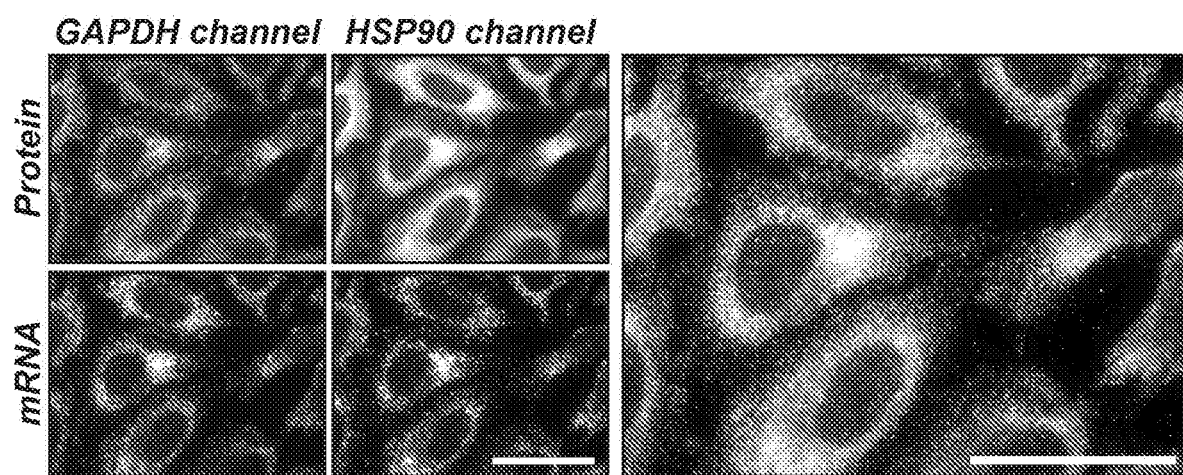
FIG. 21A and FIG. 21B show multi-omics evaluation of GAPDH and HSP90-alpha expression at mRNA and protein levels under regular cell culture conditions. To provide a reference of normal GAPDH and HSP90 expression levels to RNAi experiments, cells are grown under regular cell culture conditions for (FIG. 21A) 24 Hrs and (FIG. 21B) 48 Hrs. All targets of interest are labeled via a 2+2 encoding procedure to produce a 4-plex staining. Consistent with expected fast growth of HeLa cells, cell density increases with time. However, GAPDH and HSP90 expression remains constant through 48 Hrs of incubation, as evident from consistent intensity of mRNA and protein labeling. Multiplex images are obtained with HSI, and individual channels are normalized for direct comparison of signal intensity. GAPDH mRNA channel is false-colored green, HSP90 mRNA—red, GAPDH protein—yellow, and HSP90 protein—blue in a composite 4-color image. Scale bar, 50 µm.
Figure 21B:
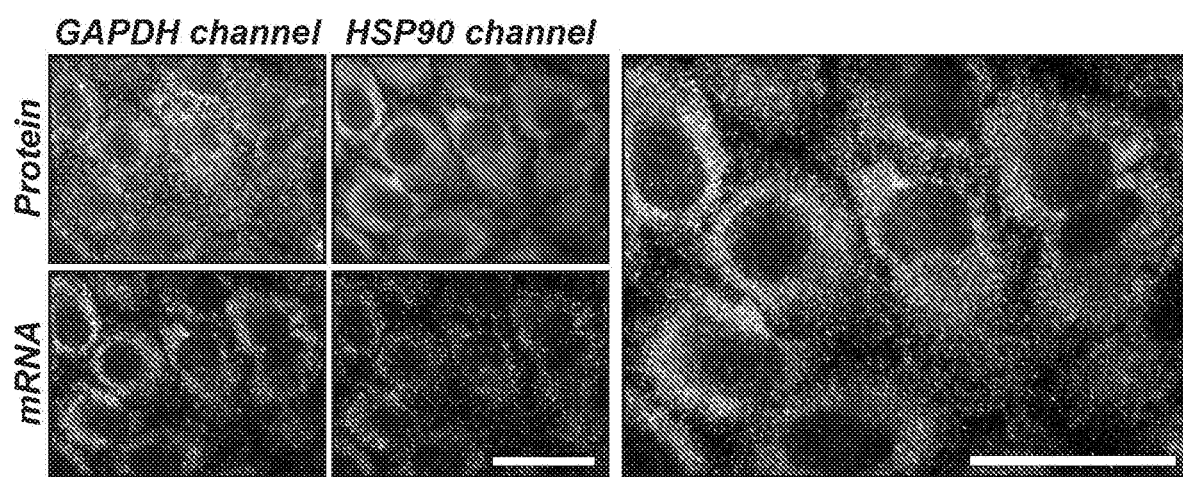
Figures 23A, 23B:
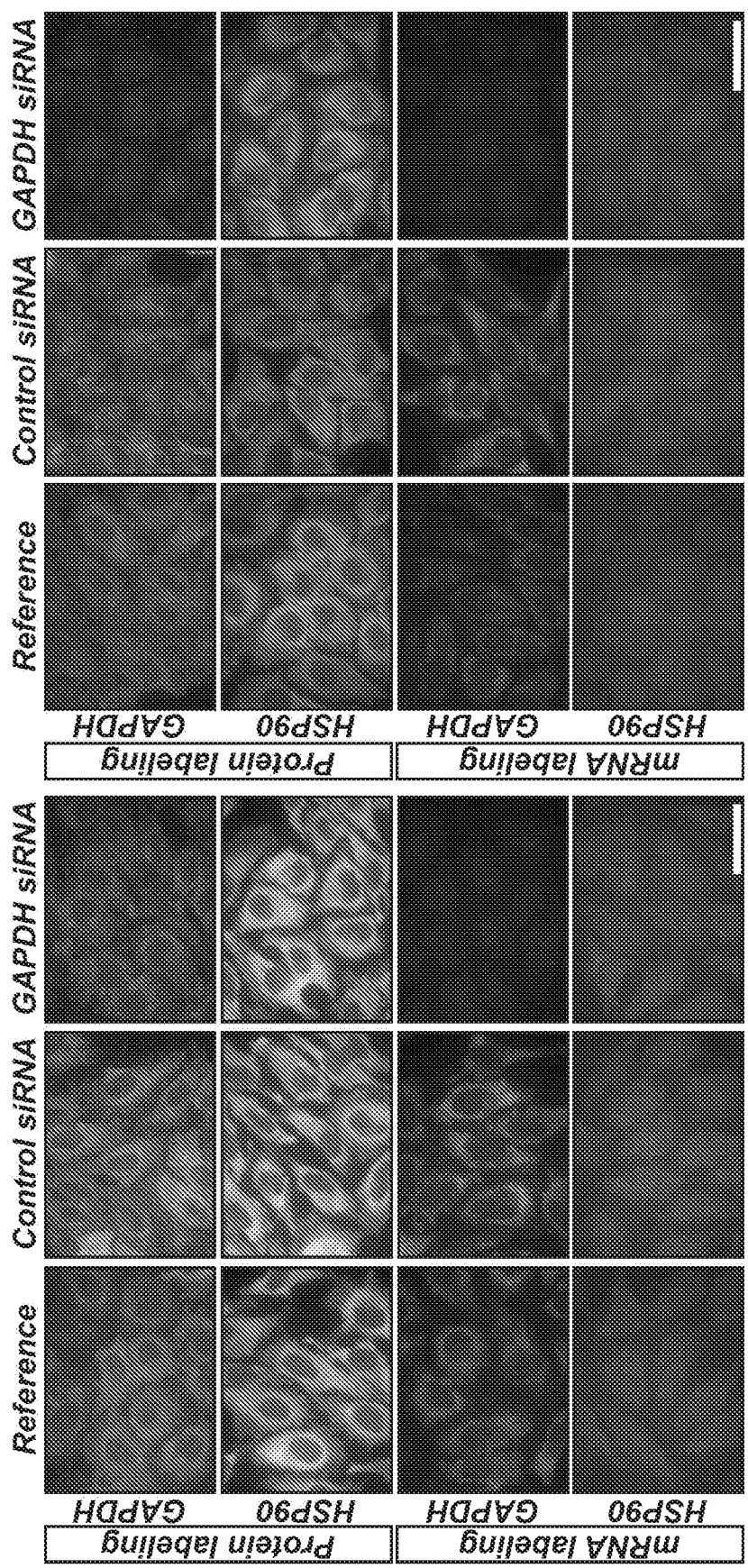
FIG. 23A and FIG. 23B show direct visualization of GAPDH RNAi effect and kinetics via single-plex labeling of individual protein and mRNA targets. To eliminate any potential effect of multi-omics labeling methodology and artifacts of HSI analysis, GAPDH RNAi experiment along with reference and control is performed on separate specimens in parallel (different wells of the same 24-well plate), followed by a single-plex labeling of individual targets and direct true-color imaging under consistent imaging conditions. Cells are reverse transfected for (FIG. 23A) 24 Hrs and (FIG. 23B) 48 Hrs prior to fixation and staining. Consistent with multi-omics analysis, single-plex imaging confirms efficient and specific degradation of GAPDH mRNA within 24 Hrs post-transfection, whereas RNAi effect on GAPDH protein level can be observed only 48 Hrs post-transfection. Scale bar, 50 µm.

Imaging of mRNA unambiguously demonstrated heterogeneity in RNAi stemming from incomplete cell transfection with siRNA. However, such heterogeneity could not be detected at the protein level, as GAPDH protein remained unperturbed 24 Hrs post-transfection in both transfected and non-transfected cells, as was evident from dual labeling of GAPDH mRNA and protein (FIG. 19). To further investigate the disparity between RNAi effect at mRNA and protein levels, HeLa cells were reverse transfected with GAPDH-targeting siRNA for 24 and 48 Hrs and processed for multiplexed imaging of GAPDH and HSP90-alpha mRNA and their respective protein products. Consistent with studies discussed earlier, 24 Hrs post-transfection a complete degradation of GAPDH mRNA was observed, whereas GAPDH protein level remained unperturbed (FIG. 20A). In contrast, 48 Hrs post-transfection a substantial reduction of GAPDH protein level could be observed, with GAPDH mRNA remaining below the detection limit (FIG. 20B). HSP90 mRNA and protein levels remained unperturbed through 48 hours, confirming selectivity of GAPDH silencing. Further, all molecular targets exhibited consistent unperturbed levels in reference non-transfected cells (FIG. 21A and FIG. 21B) and cells transfected with non-targeting siRNA (FIG. 22A and FIG. 22B) throughout the study, corroborating that the observed GAPDH knock-down indeed resulted from RNAi mechanism. Multiplexed analysis was fully confirmed by a series of single-plex studies to mitigate any artifacts that could potentially be introduced from the multi-omics labeling methodology, HSI, and image analysis (FIG. 23A and FIG. 23B).

In some cases, delay in RNAi effect at the protein level is present, as proteins are typically degraded and cleared slower in comparison to siRNA-mediated mRNA degradation. In other cases, heterogeneity in cell transfection can modulate assessing RNAi efficiency with bulk RT-PCR measurement and downstream phenotypic and molecular signaling analysis. Non-transfected cells might gain growth advantage and achieve substantial clonal expansion during the time it takes for higher-level manifestations of RNAi to occur, thus distorting observed RNAi effect at a population level. Imaging-based analysis at a single-cell level can by-pass this ambiguity and can offer a more accurate insight into molecular processes.

TABLE 4

List of ssDNA/ssDNA' tag pairs for encoding of molecular targets

| | Tag ID | Sequence* | SEQ ID NO: |
|---|---|---|---|
| QDot- | 1A | 5'-/5AmMC6/iSp18/CGTCGCACCAAGAAAT-3' | 936 |
| | 2A | 5'-/5AmMC6/iSp18/TAGACTTGCCATACGT-3' | 937 |
| | 3A | 5'-/5AmMC6/iSp18/AATTCTTGAGACCAGG-3' | 938 |
| | 4A | 5'-/5AmMC6/iSp18/ATCTGCCCAAACTCCA-3' | 939 |
| | 5A | 5'-/5AmMC6/iSp18/TTCCCAAGCGTCATCT-3' | 940 |
| | 6A | 5'-/5AmMC6/iSp18/TCTATCGGACGCTGTA-3' | 941 |
| IgG-compound | 1B | 5'-/5AmMC6/AAAAAAAAAAATTTCTTGGTGCGACG-3' | 942 |
| | 2B | 5'-/5AmMC6/AAAAAAAAAAACGTATGGCAAGTCTA-3' | 943 |
| | 3B | 5'-/5AmMC6/AAAAAAAAAAACCTGGTCTCAAGAATT-3' | 944 |
| | 4B | 5'-/5AmMC6/AAAAAAAAAATGGAGTTTGGGCAGAT-3' | 945 |
| | 5B | 5'-/5AmMC6/AAAAAAAAAAAGATGACGCTTGGGAA-3' | 946 |
| | 6B | 5'-/5AmMC6/AAAAAAAAAATACAGCGTCCGATAGA-3' | 947 |

*all ssDNA tags have 5' terminal amine group /5AmMC6/ for bioconjugation separated from the pairing sequence by either a hexa-ethyleneglycol spacer /iSp18/ for QDot-coupled tags or 10A oligonucleotide spacer for IgG-coupled tags.

TABLE 5

Sequences of GAPDH mRNA ISH probes (with 2B encoding tag)

| # | mRNA-recognition region | encoding tag 2B | SEQ ID NO: |
|---|---|---|---|
| 1 | 5'-ATTTATAGAAACCGGGGCG- | AAAAA-ACGTATGGCAAGTCTA-3' | 947 |
| 2 | 5'-CGAACAGGAGGAGCAGAGAG- | AAAAA-ACGTATGGCAAGTCTA-3' | 949 |
| 3 | 5'-GCTGGCGACGCAAAAGAAGA- | AAAAA-ACGTATGGCAAGTCTA-3' | 950 |
| 4 | 5'-CATGGTGTCTGAGCGATGTG- | AAAAA-ACGTATGGCAAGTCTA-3' | 951 |
| 5 | 5'-TACGACCAAATCCGTTGACT- | AAAAA-ACGTATGGCAAGTCTA-3' | 952 |
| 6 | 5'-CAGAGTTAAAAGCAGCCCTG- | AAAAA-ACGTATGGCAAGTCTA-3' | 953 |
| 7 | 5'-GGGTCATTGATGGCAACAAT- | AAAAA-ACGTATGGCAAGTCTA-3' | 954 |
| 8 | 5'-AACCATGTAGTTGAGGTCAA- | AAAAA-ACGTATGGCAAGTCTA-3' | 955 |

TABLE 5-continued

Sequences of GAPDH mRNA ISH probes (with 2B encoding tag)

| # | mRNA-recognition region   encoding tag 2B | SEQ ID NO: |
|---|---|---|
| 9 | 5'-GGGTGGAATCATATTGGAAC-AAAAA-ACGTATGGCAAGTCTA-3' | 956 |
| 10 | 5'-TTGACGGTGCCATGGAATTT-AAAAA-ACGTATGGCAAGTCTA-3' | 957 |
| 11 | 5'-CATTGATGACAAGCTTCCCG-AAAAA-ACGTATGGCAAGTCTA-3' | 958 |
| 12 | 5'-TCCTGGAAGATGGTGATGGG-AAAAA-ACGTATGGCAAGTCTA-3' | 959 |
| 13 | 5'-CCACTTGATTTTGGAGGGAT-AAAAA-ACGTATGGCAAGTCTA-3' | 960 |
| 14 | 5'-GGACTCCACGACGTACTCAG-AAAAA-ACGTATGGCAAGTCTA-3' | 961 |
| 15 | 5'-TTCTCCATGGTGGTGAAGAC-AAAAA-ACGTATGGCAAGTCTA-3' | 962 |
| 16 | 5'-AGAGATGATGACCCTTTTGG-AAAAA-ACGTATGGCAAGTCTA-3' | 963 |
| 17 | 5'-GACGAACATGGGGGCATCAG-AAAAA-ACGTATGGCAAGTCTA-3' | 964 |
| 18 | 5'-CATACTTCTCATGGTTCACA-AAAAA-ACGTATGGCAAGTCTA-3' | 965 |
| 19 | 5'-ATTGCTGATGATCTTGAGGC-AAAAA-ACGTATGGCAAGTCTA-3' | 966 |
| 20 | 5'-CTAAGCAGTTGGTGGTGCAG-AAAAA-ACGTATGGCAAGTCTA-3' | 967 |
| 21 | 5'-CCACGATACCAAAGTTGTCA-AAAAA-ACGTATGGCAAGTCTA-3' | 968 |
| 22 | 5'-TCTTCTGGGTGGCAGTGATG-AAAAA-ACGTATGGCAAGTCTA-3' | 969 |
| 23 | 5'-TAGAGGCAGGGATGATGTTC-AAAAA-ACGTATGGCAAGTCTA-3' | 970 |
| 24 | 5'-TCAGCTCAGGGATGACCTTG-AAAAA-ACGTATGGCAAGTCTA-3' | 971 |
| 25 | 5'-CACTGACACGTTGGCAGTGG-AAAAA-ACGTATGGCAAGTCTA-3' | 972 |
| 26 | 5'-CAGGTTTTTCTAGACGGCAG-AAAAA-ACGTATGGCAAGTCTA-3' | 973 |
| 27 | 5'-CACCTTCTTGATGTCATCAT-AAAAA-ACGTATGGCAAGTCTA-3' | 974 |
| 28 | 5'-GCTGTTGAAGTCAGAGGAGA-AAAAA-ACGTATGGCAAGTCTA-3' | 975 |
| 29 | 5'-CGTCAAAGGTGGAGGAGTGG-AAAAA-ACGTATGGCAAGTCTA-3' | 976 |
| 30 | 5'-AGTGGTCGTTGAGGGCAATG-AAAAA-ACGTATGGCAAGTCTA-3' | 977 |
| 31 | 5'-TCATACCAGGAAATGAGCTT-AAAAA-ACGTATGGCAAGTCTA-3' | 978 |
| 32 | 5'-CCTGTTGCTGTAGCCAAATT-AAAAA-ACGTATGGCAAGTCTA-3' | 979 |
| 33 | 5'-TGAGGAGGGGAGATTCAGTG-AAAAA-ACGTATGGCAAGTCTA-3' | 980 |
| 34 | 5'-CTCTTCAAGGGGTCTACATG-AAAAA-ACGTATGGCAAGTCTA-3' | 981 |
| 35 | 5'-TACATGACAAGGTGCGGCTC-AAAAA-ACGTATGGCAAGTCTA-3' | 982 |
| 36 | 5'-TGAGCACAGGGTACTTTATT-AAAAA-ACGTATGGCAAGTCTA-3' | 983 |

Note:
mRNA-recognition region and encoding tag are separated by a spacer SP. Shorter 41 nt mRNA ISH probes contain -AAAAA- single-stranded spacer. Longer 60 nt mRNA ISH probes contain pre-hybridized 16 bp double-stranded spacer flanked by -AAAA- single-stranded linkers.

TABLE 6

Sequences of HSP90-alpha mRNA ISH probes (with 4B encoding tag)

| # | mRNA-recognition region   encoding tag 4B | SEQ ID NO: |
|---|---|---|
| 1 | 5'-AGGAGTATGATTGTCAACCC-AAAAA-TGGAGTTTGGGCAGAT-3' | 984 |
| 2 | 5'-CCTATATAAGGCGAAGCAC-AAAAAA-TGGAGTTTGGGCAGAT-3' | 985 |

TABLE 6-continued

Sequences of HSP90-alpha mRNA ISH probes (with 4B encoding tag)

| # | mRNA-recognition region   encoding tag 4B | SEQ ID NO: |
|---|---|---|
| 3 | 5'-GAGTGACTCGAGAGAGCT-ACAAAAA-TGGAGTTTGGGCAGAT-3' | 986 |
| 4 | 5'-ATAGTGAGCAACGTAGGCTT-AAAAA-TGGAGTTTGGGCAGAT-3' | 987 |
| 5 | 5'-GGACATGAGTTGGGCAATTT-AAAAA-TGGAGTTTGGGCAGAT-3' | 988 |
| 6 | 5'-GAGATCAACTCCCGAAGGAA-AAAAA-TGGAGTTTGGGCAGAT-3' | 989 |
| 7 | 5'-AATCTTGTCCAAGGCATCAG-AAAAA-TGGAGTTTGGGCAGAT-3' | 990 |
| 8 | 5'-AACTTCGAAGGGTCTGTCAG-AAAAA-TGGAGTTTGGGCAGAT-3' | 991 |
| 9 | 5'-GGTTGGGGATGATGTCAATT-AAAAA-TGGAGTTTGGGCAGAT-3' | 992 |
| 10 | 5'-TACCAAAGTCAGGGTACGTT-AAAAA-TGGAGTTTGGGCAGAT-3' | 993 |
| 11 | 5'-TGAGATCAGCTTTGGTCATG-AAAAA-TGGAGTTTGGGCAGAT-3' | 994 |
| 12 | 5'-TTGGCAATGGTTCCCAAATT-AAAAA-TGGAGTTTGGGCAGAT-3' | 995 |
| 13 | 5'-CTGAAGAGCCTCCATGAATG-AAAAA-TGGAGTTTGGGCAGAT-3' | 996 |
| 14 | 5'-CCACCAAGTAGGCAGAATAA-AAAAA-TGGAGTTTGGGCAGAT-3' | 997 |
| 15 | 5'-TGCTTTGTGATCACAACCAC-AAAAA-TGGAGTTTGGGCAGAT-3' | 998 |
| 16 | 5'-CAGAAGACTCCCAAGCATAC-AAAAA-TGGAGTTTGGGCAGAT-3' | 999 |
| 17 | 5'-AGCACGCACAGTGAAGGAAC-AAAAA-TGGAGTTTGGGCAGAT-3' | 1000 |
| 18 | 5'-TCTAGGTACTCTGTCTGATC-AAAAA-TGGAGTTTGGGCAGAT-3' | 1001 |
| 19 | 5'-TAAAGGGTGATGGGATAGCC-AAAAA-TGGAGTTTGGGCAGAT-3' | 1002 |
| 20 | 5'-TGTTTAGTTCTTCCTGATCA-AAAAA-TGGAGTTTGGGCAGAT-3' | 1003 |
| 21 | 5'-AGGGTTTCTGGTCCAAATAG-AAAAA-TGGAGTTTGGGCAGAT-3' | 1004 |
| 22 | 5'-TCATTAGTGAGGCTCTTGTA-AAAAA-TGGAGTTTGGGCAGAT-3' | 1005 |
| 23 | 5'-AAAGTGCTTGACTGCCAAGT-AAAAA-TGGAGTTTGGGCAGAT-3' | 1006 |
| 24 | 5'-TGAATTCCAACTGACCTTCT-AAAAA-TGGAGTTTGGGCAGAT-3' | 1007 |
| 25 | 5'-GAGCCCGACGAGGAATAAAT-AAAAA-TGGAGTTTGGGCAGAT-3' | 1008 |
| 26 | 5'-TGAACACACGGCGGACATAG-AAAAA-TGGAGTTTGGGCAGAT-3' | 1009 |
| 27 | 5'-ATCAACTCATCACAGCTGTC-AAAAA-TGGAGTTTGGGCAGAT-3' | 1010 |
| 28 | 5'-AAGATTTTGCTCTGCTGGAG-AAAAA-TGGAGTTTGGGCAGAT-3' | 1011 |
| 29 | 5'-AGAGAAGAGCTCAAGGCACT-AAAAA-TGGAGTTTGGGCAGAT-3' | 1012 |
| 30 | 5'-GTGGATTCCAAGCTTGAGAT-AAAAA-TGGAGTTTGGGCAGAT-3' | 1013 |
| 31 | 5'-AGACTGGGAGGTATGATAGC-AAAAA-TGGAGTTTGGGCAGAT-3' | 1014 |
| 32 | 5'-CTCTGACAGAGATGTCATCT-AAAAA-TGGAGTTTGGGCAGAT-3' | 1015 |
| 33 | 5'-TAGATGGACTTCTGTGTCTC-AAAAA-TGGAGTTTGGGCAGAT-3' | 1016 |
| 34 | 5'-GCTCCACAAAAGCTGAGTTG-AAAAA-TGGAGTTTGGGCAGAT-3' | 1017 |
| 35 | 5'-CATATATACCACCTCGAAGC-AAAAA-TGGAGTTTGGGCAGAT-3' | 1018 |
| 36 | 5'-ACACAGTACTCGTCAATGGG-AAAAA-TGGAGTTTGGGCAGAT-3' | 1019 |
| 37 | 5'-TTCCCATCAAATTCCTTGAG-AAAAA-TGGAGTTTGGGCAGAT-3' | 1020 |
| 38 | 5'-GAGATTGTCACCTTCTCAAC-AAAAA-TGGAGTTTGGGCAGAT-3' | 1021 |
| 39 | 5'-TGCAGCAAGGTGAAGACACA-AAAAA-TGGAGTTTGGGCAGAT-3' | 1022 |

TABLE 6-continued

Sequences of HSP90-alpha mRNA ISH probes (with 4B encoding tag)

| # | mRNA-recognition region   encoding tag 4B | SEQ ID NO: |
|---|---|---|
| 40 | 5'-GCTTTTTGGCCATCATATAG-AAAAA-TGGAGTTTGGGCAGAT-3' | 1023 |
| 41 | 5'-AACTGCCTTATCATTCTTGT-AAAAA-TGGAGTTTGGGCAGAT-3' | 1024 |
| 42 | 5'-ATCCTCAAGGGAAAAGCCAG-AAAAA-TGGAGTTTGGGCAGAT-3' | 1025 |
| 43 | 5'-TGATCATGCGATAGATGCGG-AAAAA-TGGAGTTTGGGCAGAT-3' | 1026 |
| 44 | 5'-CATCAGGAACTGCAGCATTG-AAAAA-TGGAGTTTGGGCAGAT-3' | 1027 |
| 45 | 5'-CAAGGGCACAAGTTTTCCAA-AAAAA-TGGAGTTTGGGCAGAT-3' | 1028 |
| 46 | 5'-TACTGCCTTCAACACAAGGA-AAAAA-TGGAGTTTGGGCAGAT-3' | 1029 |
| 47 | 5'-AGAGTAGAGAGGGAATGGGG-AAAAA-TGGAGTTTGGGCAGAT-3' | 1030 |
| 48 | 5'-TACACAACATCCAATCCTGC-AAAAA-TGGAGTTTGGGCAGAT-3' | 1031 |

Note:
mRNA-recognition portion and encoding tag are separated by a spacer. Shorter 41 nt mRNA ISH probes contain -AAAAA- single-stranded spacer. Longer 60 nt mRNA ISH probes contain pre-hybridized 16 bp double-stranded spacer flanked by -AAAA- single-stranded linkers.

Example 3

Global In Situ Visualization of the DNaseI Hypersensitivity Site (DHS) Compartment of a Cell This example shows the global in situ visualization of the DNaseI Hypersensitivity Site (DHS) compartment of a cell, which allows for identification of nuclear compartments where regulatory DNA activation occurs. As shown in the graphic on the left side of FIG. 24, K562 cells were fixed with Paxgene reagent, treated with DNaseI, DNaseI-induced nicks were labeled using terminal transferase (TdT) and ethynyl-dUTP (EdUTP) (TUNEL assay), Alexafluor-488 (AF488) was conjugated to the EdUTP via copper click chemistry, and then SPDM imaging was performed. FIG. 24 shows multiple images of this. The top left image is of the raw signal data. The local density map image (top middle) shows a ring of condensation at the nuclear lamina, which is similar to findings reported by the Weintraub lab 30 years ago (Weintraub, Cell (1985) 43:471-482); see FIG. 24 top right reproduced image). Approximately 18.4% of the localized points are within the ring density at the nuclear lamina, as shown the calculations in the lower right box, in which the image data calculation was based off the image on the lower left of FIG. 24. The image data calculation is similar to the proportion of K562 DHS within lamina-associated domains (LADS). These findings indicate labeling of DNaseI cut sites in a cell's nucleus using a TUNEL assay may be used for better understanding of the nuclear localization of regulatory DNA activation.

Example 4

Nano-FISH Methods

This example shows how nano-FISH was used to detect the presence or absence of the locus control region in human erythroleukemia K562 cells.

Cells and Tissue Culture

Human erythroleukemia K562 cells and their derivative lacking the locus control region (ΔLCR) were maintained in RPMI 1640 media supplemented with 2 mM L-glutamine (0.3 g/L), 10% Fetal Bovine Serum, penicillin, and streptomycin at 37° C. in 5% $CO_2$.

In Silico Design of Nano-FISH Probe Pools

Tiled 40 bp probe pools with a minimum of 2 bp spacing between consecutive probes were designed using Primer3 with default parameters. The resulting tiled probe sets were compared to a 16-mer database of genomic sequences in each register to model partial matches of probes to genomic sequences that could result in inappropriate background staining. A uniquely mapping oligonucleotide would therefore have a total of 24 matches to the 16-mer database. Individual probe sets with >100 16-mer database matches were empirically discarded from consideration. For the genomic target regions examined in this study, a pool of at least 30 oligonucleotides that satisfied these design criteria was used.

Nano-FISH Protocol

Cells were harvested, washed once in phosphate buffered saline (PBS), re-suspended in a small volume of PBS and subsequently seeded on 18 mm×18 mm coverslips in a 6-well plate that had been coated with poly-L-lysine (Sigma P1399). After allowing cells to adhere for 5 to 10 minutes at room temperature they were fixed by the addition of 4% formaldehyde (Polysciences 18814-10) in PBS for 10 minutes, washed with PBS, and then permeabilized for 15 minutes with 0.5% detergent Triton™ X-100 in PBS. Following two washes in PBS, the cells were subjected to a 5 minute treatment of 0.1 M HCl and subsequently washed twice in saline sodium citrate (2×SSC) before incubation with RNase A (25 ug/mL in 2×SSC) at 37° C. for 30 minutes. The cover slips were washed in 2×SSC again and then pre-equilibrated for at least one hour in 50% formamide (Amresco 0606), 2×SSC (pH 7.0) at room temperature. To denature the cellular DNA the cover slips were incubated for 4.5 minutes in 70% formamide, 2×SSC (pH 7.0) preheated to 78° C. in a 6-well plate on a heat block equipped with an aluminum block designed for tissue culture plates. For consistency, only the center two wells were used for denaturations and the temperature allowed to re-equilibrate before the next batch. Cover slips were then inverted onto 80 µl of hybridization solution (50% formamide, 10% dextran sulfate, 2×SSC, 250 pM oligonucleotide pool) on parafilm in a humid chamber and incubated overnight at 37° C. Post-hybridization washes included two 15 minute incubations in 2×SSC followed by two 7 minute washes in 0.2×SSC/0.2% Tween-20 at 56° C. on a heat block and one wash in 4×SSC/0.2% Tween-20 at room temperature. Cellular DNA was counterstained with DAPI (100 ng/ml in 2×SSC), followed by two more washes in 2×SSC. Cover slips were then mounted on slides for imaging with Prolong Gold (Molecular Probes P36930).

Imaging

For standard widefield microscopy, slides were imaged on an inverted Nikon Eclipse Ti widefield microscope with a 60× Nikon Plan Apo lambda NA 1.40 oil objective and an Andor Zyla 4.2CL10 CMOS camera.

Example 5

Nano-FISH Detection of a 1.8 kb Nucleic Acid Sequence

This example and FIG. 33 shows the use of Nano-FISH to detect a 1.8 kb nucleic acid sequence. FIG. 33A shows a schematic of a Nano-FISH experiment. FIG. 33B shows the application of the Nano-FISH strategy to detect a 1.8 kb region encompassing the HS2 hypersensitive site of the β-globin locus control region (LCR) in triploid K562 erythroleukemia cells. FIG. 33C shows colocalization of the Nano-FISH signals (~1.8 kb target region) with those from standard BAC-derived probes (conventional DNA-FISH; ~170 kb target region), confirming the specificity of the detected Nano-FISH signal. Compared to the large size of BAC probes used to detect the β-globin LCR, Nano-FISH probes targeting HS2 covered a target region that was approximately 2 orders of magnitude smaller in size. Although most, but not all spots corresponding to the alleles in the triploid cell, were consistently detected using 30 tiled 40 bp oligonucleotide probes targeting the HS2 hypersensitive site, increasing the number of probes and expanding the corresponding labeled genomic DNA target region, Nano-FISH was shown to be tunable. A modest increase in the number of probes (~90), the frequency of allele detecting by Nano-FISH matches the performa of the BAC-probe based golda performance benchmark of Nano-FISH versus standard BAC probes. Conversely, decreasing the number probes below 30 drastically reduced allele detection sensitivity. Therefore, as shown in FIG. 33D, the sensitivity of efficiency and resolution of detection using Nano-FISH may be tuned according to the number of probes being used.

Using an efficient and robust automated image processing pipeline, results from hundreds of cells across multiple replicates were quantified. These studies showed that the diffraction-limited signals produced by Nano-FISH were smaller and dimmer than those generated by BAC-based probes (FIG. 33E and FIG. 33E). Despite this, Nano-FISH still showed robust detection of genomic regions with varying size, such as genomic region size ranging from about 800 bp to 2.1 kb, as shown if FIG. 33G. Thus, Nano-FISH is able to successfully label endogenous non-repetitive DNA loci that are much smaller than the current limit of resolution of BAC- and fosmid-based DNA-FISH approaches.

Example 6

Fine Structural Analysis Using Nano-FISH

This example and FIG. 34 show the use of Nano-FISH to perform fine structural analysis of specific genomic loci within the nucleus. Probe pools were designed to target a 1.6 kb region of chromosome 19 and a 1.4 kb region of chromosome 18. These chromosomes were chosen since chromosome 19 is known to occupy a central position within the nucleus while chromosome 18 is more marginally located. FIG. 34A shows the distinct spots produced by Nano-FISH probes targeting specific loci on these chromosomes. To measure the relative localization of the detected loci, the relative radial distance (RRD), a normalized measure of the position of the detected spot with respect to the nuclear centroid, was calculated. FIG. 34B shows a schematic of the relative radial distance. FIG. 34C shows that the chromosome 18 Nano-FISH signals are closer to the nuclear periphery. The distributions were obtained across 2,396 chromosome 18 signals and 3,388 chromosome 19 signals. FIG. 34D shows radial histograms of the two target loci. The differences in the distribution of signals with respect to the nuclear centroid are readily apparent in the histograms.

Example 7

Examination of Enhancer-Promoter Interactions Using Nano-FISH

This example and FIG. 35 show the use of Nano-FISH for examining the interaction of a gene enhancer with its target gene promoter. The positioning of a known enhancer of the CCND1 gene in 786-0 and MCF-7 cells was examined. Based on DNaseI hypersensitivity mapping, this enhancer is active in 786-0 cells, but is inactive in MCF-7 cells. Using large (~225 kb) probes, others have demonstrated that this enhancer is located in proximity to the CCND1 gene promoter in 786-0 cells, but not in MCF-7 cells. Nano-FISH probes targeting the enhancer and promoter were designed and synthesized. FIG. 35A shows two-color Nano-FISH in 786-0 and MCF-7 cells. The normalized inter-spot distance (NID) between these two genomic loci were compared. FIG. 35B shows a schematic of the normalized inter-spot distance. FIG. 34C shows that, on average, the spots are situated closer together in 786-0 cells compared to MCF-7 cells. FIG. 35D shows that, in spite of this, absolute colocalization (NID=0) was actually a rare event in both cell types. Thus, the small size of genomic regions targeted by Nano-FISH permits fine scale localization of regulatory DNA regions and provides a granular view of their spatial localizations within nuclei.

Example 8

Detection of Small Genomic Structural Variations Using Nano-FISH

This example and FIG. 36 show the use of Nano-FISH to detect small genomic structural variations such as small losses or gains of DNA. ZFN-mediated genome editing was used to generate a triploid homozygous deletion of the β-globin locus control region (LCR, ~18 kb) in K562 cells, as shown in FIG. 36A. Cells imbued with this deletion are referred to as ΔLCR. Probes targeting either the HS2 or HS3 hypersensitive sites within the deleted region were utilized to detect loss of LCR in the genome edited cells, as shown in FIG. 36B and FIG. 36C. For the converse scenario, using TALEN-mediated homology directed repair, a sequence encoding for eGFP was inserted into the AAVS1 safe harbor locus on chromosome 19, as shown in FIG. 36D. This exogenously-derived sequenced was readily identified by Nano-FISH, as shown in FIG. 36E and FIG. 36F.

Example 9

Fine Scale Genome Localization Using Nano-FISH and Super-Resolution Microscopy

This example and FIG. 37 show the combination of Nano-FISH and super-resolution microscopy to obtain very fine-scale genome localization. A custom automated stimulated emission and depletion (STED) microscope was utilized to efficiently acquire multiple measurements of the physical distance between the HS2 and HS3 genomic loci, which are separated by 4.1 kb of linear genomic distance. FIG. 37A shows that these closely apposed loci are readily discernible as distinct spots by STED microscopy. Pair-wise measurements of other closely situated genomic segments such as HS1-HS4 (~12 kb) and HS2-HGB2 (~25 kb) were also readily obtained and revealed non-linear compaction of the β-globin locus control region and the surrounding genome which contains its target genes, as shown in FIG. 37B. Importantly, the high-throughput STED microscopy approach enables calculation of the distribution of actual distances between these various loci, as shown in FIG. 37C. These results demonstrated the suitability of Nano-FISH for super-resolution STED microscopy experiments.

Example 10

Optimal Nano-FISH Parameters

This example and FIG. 38 show a series of experiments to determine the optimal operating parameters for a Nano-FISH experiment. FIG. 38A shows how the labeling efficiency of the Nano-FISH procedure depends on denaturation temperature. With increasing temperature, the efficiency of Nano-FISH labeling increases, until a plateau is reached at a temperature of 78° C. FIG. 38B shows that the Nano-FISH labeling procedure is repeatable across experiments. FIG. 38C shows Nano-FISH detected for genomic regions with varying size, such as genomic region size ranging from about 800 bp to 2.1 kb. FIG. 38D shows how the labeling efficiency of the Nano-FISH experiment depends on the number of oligo probes used. The labeling efficiency increases with the number of oligo probes used, attaining a maximum efficiency when 30 oligo probes are utilized. FIG. 38E shows how the detected fluorescence spot size depends on the number of oligo probes. FIG. 38F shows how the intensity of the fluorescence spot size depends on the number of oligo probes.

Example 11

Comparison of Nano-FISH and Conventional FISH

This example and FIG. 39 show a comparison of Nano-FISH and conventional FISH. FIG. 39A shows fluorescence images of β-globin lacking the LCR using conventional BAC probes (left panel), a pool of HS1-5 probes (middle panel), and the HS2 Nano-FISH technique (right panel). FIG. 39B shows the size of the probe sets used for the BAC, HS1-5, and HS2 experiments. As can be seen, the HS2 Nano-FISH experiment utilizes a significantly smaller nucleic acid sequence than conventional FISH techniques. FIG. 39C shows the labeling efficiency of the BAC, HS1-5, and HS2 experiments. FIG. 39D shows the size of the FISH spots for the BAC, HS1-5, and HS2 experiments. FIG. 39E shows the intensity of the FISH signals for the BAC, HS1-5, and HS2 experiments. As can be seen, the Nano-FISH experiment produces a lower signal-to-noise ratio (SNR) than conventional methods, with the Nano-FISH experiment producing a SNR smaller than the BAC method by a factor of approximately 2. The loss in SNR comes with a reduction in the size of the nucleic acid sequence by a factor of approximately 100. Thus, the tradeoff in SNR is well worth the significant reduction in size of nucleic acid sequence.

Example 12

Discovery of Novel Biomarkers Using Nano-FISH

This example shows the discovery of the expression of novel biomarkers that correlate the number of the target nucleic acid sequence in a cell. A sample with a population of cells that is heterogenous for the number of target nucleic acid sequences in a cell is obtained. Individual cells from the sample are distributed into a single well of a plate and are allowed to clonally expand. Samples of cells from each clone is then characterized for the number of target nucleic acid sequences in a cell using Nano-FISH and is characterized by RNA-Seq to determine novel biomarkers that correlate with the number of target nucleic acid sequences. If a novel biomarker is found to be a surface protein, then the surface protein is used as a selectable marker/sortable marker to isolate cells with the desired number of target nucleic acid sequences from the sample.

The examples and embodiments described herein are for illustrative purposes only and various modifications or changes suggested to persons skilled in the art are to be included within the spirit and purview of this application and scope of the appended claims.

What is claimed is:

1. A high-throughput method for detecting presence of a 800 nucleotides to 2.1 kb long target nucleic acid sequence in a genome of mammalian cells with high resolution, the method comprising:
contacting the mammalian cells with a plurality of probes comprising a detectable label and a probe sequence that binds to a portion of the target nucleic acid sequence; and
detecting a presence of the detectable label localized to a region in the genome in the nucleus of the mammalian cells, wherein the presence of the detectable label indicates the presence of the target nucleic acid sequence,
wherein the target nucleic acid is an endogenous nucleic acid sequence present in the genome of the cells, an exogenous nucleic acid sequence integrated into the genome of the cells, or a combination thereof,
wherein the probe sequence is between 30 and 50 nucleotides in length,
wherein the plurality of probes comprises at least 30 probes to less than 50 probes, and
wherein high resolution comprises delineation of 800 nucleotides to 2.1 kb long target sequences separated by a 4 kb intervening sequence on a chromosome.

2. The method of claim 1, wherein the mammalian cells comprise cancer cells.

3. The method of claim 1, wherein the target nucleic acid sequence is an exogenous nucleic acid sequence integrated into the genome of the cells or a combination of an endogenous nucleic acid sequence present in the genome of the cells and an exogenous nucleic acid sequence integrated into the genome of the cells.

4. The method of claim 3, the mammalian cells have been genetically modified to introduce the exogenous sequence.

5. The method of claim 4, wherein the target sequence is less than 2.5 kb long.

6. The method of claim 5, further comprising determining a phenotype of the genetically modified cells; and correlating the phenotype of the genetically modified cells with the presence of the target nucleic acid sequence.

7. The method of claim 4, wherein the method further comprises determining a number or location of the exogenous sequence in the genetically modified cells.

8. The method of claim 1, wherein the target sequence is less than 2.5 kb long.

9. The method of claim 1, wherein the detectable label is a fluorescent label.

10. The method of claim 1, wherein the mammalian cells are treated with RNase prior to the contacting.

11. The method of claim 1, wherein the mammalian cells are genetically modified cells and the method comprises genetically modifying the cells by genetic editing prior to the contacting.

12. The method of claim 1, wherein the genome of the cell is denatured at a temperature of no higher than 78° C.

13. A method of determining a localization of a regulatory element, the method comprising:
a) contacting a regulatory element with a first set of detection agents;

b) photobleaching the first set of detection agents for a first time point at a first wavelength to generate a second set of detection agents capable of generating a light at a second wavelength;
c) detecting at least one burst generated by the second set of detection agents to generate a detection profile; and
d) based on step c), analyzing the detection profile to determine the localization of the regulatory element.

14. The method of claim 13, wherein the first set of detection agents comprise fluorescently labeled probes.

* * * * *